US009562060B2

(12) United States Patent
Cheng et al.

(10) Patent No.: US 9,562,060 B2
(45) Date of Patent: Feb. 7, 2017

(54) HETEROCYCLIC PYRIDONE COMPOUND, AND INTERMEDIATE, PREPARATION METHOD AND USE THEREOF

(75) Inventors: Jianjun Cheng, Shanghai (CN); Jihong Qin, Shanghai (CN); Bin Ye, Moraga, CA (US)

(73) Assignee: SHANGHAI HUILUN LIFE SCIENCE & TECHNOLOGY CO., LTD, Shanghai (CN)

( * ) Notice: Subject to any disclaimer, the term of this patent is extended or adjusted under 35 U.S.C. 154(b) by 178 days.

(21) Appl. No.: 14/124,628

(22) PCT Filed: May 28, 2012

(86) PCT No.: PCT/CN2012/000741

§ 371 (c)(1), (2), (4) Date: Mar. 28, 2014

(87) PCT Pub. No.: WO2012/167600

PCT Pub. Date: Dec. 13, 2012

(65) Prior Publication Data

US 2014/0206679 A1 Jul. 24, 2014

(30) Foreign Application Priority Data

Jun. 9, 2011 (CN) .......................... 2011 1 0154250

(51) Int. Cl.

| | |
|---|---|
| ***A61K 31/4439*** | (2006.01) |
| ***C07D 513/04*** | (2006.01) |
| ***C07D 471/04*** | (2006.01) |
| ***C07D 498/04*** | (2006.01) |

(52) U.S. Cl.

CPC ........... *C07D 513/04* (2013.01); *C07D 471/04* (2013.01); *C07D 498/04* (2013.01)

(58) Field of Classification Search

CPC .................................................... C07D 513/04

See application file for complete search history.

(56) References Cited

FOREIGN PATENT DOCUMENTS

| | | |
|---|---|---|
| CN | 101128199 A | 2/2008 |
| CN | 101779124 A | 7/2010 |

OTHER PUBLICATIONS

Milburn, R. R. et al. (2011). Development of a practical synthesis of a pyrazotopyridinone-based p38 MAP kinase inhibitor. *Organic Process Research & Development*, 15, 31-43.

International Search Report, mailed Sep. 20, 2012 in connection with PCT International Application No. PCT/CN2012/000741, filed May 28, 2012.

Written Opinion of the International Searching Authority, mailed Sep. 20, 2012 in connection with PCT International Application No. PCT/CN2012/000741, filed May 28, 2012.

Notification Concerning Transmittal of International Preliminary Report on Patentability (Chapter I of the Patent Cooperation Treaty), including an International Preliminary Report on Patentability and Written Opinion of the International Searching Authority, mailed Dec. 27, 2013 by The International Bureau of WIPO in connection with PCT International Application No. PCT/CN2012/000741, filed May 28, 2012.

*Primary Examiner* — Brian McDowell

(74) *Attorney, Agent, or Firm* — John P. White; Cooper & Dunham LLP

(57) ABSTRACT

The present invention relates to a heterocyclic pyridone compound represented by General Formula (I), where the heterocyclic pyridone compound is used as a tyrosine kinase inhibitor, and particularly a c-Met inhibitor. The present invention also relates to intermediates for preparing heterocyclic pyridone compound and a preparation method. The present invention further relates to a pharmaceutical composition containing the heterocyclic pyridone compound as an active ingredient, and a use of the pharmaceutical composition in treatment of diseases associated with tyrosine kinase c-Met, especially cancer associated with c-Met, as a medicament.

(I)

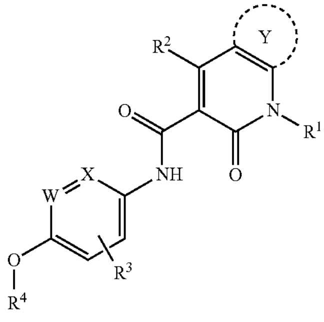

10 Claims, No Drawings

HETEROCYCLIC PYRIDONE COMPOUND, AND INTERMEDIATE, PREPARATION METHOD AND USE THEREOF

CROSS-REFERENCE TO RELATED APPLICATIONS

This application is a §371 national stage of PCT International Application No. PCT/CN2012/000741, filed May 28, 2012, claiming priority of Chinese Patent Application No. 201110154250.7, filed Jun. 9, 2011, the contents of each of which are hereby incorporated by reference in their entirety.

BACKGROUND

Technical Field

The present invention relates to a heterocyclic pyridone compound, an intermediate and a preparation method thereof, a pharmaceutical composition containing the heterocyclic pyridone compound as an active ingredient, and a use of the pharmaceutical composition in treatment of diseases associated with tyrosine kinase c-Met, especially cancer associated with c-Met, as a medicament.

Related Art

Cancer is the number one killer that threatens human life and health worldwide. Although medical advances enable human to have many new methods for treatment of cancer, presently, cancer is still considered as an unsolved medical problem. Cancer may be caused by many causes, and in recent years, people is enabled to gradually clarify the nature of tumor by means of the development of disciplines such as molecular oncology and molecular pharmacology, and people gradually realize that the nature of carcinogenesis is unlimited cell proliferation caused by cellular signaling pathway disorder. As the most important member involved in cellular signaling, protein tyrosine kinases (PTKs, tyrosine kinases for short) are the most common growth factor receptors, and are closely correlated to occurrence and development of tumor. An excessively high activity of tyrosine kinases leads to activation of a downstream signaling pathway, thereby leading to cell transformation, proliferation, inhibition to apoptosis, and promotion of cell survival, and finally resulting in formation of tumor. Therefore, in recent years, the development trend of antineoplastic agents begins to turn to drugs for abnormal intracellular signaling from conventional cytotoxic drugs, and some relevant drugs have been used in clinic in succession. Compared with conventional cytotoxic antineoplastic agents, this type of molecular targeted agents have strong efficacy and less toxic and side effects, and have gradually become hot issues in current research and development of antineoplastic agents.

The tyrosine kinases are classified into receptor tyrosine kinases and non-receptor tyrosine kinases. The receptor tyrosine kinases include epithelial growth factor receptor (EGFR) family, vascular endothelial growth factor (VEGFR) family, platelet derived growth factor receptor (PDGFR) family, fibroblast growth factor receptor (FGFR) family, and so on. The non-receptor tyrosine kinases include Src kinase family, Jak, FAK, and so on. Each kinase family further includes a variety of subtypes.

Hepatocyte growth factor receptor c-Met is a type of receptor tyrosine kinase (Park et al., Proc. Natl. Acad. Sci. USA 84: 6379-83, 1987; Bottaro et al., Science 2S 1: 802-4, 1991), and includes highly glycosylated outer α subunits and β subunits, and extracellular domains, transmembrane segments and cytoplasmic tyrosine kinase domains. The endogenous ligand for c-Met is hepatocyte growth factor (HGF) (Nature, 327: 239-242 (1987); J. Cell Biol., 111: 2097-2108 (1990)), and c-Met binds with the ligand to induce dimerization of c-Met, so as to generate an autophosphorylated activated receptor, promote downstream signaling, and mediate a variety of responses in tumor cells, including proliferation of epithelial cells and endothelial cells, stimulation of epithelial cell motility, cell survival and morphological changes and promotion of invasion. In addition, HGF regulates angiogenesis, has important meaning for tumor growth and spread. Overexpression of c-Met and the ligand thereof in a variety of tumors (including thyroid cancer, ovarian cancer and pancreatic cancer) also indicates the role of c-Met and the ligand thereof in the development of these tumors.

Presently, in primary tumor and secondary tumor metastasis that c-Met receptor activation plays a key role, a biomass (ribozyme, antibody and antisense RNA) of targeting HGF or c-Met can inhibit tumorigenesis, and it is predicted that selective small-molecular inhibitors of targeting c-Met has therapeutic potential. Patents WO2004/076412, WO2006/021881, WO2010/011538, WO2010/059771 and WO2010/048131 disclose selective c-Met small-molecular inhibitors, and preparation methods and uses thereof.

The heterocyclic pyridone compound disclosed in the present invention has not been reported as a tyrosine kinase inhibitor, a tyrosine kinase inhibitor, especially a c-Met inhibitor.

SUMMARY

A first technical problem to be solved by the present invention is to provide a heterocyclic pyridone compound.

A second technical problem to be solved by the present invention is to provide an intermediate for preparing heterocyclic pyridone compound.

A third technical problem to be solved by the present invention is to provide a method for preparing the intermediate.

A fourth technical problem to be solved by the present invention is to provide a preparation method of the heterocyclic pyridone compound.

A fifth technical problem to be solved by the present invention is to provide a pharmaceutical composition with the heterocyclic pyridone compound as an active ingredient.

A sixth technical problem to be solved by the present invention is to provide a use of the heterocyclic pyridone compound.

As a first aspect of the present invention, the heterocyclic pyridone compound is a compound represented by General formula (I) below:

(I)

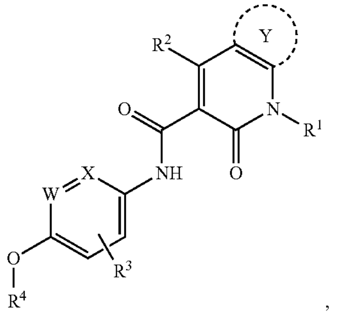

, where $R^1$ is selected from hydrogen, alkyl, substituted alkyl, cycloalkyl, substituted cycloalkyl, aryl, substituted aryl, heteroaryl, substituted heteroaryl, arylalkyl, substituted arylalkyl, heteroarylalkyl, substituted heteroarylalkyl and $C(=O)NR^{10}R^{11}$;

$R^2$ is selected from hydrogen, halogen, alkoxy, amino, alkyl, substituted alkyl, cycloalkyl, substituted cycloalkyl, hydroxy alkyl, amino alkyl, aryl, substituted aryl, heteroaryl, substituted heteroaryl, arylalkyl, substituted arylalkyl, heteroarylalkyl, substituted heteroarylalkyl, heterocyclic group, and substituted heterocyclic group;

$R^3$ is selected from hydrogen, halogen, alkyl and heteroaryl;

$R^4$ is selected from groups having Structural Formulas (1) to (5) below, where Z═CH or N;

(1)

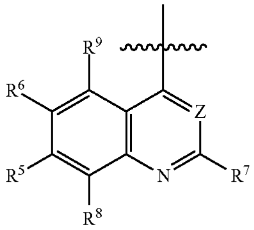

(2)

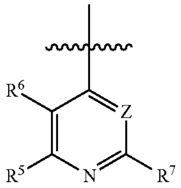

(3)

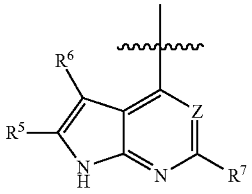

(4)

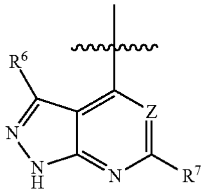

(5)

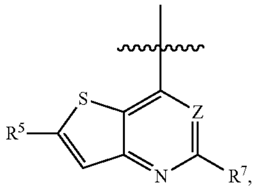

$R^5$ is selected from $NH_2$, $NH(C{=}O)R^{12}$, $NHC({=}O)NR^{10}R^{11}$, $O(CH_2)_nOR^{12}$ (n is 1 to 4), and $NR^{10}R^{11}$ or a heterocyclic ring and an aromatic heterocyclic ring;

$R^6$, $R^7$, $R^8$, $R^9$, $R^{10}$, $R^{11}$ and $R^{12}$ are simultaneously or non-simultaneously selected from hydrogen, alkyl, substituted alkyl, cycloalkyl, substituted cycloalkyl, aryl, substituted aryl, heteroaryl, substituted heteroaryl, alkenyl, substituted alkenyl, alkynyl, substituted alkynyl, substituted aminoalkyl, substituted alkylamino, arylamino, substituted arylamino, heteroaryl amino, substituted heteroaryl amino, a heterocyclic group and a substituted heterocyclic group;

W and X are selected from CH and N; and

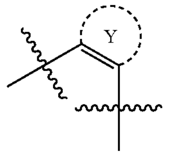

is selected from groups having Structural Formulas (6) to (38) below:

(6)

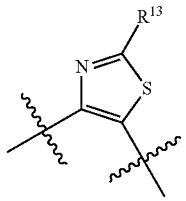

(7)

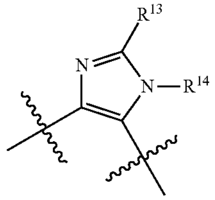

(8)

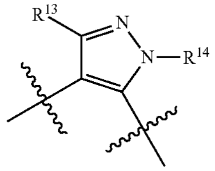

(9)

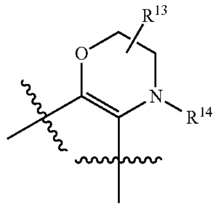

(10)

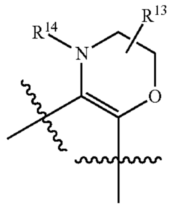

-continued
(11)
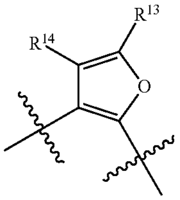
(12)
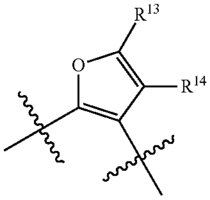
(13)
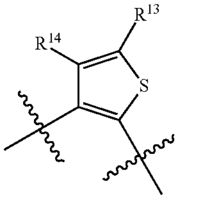
(14)
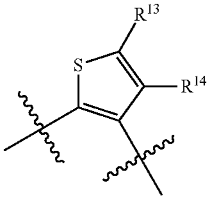
(15)
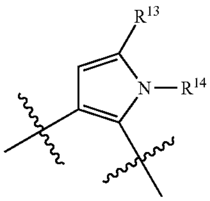
(16)
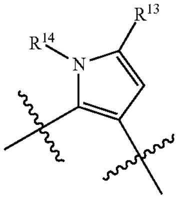
(17)
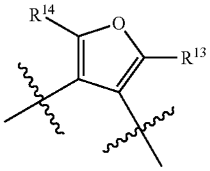
(18)
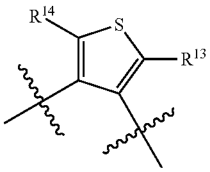
-continued
(19)
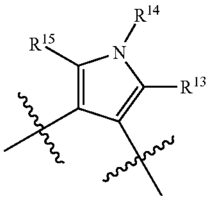
(20)
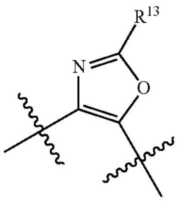
(21)
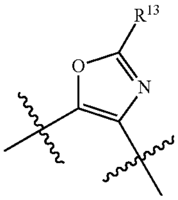
(22)
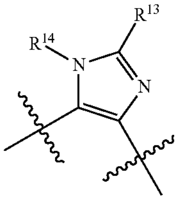
(23)
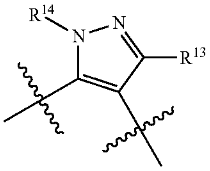
(24)
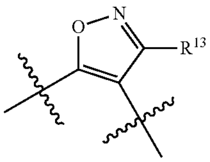
(25)
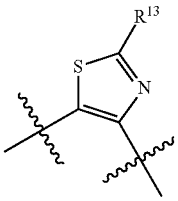
(26)
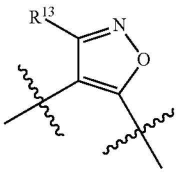

-continued (27)

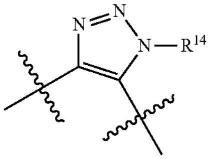

(28)

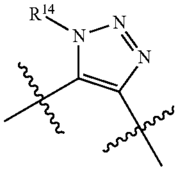

(29)

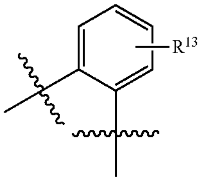

(30)

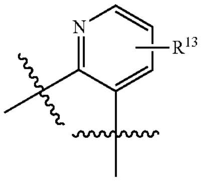

(31)

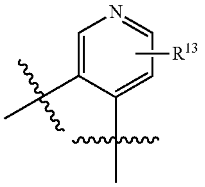

(32)

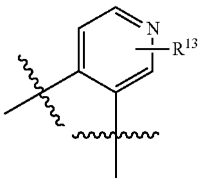

(33)

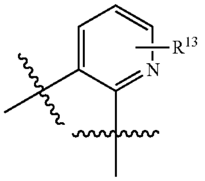

(34)

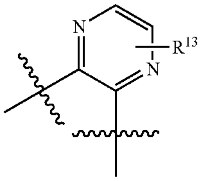

-continued (35)

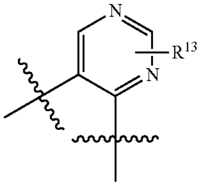

(36)

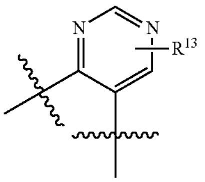

(37)

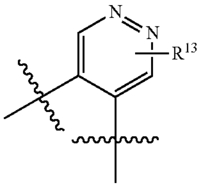

(38)

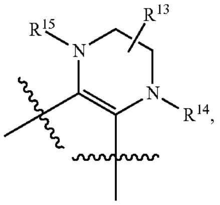

where $R^{13}$, $R^{14}$ and $R^{15}$ are independently selected from hydrogen, alkyl, substituted alkyl, cycloalkyl, substituted cycloalkyl, alkoxyl, aryl, substituted aryl, heteroaryl, substituted heteroaryl, alkenyl, substituted alkenyl, alkynyl, substituted alkynyl, substituted aminoalkyl, substituted alkylamino, arylamino, substituted arylamino, heteroaryl amino, substituted heteroaryl amino, a heterocyclic group and a substituted heterocyclic group.

In some preferred embodiments of the present invention,

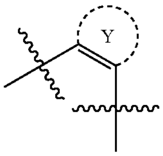

is selected from groups having Structural Formulas (6) to (10) below:

(6)

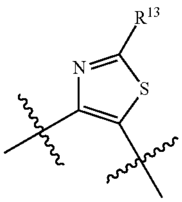

-continued (7)

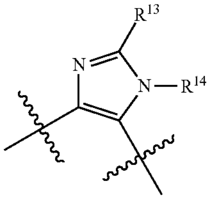

(8)

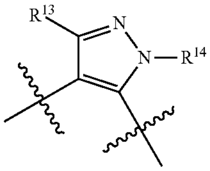

(9)

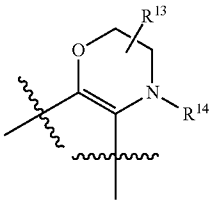

(10)

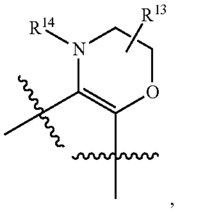

, where, $R^{13}$ and $R^{14}$ are defined as above.

In some preferred embodiments of the present invention,

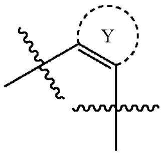

is selected from groups having Structural Formulas (39) to (44) below:

(39)

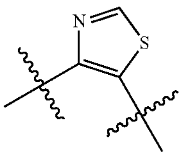

(40)

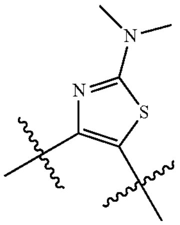

-continued (41)

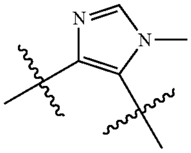

(42)

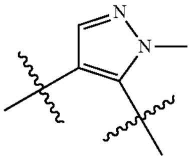

(43)

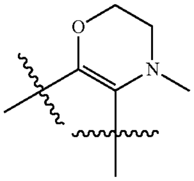

(44)

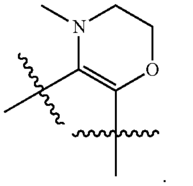

.

In some preferred embodiments of the present invention, Z is preferably CH; and $R^7$, $R^8$ and $R^9$ are respectively H.

In some preferred embodiments of the present invention, $R^4$ is selected from groups having Structural Formulas (45) to (52) below:

(45)

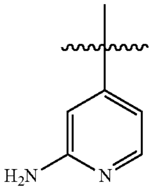

(46)

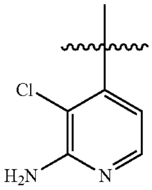

(47)

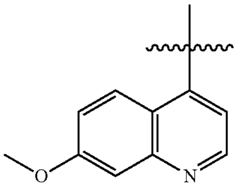

-continued (48)

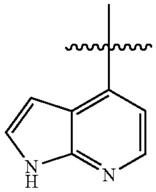

(49)

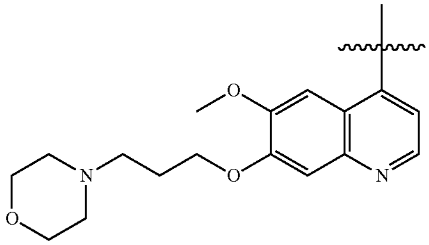

(50)

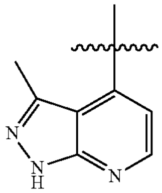

(51)

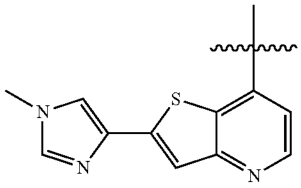

(52)

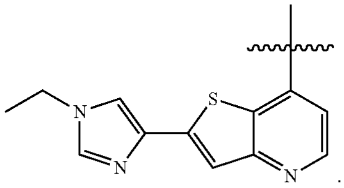

.

In some preferred embodiments of the present invention, $R^4$ is selected from groups having Structural Formulas (53) to (54) below:

(53)

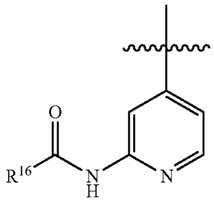

-continued (54)

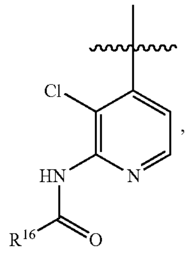

where $R^{16}$ is selected from hydrogen, alkyl, substituted alkyl, cycloalkyl, substituted cycloalkyl, alkoxy, aryl, substituted aryl, heteroaryl, substituted heteroaryl, alkenyl, substituted alkenyl, alkynyl, substituted alkynyl, substituted aminoalkyl, substituted alkylamino, arylamino, substituted arylamino, heteroaryl amino, substituted heteroaryl amino, a heterocyclic group and a substituted heterocyclic group.

Specifically, $R^{16}$ is preferably groups having Structural Formulas (55) to (61) below:

(55)

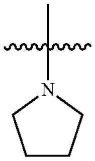

(56)

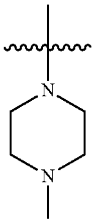

(57)

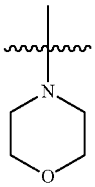

(58)

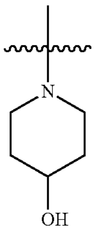

-continued (59)

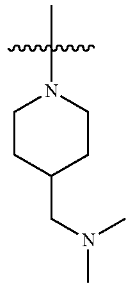

(60)

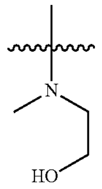

-continued (61)

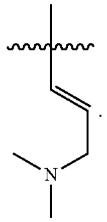

In some preferred embodiments of the present invention, $R^1$ is selected from phenyl, p-fluorophenyl, 2-hydroxyethyl phenyl and benzyl.

In some preferred embodiments of the present invention, $R^2$ is selected from hydrogen, halogen, alkoxy and amino.

In some preferred embodiments of the present invention, W and X are preferably CH, and $R^3$ is preferably fluorine.

In some preferred embodiments of the present invention, the compound represented by General Formula (I) is selected from compounds having Structural Formulas (I-1) to (I-59) below:

I-1

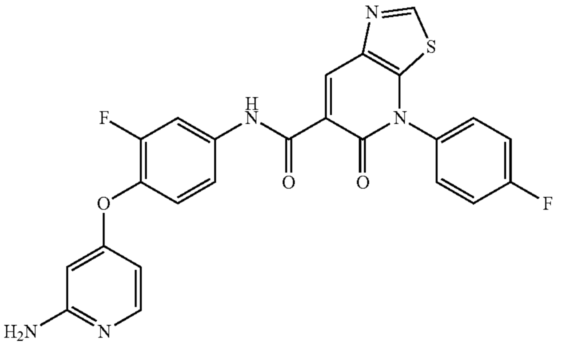

I-2

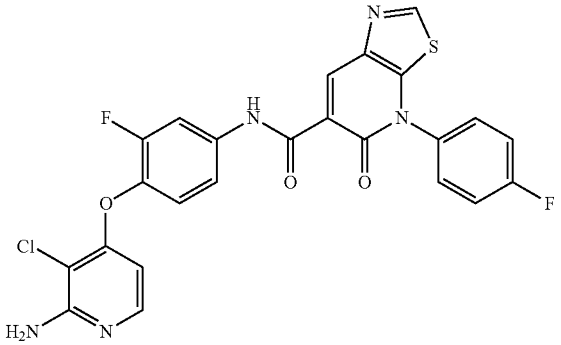

I-3

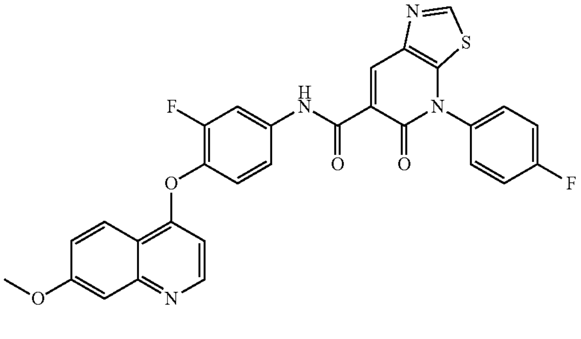

I-4

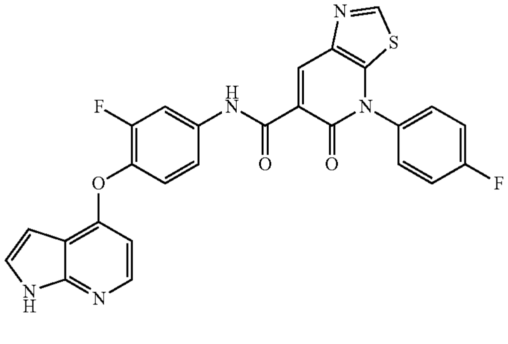

-continued
I-5
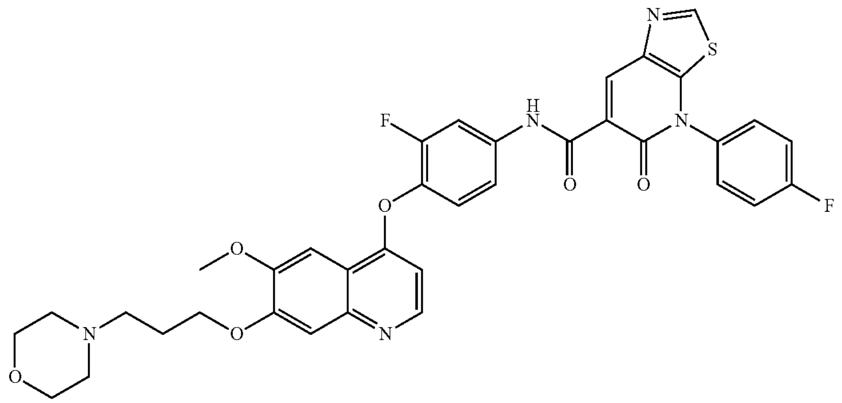
I-6
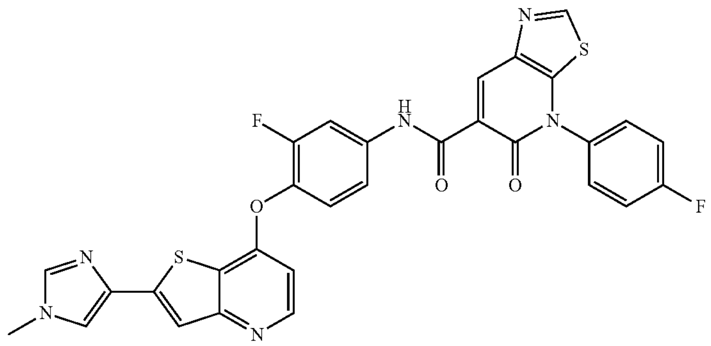
I-7
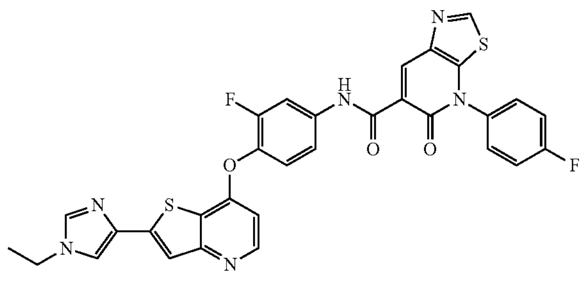
I-8
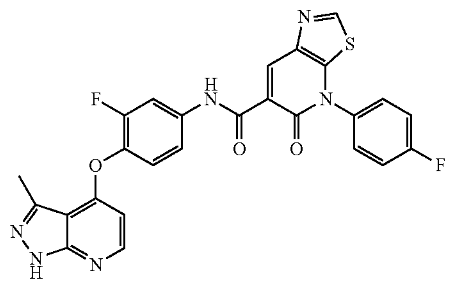
I-9
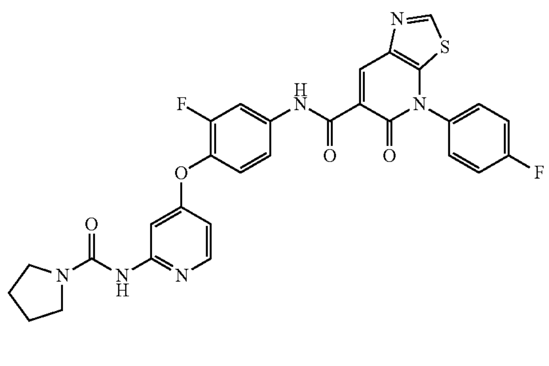
I-10
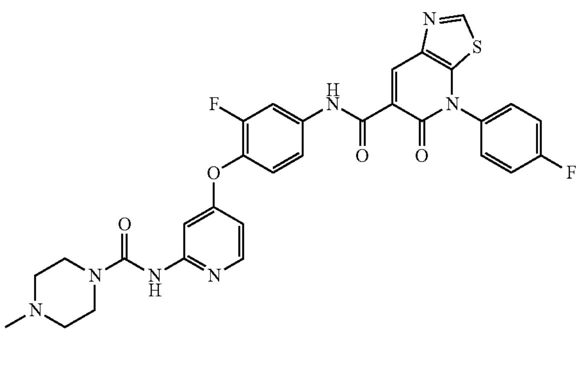

-continued
I-11
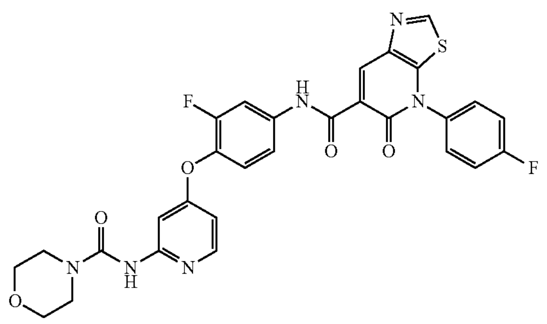
I-12
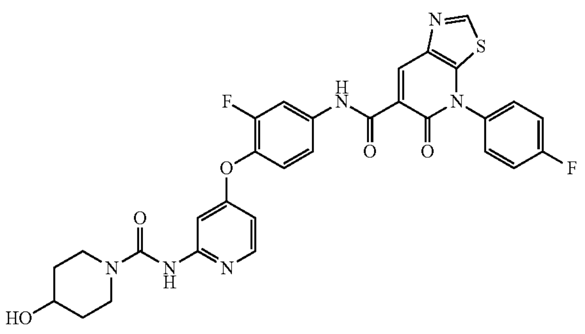
I-13
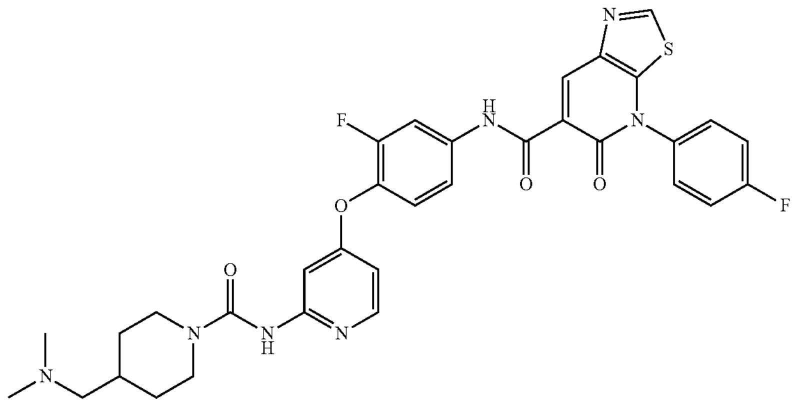
I-14
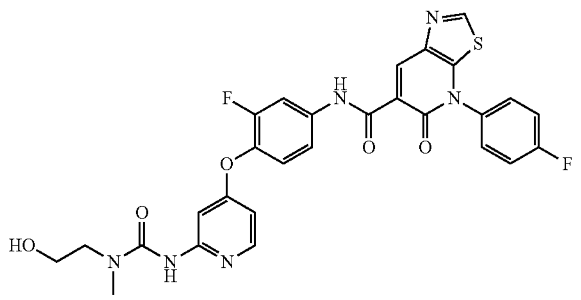
I-15
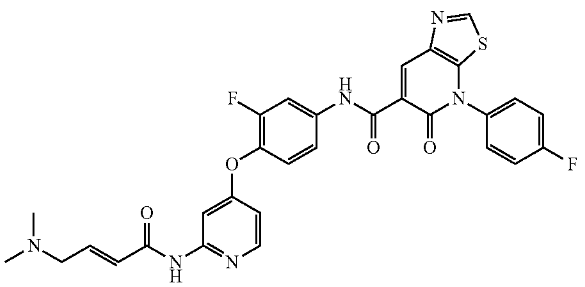
I-16
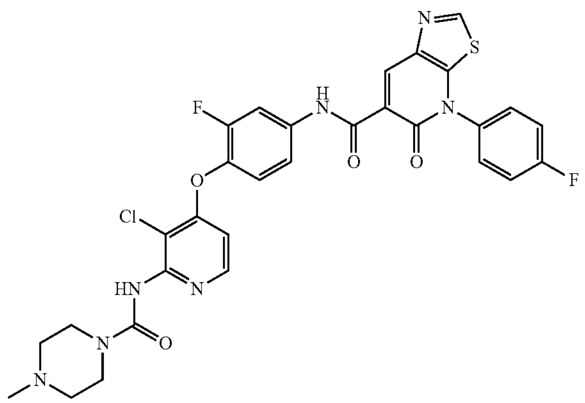
I-17
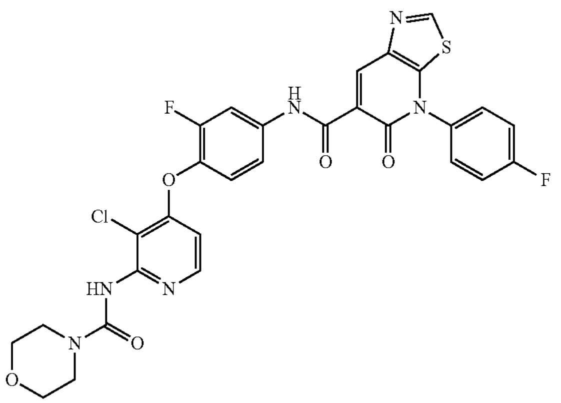

-continued
I-18
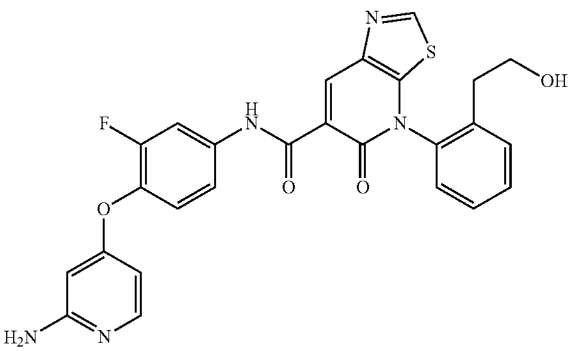
I-19
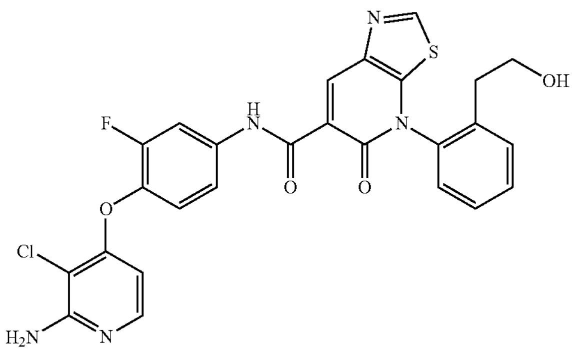
I-20
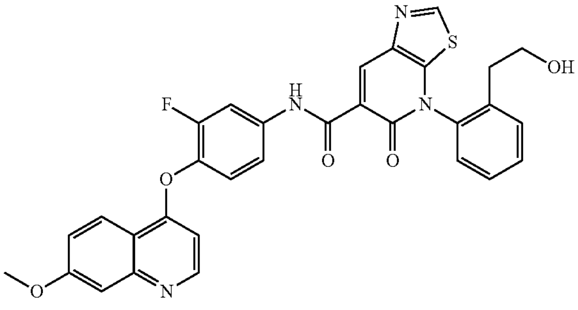
I-21
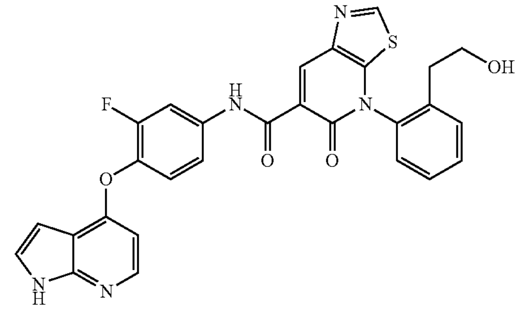
I-22
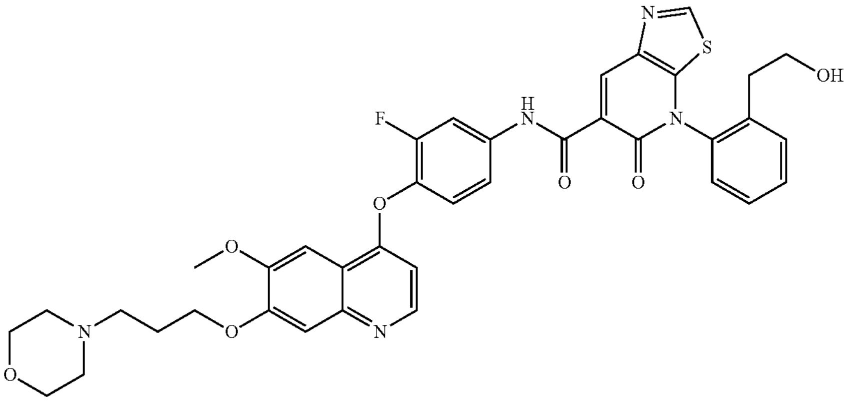
I-23
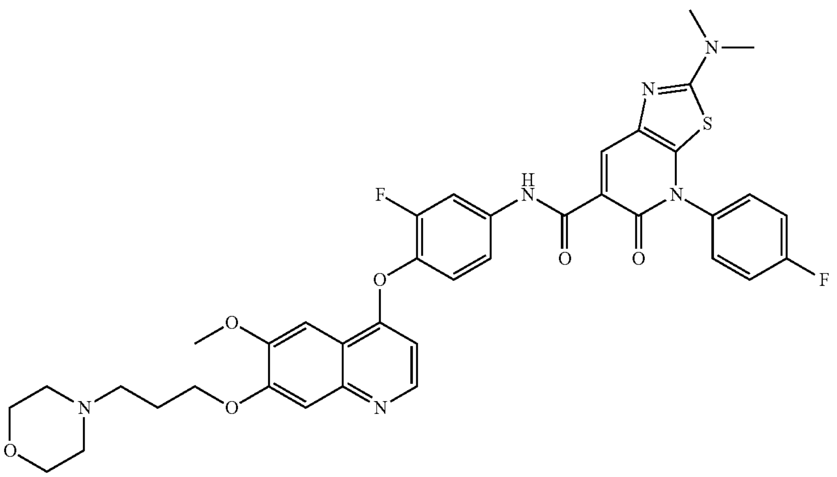

-continued
I-24
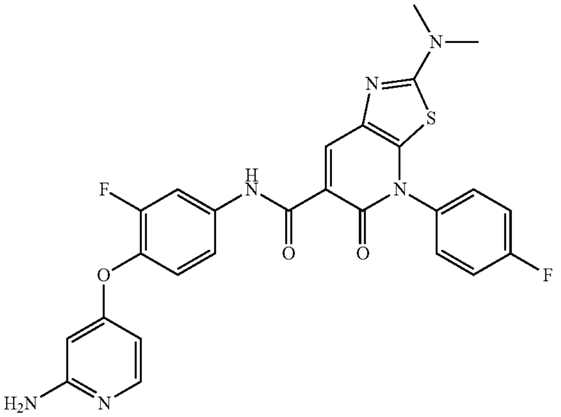
I-25
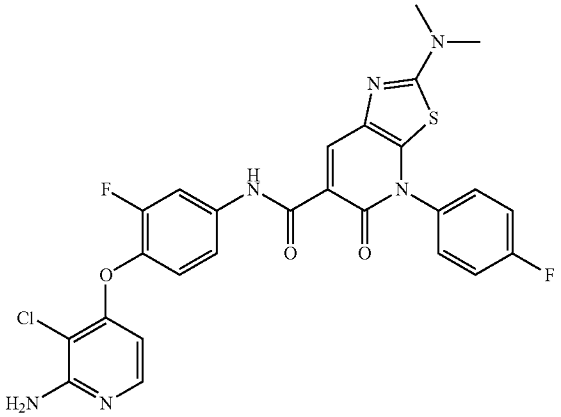
I-26
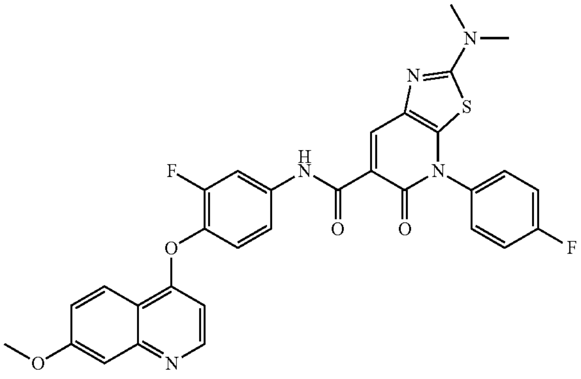
I-27
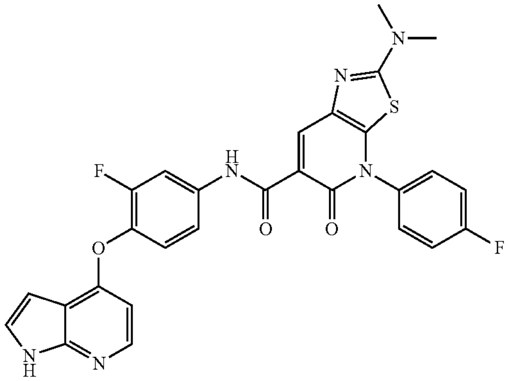
I-28
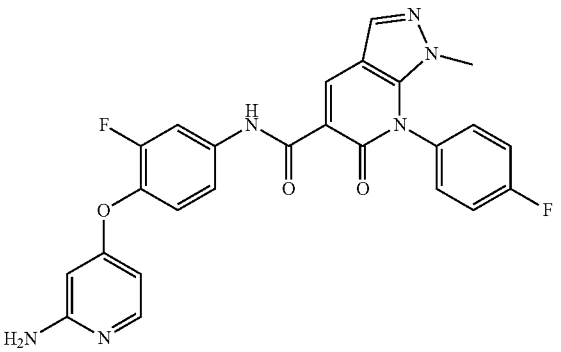
I-29
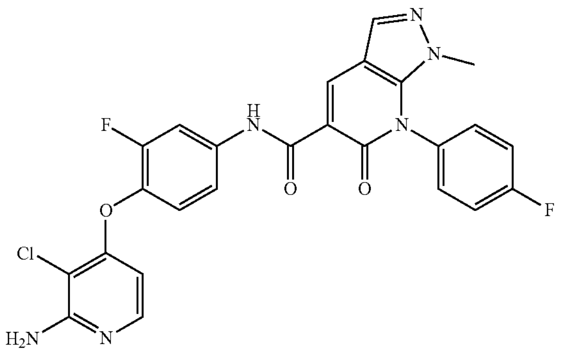
I-30
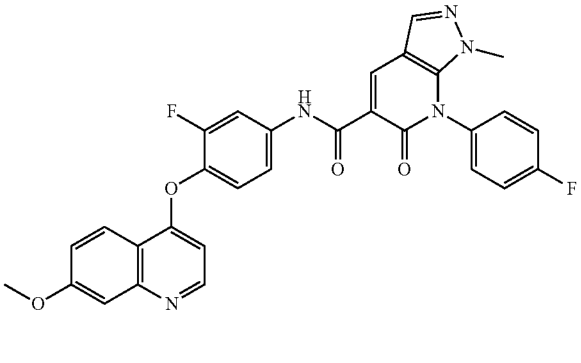
I-31
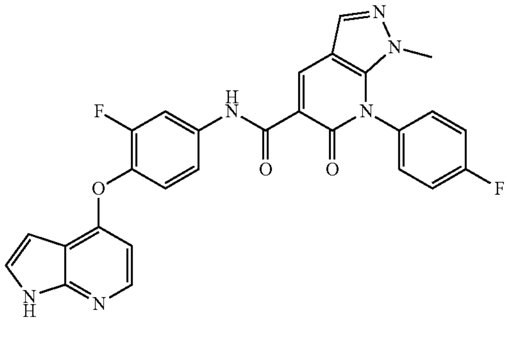

-continued
I-32
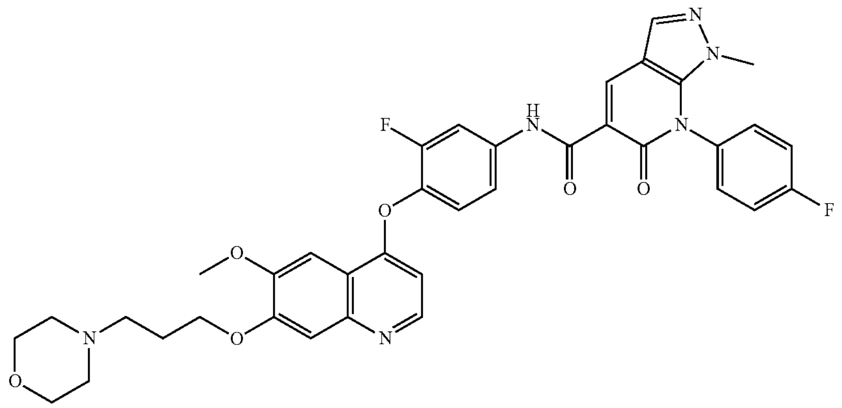
I-33
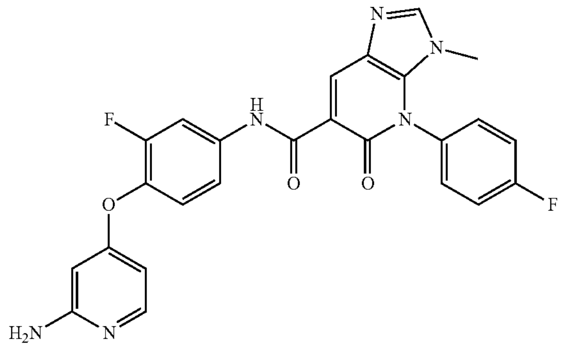
I-34
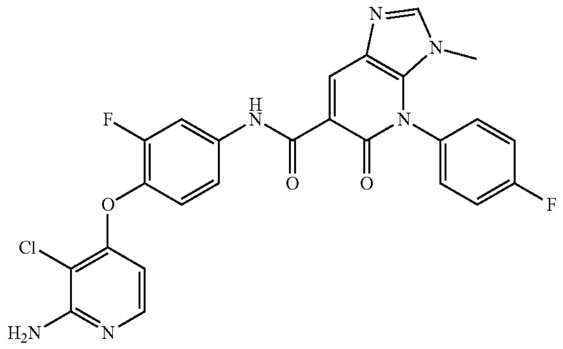
I-35
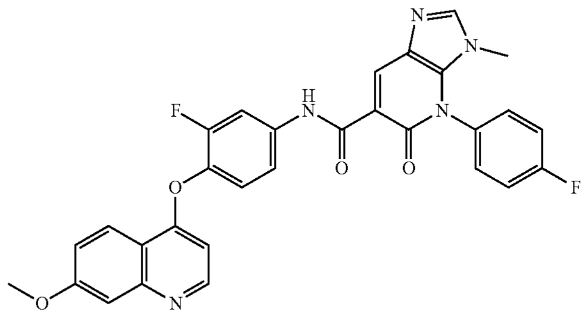
I-36
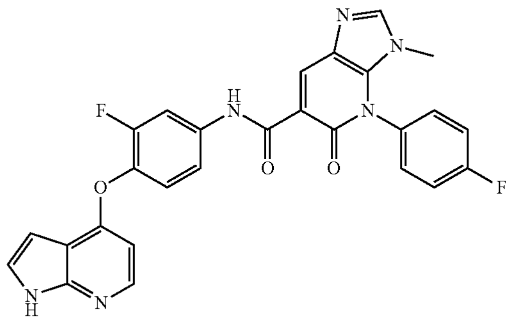
I-37
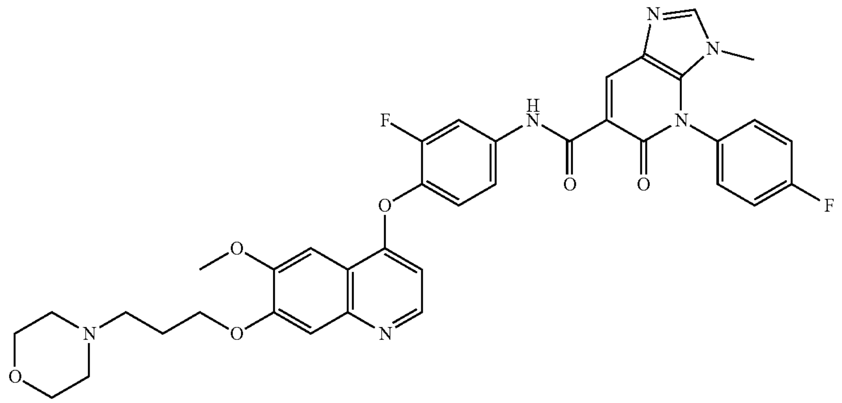

-continued
I-38
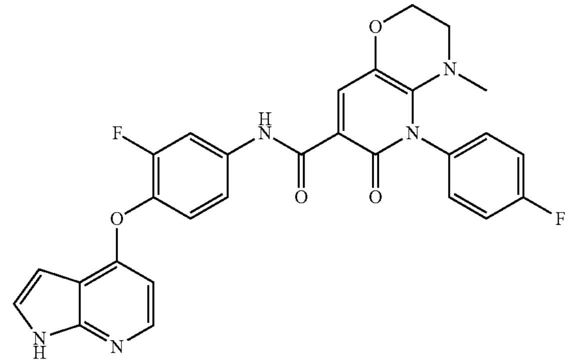
I-39
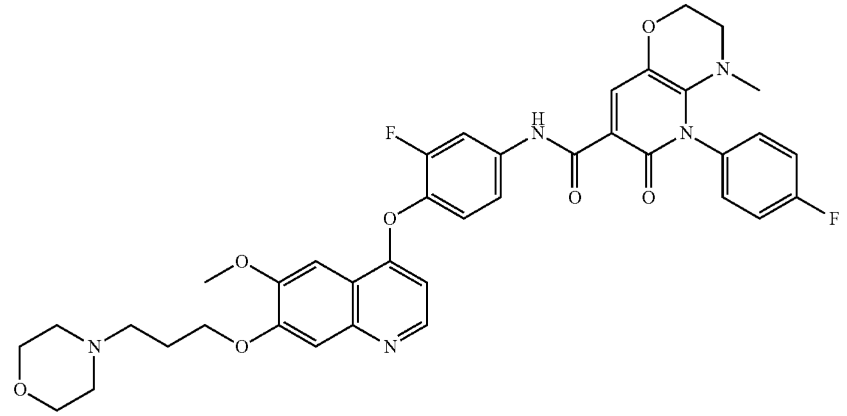
I-40
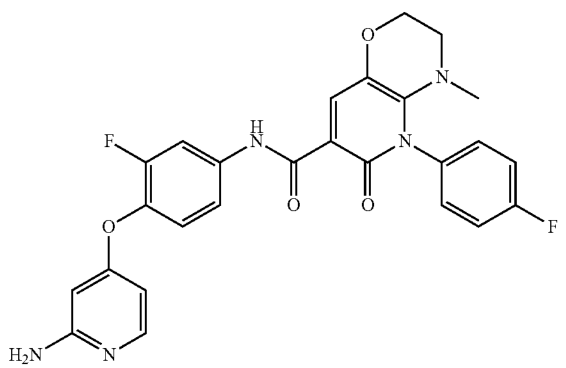
I-41
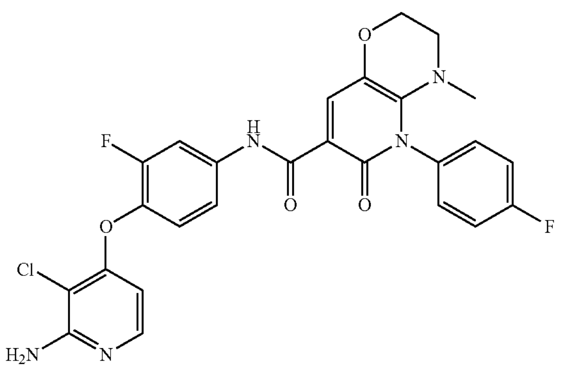
I-42
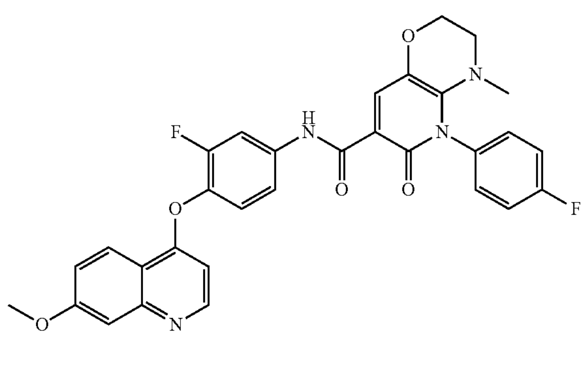
I-43
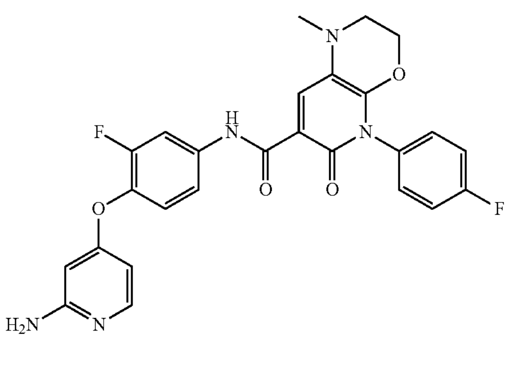

-continued
I-44
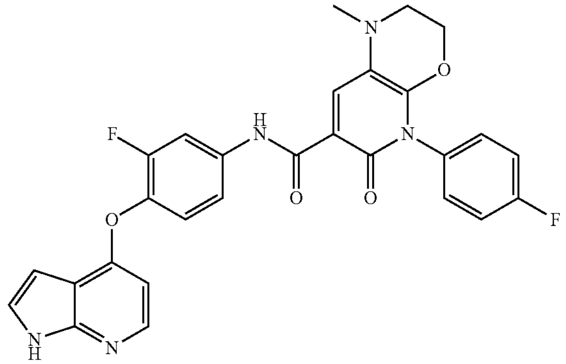
I-45
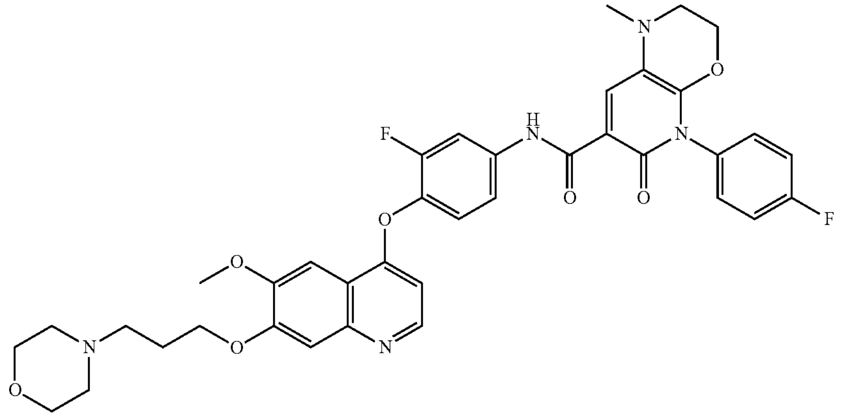
I-46
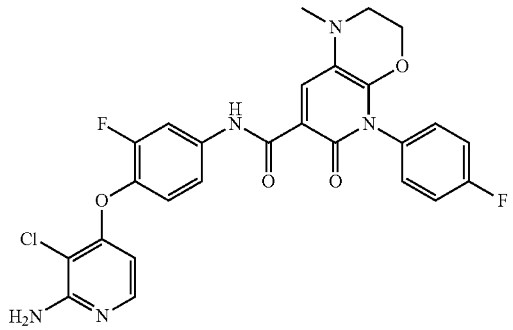
I-47
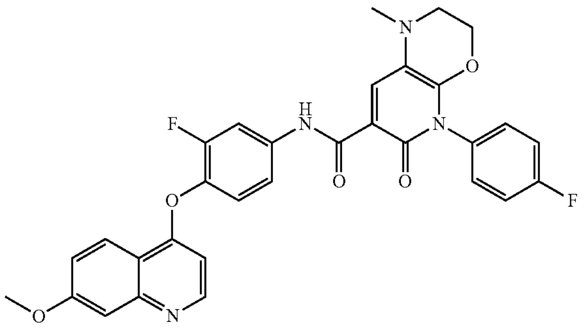
I-48
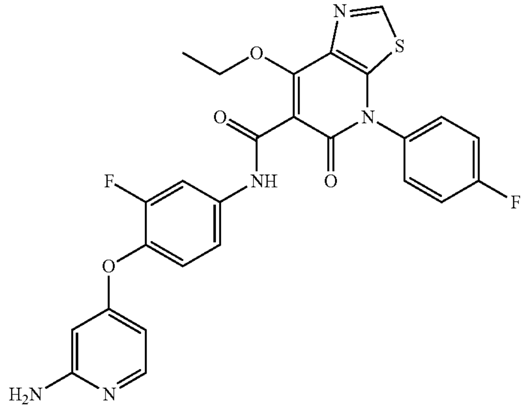
I-49
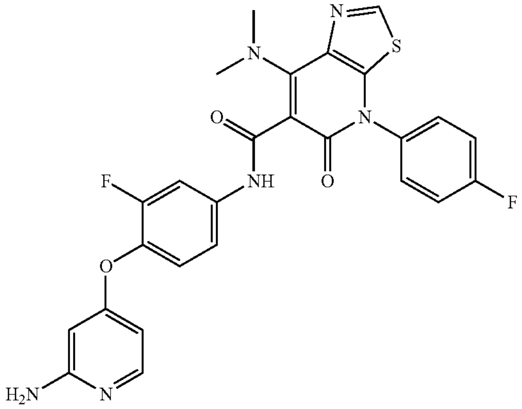

-continued
I-50
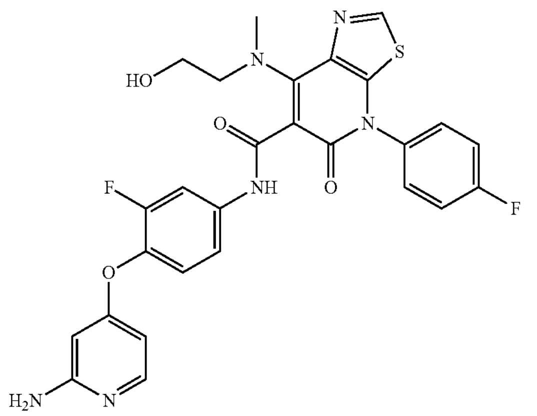
I-51
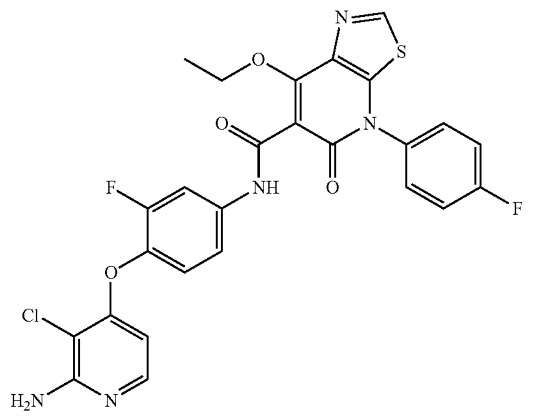
I-52
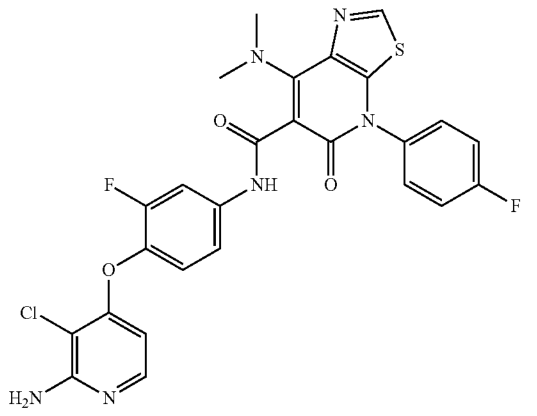
I-53
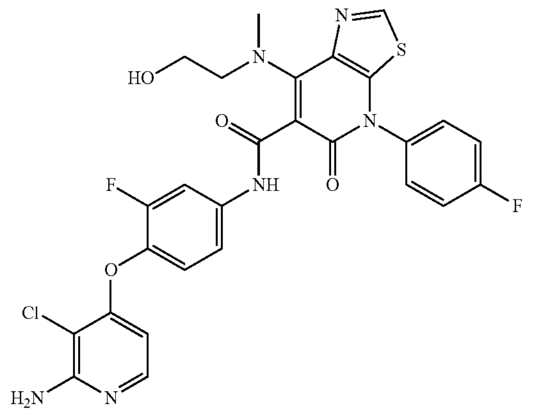
I-54
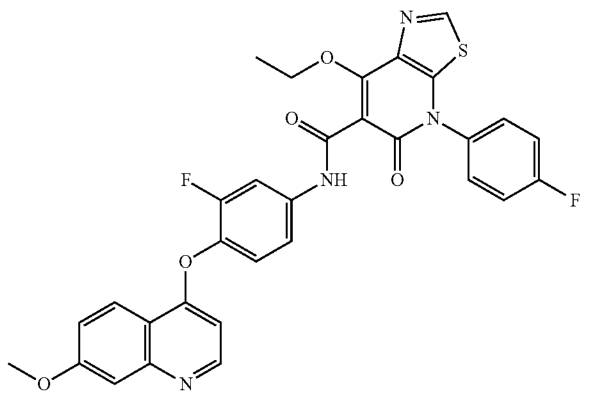
I-55
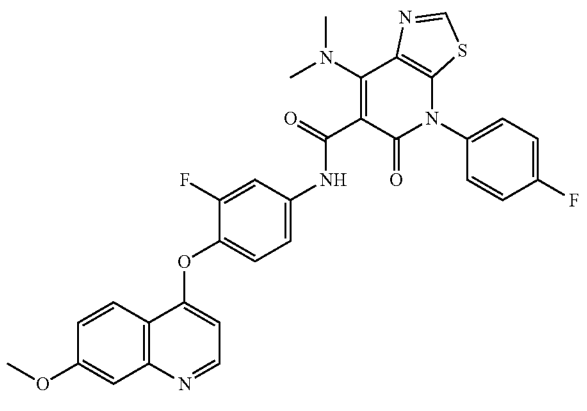

-continued

I-56

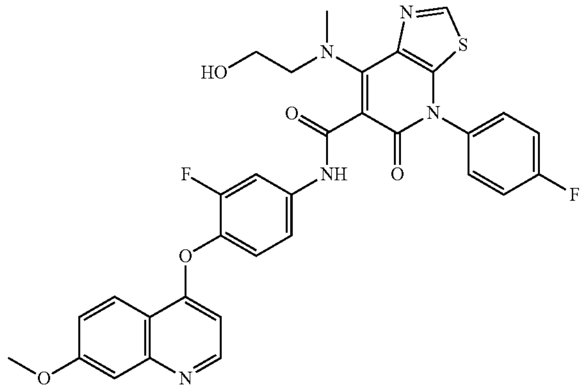

I-57

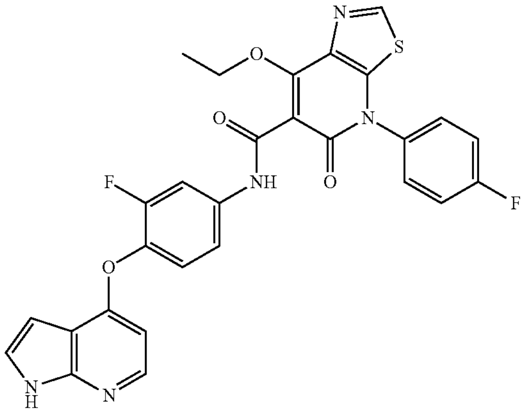

I-58

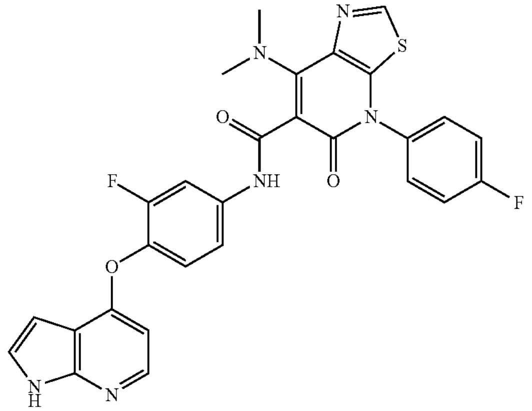

I-59

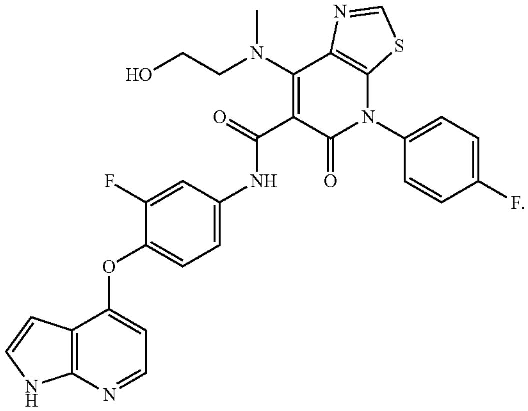

The heterocyclic pyridone compound represented by General Formula (I) is an enantiomer, a diastereomer, a conformational isomer, or a mixture thereof.

The heterocyclic pyridone compound represented by General Formula (I) is a pharmaceutically acceptable derivative.

The compound represented by General Formula (I) of the present invention may exist in the form of a pharmaceutically acceptable salt.

The pharmaceutically acceptable salt of the present invention is a hydrochloride, sulfate, phosphate, trifluoroacetate, methanesulfonate, trifluoromethanesulfonate, p-toluenesulfonate, tartrate, maleate, fumarate, succinate or malate of the compound represented by General Formula (I).

As a second aspect of the present invention, the intermediate is a compound represented by General Formula (II) below:

II

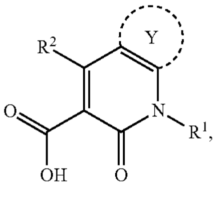

where $R^1$ is selected from hydrogen, alkyl, substituted alkyl, cycloalkyl, substituted cycloalkyl, aryl, substituted aryl, heteroaryl, substituted heteroaryl, arylalkyl, substituted arylalkyl, heteroarylalkyl, substituted heteroarylalkyl and $C(=O)NR^{10}R^{11}$;

$R^2$ is selected from hydrogen, halogen, alkoxy, amino, alkyl, substituted alkyl, cycloalkyl, substituted cycloalkyl, hydroxy alkyl, amino alkyl, aryl, substituted aryl, heteroaryl, substituted heteroaryl, arylalkyl, substituted arylalkyl, heteroarylalkyl, substituted heteroarylalkyl, heterocyclic group, and substituted heterocyclic group; and

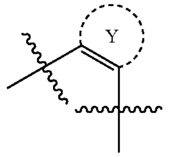

is selected from groups having a Structural Formulas (6) to (38) below:

(6)
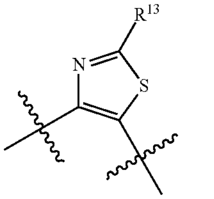
(7)
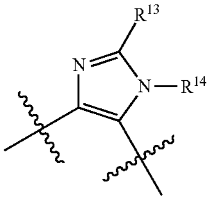
(8)
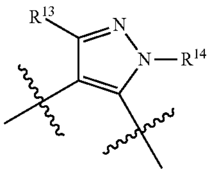
(9)
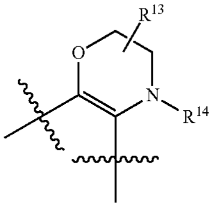
(10)
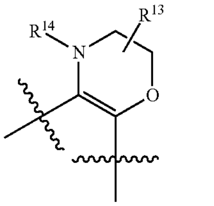
(11)
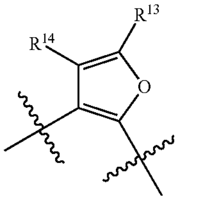
(12)
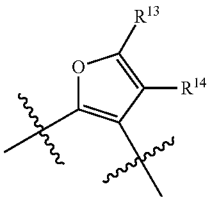
-continued
(13)
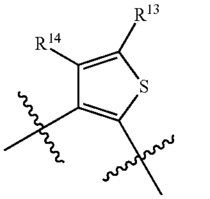
(14)
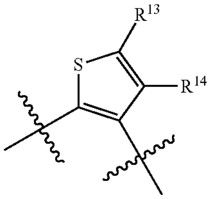
(15)
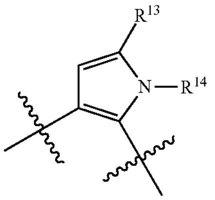
(16)
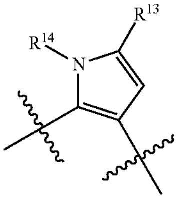
(17)
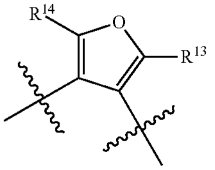
(18)
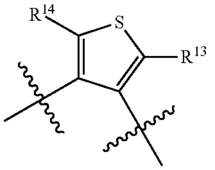
(19)
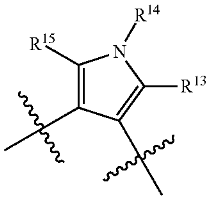
(20)
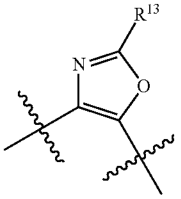

-continued
(21)
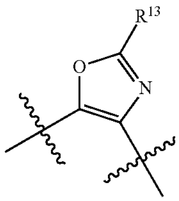
(22)
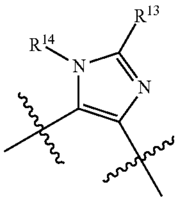
(23)
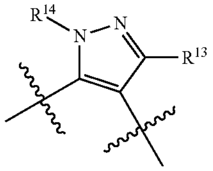
(24)
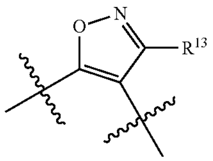
(25)
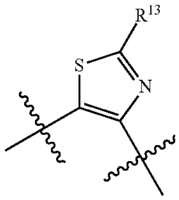
(26)
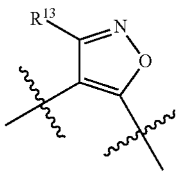
(27)
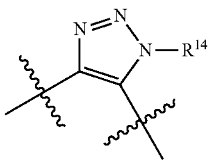
(28)
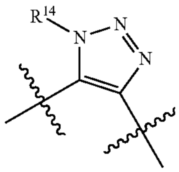
-continued
(29)
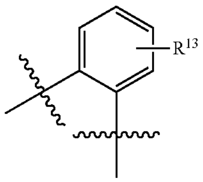
(30)
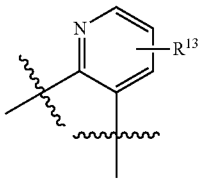
(31)
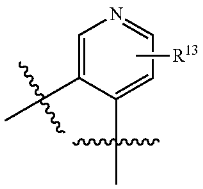
(32)
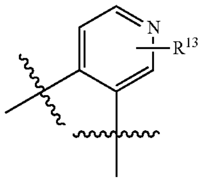
(33)
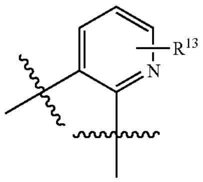
(34)
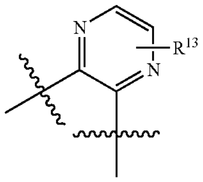
(35)
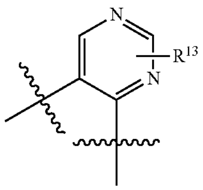
(36)
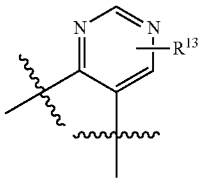

-continued (37)

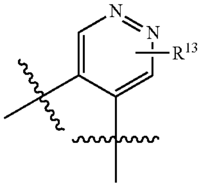

(38)

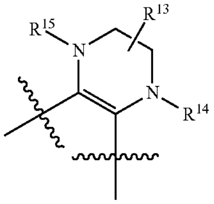

where $R^{13}$, $R^{14}$ and $R^{15}$ are independently selected from hydrogen, alkyl, substituted alkyl, cycloalkyl, substituted cycloalkyl, aryl, substituted aryl, heteroaryl, substituted heteroaryl, alkenyl, substituted alkenyl, alkynyl, substituted alkynyl, substituted aminoalkyl, substituted alkylamino, arylamino, substituted arylamino, heteroaryl amino, substituted heteroaryl amino, a heterocyclic group and a substituted heterocyclic group.

In some preferred embodiments of the present invention, $R^1$ is preferably selected from phenyl, substituted phenyl, benzyl; and $R^2$ is preferably selected from hydrogen, halogen, alkoxy and amino.

In some preferred embodiments of the present invention,

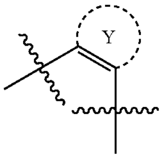

is selected from groups having Structural Formulas (39) to (44) below:

(39)

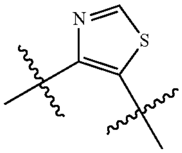

(40)

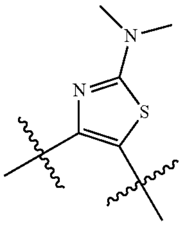

-continued (41)

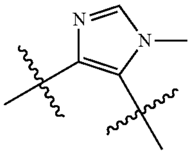

(42)

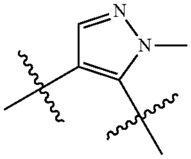

(43)

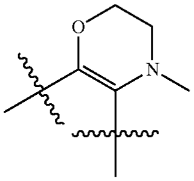

(44)

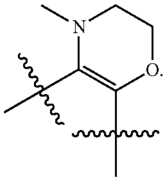

In some preferred embodiments of the present invention, the intermediate (II) is one selected from the following compounds:

II-1

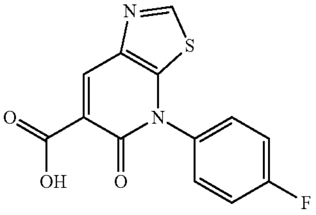

II-2

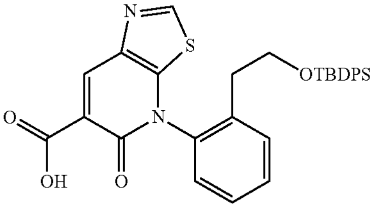

II-3

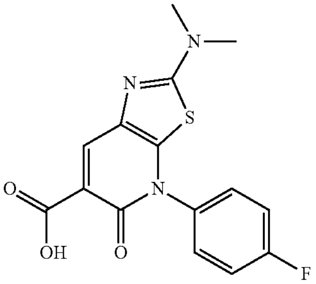

-continued

II-4

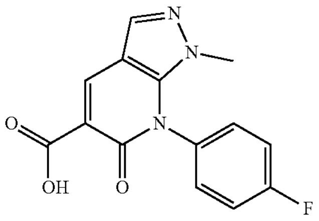

II-5

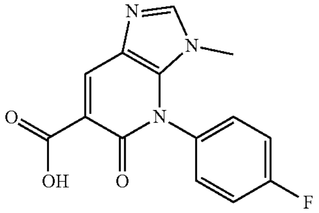

II-6

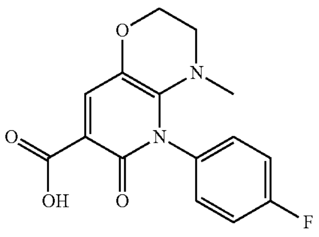

II-7

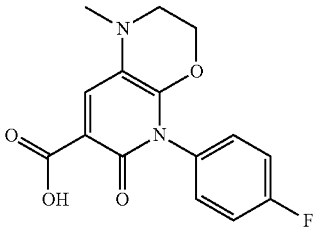

II-8

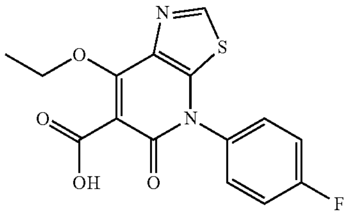

II-9

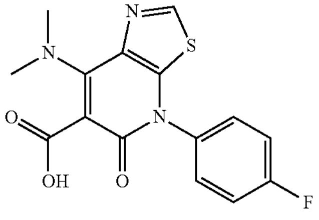

II-10

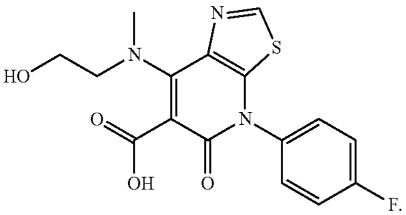

The intermediate represented by General Formula (II) is an enantiomer, a diastereomer, a conformational isomer, or a mixture thereof.

The intermediate represented by General Formula (II) is a pharmaceutically acceptable derivative.

The intermediate represented by General Formula (II) of the present invention may exist in the form of a pharmaceutically acceptable salt.

The pharmaceutically acceptable salt of the present invention is a hydrochloride, sulfate, phosphate, trifluoroacetate, methanesulfonate, trifluoromethanesulfonate, p-toluenesulfonate, tartrate, maleate, fumarate, succinate or malate of the intermediate represented by General Formula (II).

As a third aspect of the present invention, when

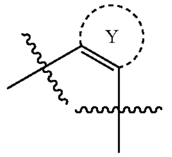

is a thiazole ring and $R^2$ is hydrogen, the preparation method for the intermediate represented by General Formula (II) includes: reacting an alkylamine or arylamine (M-1) with carbon disulfide or thiophosgene, to obtain an isothiocyanate (M-2); subjecting the isothiocyanate (M-2) to an addition reaction with ethyl isocyanoacetate in the presence of potassium tert-butoxide, to obtain an intermediate (M-3); reacting the intermediate (M-3) with methyl malonyl chloride, to obtain an amide (M-4); treating the amide (M-4) with sodium methoxide, to cyclize the amide (M-4), so as to obtain pyridone (M-5); reacting pyridone (M-5) with N-phenylbis(trifluoromethanesulphonimide), to form a trifluoromethanesulfonate (M-6); subjecting the trifluoromethanesulfonate (M-6) to reduction deoxidation, to obtain an intermediate (M-7); and hydrolyzing the ester group in the intermediate (M-7), to obtain a carboxylic acid represented by General Formula (IIa); where the definition of $R^1$ is the same as the above, and the specific reaction equations are as follows:

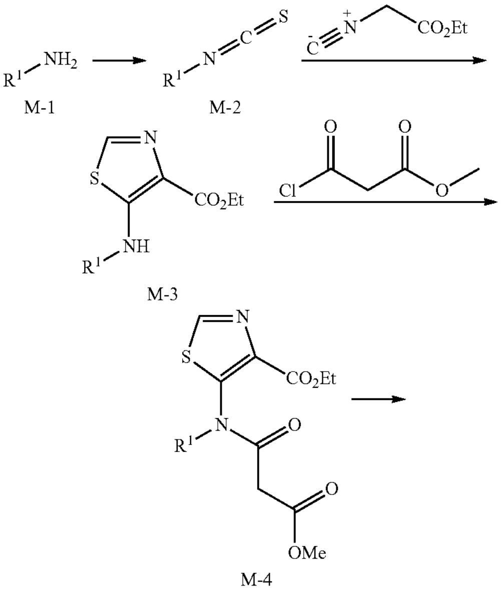

M-1

M-2

M-3

M-4

-continued

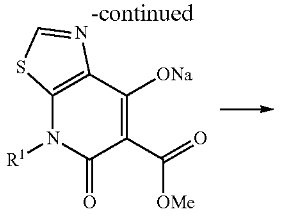

M-5

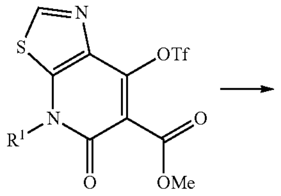

M-6

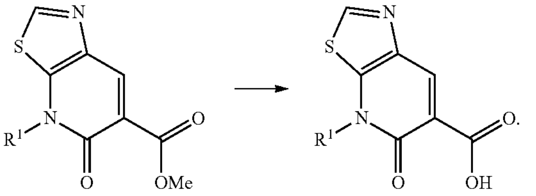

M-7 IIa

As the third aspect of the present invention, when

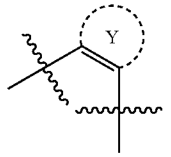

is a 2-dimethylaminothiazole ring and $R^2$ is hydrogen, the preparation method of the intermediate represented by General Formula (II) includes: converting 2-methoxy-5-aminopyridine (M-8) into an intermediate (M-9) in the presence of potassium thiocyanate and liquid bromine; subjecting the intermediate (M-9) to a Sandmeyer reaction, to convert the amino group of the intermediate (M-9) into a bromide (M-10); reacting the bromide (M-10) with dimethylamine, to obtain an intermediate (M-11); subjecting the intermediate (M-11) to bromization, cyanidation and hydrolysis, to convert the intermediate (M-11) into an intermediate (M-14); reacting the intermediate (M-14) with thionyl chloride and methanol, to convert the intermediate (M-14) into a corresponding methyl ester (M-15); and subjecting the methyl ester (M-15) to coupling and hydrolysis, to obtain a carboxylic acid represented by General Formula (IIb), where the definition of $R^1$ is the same as the above, and the specific reaction equations are as follows:

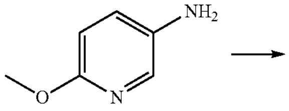

M-8

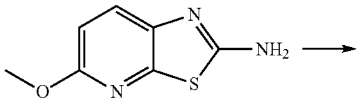

M-9

-continued

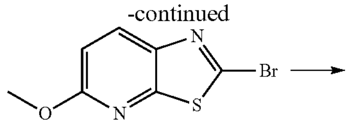

M-10

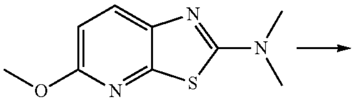

M-11

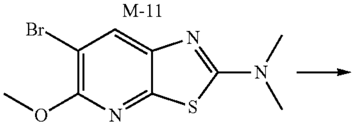

M-12

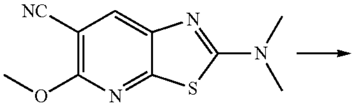

M-13

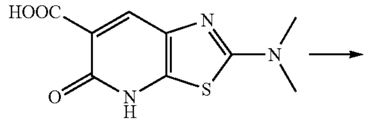

M-14

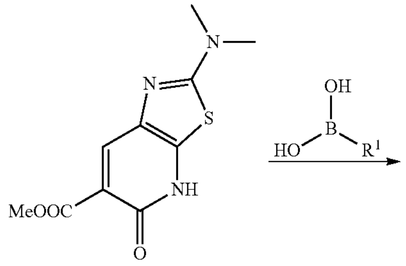

M-15

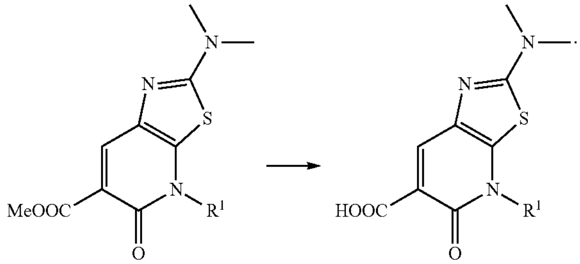

M-16 IIb

As the third aspect of the present invention, when

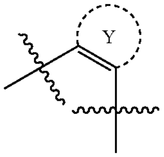

is an imidazole ring and $R^2$ is hydrogen, the preparation method of the intermediate represented by General Formula (II) includes: preparing a starting material (M-17) with reference to a reported method (Letters in Organic Chemistry, 2004, 1, 326-330); reducing the starting material (M-17) with iron powder, to obtain an intermediate (M-18); coupling the intermediate (M-18) with boronic acid [$R^1$—$B(OH)_2$], to obtain an intermediate (M-19); and hydrolyzing the ester group in the intermediate (M-19), to obtain a carboxylic acid represented by General Formula (IIc), where the definition of $R^1$ is the same as the above, and the specific reaction equations are as follows:

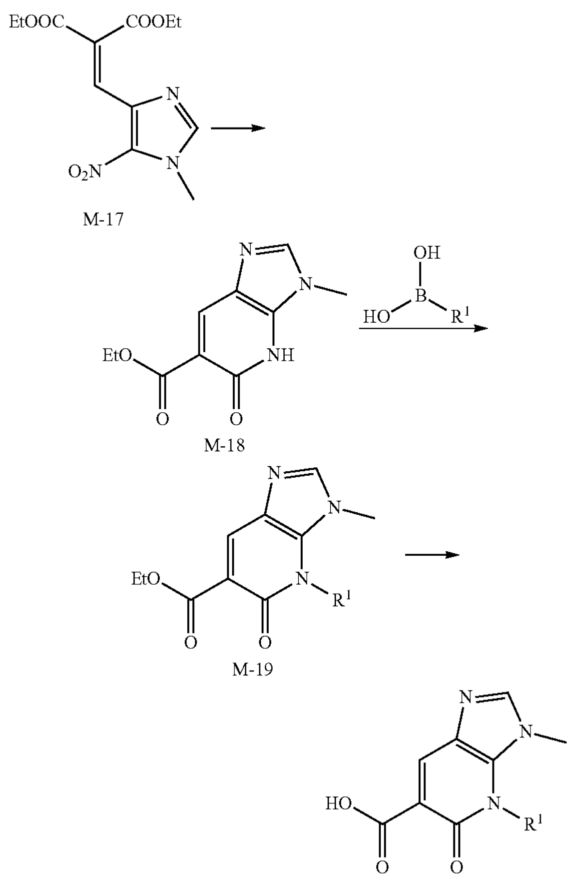

M-17

M-18

M-19

IIc

As the third aspect of the present invention, when

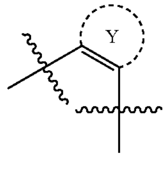

is a pyrazole ring and $R^2$ is hydrogen, the preparation method of the intermediate represented by General Formula (II) includes: reacting 2-ethoxymethylenemalononitrile (M-20) with methylhydrazine in ethanol at reflux, to obtain pyrazole (M-21); reducing the cyano group in pyrazole (M-21), to obtain an intermediate (M-22); reacting the intermediate (M-22) with diethyl malonate in the presence of a base, to cyclize the intermediate (M-22), so as to obtain pyridone (M-23); and subjecting pyridone (M-23) to coupling with a suitable alkylboronic acid or arylboronic acid and hydrolysis, to obtain a carboxylic acid represented by General Formula (IId), where the definition of $R^1$ is the same as the above, and the specific reaction equations are as follows:

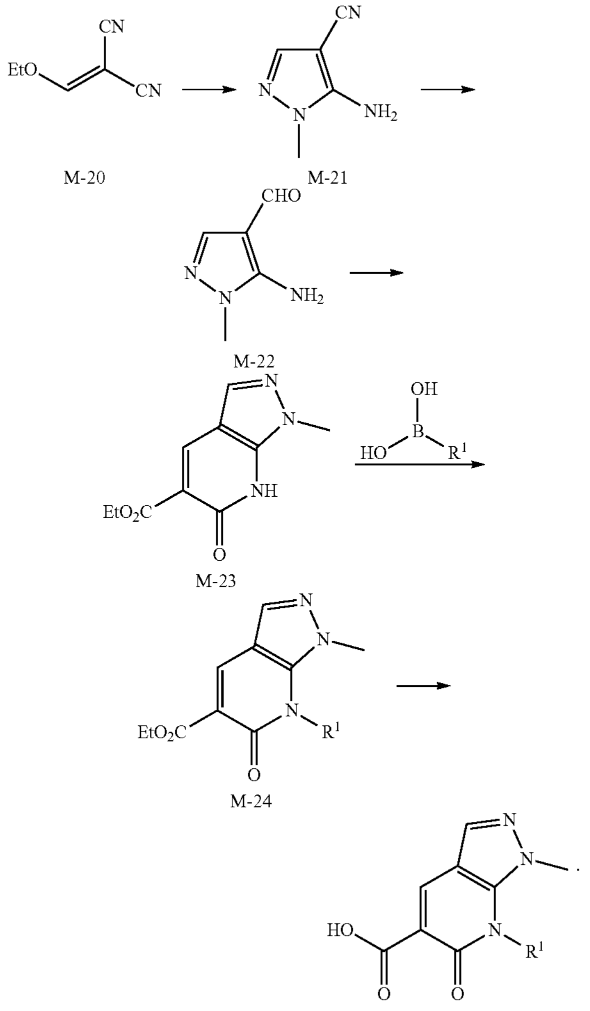

M-20

M-21

M-22

M-23

M-24

IId

As the third aspect of the present invention, when

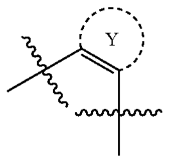

is a morpholine ring and $R^2$ is hydrogen, the preparation method of the intermediate represented by General Formula (II) includes: preparing a compound (M-25) with reference to a document method (Journal of Medicinal Chemistry, 2007, 50, 3730-3742.), which serves as a raw material; subjecting the compound (M-25) to bromization, cyanidation and hydrolysis, to convert the compound (M-25) into an intermediate (M-28); converting the intermediate (M-28) into a methyl ester (M-29) in the presence of thionyl chloride and methanol; methylating the amino group of the methyl ester (M-29) in the presence of sodium hydride/methyl iodide, to obtain a compound (M-30); subjecting the compound (M-30) to oxidation rearrangement by using pyridine, to convert the compound (M-30) into pyridone (M-31); and subjecting pyridone (M-31) to coupling with boronic acid and hydrolysis, to obtain a carboxylic acid represented by General Formula (IIe), where the definition of $R^1$ is the same as the above, and the specific reaction equations are as follows:

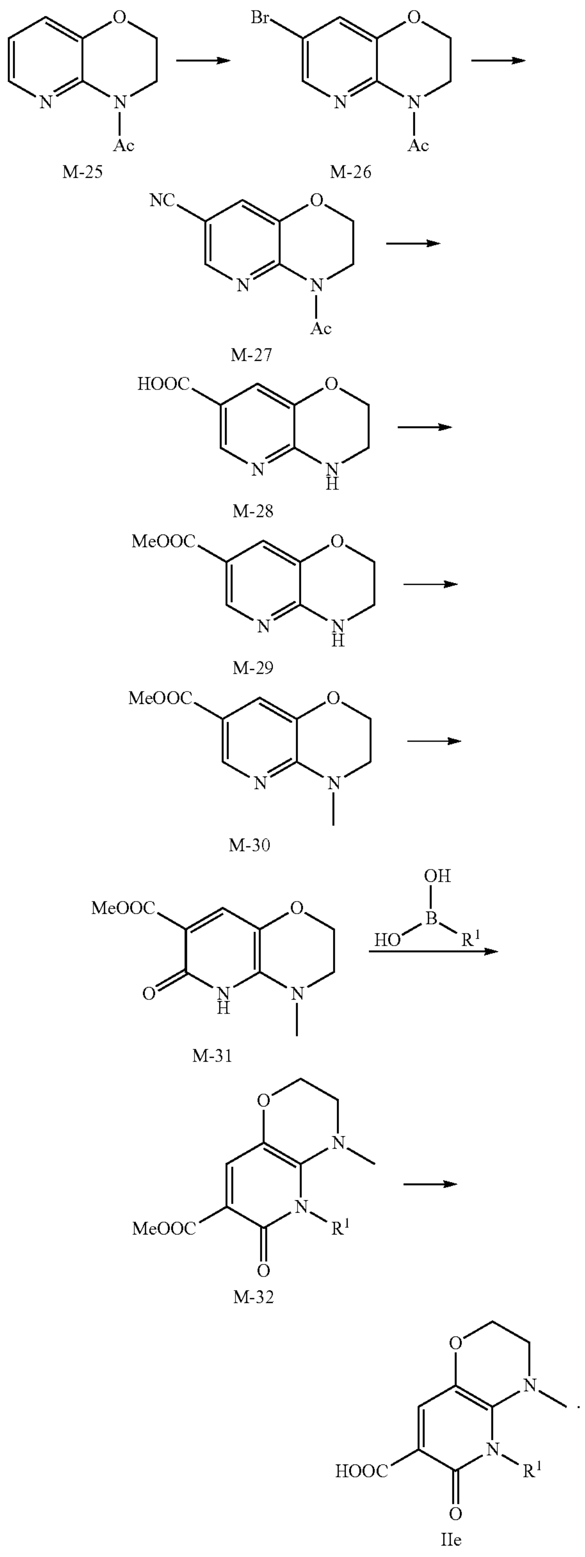

M-25 M-26 M-27 M-28 M-29 M-30 M-31 M-32 IIe

As the third aspect of the present invention, when

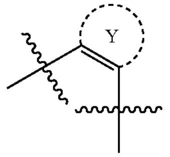

is a morpholine ring and $R^2$ is hydrogen, the preparation method of the intermediate represented by General Formula (II) includes: reacting a starting material (M-33) with phosphorus oxychloride and methanol, to prepare a compound (M-34); substituting the chlorine atom in the compound (M-34) with methyl glycolate, to obtain a compound (M-35); subjecting the compound (M-35) to reduction and cyclization in the presence of iron powder and acetic acid, to obtain an intermediate (M-36); methylating the amide nitrogen atom of the intermediate (M-36) with iodomethane, to obtain a compound (M-37); reducing the amide bond in the compound (M-37), to obtain a compound (M-38); subjecting the compound (M-38) to oxidation rearrangement by using pyridine, to convert the compound (M-38) into pyridone (M-39); and subjecting pyridone (M-39) to coupling with boronic acid and hydrolysis, to obtain a carboxylic acid represented by General Formula (IIf), where the definition of $R^1$ is the same as the above, and the specific reaction equations are as follows:

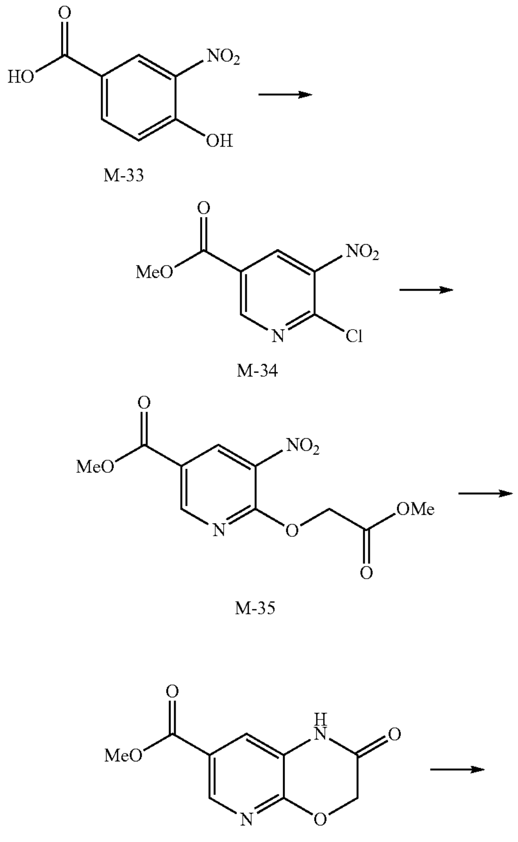

M-33 M-34 M-35 M-36

-continued

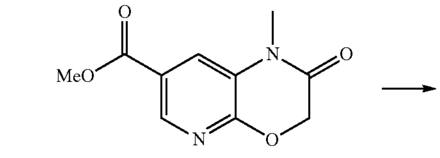

M-37

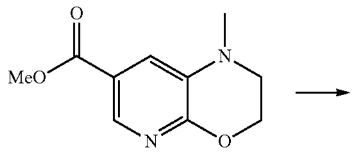

M-38

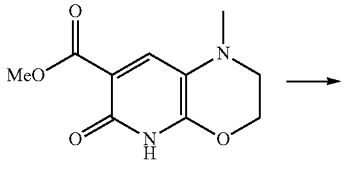

M-39

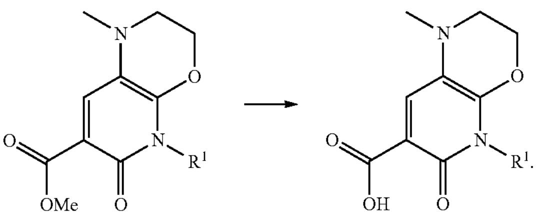

M-40 IIf

As the third aspect of the present invention, when

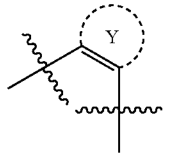

is a thiazole ring and $R^2$ is ethoxy, the preparation method of the intermediate represented by General Formula (II) includes: with an alkylamine or arylamine (M-1) as a starting material, converting the starting material into pyridone (M-5); alkylating pyridone (M-5) with iodomethane, to obtain an intermediate (M-41); and hydrolyzing the ester group in the intermediate (M-41), to obtain a carboxylic acid represented by General Formula (IIg), where the definition of $R^1$ is the same as the above, and the specific reaction equations are as follows:

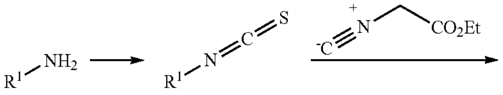

M-1 M-2

-continued

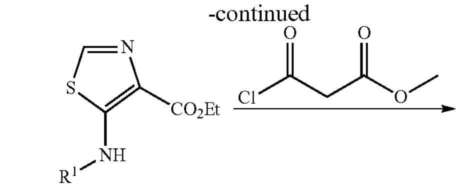

M-3

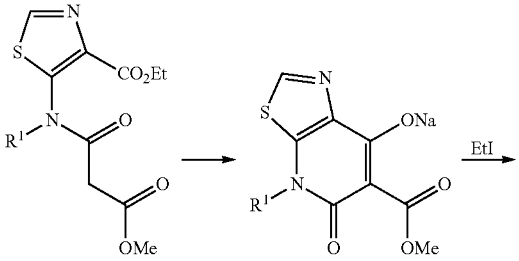

M-4 M-5

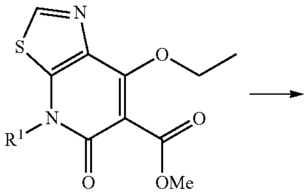

M-41

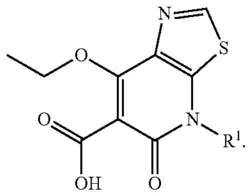

IIg

As the third aspect of the present invention, when

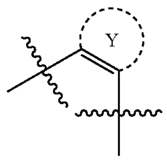

is a thiazole ring and $R^2$ is dimethylamino or N-methyl-2-hydroxyethnylamino, the preparation method of the intermediate represented by General Formula (II) includes: with an alkylamine or arylamine (M-1) as a starting material, converting the starting material into an intermediate (M-6); subjecting the intermediate (M-6) to substitution with dimethylamino or N-methyl-2-hydroxyethnylamino, to obtain an intermediate (M-42); and hydrolyzing the ester group in the intermediate (M-42), to obtain a carboxylic acid represented by General Formula (IIh), where the definition of $R^1$ is the same as the above, $R^1$ is A=-$CH_3$ or —$CH_2CH_2OH$, and the specific reaction equations are as follows:

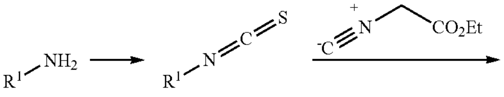

M-1 M-2

-continued

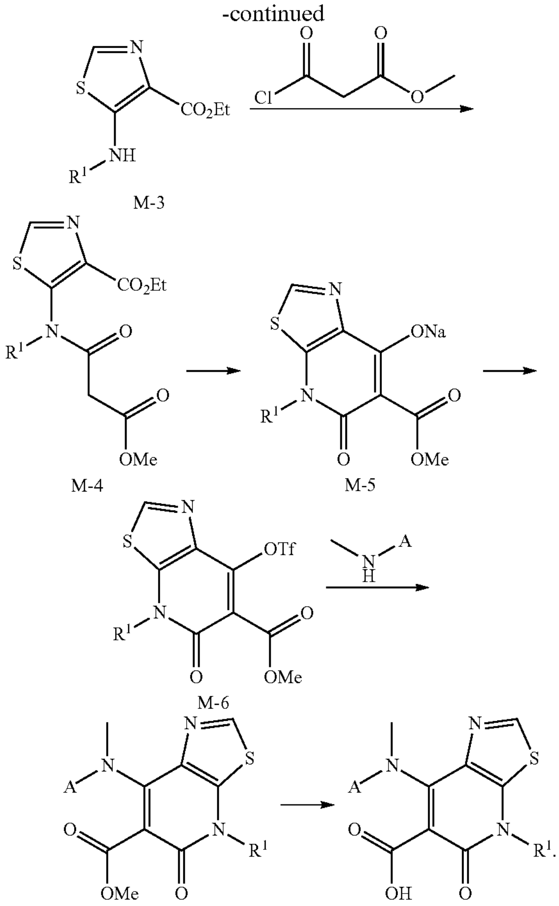

M-3, M-4, M-5, M-6, M-42, IIh.

As a fourth aspect of the present invention, the preparation method of the heterocyclic pyridone compound represented by General Formula (I) includes an amide condensation reaction of the intermediate represented by General Formula (II) and an arylamine (III), where the specific reaction equation is as follows:

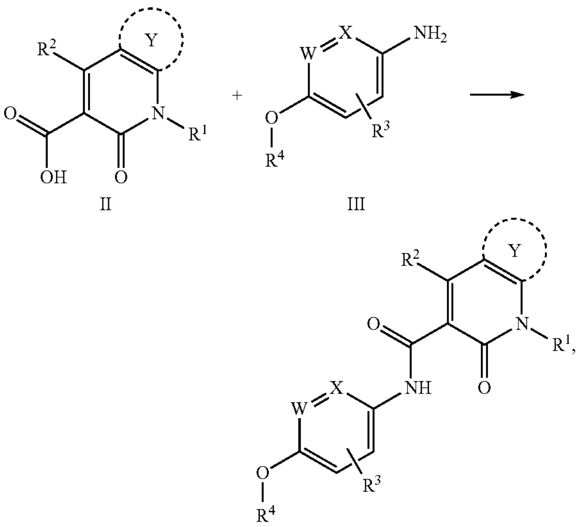

II III I where arylamine (III) may be obtained by subjecting a substituted phenol compound to nucleophilic substitution reaction with a halide, to obtain a nitro compound; and reducing the nitro compound, and the specific reaction equation are as follows:

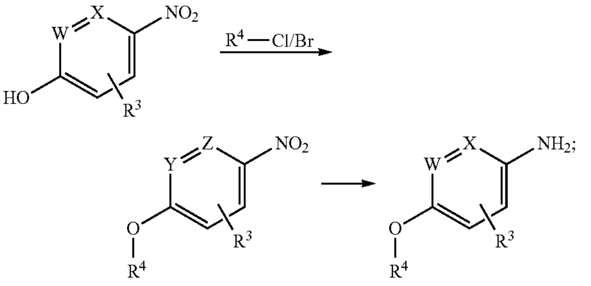

III where the definitions of $R^1$, $R^2$, $R^3$ and $R^4$ are consistent with the above.

As the fourth aspect of the present invention, when

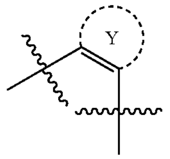

is a thiazole ring and $R^2$ is hydrogen, the preparation method of the compound represented by General Formula (I) includes: reacting an alkylamine or arylamine (M-1) with carbon disulfide or thiophosgene, to obtain an isothiocyanate (M-2); subjecting the isothiocyanate (M-2) to an addition reaction with ethyl isocyanoacetate in the presence of potassium tert-butoxide, to obtain an intermediate (M-3); reacting the intermediate (M-3) with methyl malonyl chloride, to obtain an amide (M-4); treating the amide (M-4) with sodium methoxide, to cyclize the amide (M-4) into pyridone (M-5); reacting pyridone (M-5) with N-phenylbis(trifluoromethanesulphonimide), to form a trifluoromethanesulfonate (M-6); subjecting the trifluoromethanesulfonate (M-6) to reduction deoxidation, to obtain an intermediate (M-7); hydrolyzing the ester group in the intermediate (M-7), to obtain a carboxylic acid represented by General Formula (IIa); and condensing the carboxylic acid represented by General Formula (IIa) with a corresponding arylamine in the presence of an amino acid condensing agent, to obtain a compound represented by General Formula (Ia), where the definitions of $R^1$, $R^3$ and $R^4$ are the same as the above, and the specific reaction equations are as follows:

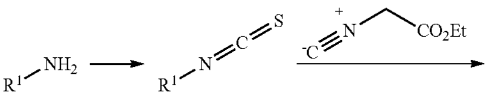

M-1 M-2

-continued

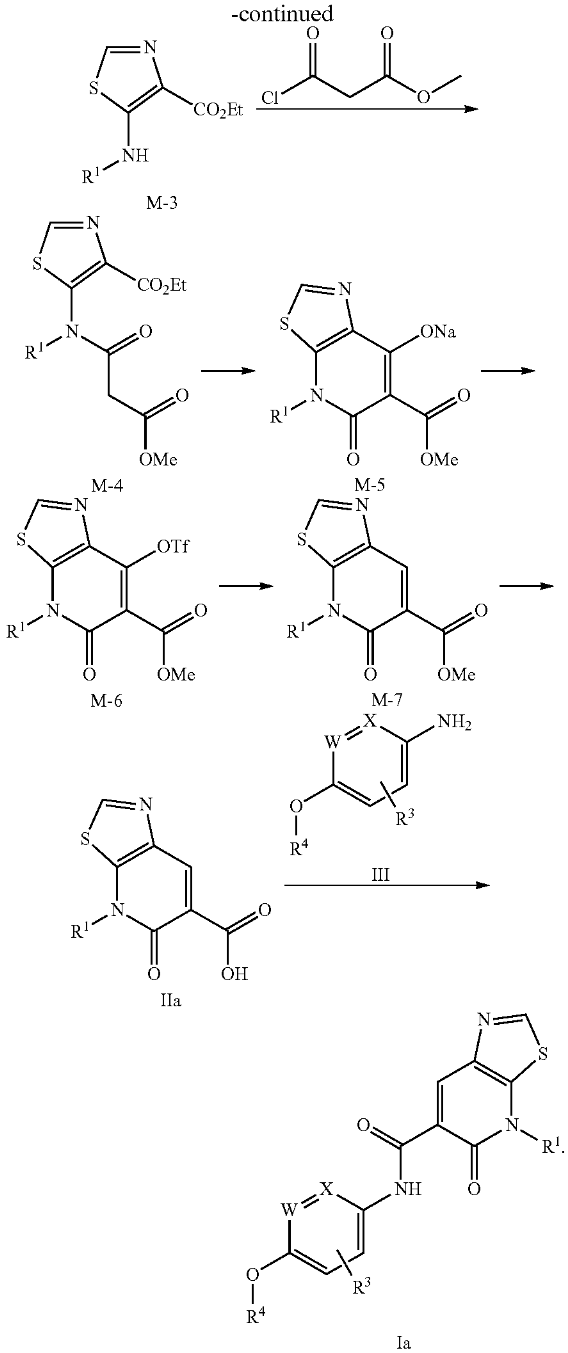

M-3, M-4, M-5, M-6, M-7, IIa, Ia

As the fourth aspect of the present invention, when

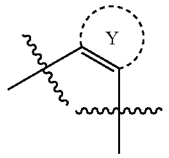

is a 2-dimethylaminothiazole ring and $R^2$ is hydrogen, the preparation method of the compound represented by General Formula (I) includes: converting 2-methoxy-5-aminopyridine (M-8) into an intermediate (M-9) in the presence of potassium thiocyanate and liquid bromine; subjecting the intermediate (M-9) to a Sandmeyer reaction, to convert the amino group of the intermediate (M-9) into a bromide (M-10); reacting the bromide (M-10) with dimethylamine, to obtain an intermediate (M-11); subjecting the intermediate (M-11) to bromization, cyanidation and hydrolysis, to convert the intermediate (M-11) into an intermediate (M-14); reacting the intermediate (M-14) with thionyl chloride and methanol, to convert the intermediate (M-14) into a corresponding methyl ester (M-15); subjecting the methyl ester (M-15) to coupling and hydrolysis, to obtain a carboxylic acid represented by General Formula (IIb); and condensing the carboxylic acid represented by General Formula (IIb) with a corresponding arylamine, to obtain a compound represented by General Formula (Ib), where the definitions of $R^1$, $R^3$ and $R^4$ are the same as the above, and the specific reaction equations are as follows:

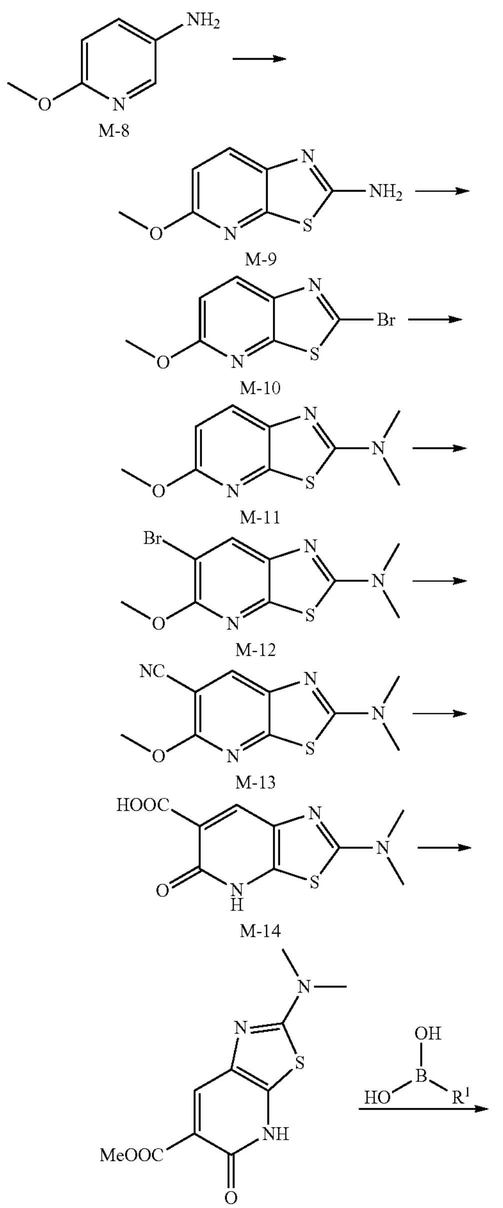

M-8, M-9, M-10, M-11, M-12, M-13, M-14, M-15

-continued

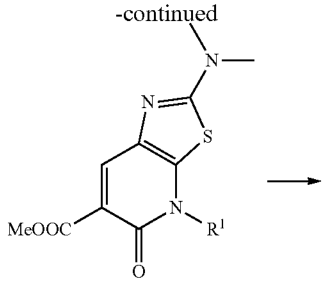

M-16

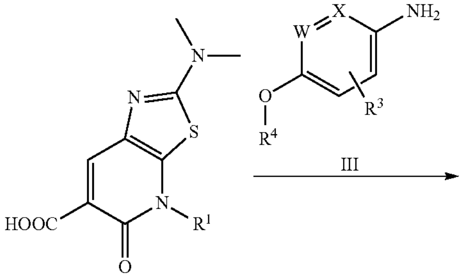

IIb

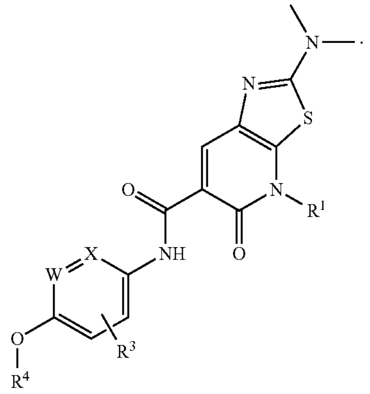

Ib

As the fourth aspect of the present invention, when

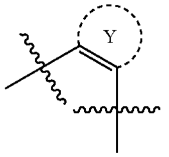

is an imidazole ring and $R^2$ is hydrogen, the preparation method of the compound represented by General Formula (I) includes: preparing a starting material (M-17) with reference to a reported method (Letters in Organic Chemistry, 2004, 1, 326-330); reducing the starting material (M-17) with iron powder, to obtain an intermediate (M-18); coupling the intermediate (M-18) with boronic acid [$R^1$—$B(OH)_2$], to obtain an intermediate (M-19); hydrolyzing the ester group in the intermediate (M-19), to obtain a carboxylic acid represented by General Formula (IIc); and condensing the carboxylic acid represented by General Formula (IIc) with a corresponding arylamine, to obtain a compound represented by General Formula (Ic), where the definitions of $R^1$, $R^3$ and $R^4$ are the same as the above, and the specific reaction equations are as follows:

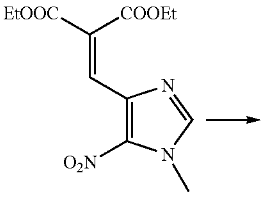

M-17

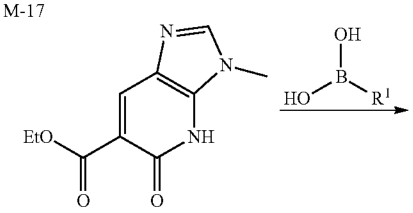

M-18

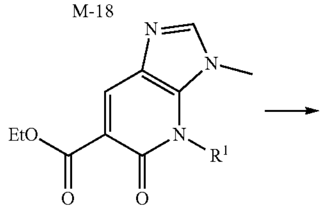

M-19

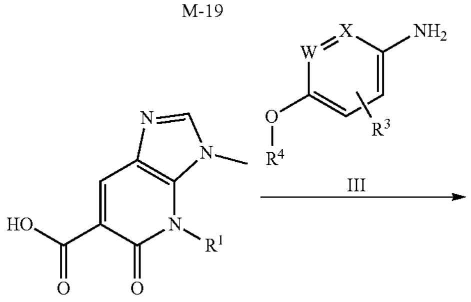

IIc

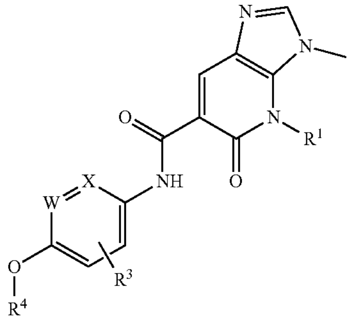

Ic

As the fourth aspect of the present invention, when

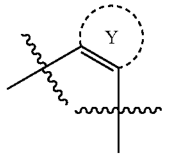

is a pyrazole ring and $R^2$ is hydrogen, the preparation method of the compound represented by General Formula (I) includes: reacting 2-ethoxymethylenemalononitrile (M-20) with methylhydrazine in ethanol at reflux, to obtain pyrazole (M-21); reducing the cyano group in pyrazole (M-21), to obtain an intermediate (M-22); reacting the intermediate (M-22) with diethyl malonate in the presence of a base, to cyclize the intermediate (M-22), so as to obtain pyridone (M-23); subjecting pyridone (M-23) to coupling with a suitable alkylboronic acid or arylboronic acid and hydrolysis, to obtain a carboxylic acid represented by General Formula (IId); and condensing the carboxylic acid represented by General Formula (IId) with a corresponding arylamine, to obtain a compound represented by General Formula (Id), where the definition of $R^1$, $R^3$ and $R^4$ are the same as the above, and the specific reaction equations are as follows:

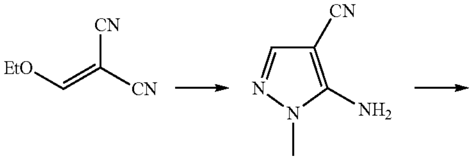

M-20 M-21

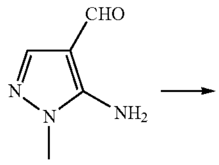

M-22

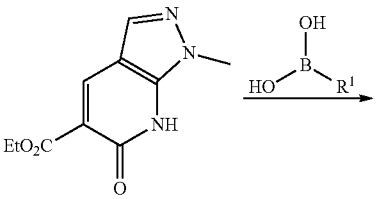

M-23

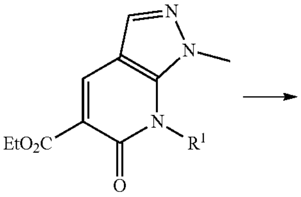

M-24

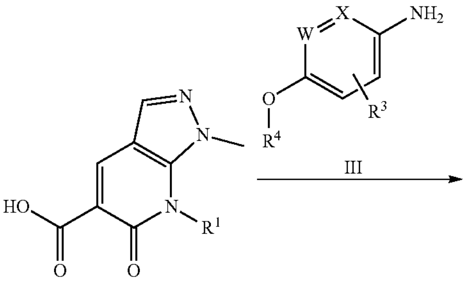

IId

-continued

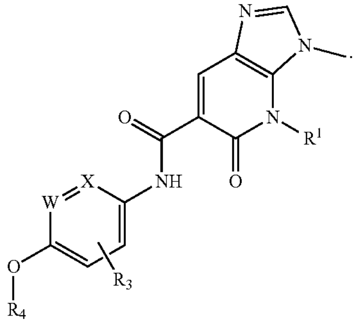

Id

As the fourth aspect of the present invention, when

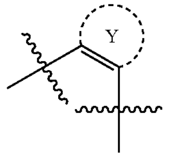

is a morpholine ring and $R^2$ is hydrogen, the preparation method of the compound represented by General Formula (I) includes: preparing a compound (M-25) with reference to a document method (Journal of Medicinal Chemistry, 2007, 50, 3730-3742.), which serves as a raw material; subjecting the compound (M-25) to bromization, cyanidation and hydrolysis, to convert the compound (M-25) into an intermediate (M-28); converting the intermediate (M-28) into a methyl ester (M-29) in the presence of thionyl chloride and methanol; methylating the amino group of the methyl ester (M-29) in the presence of sodium hydride/methyl iodide, to obtain a compound (M-30); subjecting the compound (M-30) to oxidation rearrangement by using pyridine, to convert the compound (M-30) into pyridone (M-31); subjecting pyridone (M-31) to coupling with boronic acid and hydrolysis, to obtain a carboxylic acid represented by General Formula (IIe); and condensing the carboxylic acid represented by General Formula (IIe) with a corresponding arylamine, to obtain a compound represented by General Formula (Ie), where the definitions of $R^1$, $R^3$ and $R^4$ are the same as the above, and the specific reaction equations are as follows:

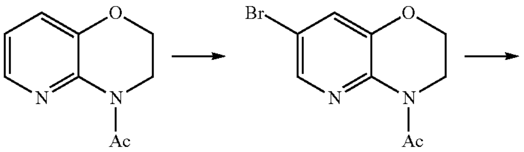

M-25 M-26

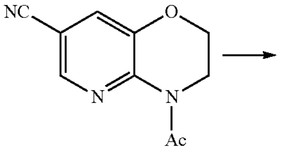

M-27

-continued

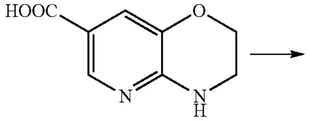

M-28

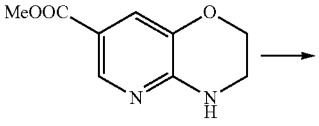

M-29

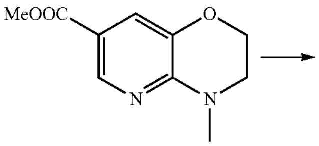

M-30

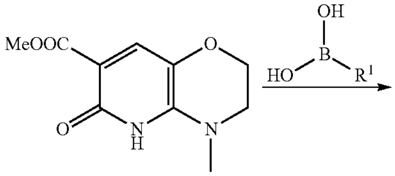

M-31

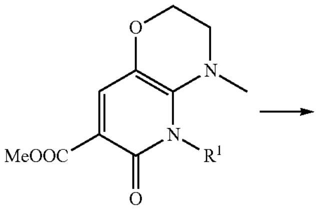

M-32

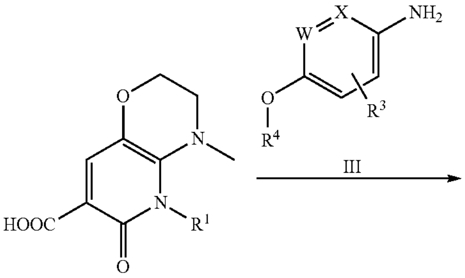

IIe

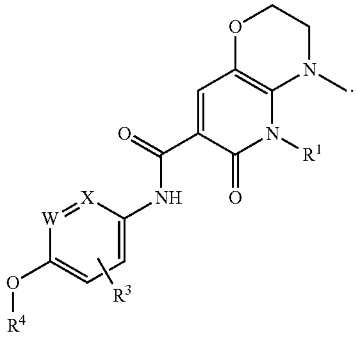

Ie

As the fourth aspect of the present invention, when

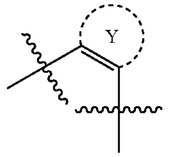

is a morpholine ring and $R^2$ is hydrogen, the preparation method of the intermediate represented by General Formula (I) includes: reacting a starting material (M-33) with phosphorus oxychloride and methanol, to prepare a compound (M-34); substituting the chlorine atom in the compound (M-34) with methyl glycolate, to obtain a compound (M-35); subjecting the compound (M-35) to reduction and cyclization in the presence of iron powder and acetic acid, to obtain an intermediate (M-36); methylating the amide nitrogen atom of the intermediate (M-36) with iodomethane, to obtain a compound (M-37); reducing the amide bond in the compound (M-37), to obtain a compound (M-38); subjecting the compound (M-38) to oxidation rearrangement by using pyridine, to convert the compound (M-38) into pyridone (M-39); subjecting pyridone (M-39) to coupling with boronic acid and hydrolysis, to obtain a carboxylic acid represented by General Formula (IIf); and condensing the carboxylic acid represented by General Formula (IIf) with a corresponding arylamine (III), to obtain a compound represented by General Formula (If), where the definitions of $R^1$, $R^3$ and $R^4$ are the same as the above, and the specific reaction equations are as follows:

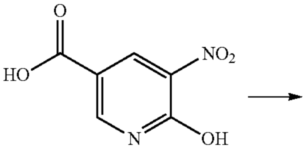

M-33

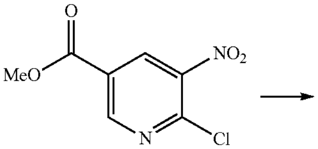

M-34

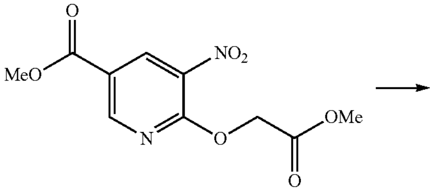

M-35

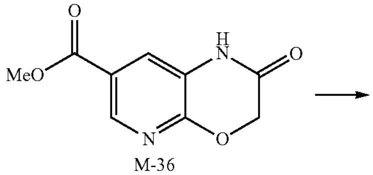

M-36

-continued

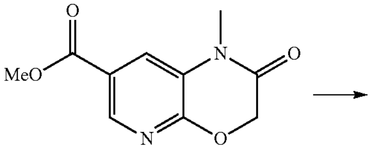

M-37

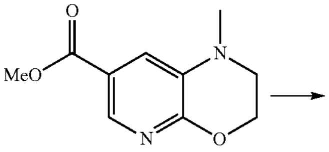

M-38

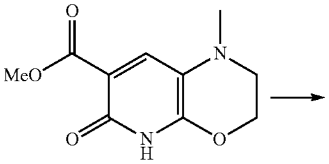

M-39

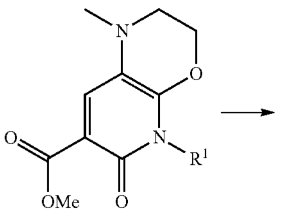

M-40

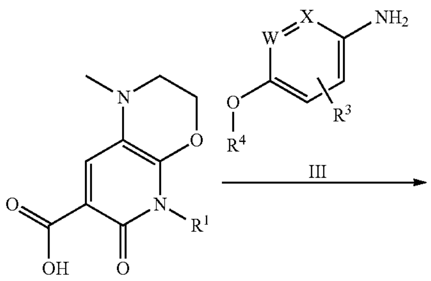

IIf

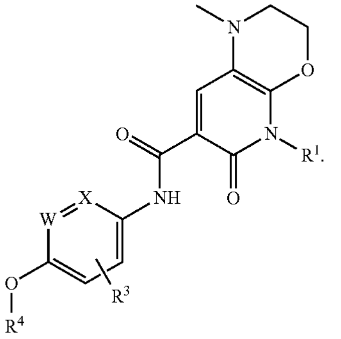

If

As the fourth aspect of the present invention, when

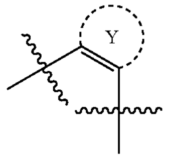

is a thiazole ring and $R^2$ is ethoxy, the preparation method of the intermediate represented by General Formula (I) includes: with an alkylamine or arylamine (M-1) as a starting material, converting the starting material into pyridone (M-5); alkylating pyridone (M-5) with iodomethane, to obtain an intermediate (M-41); hydrolyzing the ester group in the intermediate (M-41), to obtain a carboxylic acid represented by General Formula (IIg); and condensing the carboxylic acid represented by General Formula (IIg) with a corresponding arylamine (III), to obtain a compound represented by General Formula (Ig), where the definitions of $R^1$, $R^3$ and $R^4$ are the same as the above, and the specific reaction equations are as follows:

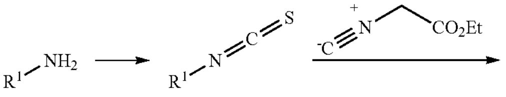

M-1 M-2

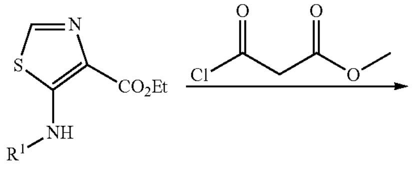

M-3

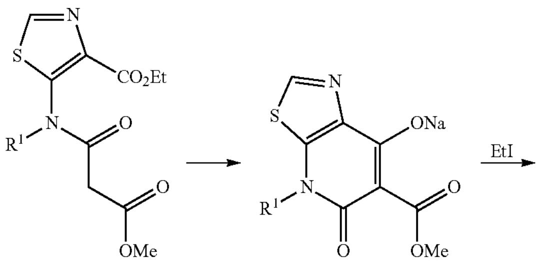

M-4 M-5

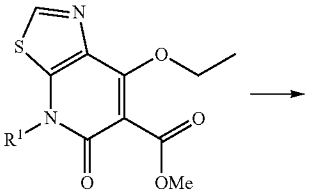

M-41

-continued

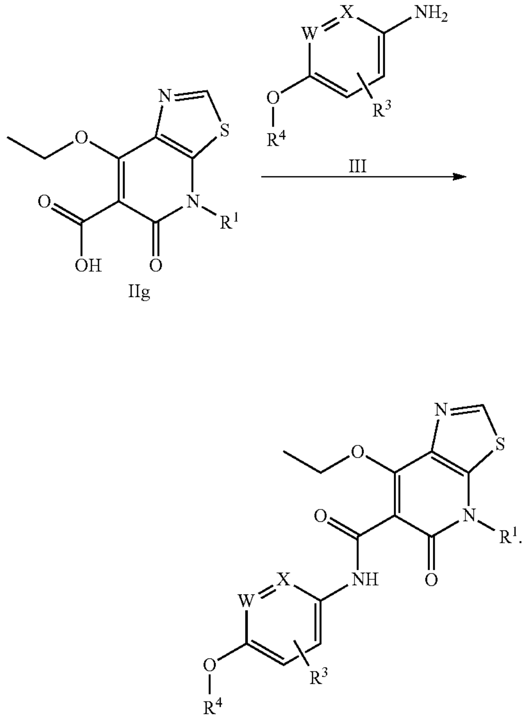

IIg

Ig

As the fourth aspect of the present invention, when

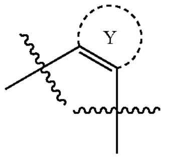

is a thiazole ring and $R^2$ is dimethylamino or N-methyl-2-hydroxyethnylamino, the preparation method of the intermediate represented by General Formula (I) includes: with an alkylamine or arylamine (M-1) as a starting material, converting the starting material into an intermediate (M-6); subjecting the intermediate (M-6) to substitution with dimethylamino or N-methyl-2-hydroxyethnylamino, to obtain an intermediate (M-42); hydrolyzing the ester group in the intermediate (M-42), to obtain a carboxylic acid represented by General Formula (IIh); and condensing the carboxylic acid represented by General Formula (IIh) with a corresponding arylamine (III), to obtain a compound represented by General Formula (Ih), where the definitions of $R^1$, $R^3$ and $R^4$ are the same as the above, $R^1$, $R^3$ and $R^4$ are A=-$CH_3$ or —$CH_2CH_2OH$, and the specific reaction equations are as follows:

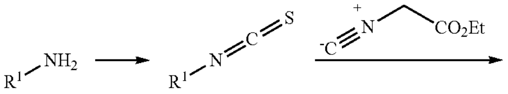

M-1 M-2

-continued

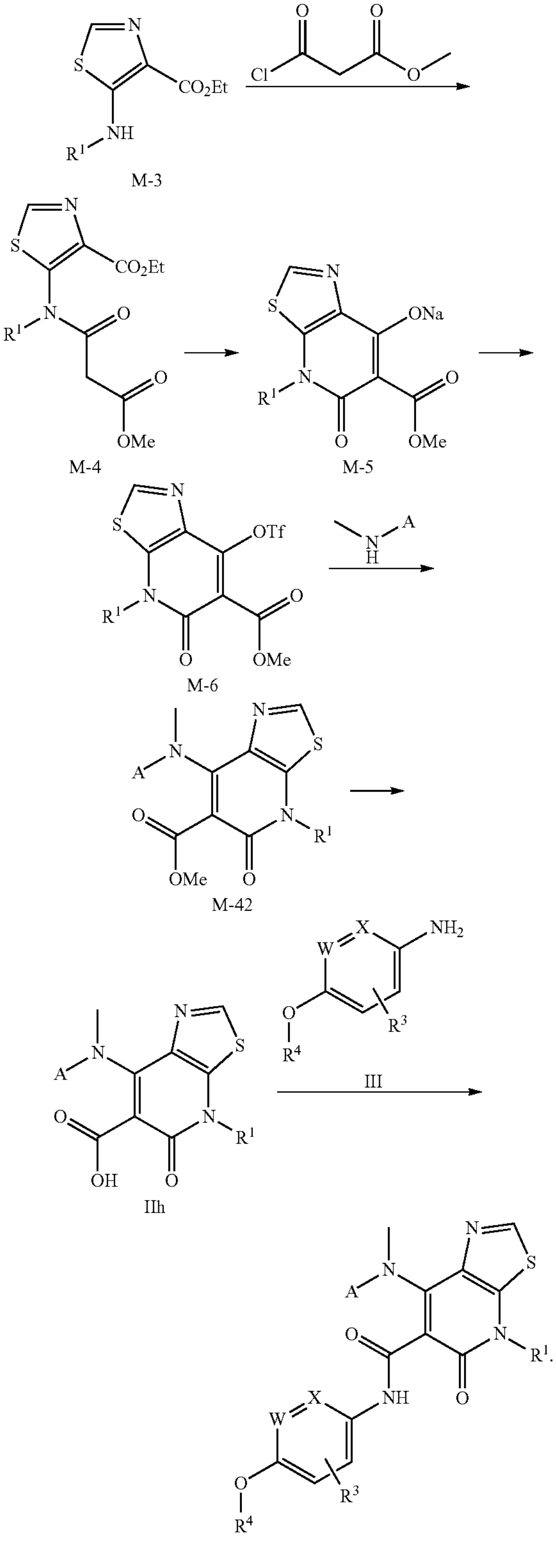

M-3

M-4 M-5

M-6

M-42

IIh

Ih

As a fifth aspect of the present invention, the pharmaceutical composition contains a therapeutically effective amount of the heterocyclic pyridone compound represented by General Formula (I) and a pharmaceutically acceptable excipient.

As the fifth aspect of the present invention, the pharmaceutical composition contains a therapeutically effective amount of a pharmaceutically acceptable derivative of the heterocyclic pyridone compound represented by General Formula (I) and a pharmaceutically acceptable excipient.

As the fifth aspect of the present invention, the pharmaceutical composition contains a therapeutically effective amount of a pharmaceutically acceptable salt of the heterocyclic pyridone compound represented by General Formula (I) and a pharmaceutically acceptable excipient.

The pharmaceutical composition is prepared in the form of tablet, capsule, aqueous suspension, oily suspension, dispersible powder, granule, troche, emulsion, syrup, cream, ointment, suppository and injection.

As a sixth aspect of the present invention, the use is a use of the heterocyclic pyridone compound represented by General Formula (I) in preparation of a product for adjusting catalytic activity of protein kinases.

As the six aspect of the present invention, the use is a use of a pharmaceutically acceptable derivative of the heterocyclic pyridone compound represented by General Formula (I) in preparation of a product for adjusting catalytic activity of protein kinases.

As the six aspect of the present invention, the use is a use of a pharmaceutically acceptable salt of the heterocyclic pyridone compound represented by General Formula (I) in preparation of a product for adjusting catalytic activity of protein kinases.

As the six aspect of the present invention, the use is a use of a pharmaceutical composition in preparation of drugs for treatment of diseases associated with protein kinases.

The protein kinases are c-Met receptor tyrosine kinase.

The cancer selected from thyroid cancer, colon cancer, gastric cancer, kidney cancer, liver cancer, lung cancer, ovarian cancer, breast cancer, prostate cancer, bladder cancer, head and neck cancer, pancreatic cancer, gallbladder cancer, osteosarcoma, rhabdomyosarcoma, MFH/fibrosarcoma, glioblastoma/astrocytoma, melanoma and mesothelioma.

The heterocyclic pyridone compound represented by General Formula (I) according to the present invention can also be used in researches of biological or pharmacological phenomenon, researches of tyrosine kinase involved signaling pathway, and comparison and evaluation of new tyrosine kinase inhibitors.

BRIEF DESCRIPTION OF THE DRAWINGS

Detailed Description

The present invention provides a heterocyclic pyridone compound represented by General Formula (I) defined in the above, a pharmaceutical composition containing the compound, a method for preparing the compound and a method for using the compound.

Definitions of various terms used for description of the compound of the present invention are listed below. The definitions are applied in terms used in the specification (unless otherwise specified in some specific conditions), regardless of the terms are used alone or used as a part of a greater group.

Unless otherwise defined, the term "alkyl" (used alone or used as a part of another group) used in this application refers to a monovalent group having 1 to 12 carbon atoms and derived from an alkane. A preferred alkyl group has 1 to 6 carbon atoms. The alkyl group is a substituted straight-chain, branched-chain or cyclic saturated hydrocarbyl group. An exemplary alkyl group includes methyl, ethyl, propyl, isopropyl, n-butyl, t-butyl, isobutyl, pentyl, hexyl, isohexyl, heptyl, 4,4-dimethyl-pentyl, octyl, 2,2,4-trimethylpentyl, nonyl, decyl, undecyl and dodecyl. A substituent of "substituted alkyl" is selected from the following groups: alkyl, aryl, aryloxy, halogen (such as fluorine, chlorine, bromine and iodine), haloalkyl (such as trichloromethyl and trifluoromethyl), alkoxy, alkylthio, hydroxy, cyano, nitro, carboxy, alkoxycarbonyl, alkylcarbonyloxy, amino, carbomoyl, ureido and merapto.

The term "alkenyl" (used alone or used as a part of another group) used in this application refers to a straight-chain, branched chain or cyclic hydrocarbyl group having 2 to 12 carbon atoms and at least one C—C double bond. The alkenyl group may also be substituted at any available connection point. Exemplary substituents for alkenyl include the substituents listed for alkyl, and especially include $C_3$-$C_7$ cycloalkyl, such as cyclopropyl, cyclopentyl and cyclohexyl, where the cycloalkyl groups may be further substituted with, for example, amino, oxo and hydroxy.

The term "alkynyl" (used alone or used as a part of another group) used in this application refers to a straight-chain, branched chain or cyclic hydrocarbyl group having 2 to 12 carbon atoms and at least one C—C triple bond. The alkynyl group may also be substituted at any available connection point. Exemplary substituents for alkynyl include the substituents listed for alkyl, such as amino and alkylamino.

A subscript number following the symbol "C" defines the number of carbon atoms contained in a specific group. For example, a "$C_1$-$C_6$ alkyl" refers to a straight or branched carbon chain having 1 to 6 carbon atoms, and examples include methyl, ethyl, n-propyl, isopropyl, n-butyl, sec-butyl, iso-butyl, tert-butyl, n-pentyl, sec-pentyl, iso-pentyl and n-hexyl. Based on the context, "$C_1$-$C_6$ alkyl" may also refer to $C_1$-$C_6$ alkylene for connecting two groups, and examples include propane-1,3-diyl, butane-1,4-diyl and 2-methyl-butyane-1,4-diyl. "$C_2$-$C_6$ alkenyl" refers to a straight or branched carbon chain having at least C—C double bond and 2 to 6 carbon atoms, and examples include ethenyl, propenyl, isopropenyl, butenyl, isobutenyl, pentenyl and hexenyl. Based on the context, "$C_2$-$C_6$ alkenyl" may also refer to $C_2$-$C_6$ alkenylene for connecting two groups, and examples include ethylene-1,2-diyl (vinylene), 2-methyl-2-butylene-1,4-diyl and 2-hexene-1,6-diyl. "$C_2$-$C_6$ alkynyl" refers to a straight or branched carbon chain having at least one C—C triple bond and 2 to 6 carbon atoms, and examples include ethynyl, propynyl, butynyl and hexynyl.

The term "acyl" (used alone or used as a part of another group) used in this application refers to an alkyl group connected through a carbonyl group or —C(═O)R, where R is the alkyl group.

The term "alkoxy" (used alone or used as a part of another group) used in this application refers to an alkyl group preferably having 1 to 6 carbon atoms and connected through an oxygen atom, such as —OR, where R is the alkyl group.

The term "alkoxycarbonyl" (used alone or used as a part of another group) used in this application refers to —C(═O)OR, wherein R is the alkyl group.

The term "arylalkyl" (used alone or used as a part of another group) used in this application refers to an aromatic ring connected through the alkyl group described above (for example, benzyl).

The term "haloalkyl" (used alone or used as a part of another group) used in this application refers to a halogen atom connected through an alkyl group, such as —$CF_3$.

The term "aminoalkyl" (used alone or used as a part of another group) used in this application refers to an amino group connected through an alkyl group (—NR'R").

The term "arylalkylamino" (used alone or used as a part of another group) used in this application refers to an aryl group connected through an alkyl group, where the alkyl is connected through an amino group.

The term "aryl" (used alone or used as a part of another group) used in this application refers to a monocyclic aromatic ring or a bicyclic aromatic ring, for example, phenyl, substituted phenyl and a fused group such as naphthyl and phenanthryl. Therefore, the aryl group contains at least one ring having at least 6 atoms, and contains at most five rings of this type (that is, contains at most 22 atoms), and alternating (conjugated) double bonds exist between adjacent carbon atoms or suitable heteroatoms. A preferably aryl group contains 6 to 14 carbon atoms in the ring. The aryl group may be substituted with one or more groups, where the groups include, but not limited to, halogen (such as F, Cl and Br), alkyl (such as methyl, ethyl and propyl), alkoxy (such as methoxy and ethoxy), hydroxy, carboxy, carbamoyl, alkoxycarbonyl, nitro, alkenyloxy, trifluoromethyl, amino, cycloalkyl, aryl, heteroaryl, cyano, alkyl S(═O)$_m$ (m=0, 1, 2) and mercapto.

The term "amino" (used alone or used as a part of another group) used in this application refers to —$NH_2$. "Amino" may be substituted with one or two substituents (NR'R"), where R' and R" may be the same or different, such as alkyl, aryl, arylalkyl, alkenyl, alkynyl, heteroaryl, heteroarylalkyl, heterocycloalkyl, alkyl, heterocycloalkylalkyl, cycloalkyl, cycloalkylalkyl, haloalkyl, hydroxyalkyl, alkoxyalkyl, alkylthio, carbonyl and carboxyl. These substituents may be further substituted with a carboxylic acid or any one of substituents for alkyl or aryl listed in this application. In some implementation manners, the amino group is substituted with carboxyl or carbonyl, to form an N-acyl or N-carbamoyl derived group.

The term "cycloalkyl" (used alone or used as a part of another group) used in this application refers to a fully saturated or partially unsaturated hydrocarbon ring group having 3 to 9 carbon atoms, and preferably 3 to 7 carbon atoms. In addition, cycloalkyl may be substituted. Substituted cycloalkyl refers to a ring having one, two or three substituents selected from: halogen, alkyl, substituted alkyl (where the substituent is as defined for the substituents for alkyl), alkenyl, alkynyl, nitro, cyano, oxo (═O), hydroxy, alkoxy, alkylthio, —$CO_2$H, —C(═O)H, —$CO_2$-alkyl, —C(═O)alkyl, keto, ═N—OH, ═N—O-alkyl, aryl, heteroaryl, five- or six-membered ketal (that is, 1,3-dioxane), —NR'R", —C(═O)NR'R", —$CO_2$NR'R", —C(═O) NR'R", —NR'$CO_2$R", —NR'C(═O)R", —$SO_2$NR'R" and —NR'$SO_2$R", where R' and R" are independently selected from hydrogen, alkyl, substituted alkyl and cycloalkyl; or, R' and R" together form a heterocycloalkyl group or a heteroaryl ring.

The term "heteroaryl" (used alone or used as a part of another group) used in this application refers to a substituted or unsubstituted aromatic 5- or 6-membered monocyclic group, 9- or 10-membered bicyclic group or a 11- to 14-membered tricyclic group, at least one ring of theses groups contains at least one heteroatom (O, S or N). Each ring of the heteroaryl group containing a heteroatom may contain one or more oxygen atoms or sulfur atoms, or one to four nitrogen atoms, provided that the total number of heteroatoms in each ring is four or less, and each ring has at least one carbon atom. The fused ring for forming the bicyclic group or tricyclic group may only contain carbon atoms, and may be saturated or partial saturated. The nitrogen atom and the nitrogen atom may be oxidated, and the nitrogen atom may be quaternized. The bicyclic or tricyclic heteroaryl group must contain at least one fully aromatic group, but other fused ring or multiple rings may be aromatic rings or non-aromatic rings. The heteroaryl group may be connected at any available nitrogen atom or carbon atom of any ring. The heteroaryl ring may contain zero, one, two or three substituents selected from: halogen, alkyl, substituted alkyl, alkenyl, alkynyl, aryl, nitro, cyano, hydroxyl, alkoxy, alkylthio, —$CO_2$H, —C(═O)H, —$CO_2$-alkyl, —C(═O)alkyl, phenyl, benzyl, phenylethyl, phenyloxy, phenylthio, cycloalkyl, substituted cycloalkyl, heterolcycloalkyl, heteroaryl, —NR'R", —C(═O)NR'R", —$CO_2$NR'R", —C(═O) NR'R", —NR'$CO_2$R", —NR'C (═O)R", —$SO_2$NR'R" or —NR'$SO_2$R", wherein R' and R" are independently selected from hydrogen, alkyl, substituted alkyl and cycloalkyl, or R' and R" together form a heterocycloalkyl or heteroaryl ring.

Examples of monocyclic heteroaryl include pyrrolyl, pyrazolyl, pyrazolinyl, imidazolyl, oxazolyl, oxadiazolyl, isoxazolyl, thiazolyl, thiadiazolyl, isothiazolyl, furyl, thienyl, oxadiazolyl, pyridyl, pyrazinyl, pyrimidinyl, pyridazinyl, and triazinyl.

Examples of bicyclic heteroaryl include indolyl, benzothiazolyl, benzodioxol, benzoxazolyl, benzothienyl, quinolinyl, tetrahydroisoquinolinyl, isoquinolinyl, benzimidazolyl, benzopyranyl, indolizinyl, benzofuranyl, chromonyl group, coumarinyl, benzofuranyl, quinoxalinyl, indazolyl, pyrrolopyridyl, furopyridyl, dihydroisoindolyl and tetrahydroquinolinyl.

Examples of tricyclic heteroaryl include carbazolyl, benzo indolyl, phenanthrolinyl, acridinyl and phenanthridinyl.

The term "heterocyclic group" (used alone or used as a part of another group) used in this application refers to a cycloalkyl group (non-aromatic group) in which a carbon atom in the ring is substituted with a heteroatom selected from O, S and N and at least three other carbon atoms are substituted by the heteroatoms. The term "heterocyclic group" (used alone or used as a part of another group) used in this application refers to a stable saturated or partially saturated monocyclic ring containing 5 to 7 ring atoms (carbon atoms and other atoms selected from nitrogen, sulfur and/or oxygen). The heterocylic ring may be a 5-, 6- or 7-membered monocyclic ring containing one, two or three heteroatoms selected from nitrogen, oxygen and/or sulfur. The heterocylic ring may be optionally substituted, which means that the heterocylic ring may be substituted at one or more substitutable positions with one or more groups independently selected from: alkyl (preferably lower alkyl), heterocycloalkyl, heteroaryl, alkoxy (preferably lower-alkoxy), nitro, monoalkylamino (preferably lower alkylamino), dialkylamino (preferably di[lower]alkylamino), cyano, halogen, haloalkyl (preferably trifluoromethyl), alkylacyl, aminocarbonyl, monoalkylaminocarbonyl, dialkylaminocarbonyl, alkylacylamino (preferably lower alkylacylamino), alkoxyalkyl (preferably lower alkoxy lower alkyl), alkoxycarbonyl(preferably lower alkoxycarbonyl), alkylcarbonyloxy(preferably lower alkylcarbonyloxy) and aryl (preferably phenyl), where the aryl is optionally substituted with halogen, lower alkyl and lower alkoxy. Examples of these heterocycloalkyl groups include piperazine, piperidine, morpholine, homomorpholine, thiomorpholine, pyrrolidine and azetidine.

The term "heteroatom" refers to independently selected O, S or N. It should be noted that, any heteroatom with satisfied valence is considered as being connected with hydrogen atoms, so as to satisfy the valence.

The term "halogen" refers to independently selected fluorine, chlorine, bromine or iodine.

The term "anti-cancer drug" includes any known drugs applicable in treatment of cancer, and includes: (1) cytotoxic drugs: nitrogen mustard drugs, such as melphalan and cyclophosphamide; platinum coordination complexes, such as cisplatin, carboplatin and oxaliplatin; (2) antimetabolite antineoplastic agents: 5-fluorouracil, capecitabine, methotrexate, leucovorin, raltitrexed and purine antagonists (for example, 6-thioguanine and 6-mercaptopurine); (3) hormones: 17α-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesterone acetate and toremifene; (4) tyrosine kinase inhibitors: EGFR inhibitors, including gefitinib, erlotinib, cetuximab and Herceptin); VEGF inhibitors, such as anti-VEGF antibodies (Avastin) and small molecules such as Vandetanib and Cediranib, BAY 43-9006, SU11248, CP-547632 and CEP-7055; Bcr-Abl inhibitors (Gleevac); Src inhibitors BMS-354825, AZD-0530, SKI-606 and AP-23464; and MEK-1 kinase inhibitors, MAPK kinase inhibitors, PI3 kinase inhibitors, c-Met inhibitors, aurora kinase inhibitors, and PDGF inhibitors (such as imatinib); (5) agents acting on tubulin, such as vinblastine agents, paclitaxel agents, epothilone agents such as ixabepilone; (6) topoisomerase I inhibitor, such as topotecan and irinotecan; (7) and others: biological response modifiers; growth inhibitors; glutamine antagonists; anti-angiogenic and anti-vascular drugs; and matrix metalloproteinases inhibitors.

"Mammal" includes human and domestic animals such as cats, dogs, pigs, cattle, sheep, goats, horses, rabbits, etc. Preferably, for the objectives of the present invention, the mammal refers to human.

"Optional" or "optionally" indicates that the subsequently described environment or event may or may not exist, and the description includes the case that the event or environment occurs and the case that the event or environment does not occur. For example, "optionally substituted aryl" indicates that the aryl may or may not be substituted and the description includes substituted aryl and unsubstituted aryl.

"Pharmaceutically acceptable derivative" indicates that when being administered to a patient, any non-toxic salt, ester, salt, ester or other derivative of the compound of the present invention or an inhibitory active metabolite or residue thereof can be directly or indirectly provided.

"Pharmaceutically acceptable excipient" includes, but not limited to, any auxiliary agent, carrier, excipient, glidant, sweetener, dispersants, diluent, preservative, suspending agent, stabilizer, dye/colorant, flavoring agent, surfactant, wetting agent, isotonic agent, solvent or emulsifier applicable to human or domestic animals that have been approved by State Food and Drug Administration.

"Pharmaceutically acceptable salt" includes an acid addition salt and a base addition salt.

"Pharmaceutically acceptable acid addition salt" refers to such a salt that the salt retains the biological effects and nature of a free base and will not cause biological or other adverse consequences, and is formed from an inorganic acid including, but not limited to, hydrochloric acid, hydrobromic acid, sulfuric acid, nitric acid and phosphoric acid, and an organic acid including, but not limited to, formic acid, acetic acid, trifluoroacetic acid, methanesulfonic acid, ethanesulfonic acid, 2-hydroxy-ethanesulfonic acid, benzenesulfonic acid, p-toluenesulfonic acid, 2,2-dichloroacetic acid, adipic acid, alginic acid, ascorbic acid, aspartic acid, benzoic acid, acetaminophen acid, camphorsulfonic acid, camphor-10-sulfonic acid, capric acid, caproic acid, caprylic acid, carbonic acid, cinnamic acid, citric acid, cyclamic acid, dodecyl sulfuric acid, ethane-1,2-disulfonic acid, fumaric acid, galacturonic acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, mucic acid, naphthalene-2-sulfonic acid, naphthalene-1,5-disulfonate, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-amino salicylic acid, sebacic acid, stearic acid, fumaric acid, succinic acid, tartaric acid, thiocyanic acid and undecylenic acid.

"Pharmaceutically acceptable base addition salt" refers to such a salt that the salt retains the biological effects and nature of a free acid and will cause biological or other adverse consequences. The salt is obtained by add an inorganic base or organic base to a free acid. Salts from an inorganic base include, but not limited to, sodium, potassium, lithium, ammonium, calcium, magnesium, iron, zinc, copper, manganese and aluminum salts. Preferably inorganic salt are ammonium, sodium, potassium, calcium and magnesium salts. Salts from an organic base include, but not limited to, salts of the following substances primary amines, secondary amines and tertiary amines, substituted amines including naturally existing substituted amines, cyclic amines and basic ion exchange resins, such as ammonia, methylamine, dimethylamine, trimethylamine, diethylamine, triethylamine, propylamine, isopropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, ethylenediamine, glucosamine, methylglucamine, theobromine, triethanolamine, tromethamine, purines, piperidine, piperazine, N-ethyl-piperidine and polyamine resins. Preferred organic bases are isopropylamine, diethylamine, ethanolamine, trimethylamine, dicyclohexylamine, choline and caffeine.

"Pharmaceutical composition" refers to a preparation of the compound of the present invention and a medium that is commonly acceptable in the field of delivering a biologically active compound to a mammal such as human. Such medium includes all pharmaceutically acceptable carriers, diluents or excipients.

"Therapeutically effective amount" refers to an amount of the compound of the present invention that is capable of achieving the treatment defined in the following on a related disease or disorder of a mammal (preferably human) when being administered to the mammal (preferably human). The amount of the compound of the present invention forming the "therapeutically effective amount" varies with, for example, the activity of the specific compound used: metabolic stability and length of action of the compound; the age, body weight, general health, gender and diet of the patient; mode and time of administration; rate of excretion; combination therapy; the severity of a particular disease or disorder; and individuals experiencing the treatment, but can be routinely determined by persons of ordinary skill in the art according to knowledge and this disclosure.

"Treatment" when being used herein contains the treatment of a related disease or disorder of mammal preferably human with the related disease or disorder, and includes:

(i) preventing occurrence of a disease or disorder in mammal, especially when the mammal is susceptible to the disease but not yet diagnosed with the disease;

(ii) suppressing a disease or disorder, that is, prevent the development of a disease or disorder;

(iii) relieving a disease or disorder, that is, cause regression of a disease or disorder; and (iv) stabilizing a disease or disorder.

When being used herein, the terms "disease" and "disorder" can be used interchangeably or may be different. Because a specific disease or disorder may not have known inducement (so the cause has not be studied out), the specific disease or disorder has not been considered as a disease, but be considered as an abnormal condition or syndrome, while clinicians have identified specific syndromes more or less.

The compound of the present invention and the structure thereof herein further indicate that all isomers (for example, enantiomers, diastereomers and geometric isomers (or conformers) are included, which may be defined as (R)-, (S)-, (D)- or (L)-according to absolute stereochemistry of amino acids. The present invention indicates that all potential isomers and their racemic form, enantiomerically enriched form and optionally pure form are included. optical activity (+) and (−), (R)- and (S)- or (D)- and (L)-isomers may be prepared by using chiral synthesis or chiral reagents, or may be split by using a conventional technology, for example, but not limited to, HPLC using a chiral column. When compound of the present invention contains an alkenyl double bond or other geometric asymmetric centers, unless otherwise stated, it is expected that the compound includes both E and Z geometric isomers. Similarly, it is expected that the compound includes all tautomeric form.

"Stereoisomers" refer to compounds formed by the same atoms and the same bonds but having different three-dimensional structures, and are not interchangeable. The present invention covers various stereoisomers and a mixture thereof, and includes "enantiomers", in which enantiomers refer to two stereoisomers whose molecules are non-overlapping mirror images.

"Tautomers" refer to a proton moves from an original position of an atom of a molecule to another position of the same molecule. The present invention includes any tautomers of the compound.

In addition, unless other stated, the compound of the present invention is further intended to include compounds having a difference in structure merely in having one or more isotopically enriched atoms. For example, a compound having the structure of the present invention, with hydrogen replaced by "deuterium" or "tritium", or fluorine replaced by $^{18}$F-fluorine label ($^{18}$F isotope), or carbon replaced by $^{11}$C—, $^{13}$C— or $^{14}$C-enriched carbon ($^{11}$C-, $^{13}$C- or $^{14}$C-carbon label; $^{11}$C-, $^{13}$C- or $^{14}$C-isotope) are within the scope of the present invention. Such compounds can be used as an analytical tool or probe in biology tests, or used as an imaging tracer of in vivo diagnosis of diseases, or used as an imaging tracer in pharmacodynamics, pharmacokinetics or receptor studies.

An implementation manner of the present invention provides a method as follows: administering a therapeutically effective amount of the compound represented by General Formula (I) defined above and at least one other anti-cancer drugs in combination (at the same time or in succession) to a patient needing the treatment, to adjust c-Met kinases, so as to treatment proliferative diseases (such as cancer). In a preferred implementation manner, the proliferative disease is cancer.

Particularly, the compound represented by General Formula (I) can be used in treatment of various cancers, and specifically cancers dependent on activation of c-Met. The activation of c-Met can be adjusted by gene amplification, mutation (multiple mutant), and/or HGF stimulation, in which HGF is provided by tumor (autocrine) or host (paracrine) tissues. Generally, the compound of the present invention can be used in treatment of the following cancers:

A) solid tumors, including bladder cancer, breast cancer, colon cancer, kidney cancer, liver cancer, lung cancer (including small cell lung cancer, non-small cell lung cancer), esophageal cancer, gallbladder cancer, ovarian cancer, pancreatic cancer, stomach cancer, cervical cancer, thyroid cancer, prostate cancer and skin cancer (including squamous cell carcinoma);

B) hematopoietic tumors of lymphoid lineage, including leukemia, acute lymphoblastic leukemia (ALL), acute lymphoblastic leukemia primitive, B-cell lymphoma, T-cell lymphoma, Hodgkin's lymphoma, non-Hodgkin's lymphoma, hairy lymphoma and Burkett's lymphoma;

C) hematopoietic tumors of bone marrow lineage, including acute and chronic myelogenous leukemia, myelodysplastic syndrome and promyelocytic leukemia;

D) tumors of mesenchymal origin, including fibrosarcoma and rhabdomyosarcoma;

E) central and peripheral nervous system tumors, including astrocytoma, neuroblastoma, glioma and nerve sheath tumors; and F) other tumors, including melanoma, seminoma, teratocarcinoma, osteosarcoma, xeroderma pigmentosum disease, keratoacanthoma, follicular thyroid carcinoma and Kaposi's sarcoma.

The compound represented by General Formula (I) can further be used in treatment process of any diseases characterized by abnormal cell proliferation, for example, benign prostatic hyperplasia, neurofibromatosis, atherosclerosis, pulmonary fibrosis, arthritis, psoriasis, glomerulonephritis, vascular restenosis after angioplasty or vascular surgery, inflammatory bowel disease, transplantation rejection, endotoxic shock, and fungal infections.

The compound represented by General Formula (I) can adjust the level of cellular RNA and DNA synthesis. Therefore, these substances can be used in treatment of viral infections (including, but not limited to, HIV, human papillomavirus, herpes virus, pox virus, EB virus, Sindbis virus and adenovirus).

The compound represented by General Formula (I) can be used in chemoprevention of cancer. Chemoprevention is defined as inhibition of the progress of invasive cancers or inhibition of recurrence of tumors by blocking initial mutagenic event or blocking the progress of premalignant cells that have suffered injuries.

The compound represented by General Formula (I) can be used in inhibiting tumor angiogenesis and metastasis.

The compound of the present invention may also be used in combination with known anti-cancer drugs (including, but not limited to, those mentioned in the "anti-cancer drug") or anti-cancer treatment (such as radiation therapy) (administered together or in succession).

Some compounds represented by General Formula (I) generally can be prepared according to Scheme 1 to Scheme 10 below. Tautomers and solvates (such as hydrates) of the compound represented by General Formula (I) are also within the scope of the present invention. The preparation method of the solvates is generally known in the art. Therefore, the compound of the present invention may be in a free form or in the form of a hydrate, and can be obtained through a method demonstrated in the following schemes.

In the method described below, the functional groups of the intermediate compound may need to be protected by a suitable protecting group. The functional groups include hydroxyl, amino, mercapto and carboxylic acid. Suitable protecting groups for hydroxy include trialkylsilylalkyl or diarylalkylsilylalkyl (for example, tert-butyldimethylsilylalkyl, tert-butyldiphenylsilylalkyl or trimethylsilylalkyl), tetraphydropyranyl and benzyl. Suitable protecting groups for amino, amidino and guanidine include tert-butyloxycarbonyl, benzyloxycarbonyl, acetyl, benzoyl and trifluoroacetyl. Suitable protecting groups for mercapto include —C(═O)—R'' (where R'' is alkyl, aryl or arylalkyl), p-methoxybenzyl and trityl. Suitable protecting groups for carboxylic acid include alkyl, aryl and arylalkyl. Suitable protecting groups for functional group NH of heteroaryl such as indole or indazole ring include tert-butyloxycarbonyl, benzyloxycarbonyl, acetyl, benzoyl, 2-trimethylsilylethoxymethyl (SEM).

The protecting group can be added or removed according to methods known to persons of ordinary skill in the art (Greene, T. W., Protective Groups in Organic Synthesis, 1999, the third edition, Wiley) and standard technology described herein. The protecting group may also be a polymer resin such as Wang resin, Rink resin or 2-chlorotrityl chloride resin.

Meanwhile the protected derivatives of the compound of the present invention may not have pharmacological activity, but they can be administered to a mammal, and then metabolized in the body to form the compound of the present invention having the pharmacological activity. Therefore, such derivatives are described as "predrugs". All predrugs of the compound of the present invention fall within the scope of the present invention.

The heterocyclic pyridone compound represented by General Formula (I) of the present invention may be obtained through amide condensation of the intermediate represented by General Formula (II) and arylamine (III), and the specific reaction equation are shown in Scheme 1.

Scheme 1:

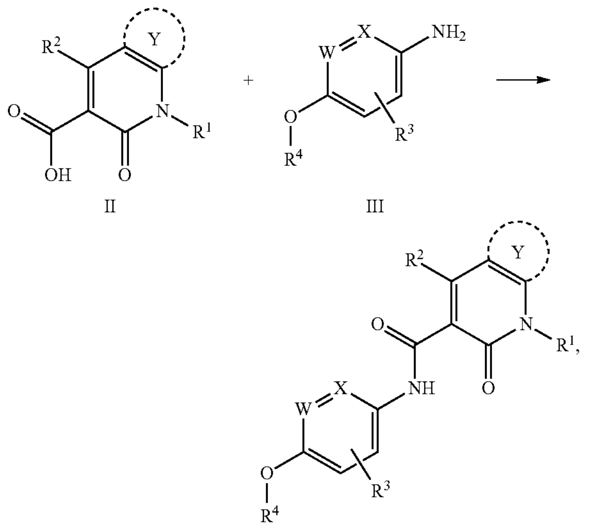

II III

I where arylamine (III) may be obtained through a nucleophilic substitution reaction of a substituted phenol compound with a halide, to obtain a nitro compound; and a reduction reaction of the nitro compound, and the specific reaction equations are shown in Scheme 2.

Scheme 2.

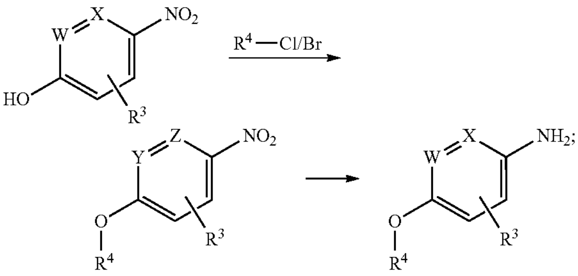

III where the definitions of $R^1$, $R^2$, $R^3$ and $R^4$ are consistent to those in the above.

When

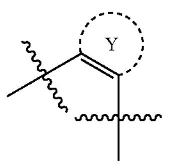

is a thiazole ring and $R^2$ is hydrogen, the preparation method of the compound represented by General Formula (I) of the present invention includes: reacting an alkylamine or arylamine (M-1) with carbon disulfide or thiophosgene, to obtain an isothiocyanate (M-2), subjecting the isothiocyanate (M-2) to an addition reaction with ethyl isocyanoacetate in the presence of potassium tert-butoxide, to obtain an intermediate (M-3); reacting the intermediate (M-3) with methyl malonyl chloride, to obtain an amide (M-4); treating the amide (M-4) with sodium methoxide, to cyclize the amide (M-4), so as to obtain pyridone (M-5); reacting pyridone (M-5) with N-phenylbis(trifluoromethanesulphonimide), to form a trifluoromethanesulfonate (M-6); subjecting the trifluoromethanesulfonate (M-6) to reduction deoxidation, to obtain an intermediate (M-7); hydrolyzing the ester group in the intermediate (M-7), to obtain a carboxylic acid represented by General Formula (IIa); and condensing the carboxylic acid represented by General Formula (IIa) with a corresponding arylamine in the presence of an amino acid condensing agent, to obtain a compound represented by General Formula (Ia), where the definitions of $R^1$, $R^3$ and $R^4$ are the same as the above, and the specific reaction equations are shown in Scheme 3.

Scheme 3:

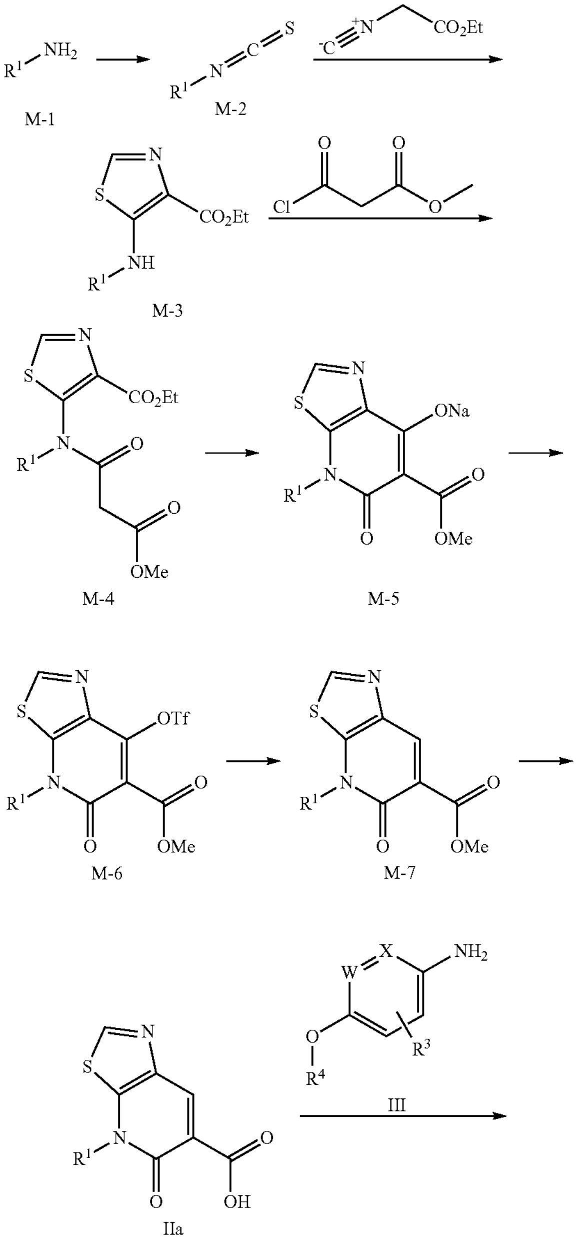

M-1, M-2, M-3, M-4, M-5, M-6, M-7, IIa

-continued

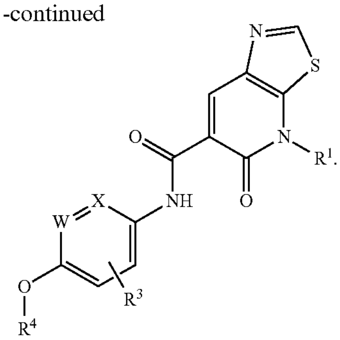

Ia

When

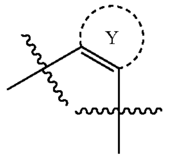

is a 2-dimethylaminothiazole ring and $R^2$ is hydrogen, the preparation method of the compound represented by General Formula (I) of the present invention includes: converting 2-methoxy-5-aminopyridine (M-8) into an intermediate (M-9) in the presence of potassium thiocyanate and liquid bromine; subjecting the intermediate (M-9) to a Sandmeyer reaction, to convert the amino group of the intermediate (M-9) into a bromide (M-10); reacting the bromide (M-10) with dimethylamine, to obtain an intermediate (M-11); subjecting the intermediate (M-11) to bromization, cyanidation and hydrolysis, to convert the intermediate (M-11) into an intermediate (M-14); reacting the intermediate (M-14) with thionyl chloride and methanol, to convert the intermediate (M-14) into a corresponding methyl ester (M-15); subjecting the methyl ester (M-15) to coupling and hydrolysis, to obtain a carboxylic acid represented by General Formula (IIb); and condensing the carboxylic acid represented by General Formula (IIb) with a corresponding arylamine, to obtain a compound represented by General Formula (Ib), where the definitions of $R^1$, $R^3$ and $R^4$ are the same as the above, and the specific reaction equations are shown in Scheme 4.

Scheme 4:

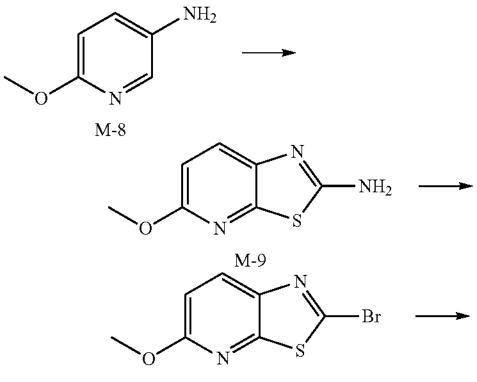

M-8, M-9, M-10

-continued

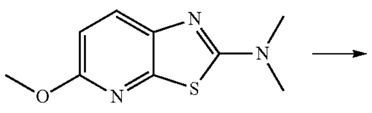
M-11

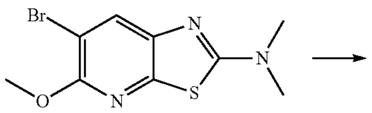
M-12

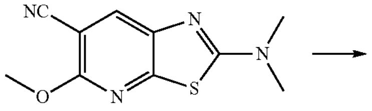
M-13

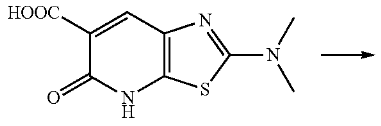
M-14

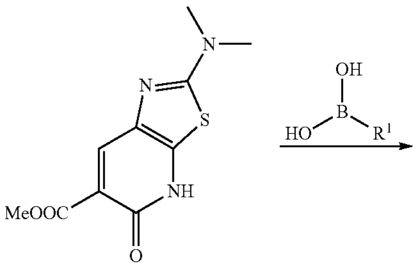
M-15

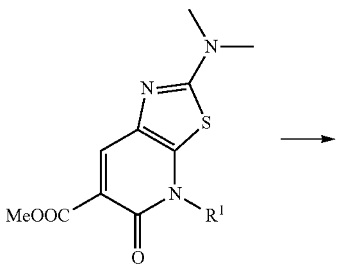
M-16

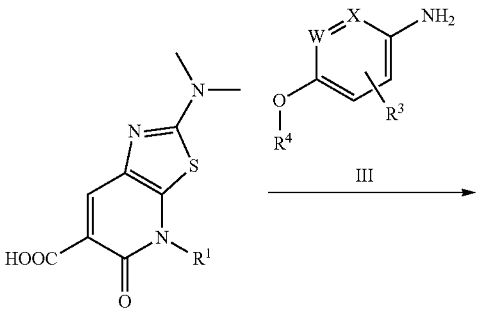

IIb

-continued

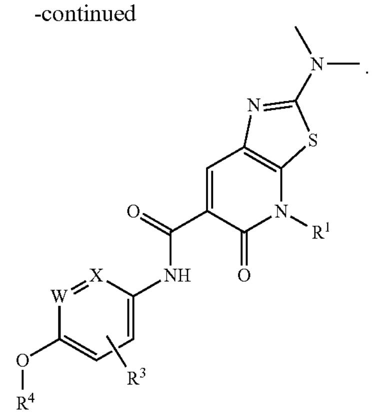
Ib

When

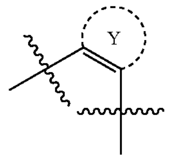

is an imidazole ring and $R^2$ is hydrogen, the preparation method of the compound represented by General Formula (I) of the present invention includes: preparing a starting material (M-17) with reference to a reported method (Letters in Organic Chemistry, 2004, 1, 326-330); reducing the starting material (M-17) with iron powder, to obtain an intermediate (M-18); coupling the intermediate (M-18) with boronic acid [$R^1$—$B(OH)_2$], to obtain an intermediate (M-19); hydrolyzing the ester group in the intermediate (M-19), to obtain a carboxylic acid represented by General Formula (IIc); and condensing the carboxylic acid represented by General Formula (IIc) with a corresponding arylamine, to obtain a compound represented by General Formula (Ic), where the definitions of $R^1$, $R^3$ and $R^4$ are the same as the above, and the specific reaction equations are shown in Scheme 5.

Scheme 5:

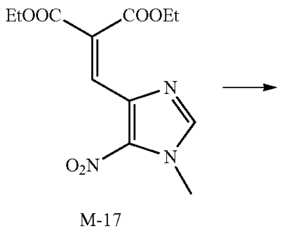
M-17

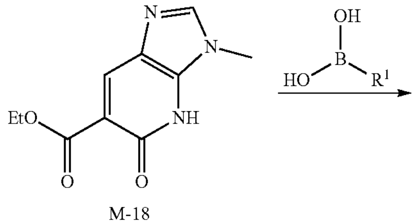
M-18

-continued

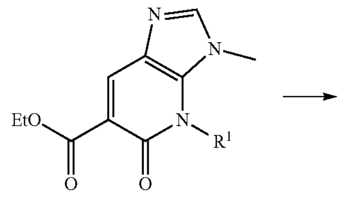

M-19

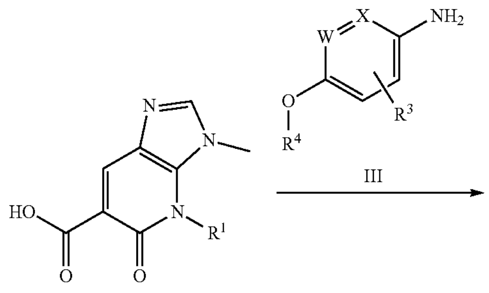

IIc

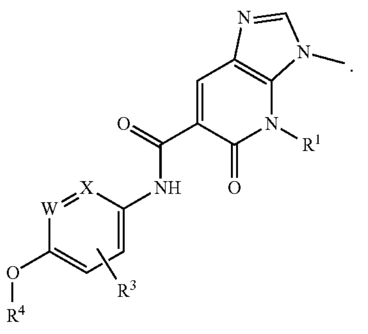

Ic

When

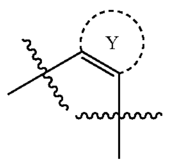

is a pyrazole ring and $R^2$ is hydrogen, the preparation method of the compound represented by General Formula (I) of the present invention includes: reacting 2-ethoxymethylenemalononitrile (M-20) with methylhydrazine in ethanol at reflux, to obtain pyrazole (M-21); reducing the cyano group in pyrazole (M-21), to obtain an intermediate (M-22); reacting the intermediate (M-22) with diethyl malonate in the presence of a base, to cyclize the intermediate (M-22), so as to obtain pyridone (M-23); subjecting pyridone (M-23) to coupling with a suitable alkylboronic acid or arylboronic acid and hydrolysis, to obtain a carboxylic acid represented by General Formula (IId); and condensing the carboxylic acid represented by General Formula (IId) with a corresponding arylamine, to obtain a compound represented by General Formula (Id), where the definition of $R^1$, $R^3$ and $R^4$ are the same as the above, and the specific reaction equations are shown in Scheme 6.

Scheme 6:

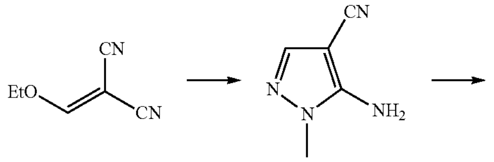

M-20 M-21

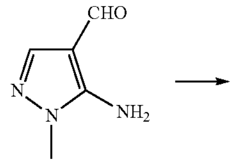

M-22

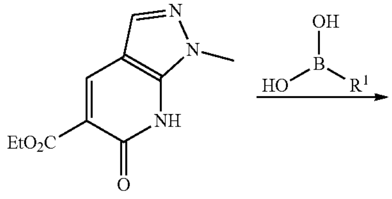

M-23

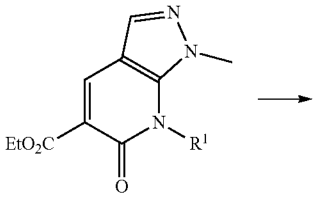

M-24

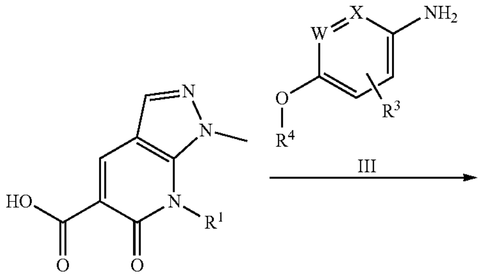

IId

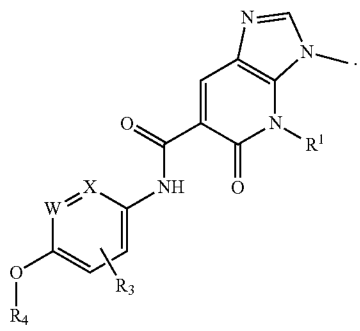

Id

When

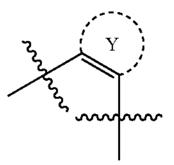

is a morpholine ring and $R^2$ is hydrogen, the preparation method of the compound represented by General Formula (I) of the present invention includes: preparing a compound (M-25) with reference to a document method (Journal of Medicinal Chemistry, 2007, 50, 3730-3742.), which serves as a raw material; subjecting the compound (M-25) to bromization, cyanidation and hydrolysis, to convert the compound (M-25) into an intermediate (M-28); converting the intermediate (M-28) into a methyl ester (M-29) in the presence of thionyl chloride and methanol; methylating the amino group of the methyl ester (M-29) in the presence of sodium hydride/methyl iodide, to obtain a compound (M-30); subjecting the compound (M-30) to oxidation rearrangement by using pyridine, to convert the compound (M-30) into pyridone (M-31); subjecting pyridone (M-31) to coupling with boronic acid and hydrolysis, to obtain a carboxylic acid represented by General Formula (IIe); and condensing the carboxylic acid represented by General Formula (IIe) with a corresponding arylamine, to obtain a compound represented by General Formula (Ie), where the definitions of $R^1$, $R^3$ and $R^4$ are the same as the above, and the specific reaction equations are shown in Scheme 7.

Scheme 7:

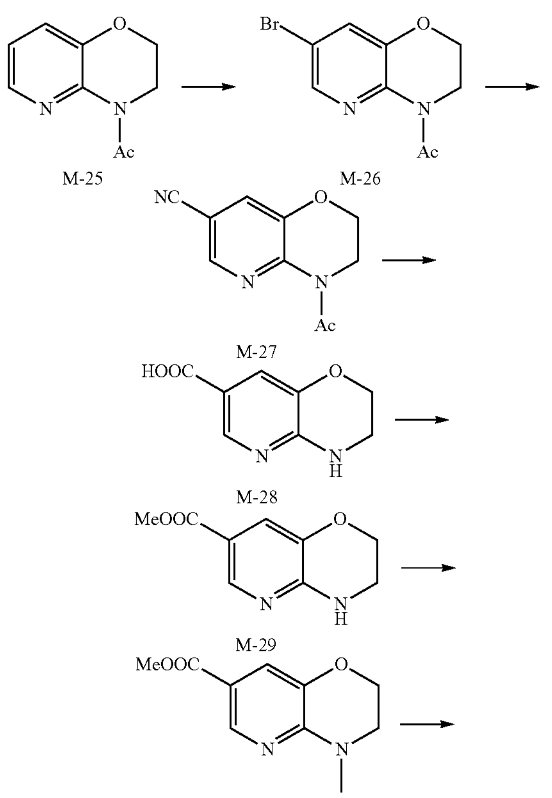

M-25 M-26 M-27 M-28 M-29 M-30

-continued

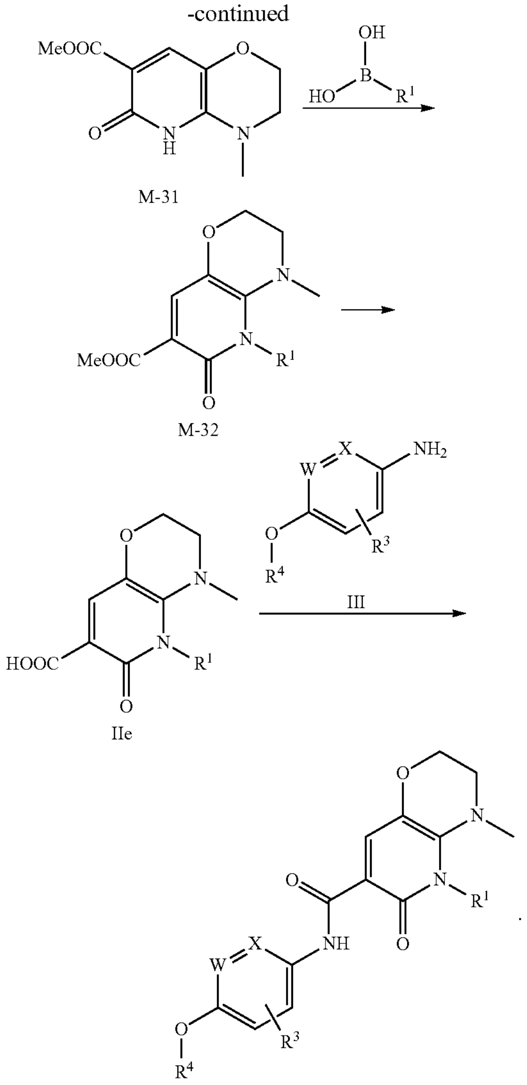

M-31 M-32 IIe Ie

When

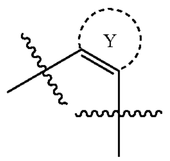

is selected from morpholine ring and $R^2$ is hydrogen, the preparation method of the compound represented by General Formula (I) of the present invention includes: reacting a starting material (M-33) with phosphorus oxychloride and methanol, to prepare a compound (M-34); substituting the chlorine atom in the compound (M-34) with methyl glycolate, to obtain a compound (M-35); subjecting the compound (M-35) to reduction and cyclization in the presence of iron powder and acetic acid, to obtain an intermediate (M-36); methylating the amide nitrogen atom of the intermediate (M-36) with iodomethane, to obtain a compound (M-37); reducing the amide bond in the compound (M-37), to obtain a compound (M-38); subjecting the compound (M-38) to oxidation rearrangement by using pyridine, to convert the compound (M-38) into pyridone (M-39); subjecting pyridone (M-39) to coupling with boronic acid and hydrolysis, to obtain a carboxylic acid represented by General Formula (IIf); and condensing the carboxylic acid represented by General Formula (IIf) with a corresponding arylamine (III), to obtain a compound represented by General Formula (If), where the definitions of $R^1$, $R^3$ and $R^4$ are the same as the above, and the specific reaction equations are shown in Scheme 8.

Scheme 8:

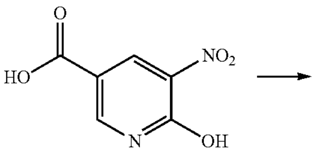

M-33

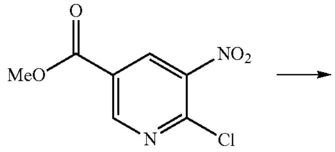

M-34

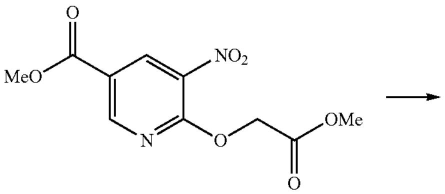

M-35

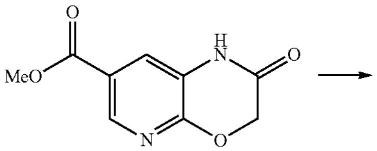

M-36

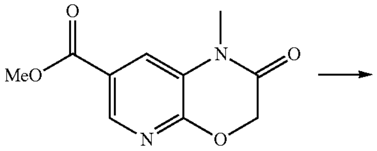

M-37

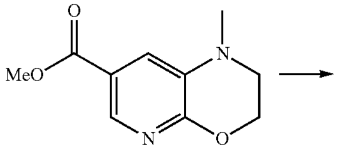

M-38

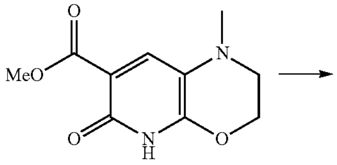

M-39

-continued

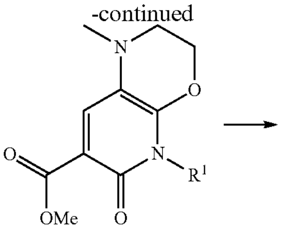

M-40

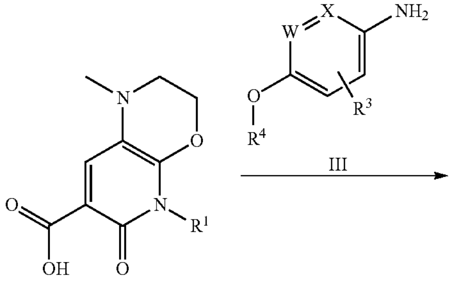

IIf

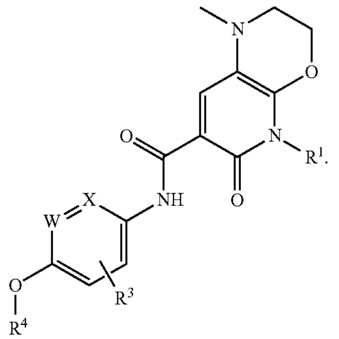

If

When

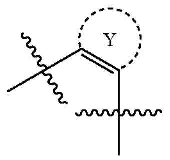

is a thiazole ring and $R^2$ is ethoxy, the preparation method of the intermediate represented by General Formula (I) of the present invention includes: with an alkylamine or arylamine (M-1) as a starting material, converting the starting material into pyridone (M-5); alkylating pyridone (M-5) with iodomethane, to obtain an intermediate (M-41); hydrolyzing the ester group in the intermediate (M-41), to obtain a carboxylic acid represented by General Formula (IIg); and condensing the carboxylic acid represented by General Formula (IIg) with a corresponding arylamine (III), to obtain a compound represented by General Formula (Ig), where the definitions of $R^1$, $R^3$ and $R^4$ are the same as the above, and the specific reaction equations are shown in Scheme 9.

Scheme 9:

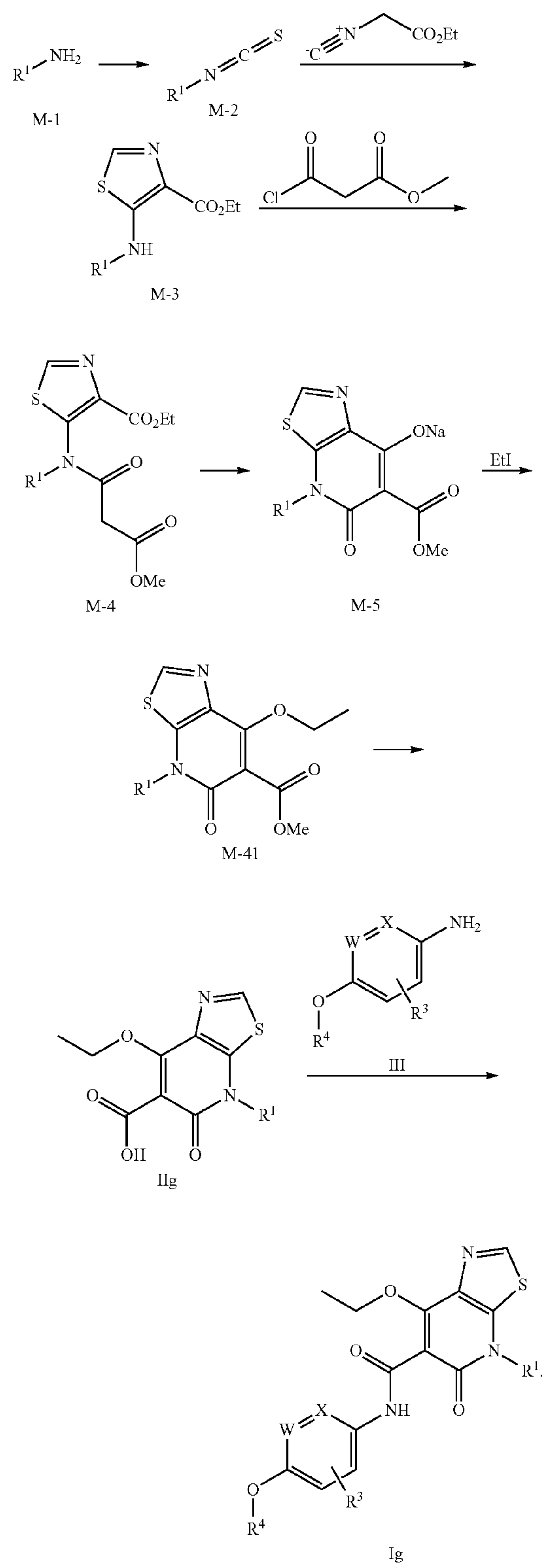

When

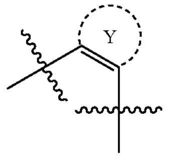

is a thiazole ring and $R^2$ is dimethylamino or N-methyl-2-hydroxyethnylamino, the preparation method of the intermediate represented by General Formula (I) of the present invention includes: with an alkylamine or arylamine (M-1) as a starting material, converting the starting material into an intermediate (M-6); subjecting the intermediate (M-6) to substitution with dimethylamino or N-methyl-2-hydroxyethnylamino, to obtain an intermediate (M-42); hydrolyzing the ester group in the intermediate (M-42), to obtain a carboxylic acid represented by General Formula (IIh); and condensing the carboxylic acid represented by General Formula (IIh) with a corresponding arylamine (III), to obtain a compound represented by General Formula (Ih), where the definitions of $R^1$, $R^3$ and $R^4$ are the same as the above, $R^1$, $R^3$ and $R^4$ are A=-$CH_3$ or —$CH_2CH_2OH$, and the specific reaction equations are shown in Scheme 10.

Scheme 10:

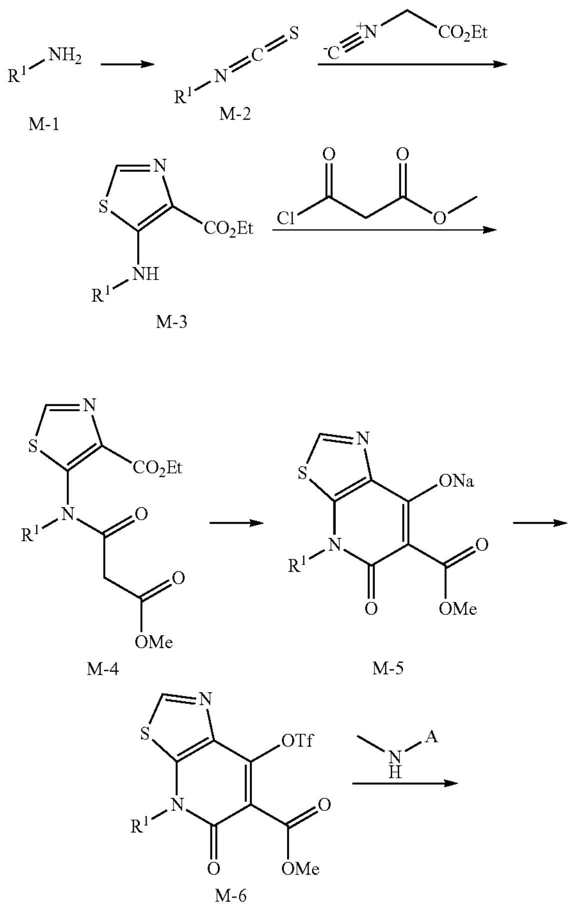

-continued

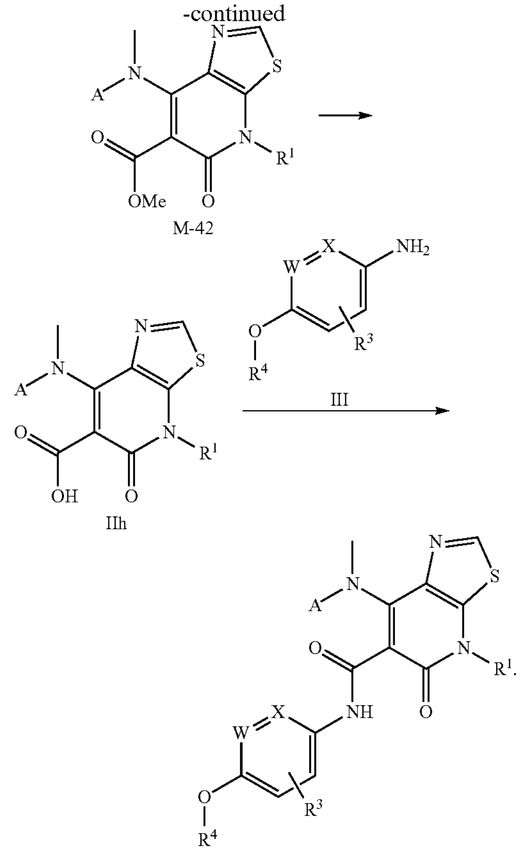

M-42

IIh

Ih

The commonly used abbreviations are defined as follows:

HATU: 2-(7-aza-1H-benzotriazole-1-yl)-N,N,N',N'-tetramethyluronium hexafluorophosphate;

TBTU: 2-(1H-benzotriazole-1-yl)-1,1,3,3-tetramethyluronium tetrafluoroborate;

TBDPS: Butyldiphenylsilyl;

DMF: N,N-dimethylformamide;

DMSO: Dimethyl sulfoxide;

$CDCl_3$: Deuterated chloroform;

$^1$H NMR: 1H Nuclear Magnetic Resonance Spectrum;

ESI-MS: Electrospray ionization mass spectrum;

s: Singlet d: Doublet t: Triplet dd: Doublet of doulblet br: Broad m: Multiplet

° C.: Celsius degree mol: Mole

TLC: Thin layer chromatography

Persons of ordinary skill in the art can prepare other compounds of the present invention that are not specifically disclosed in the above reaction schemes by using suitable raw materials and adopting similar methods.

By treating with a suitable inorganic or organic base or acid, all compounds of the present invention existing in the form of free base or acid prepared according to the above description can be converted into pharmaceutically acceptable salts thereof. The salts of the compound prepared according to the above description can be converted into free bases or acids through standard technologies.

All the compounds of the present invention mostly include all crystalline forms, amorphous forms, anhydrates, hydrates, solvates and salts thereof. In addition, all the compounds of the present invention containing an ester group and amide group can be converted into corresponding acids through methods known to persons of ordinary skill in the art or methods described herein. Similarly, the compounds of the present invention containing a carboxylic acid group can be converted into corresponding esters and amides through method known to persons of ordinary skill in the art. Other substitution on the molecule can also be performed through method known to persons of ordinary skill in the art (for example, hydrogenation, alkylation and reaction with acyl chloride).

A cyclodextrin inclusion complex of the present invention can be prepared by: dissolving the compound represented by General Formula (I) and defined in the summary of the present invention in a pharmacologically acceptable solvent, for example, but not limited to, alcohols (preferably ethanol), ketones (such as acetone) and ethers (such as diethyl ether), and mixing with an aqueous solution of α-cyclodextrin, β-cyclodextrin or γ-cyclodextrin, preferably β-cyclodextrin at temperature of 20° C. to 80° C.; or blending an acid of the compound represented by General Formula (I) defined in the summary of the present invention in the form of an aqueous solution of a salt (for example, sodium or potassium salt) with cyclodextrin, and then blending with a solution of an equivalent amount of an acid (for example, HCl and $H_2SO_4$).

At this time or when being cooled, the corresponding cyclodextrin inclusion complex crystal can be crystallized. Or, when the compound represented by General Formula (I) is an oil and is crystallized, by stirring for a long term at room temperature (for example, 1 hr to 14 days), and treating with an aqueous solution of cyclodextrin, the compound can be converted into a corresponding cyclodextrin inclusion complex. Then, the cyclodextrin inclusion complex is filtered and dried, and is separated into a solid and a crystal with fluidity.

The cyclodextrin useful in the present invention is commercially available (for example, from Aldrich Chemical Co.), or may be prepared through a method known to persons of ordinary skill in the art, and reference can be made to, for example, Croft, A. P. et al, "Synthesis of Chemically Modified Cyclodextrins", Tetrahedron 1983, 39, 9, 1417-1474. Suitable cyclodextrin includes various types of cyclodextrins capable of reacting with the compound represented by Formula (I) to prepare inclusion complexes.

By selecting suitable amount of cyclodextrin and water, an inclusion complex having a reproducible content of an active substance can be obtained according to the stoichiometric composition. The inclusion complex may be used in the form of being dry and water-absorbable or in the form of water bearing but being more water-unabsorbable. The typical molar ratio of cyclodextrin to the compound represented by General Formula (I) is 2:1 (cyclodextrin:compound).

The pharmaceutical composition containing the compound represented by General Formula (I) as an active ingredient may be in the form suitable for oral administration, for example, tablet, capsule, aqueous suspension, oily suspension, dispersible powder, granule, troche, emulsion, syrup, cream, ointment, suppository and injection. The composition for oral administration can be prepared according to any method for preparing a pharmaceutical composition known in the art, and the composition may contain one or more substances selected from sweeteners, flavoring agents, coloring agents and preservatives, so as to provide a pharmaceutically elegant and palatable preparation. The tablet contains an active ingredient, and is blended with a non-toxic and pharmaceutically acceptable excipient or carrier suitable for preparation of tablet. The excipient or carrier may be, for example, an inert diluent such as calcium carbonate, sodium carbonate, lactose, calcium phosphate and sodium phosphate; a granulating agent and disintegrating agent such as microcrystalline cellulose, sodium carboxymethyl cellulose, corn starch and alginic acid; a binding agent such as starch, gelatin, polyvinyl pyrrolidone andacacia; and a lubricant such as magnesium stearate, stearic acid and talc. The tablet may be uncoated, or may be coated by a known technology to mask an unpleasant flavor of a drug or delay disintegration and absorption in the gastrointestinal tract, so as to provide a lasting effect in a long period of time. For example, a water soluble flavor making substance (such as hydroxypropyl-methyl cellulose and hydroxypropyl-cellulose) or a time delay substance (such as ethyl cellulose and cellulose acetate butyrate) may be used.

The preparation for oral administration may be prepared in the form of hard gelatin capsule, where the active ingredient is mixed with an inert solid diluent such as calcium carbonate, calcium phosphate and kaolin. Or, the preparation for oral administration may be prepared in the form of soft gelatin capsule, where the active ingredient is mixed with a water-soluble carrier (such as polyethylene glycol) or an oil medium (such as peanut oil, liquid paraffin and olive oil).

The aqueous suspension contains the active substance, and is blended with an excipient suitable for preparing an aqueous suspension. The excipient is a suspending agent such as sodium carboxymethyl cellulose, methyl cellulose, hydroxypropylmethyl-cellulose, sodium alginate, polyvinylpyrrolidone and gum arabic; a dispersing agent or wetting agent, being naturally existing phospholipid (such as lecithin) or a condensation product (such as polyoxyethylene stearate) of ethylene oxide and fatty acid or a condensation product (such as heptadecaethylene-oxycetanol) of ethylene oxide and a long chain aliphatic alcohol, or a condensation product (such as polyoxyethylene sorbitan monooleate) of ethylene oxide and a partial ester derived from fatty acid and hexitol, or a condensation product (such as polyethylene dehydrated sorbitan monooleate) of ethylene oxide and a partial ester derived from fatty acid and a mixture of hexitol and hexitol ether. The aqueous suspension may also contain one or more preservatives (such as ethyl p-hydroxybenzoate and n-propyl p-hydroxybenzoate), one or more coloring agents, one or more flavoring agents, and one or more sweeteners (such as sucrose, saccharin and aspartame).

The oily suspension may be formulated by suspending the active ingredient in a vegetable oil (such as peanut oil, olive oil, sesame oil and coconut oil) or a mineral oil (such as liquid paraffin). The oily suspension may contain a thickener such as beeswax, hard paraffin and cetyl alcohol. A sweetener (such as those listed above) and a flavoring agent may be added, to provide a palatable oral preparation. These compositions can be preservatized by adding an antioxidant (such as butylated Hydroxyanisole and α-tocopherol).

A dispersible powder and granule suitable for preparing an aqueous suspension by adding water contains the active ingredient, and is blended with a dispersing agent or wetting agent, a suspending agent and one or more preservatives. Examples of a suitable dispersing agent or wetting agent and suspending agent are those mentioned above. The powder and granule may also contain other excipients, such as sweetener, flavoring agent and coloring agent. These compositions can be preservatized by adding an antioxidant (such as ascorbic acid).

The pharmaceutical composition of the present invention may be in the form of oil in water emulsion. The oil phase may be a vegetable oil (such as olive oil or peanut oil) or a mineral oil (such as liquid paraffin), or a mixture thereof. A suitable emulsifier may be naturally existing phospholipid (such as soya bean lecithin), an ester or partial ester (such as dehydrated sorbitan monooleate) derived from fatty acid and hexitol, and a condensation product (such as polyethylene dehydrated sorbitan monooleate) of the partial ester and ethylene oxide. The emulsion may also contain a sweetener, a flavor agent, a preservative and an antioxidant.

The syrup may be formulated by using a sweetener (such as glycerol, propylene glycol, sorbitol and sucrose). The preparations may also contain a demulcent, a preservative, a flavoring agent, a coloring agent and an antioxidant.

The pharmaceutical composition may be in the form of sterile injectable aqueous solution. Useful and acceptable carrier and solvent include water, Ringer's solution, and isotonic sodium chloride solution and glucose solution.

The sterile injectable preparation may also be a sterile injectable oil-in-water microemulsion, where the active ingredient is dissolved in the oil phase. For example, first, the active ingredient is dissolved in a mixture of soybean oil and lecithin, and then, the resulting oil phase solution was poured into a mixture of water and glycerol for treatment, so as to form a microemulsion.

The injectable solution or microemulsion may be introduced into the patient's blood through local injection. Alternatively, it may be advantageous that the solution or microemulsion is administered in some manner, so as to maintain a constant circulating concentration of the compound of the present invention. In order to maintain this constant concentration, a continuous intravenous administration device such as an infusion pump may be used.

The pharmaceutical composition may be in the form of sterile injectable aqueous solution or oily suspension for intramuscular or subcutaneous administration. The suspension may be formulated by using those suitable dispersing agents or wetting agents mentioned above according to a known technology. The sterile injectable preparation may also be a sterile injectable solution or suspension of a non-toxic pharmaceutically acceptable diluent or solvent, such as a solution of 1,3-butylene glycol. In addition, a sterile nonvolatile oil can be conveniently used as a solvent or suspension medium. For this purpose, any mild nonvolatile oil can be used, including a synthetic monoglyceride or diglyceride. In addition, a fatty acid (such as oleinic acid) can be used in preparation of an injection.

The compound represented by General Formula (I) may be administered in the form of a suppository for rectal administration. These compositions can be prepared by mixing the agent with a suitable non-irritating excipient, and the excipient is a solid at normal temperature but is a liquid at the rectal temperature, so the excipient is melted, and the agent is released. These substances include cocoa butter, glycerogelatin gum, hydrogenated vegetable oil, a mixture of polyethylene glycols of different molecular weights and fatty acid esters of polyethylene glycol.

For local use, a cream, an ointment, a jelly, a solution or a suspension containing the compound represented by General Formula (I) can be used.

The compound of the present invention may be intranasally administered through local use of a suitable nasal carrier and delivery device, or may be administered through a percutaneous route by using a transdermal skin patch well known to persons of ordinary skill in the art. For administration through a transdermal delivery system, the drug administration in the whole dosage regimen definitely should be continuous rather than intermittent. The compound of the present invention may also be administered in the form of a suppository using the following matrices: cocoa butter, glycerogelatin gum, hydrogenated vegetable oil, a mixture of polyethylene glycols of different molecular weights and fatty acid esters of polyethylene glycol.

When the compound of the present invention is administered to a human subject body, the daily dose is generally determined by a physician writing the prescription, and the dose generally varies with the age, weight, gender and response of the patient and the severity of symptoms of the patient. Generally, for a patient of 70 kg, the effective daily dose is approximately 0.001 mg/kg to 100 mg/kg, preferably 0.01 mg/kg to 50 mg/kg, and more preferably 1 mg/kg to 25 mg/kg.

If the composition is formulated into a fixed dose, the composition can use the compound of the present invention in the dose range described above and other pharmaceutically active agents in an approved dose range for treatment. When the combined preparation is not suitable, the compound represented by General Formula (I) and a known anti-cancer drug or a cytotoxic agent can be administered in sequence. The present invention is not limited to any administration sequence; the compound represented by General Formula (I) can be administered before or after the known anti-cancer drug (a variety of anti-cancer drugs) or cytotoxic agent (a variety of cytotoxic agents) is administered.

The compound of the present invention is an inhibitor for c-Met mediated diseases or c-Met mediated disorders. The terms "c-Met mediated disease" and "c-Met mediated disorder" represent any disease state or other harmful condition in which c-Met is known to play a role. The terms "c-Met mediated disease" and "c-Met mediated disorder" further represent diseases or disorders that are relieved through treatment by using a c-Met inhibitor. These diseases and disorders include, but not limited to, cancer and other proliferative disorders.

Therefore, the compound can be used in treatment of the following diseases or disorders in mammal especially in human: esophageal cancer, pancreatic cancer, renal cancer, gastric cancer, colon cancer, thyroid cancer, brain cancer, breast cancer, prostate cancer, lung cancer and other solid tumors; atherosclerosis; angiogenesis; and thrombosis and pulmonary fibrosis.

The compound of the present invention can also be used in researches of biological or pharmacological phenomenon, researches of tyrosine kinase involved signaling pathway, and comparison and evaluation of new tyrosine kinase inhibitors.

The compounds of this application include, but not limited to, the structure types given in Scheme 1 to Scheme 10, and persons skilled in the art can obtain the compounds from suitable starting materials by using similar methods.

The specific synthesis and preparation (for preparing the compound of the present invention) and biological embodiments (detections for demonstrating the use of the compound of the present invention) provided below are used to help implement the present invention, and should not be construed as limitations of the scope of the present invention.

Embodiment 1

N-(4-(2-aminopyridine-4-oxy)-3-fluorophenyl)-4-(4-fluorophenyl)-5-oxo-4,5-dihydro-thiazolo[5,4-b]pyridine-6-formamide, having the structural formula below:

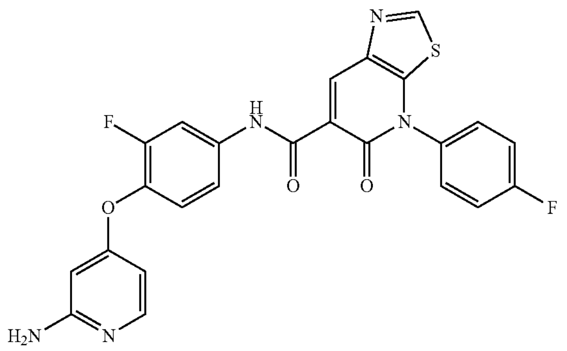 [SMILES: Nc1cc(Oc2ccc(NC(=O)c3cc4ncsc4n(-c4ccc(F)cc4)c3=O)cc2F)ccn1]

Step 1. Synthesis of 4-fluoro-phenyl isothiocyanate, through the reaction equation below:

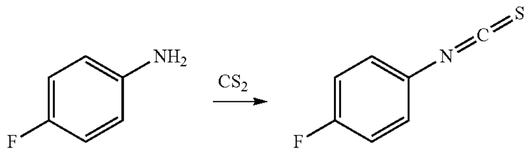

Under protection of nitrogen, 4-fluoroaniline (22 g, 198 mmol) and triethylamine (94 mL) were dissolved in anhydrous tetrahydrofuran (200 mL), carbon disulfide (21.6 mL) was added dropwise, and then the mixture was cooled to 0° C., and triethylamine (20 mL) was added, and mixture was stirred overnight at room temperature. The mixture was cooled to 0° C., p-toluenesulfonyl chloride (45.2 g, 237 mmol) was added portionwise to the reaction mixture, and the reaction system was stirred for 1 hr at room temperature. The mixture was cooled to 0° C., and 1N hydrochloric acid (100 mL) was added dropwise. The mixture was extracted with petroleum ether, the organic phase was washed with saturated brine, dried with anhydrous sodium sulfate, and condensed, and the residue was subjected to silica gel column chromatography (the eluent was petroleum ether), to obtain a white solid (27 g, 89%).

Step 2. Synthesis of ethyl 5-(4-fluorophenylamino)thiazole-4-formate, through the reaction equation below:

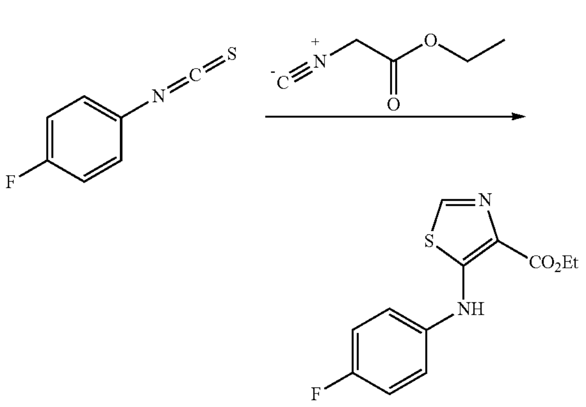

Potassium tert-butoxide (21.85 g, 195 mmol) was dissolved in anhydrous tetrahydrofuran (250 mL), and ethyl isocyanoacetate (19.5 mL, 177 mmol) was added dropwise slowly at room temperature. After stirring for a while, 4-fluoro-phenyl isothiocyanate (27.17 g, 177 mmol) was added portionwise, and the mixture was stirred for 2 hrs at room temperature. Glacial acetic acid was added dropwise to adjust the pH value to 6, the reaction solution was added with water, and extracted with ethyl acetate. The ethyl acetate phase was washed with saturated brine, dried with anhydrous sodium sulfate, and condensed, and the residue was subjected to silica gel column chromatography (petroleum ether/ethyl acetate=1/0 to 5/1), to obtain a black oil (22 g, 54%).

Step 3. Synthesis of ethyl 5-(N-(4-fluorophenyl)-2-methoxycarbonylacetamido) thiazole-4-formate, through the reaction equation below:

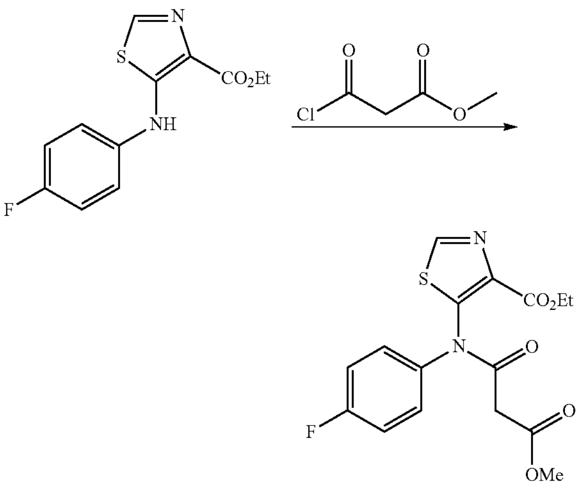

Ethyl 5-(4-fluorophenylamino)thiazole-4-formate (21 g, 79 mmol) was dissolved in 1,2-dichloroethane (200 mL), methyl malonyl chloride (13 mL, 118 mmol) was added, the reaction mixture was stirred for 2 hrs at reflux. TLC (petroleum ether/ethyl acetate=1/1) showed that the raw materials disappeared, the reaction mixture was concentrated under reduced pressure, a saturated sodium bicarbonate solution was added to the residue to adjust the pH value to be greater than 7, and the mixture was extracted with ethyl acetate. The extract was washed with saturated brine, dried with anhydrous sodium sulfate, and concentrated under reduced pressure, and the residue was subjected to silica gel column chromatography (petroleum ether/ethyl acetate=3/1), to obtain a light yellow solid (20 g, 69%).

Step 4. Synthesis of 4-(4-fluorophenyl)-6-(methoxycarbonyl)-5-oxo-4,5-dihydro-thiazolo[5,4-b]pyridine-7-oxy sodium salt, through the reaction equation below:

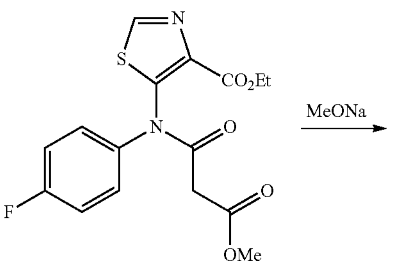

-continued

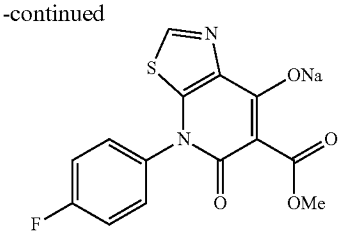

Ethyl 5-(N-(4-fluorophenyl)-2-methoxycarbonylacetamido)thiazole-4-formate (16.44 g, 44.9 mmol) was dissolved in anhydrous methanol (68 mL), the resulting solution was slowly added dropwise to a freshly prepared sodium methoxide/methanol solution (obtained by dissolving metal sodium (1.14 g, 49.6 mmol) in anhydrous methanol (22 mL)), and the mixture was stirred overnight at room temperature. The reaction mixture was filtered and dried, to obtain an offwhite solid (9.62 g, 63%).

Step 5. Methyl 4-(4-fluorophenyl)-5-oxo-4,5-dihydro-thiazolo[5,4-b]pyridine-6-formate, through reaction equations below:

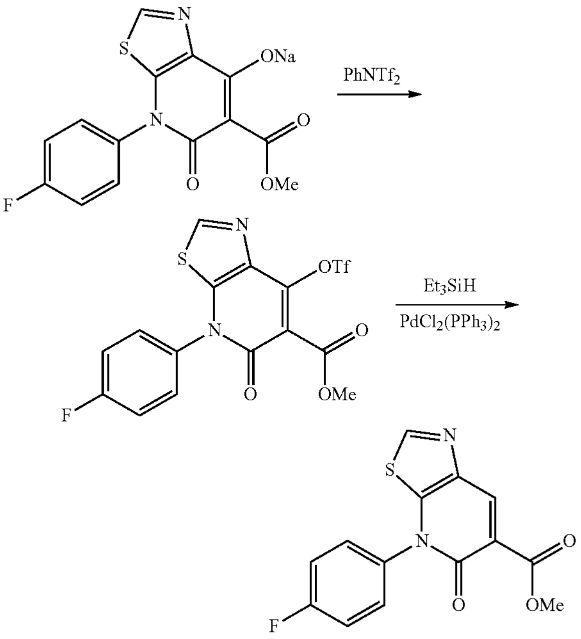

Under protection of nitrogen, 4-(4-fluorophenyl)-6-(methoxycarbonyl)-5-oxo-4,5-dihydro-thiazolo[5,4-b]pyridine-7-oxy sodium salt (7.6 g, 22.2 mmol) was suspended in anhydrous DMF (70 mL), a solution of $PhNTf_2$ (8.67 g, 26.6 mmol) in anhydrous DMF (30 mL) was added dropwise to the resulting suspension, and then the mixture was stirred overnight at room temperature. $PdCl_2(PPh_3)_2$ (779 mg, 1.11 mmol), triethylamine (9.2 mL, 66.6 mmol) and triethylsilane (5.16 g, 44.4 mmol) were added in one portion to the reaction system, the mixture was heated to 80° C. and stirred for 3 hrs. The mixture was cooled to room temperature, and ethyl acetate was added to the system. The mixture was filtered, the filtrate was condensed, and the residue was subjected to silica gel column chromatography (petroleum ether/ethyl acetate=3/1) for purification, to obtain a brown solid (5.0 g, two-step yield 74%). $^1H$ NMR (DMSO-$d_6$, 300

MHz) δ 8.91 (s, 1H), 8.67 (s, 1H), 7.67~7.61 (m, 2H), 7.51~7.44 (m, 2H), 3.78 (s, 3H).

Step 6. Synthesis of 4-(4-fluorophenyl)-5-oxo-4,5-dihydro-thiazolo[5,4-b]pyridine-6-formic acid, through the reaction equation below:

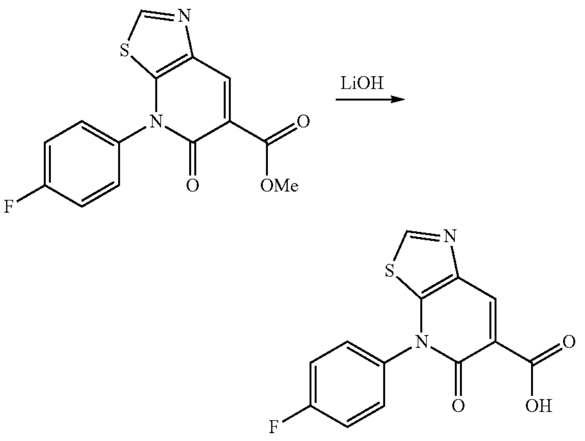

Methyl 4-(4-fluorophenyl)-5-oxo-4,5-dihydro-thiazolo[5,4-b]pyridine-6-formate (490 mg, 1.61 mmol) was suspended in a mixed solvent of tetrahydrofuran (3.5 mL) and water (3.5 mL), $LiOH.H_2O$ (136 mg, 3.24 mmol) was added to the resulting suspension, and the mixture was stirred for a half an hour at room temperature. The reaction mixture was concentrated under reduced pressure, and the residue was acidified with 1N hydrochloric acid to a pH value of 5, and filtered, to obtain a yellow solid (460 mg, approximately 100%). $^1$H NMR (DMSO-$d_6$, 300 MHz) δ 13.91 (br, 1H), 9.07 (s, 1H), 8.93 (s, 7.76~7.71 (m, 2H), 7.55~7.48 (m, 2H).

Step 7. Synthesis of N-(4-(2-aminopyridine-4-oxy)-3-fluorophenyl)-4-(4-fluorophenyl)-5-oxo-4,5-dihydro-thiazolo[5,4-b]pyridine-6-formamide, through the reaction equation below:

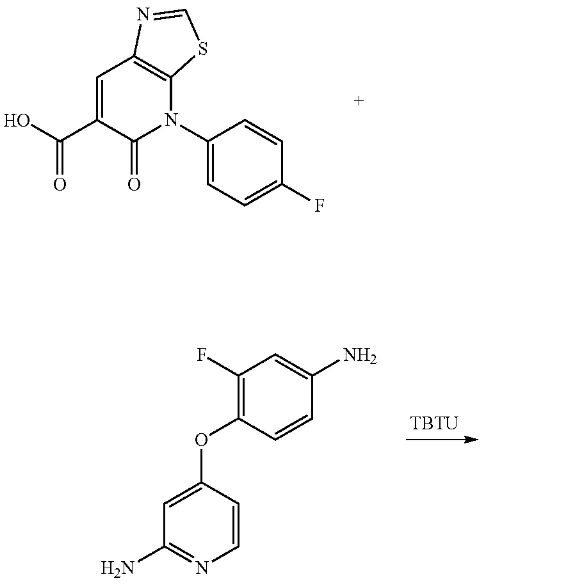

-continued

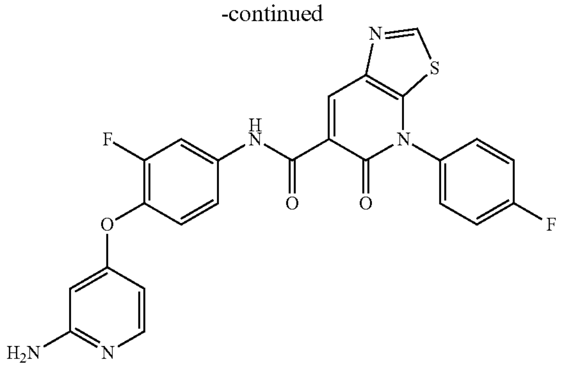

Under protection of nitrogen, 4-(4-fluorophenyl)-5-oxo-4,5-dihydro-thiazolo[5,4-b]pyridine-6-formic acid (2.26 g, 7.79 mmol) and 3-fluoro-4-(2-aminopyridine-4-oxy)aniline (1.13 g, 5.15 mmol, prepared with reference to document: US20050245530) were dissolved in anhydrous DMF together, TBTU (2.0 g, 6.23 mmol) and diisopropylethyl amine (3.4 mL, 15.6 mmol) were added, and the mixture was stirred overnight at room temperature. DMF was evaporated under reduced pressure, the residue was dissolved in dichloromethane, and the dichloromethane solution was washed in sequence with 1N hydrochloric acid, a saturated sodium bicarbonate solution and saturated brine, dried with anhydrous sodium sulfate, and concentrated under reduced pressure. The residue was subjected to silica gel column chromatography (dichloromethane/methanol=50/1), to obtain a yellow solid (470 mg, 19%). $^1$H NMR (400 MHz, DMSO-$d_6$): δ 13.48 (br, 1H), 11.97 (s, 1H), 9.06 (d, 1H), 8.09~8.14 (dd, 1H), 7.97~7.99 (d, 1H), 7.74~7.82 (m, 4H), 7.44~7.63 (m, 4H), 6.17~6.18 (dd, 1H), 5.76 (s, 1H).

Embodiment 2

N-(4-(2-amino-3-chloropyridine-4-oxy)-3-fluorophenyl)-4-(4-fluorophenyl)-5-oxo-4,5-dihydro-thiazolo[5,4-b]pyridine-6-formamide, having the structural formula below:

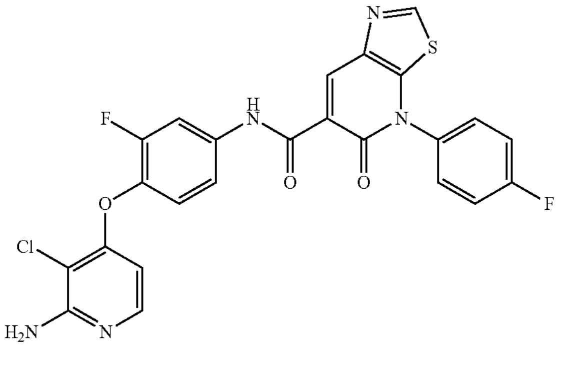 [SMILES: Nc1nccc(Oc2ccc(NC(=O)c3cc4ncsc4n(-c4ccc(F)cc4)c3=O)cc2F)c1Cl]

Step 1. Synthesis of 3-chloro-4-(2-fluoro-4-nitrophenyloxy)pyridine-2-amine, through a reaction equation below:

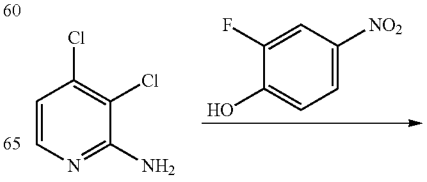

-continued

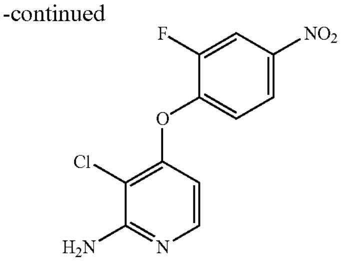

3,4-dichloro-2-aminopyridine (500 mg, 3.07 mmol, prepared with reference to document: Synthetic Communications, 1997, 27(5), 861-870.) and 2-fluoro-4-nitrophenol (1.928 g, 12.27 mmol) were heated to 120° C. and melted, and stirred for 24 hrs. The molten was cooled to room temperature, and subjected to silica gel column chromatography (the eluent was dichloromethane to dichloromethane/methanol=50/1) for purification, to obtain a white solid (137 mg, 16%). $^1$H NMR (DMSO-$d_6$, 300 MHz) δ 8.38 (dd, 1H, J=10.5, 2.4 Hz), 8.14~8.09 (m, 1H), 7.86 (d, 1H, J=5.4 Hz), 7.42~7.36 (m, 1H), 6.60 (br, 2H), 6.27 (d, 1H, J=5.4 Hz).

Step 2. Synthesis of 4-(4-amino-2-fluorophenyloxy)-3-chloropyridine-2-amine, through the reaction equation below:

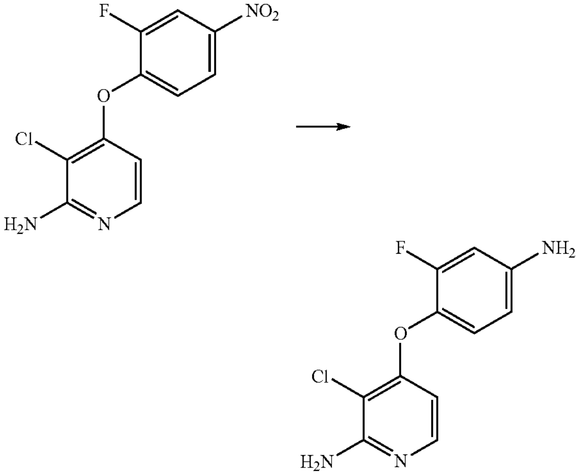

3-chloro-4-(2-fluoro-4-nitrophenyloxy)pyridine-2-amine (250 mg, 0.881 mmol) was dissolved in DMF/$H_2O$/EtOH (4 mL/4 mL/4 mL), and reduced iron powder (492 mg, 8.814 mmol) and ammonium chloride (943 mg, 17.628 mmol) were added, the mixture was heated to 100° C. and stirred for 2 hrs. The mixture was cooled to room temperature and filtered, and the filtrate was added with a small amount of water and an aqueous solution of sodium hydroxide for basification, and extracted with dichloromethane. The dichloromethane phases were combined, dried with anhydrous sodium sulfate, and concentrated under reduced pressure, to obtain a light yellow solid (190 mg, 85%). $^1$H NMR (DMSO-$d_6$, 300 MHz) δ 7.70 (d, 1H, J=5.7 Hz), 6.98~6.91 (m, 1H), 6.50~6.36 (m, 2H), 6.31 (br, 2H), 5.82 (dd, 1H, J=6.0, 1.2 Hz), 5.45 (br, 2H).

Step 3. Synthesis of N-(4-(2-amino-3-chloropyridine-4-oxy)-3-fluorophenyl)-4-(4-fluorophenyl)-5-oxo-4,5-dihydro-thiazolo[5,4-b]pyridine-6-formamide, through the reaction equation below:

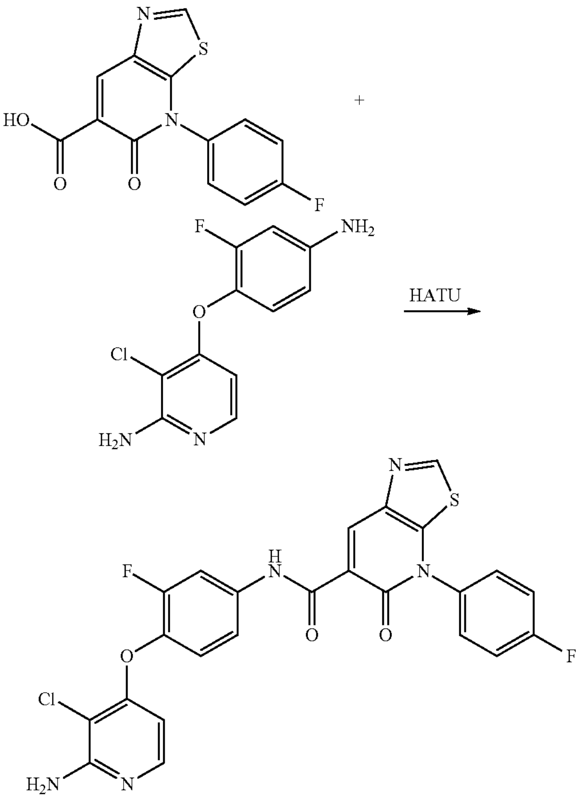

Under protection of nitrogen, 4-(4-fluorophenyl)-5-oxo-4,5-dihydro-thiazolo[5,4-b]pyridine-6-formic acid (57 mg, 0.197 mmol) was dissolved in anhydrous DMF (2 mL), HATU (75 mg, 0.197 mmol) and diisopropylethyl amine (51 mg, 0.394 mmol) were added, and the mixture was added for 10 min at room temperature. 3-fluoro-4-(2-amino-3-chloropyridine-4-oxy)aniline (50 mg, 0.197 mmol) was added, and the mixture was stirred overnight at room temperature. Water and ethyl acetate was added to the reaction system for extraction, and an ethyl acetate solution was added, the mixture was condensed, and subjected to silica gel column chromatography (eluent was dichloromethane to dichloromethane/methanol=20/1), to obtain a yellow solid (55 mg, 53%). $^1$H NMR (300 MHz, DMSO-$d_6$) δ 11.91 (s, 1H), 9.04 (s, 2H), 7.99-8.04 (m, 1H), 7.73~7.77 (m, 3H), 7.50~7.56 (m, 3H), 7.28~7.34 (t, 1H), 6.43 (s, 2H), 5.91~5.94 (d, 1H).

Embodiment 3

N-(3-fluoro-4-(7-methoxyquinoline-4-oxy)phenyl)-4-(4-fluorophenyl)-5-oxo-4,5-dihydro-thiazolo[5,4-b]pyridine-6-formamide, through the reaction equation below:

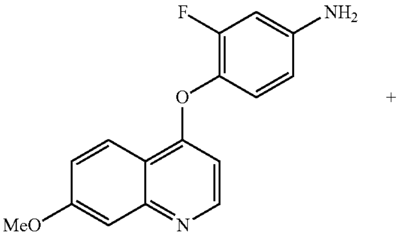

-continued

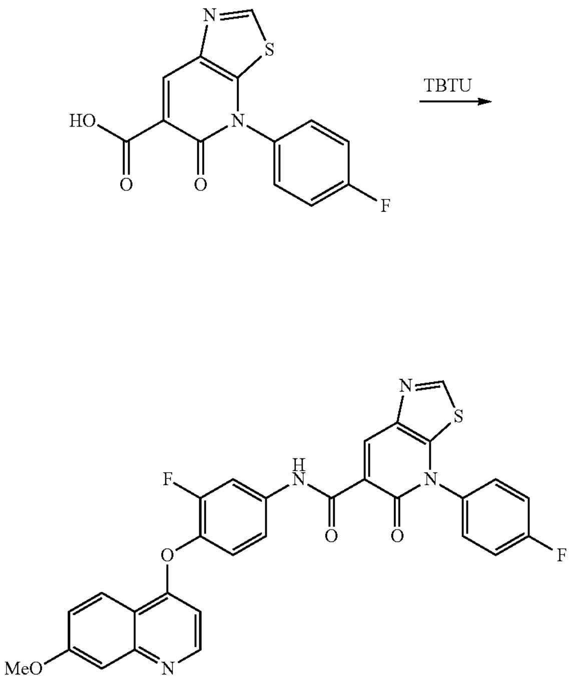

Under protection of nitrogen, 4-(4-fluorophenyl)-5-oxo-4,5-dihydro-thiazolo[5,4-b]pyridine-6-formic acid (209 mg, 0.72 mmol) and 3-fluoro-4-(7-methoxyquinoline-4-oxy)aniline (205 mg, 0.72 mmol, prepared with reference to document: Journal of Medicinal Chemistry, 2008, 51, 3688-3691) were dissolved in anhydrous DMF together, TBTU (347 mg, 1.08 mmol) and diisopropylethyl amine (279 mg, 2.16 mmol) were added, and then the mixture was stirred overnight at room temperature. DMF was evaporated under reduced pressure, and the residue was dissolved in dichloromethane, and washed with saturated brine, dried with anhydrous sodium sulfate, and concentrated under reduced pressure. The residue was subjected to silica gel column chromatography, to obtain a yellow solid (25 mg, 6%). $^1$H NMR (400 MHz, $CDCl_3$): δ 11.8 (s, 1H), 9.40 (s, 1H), 8.66 (s, 1H), 8.59~8.60 (m, 1H), 8.27 (d, 1H), 7.97 (dd, 1H), 7.47~7.50 (m, 2H), 7.25~7.42 (m, 3H), 7.19~7.24 (m, 2H), 6.42 (d, 2H), 3.97 (s, 3H); ESI-MS m/z 557 (M+H).

Embodiment 4

N-(4-(1H-pyrrolo[2,3-b]pyridine-4-oxy)-3-fluorophenyl)-4-(4-fluorophenyl)-5-oxo-4,5-dihydrothiazole[5,4-b]pyridine-6-formamide, through the reaction equation below:

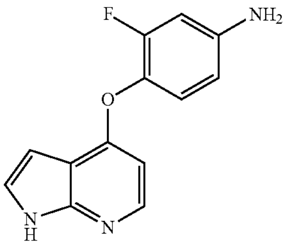

+

-continued

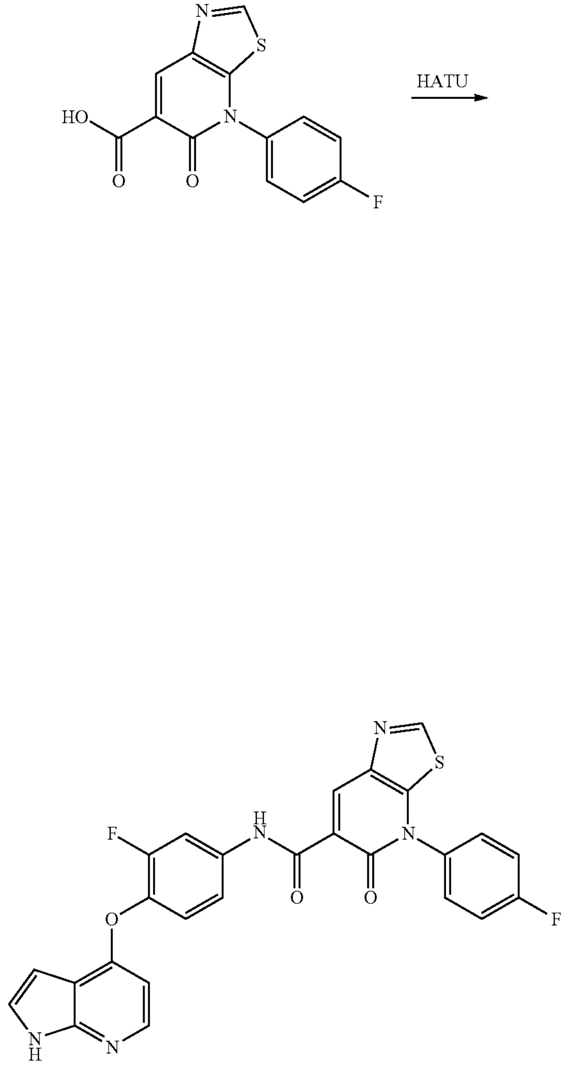

Under protection of nitrogen, 4-(4-fluorophenyl)-5-oxo-4,5-dihydro-thiazolo[5,4-b]pyridine-6-formic acid (60 mg, 0.206 mmol) was dissolved in anhydrous DMF (2 mL), HATU (78 mg, 0.206 mmol) and diisopropylethyl amine (53 mg, 0.412 mmol) were added, and the mixture was stirred for 10 min at room temperature. 3-fluoro-4-(1H-pyrrolo[2,3-b]pyridine-4-oxy)aniline (50 mg, 0.206 mmol, prepared with reference to document: Journal of Medicinal Chemistry, 2008, 51, 17, 5330-5341.) was added, and the reaction system was stirred overnight at room temperature. Water was added to the reaction system, the resulting solid was filtered off and dried, and subjected to silica gel column chromatography (dichloromethane/methanol=20/1), to obtain a light yellow solid (38 mg, 36%). $^1$H NMR (300 MHz, DMSO-$d_6$) δ 11.92 (s, 1H), 11.78 (s, 1H), 9.05 (s, 1H), 9.04 (s, 1H), 8.01~8.07 (m, 2H), 7.73~7.78 (m, 2H), 7.50~7.56 (m, 3H), 7.34~7.40 (m, 2H), 6.37-6.39 (d, 1H), 6.23~6.24 (t, 1H).

Embodiment 5

N-(3-fluoro-4-(6-methoxy-7-(3-morpholinepropoxy)quinoline-4-oxy)phenyl)-4-(4-fluorophenyl)-5-oxo-4,5-dihydro-thiazolo[5,4-b]pyridine-6-formamide, through the reaction equation below:

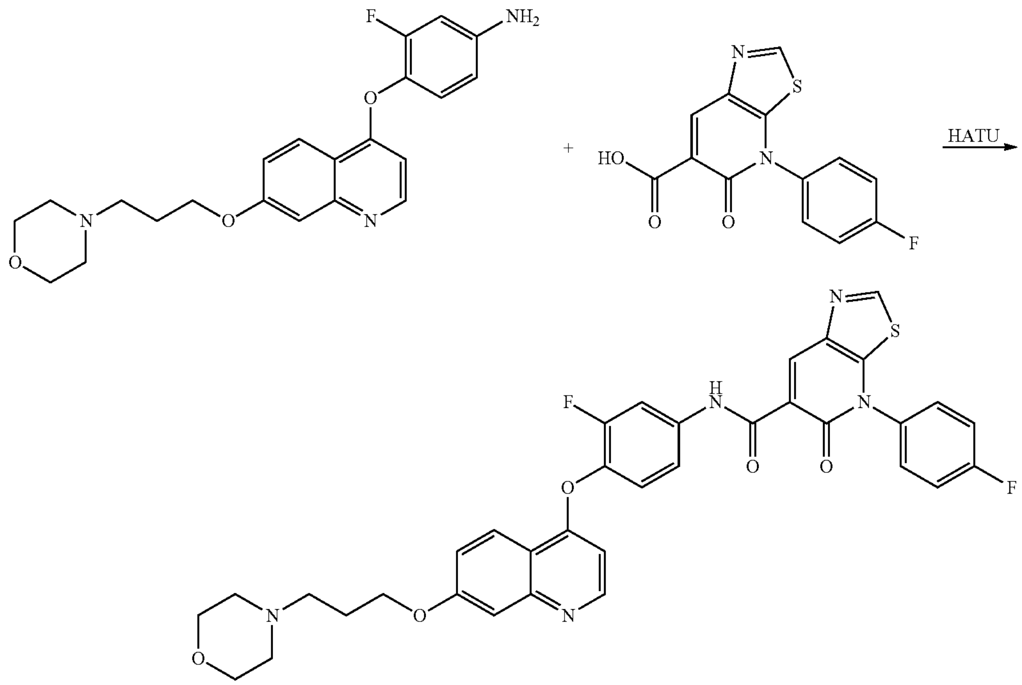

Under protection of nitrogen, 4-(4-fluorophenyl)-5-oxo-4,5-dihydro-thiazolo[5,4-b]pyridine-6-formic acid (70 mg, 0.241 mmol) was dissolved in anhydrous DMF (2 mL), HATU (94 mg, 0.241 mmol) and diisopropylethyl amine (62 mg, 0.482 mmol) were added, and the mixture was stirred for 10 min at room temperature. 3-fluoro-4-(6-methoxy-7-(3-morpholinyl propyloxy)quinoline-4-oxy)aniline (94 mg, 0.219 mmol, prepared with reference to document: US20080004273), and then the mixture was stirred overnight at room temperature. Water was added to the reaction system, the resulting solid was filtered off and dried, and subjected to silica gel column chromatography (dichloromethane/methanol=20/1), to obtain a light yellow solid (117 mg, 76%). $^1$H NMR (300 MHz, DMSO-$d_6$) δ 11.95 (s, 1H), 9.05 (s, 1H), 9.05 (s, 1H), 8.45~8.47 (d, 1H), 8.05~8.10 (m, 1H), 7.74~7.78 (m, 2H), 7.48~7.59 (m, 4H), 7.39~7.45 (m, 2H), 6.45~6.47 (d, 1H), 4.17~4.21 (t, 2H), 3.93 (s, 3H), 3.58 (m, 4H), 2.48~2.49 (t, 2H), 2.38 (t, 4H), 1.97 (m, 2H).

Embodiment 6

N-(3-fluoro-4-(2-(1-methyl-1H-imidazol-4-yl)thiophene[3,2-b]pyridine-7-oxy)phenyl)-4-(4-fluorophenyl)-5-oxo-4,5-dihydro-thiazolo[5,4-b]pyridine-6-formamide, through the reaction equation below:

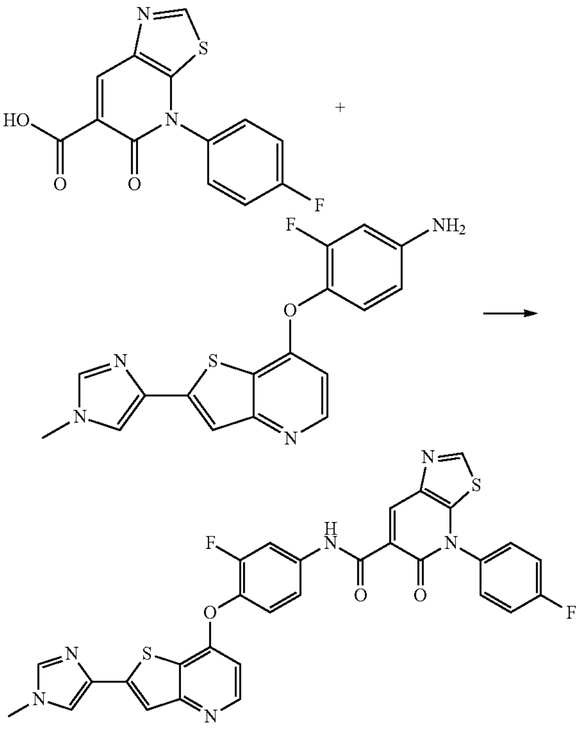

4-(4-fluorophenyl)-5-oxo-4,5-dihydro-thiazolo[5,4-b]pyridine-6-formic acid (100 mg, 0.34 mmol) was dissolved in toluene (2 mL), thionyl chloride (2 mL) was then added, and the reaction was carried out for 2 hrs with stirring at room temperature. The solvent was evaporated under reduced pressure, to obtain a yellow solid (105 mg). The yellow solid (55 mg) was added to tetrahydrofuran (2 mL) to form a suspension, and 3 drops of DMF was added dropwise, and the solution got clear and transparent, and then 2 drops of diisopropylethyl amine was added dropwise. The reaction solution was cooled to 0° C., 3-fluoro-4-(2-(1-methyl-1H-imidazol-4-yl)thienthio[3,2-b]pyridine-7-oxy) aniline (58 mg, 0.19 mmol, prepared with reference to document: WO2007054831A2), and the reaction was carried out for 1 hr with stirring at 0° C. The reaction solution was concentrated under reduced pressure, to obtain a crude product, and the crude product was subjected to column chromatography, to obtain the target product (60 mg, yield 61%). ESI-MS: m/z [M+H]=613; $^{1}$H NMR (300 MHz, DMSO-$d_6$) δ 12.09 (s, 1H), 9.08 (s, 1H), 9.06 (s, 1H), 8.16 (d, J=14.1 Hz, 1H), 7.91-7.86 (m, 2H), 7.84-7.72 (m, 3H), 7.55-7.51 (m, 2H), 6.90 (s, 1H), 6.13 (d, J=4.8 Hz, 1H), 3.62 (s, 3H).

Embodiment 7

N-(4-(2-(1-ethyl-1H-imidazol-4-yl)thienthio[3,2-b]pyridine-7-oxy)-3-fluorophenyl)-4-(4-fluorophenyl)-5-oxo-4,5-dihydro-thiazolo[5,4-b]pyridine-6-formamide

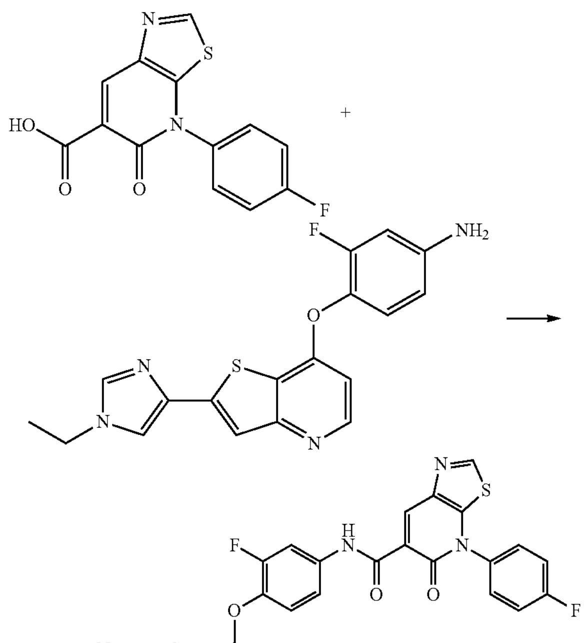

3-fluoro-4-(2-(1-ethyl-1H-imidazol-4-yl)thienthio[3,2-b]pyridine-7-oxy)aniline was prepared with reference to document: WO2007054831A2, to replace 3-fluoro-4-(2-(1-methyl-1H-imidazol-4-yl)thienthio[3,2-b]pyridine-7-oxy) aniline in Embodiment 6, so as to prepare the target compound. $^{1}$H NMR (300 MHz, DMSO-$d_6$) δ 12.09 (s, 1H), 9.08 (s, 1H), 9.06 (s, 1H), 8.16 (d, J=13.2 Hz 1H), 7.90-7.85 (m, 2H), 7.83-7.70 (m, 3H), 7.54-7.50 (m, 2H), 6.90 (s, 1H), 6.13 (d, J=7.2 Hz, 1H), 3.98-3.91 (m, 2H), 1.32 (t, 3H).

Embodiment 8

N-(3-fluoro-4-(3-methyl-1H-pyrazolo[3,4-b]pyridine-4-oxy)phenyl)-4-(4-fluorophenyl)-5-oxo-4,5-dihydro-thiazolo[5,4-b]pyridine-6-formamide, through the reaction equations below:

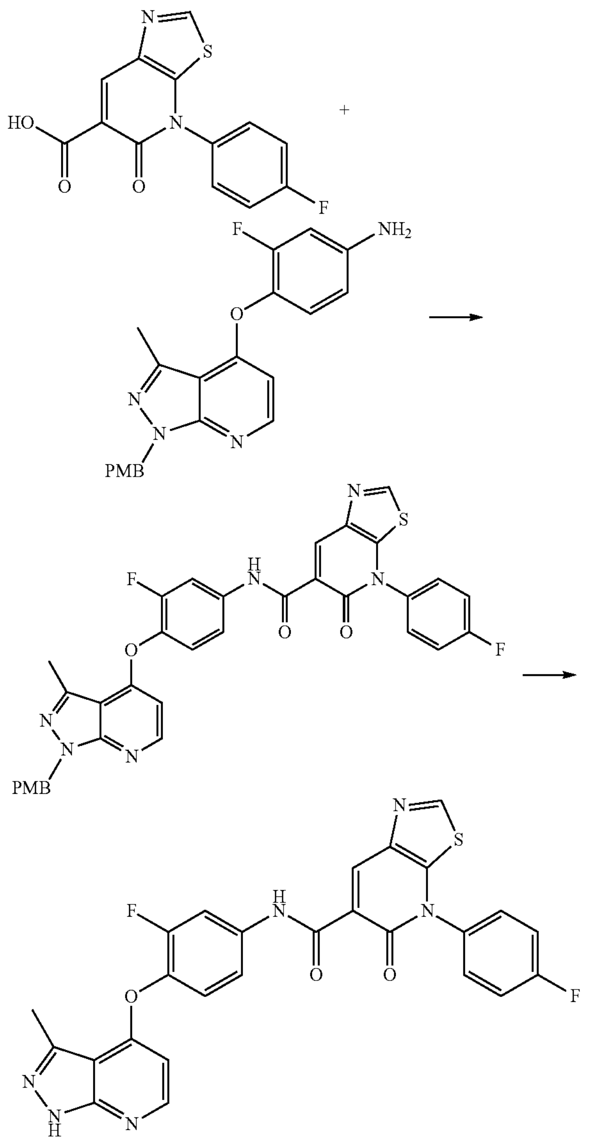

4-(4-fluorophenyl)-5-oxo-4,5-dihydro-thiazolo[5,4-b]pyridine-6-formic acid (120 mg, 0.41 mmol) was dissolved in DMF (3 mL), HATU (156 mg, 0.41 mmol) and diisopropylethyl amine (106.9 mg, 0.82 mmol) were added, and the reaction was carried out for 15 min. Then, 3-fluoro-4-(1-(4-methoxybenzyl)-3-methyl-1H-pyrazolo[3,4-b]pyridine-4-oxy)aniline (156 mg, 0.41 mmol, prepared with reference to document: WO2007103308A2) was added, and the reaction was carried out overnight with stirring at room temperature. The reaction solution was added with water (20 mL), and extracted with ethyl acetate, the organic phases were combined, dried, spin dried, and subjected to silica gel column chromatography for purification, to obtain a white solid. The white solid was dissolved in trifluoroacetic acid, and stirred for 3 hrs at 65° C. Trifluoroacetic acid was evaporated under reduced pressure, and the solution was basified with a saturated $Na_2CO_3$ solution, and extracted with ethyl acetate. The organic phases were combined, dried, and condensed, to obtain a crude product. The crude product was subjected to silica gel column chromatography for purification, to obtain the target product, as a light yellow solid (150 mg, 83%). ESI-MS: [M+H]=531; $^1$H NMR (300 MHz, DMSO-$d_6$) δ 13.29 (s, 1H), 11.60 (s, 1H), 9.06 (s, 1H), 9.05 (s, 1H), 8.25 (d, J=5.4 Hz, 1H), 8.08 (dd, J=12.6, 1.8 Hz, 1H), 7.78-7.72 (m, 2H), 7.60-7.47 (m, 4H), 6.21 (dd, J=5.4, 0.6 Hz, 1H), 2.60 (s, 3H).

Embodiment 9

N-(3-fluoro-4-(2-(tetrahydropyrrole-1-formamide)pyridine-4-oxy)phenyl)-4-(4-fluoro phenyl)-5-oxo-4,5-dihydro-thiazolo[5,4-b]pyridine-6-formamide, through the reaction equation below:

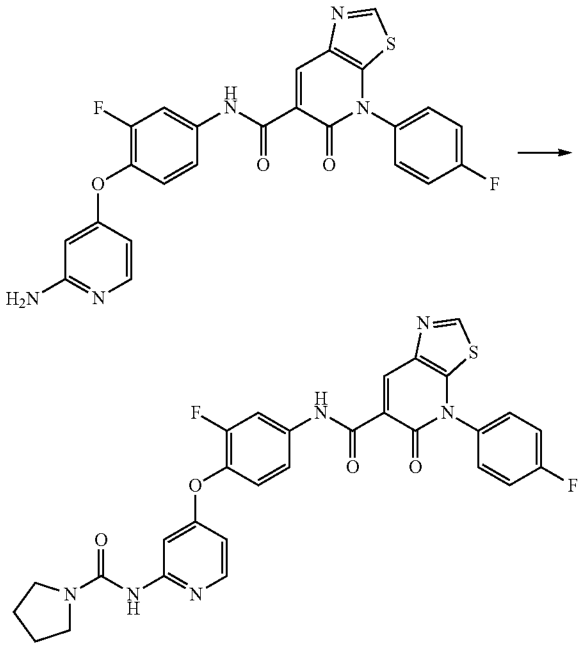

N-(4-(2-aminopyridine-4-oxy)-3-fluorophenyl)-4-(4-fluorophenyl)-5-oxo-4,5-dihydro-thiazolo[5,4-b]pyridine-6-formamide (150 mg, 0.305 mmol) was dissolved in anhydrous tetrahydrofuran (10 mL), triethylamine (62 mg, 0.61 mmol) was added, and the mixture was stirred for a while. Phenyl chloroformate (53 mg, 0.336 mmol) was added, and then the mixture was stirred for 2 hrs at room temperature. Tetrahydropyrrole (65 mg, 0.915 mmol) was added, and the mixture was stirred overnight at room temperature. A saturated aqueous solution of ammonium chloride was added to the reaction solution, and solution was extracted with dichloromethane three times. The extracts were combined, dried with anhydrous sodium sulfate, and concentrated under reduced pressure, and the residue was purified by using a silica gel preparation plate (dichloromethane/methanol=20/1), to obtain a white solid (83 mg, 46%). $^1$H NMR (300 MHz, $CDCl_3$) δ 11.93 (br, 1H), 9.05 (s, 1H), 9.04 (s, 1H), 8.73 (br, 1H), 8.00~8.11 (m, 2H), 7.73~7.78 (m, 2H), 7.46~7.56 (m, 4H), 7.34 (t, 1H, J=8.1 Hz), 6.60 (dd, 1H, J=5.7, 6.0 Hz), 3.33 (s, 4H), 1.79 (s, 4H).

Embodiment 10

N-(3-fluoro-4-(2-(4-methylpiperazine-1-formamide)pyridine-4-oxy)phenyl)-4-(4-fluorophenyl)-5-oxo-4,5-dihydro-thiazolo[5,4-b]pyridine-6-formamide, having the structural formula below:

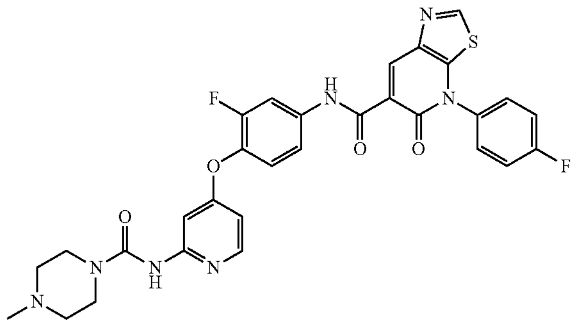 [SMILES: CN1CCN(C(=O)Nc2cc(Oc3ccc(NC(=O)c4cc5ncsc5n(-c5ccc(F)cc5)c4=O)cc3F)ccn2)CC1]

Following the method for preparing N-(3-fluoro-4-(2-(tetrahydropyrrole-1-formamide) pyridine-4-oxy)phenyl)-4-(4-fluorophenyl)-5-oxo-4,5-dihydro-thiazolo[5,4-b]pyridine-6-formamide in Embodiment 9, tetrahydropyrrole was replaced with methylpiperazine, so as to obtain the target product. $^1$H NMR (300 MHz, $CDCl_3$) δ 11.92 (br, 1H), 9.25 (br, 1H), 9.05 (s, 1H), 9.04 (s, 1H), 8.11 (d, 1H, J=6.6 Hz), 8.03 (d, 1H, J=12.9 Hz), 7.74~7.78 (m, 2H), 7.51~7.56 (m, 3H), 7.31~7.37 (m, 2H), 6.60 (dd, 1H, J=3.0, 1.8 Hz), 3.38 (t, 4H, J=3.9 Hz), 2.23 (t, 4H, J=4.1 Hz).

Embodiment 11

N-(3-fluoro-4-(2-(morpholine-1-formamide)pyridine-4-oxy)phenyl)-4-(4-fluorophenyl)-5-oxo-4,5-dihydro-thiazolo [5,4-b]pyridine-6-formamide, having the structural formula below:

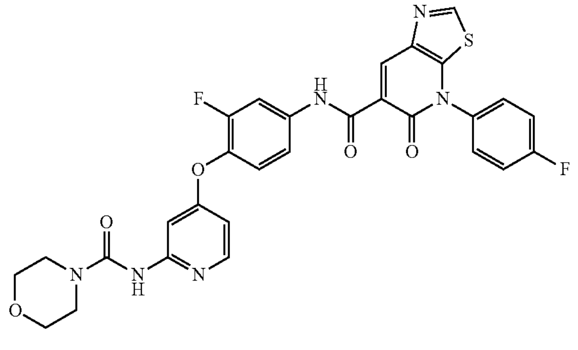 [SMILES: O=C(Nc1ccc(Oc2ccnc(NC(=O)N3CCOCC3)c2)c(F)c1)c1cc2ncsc2n(-c2ccc(F)cc2)c1=O]

Following the method for preparing N-(3-fluoro-4-(2-(tetrahydropyrrole-1-formamide) pyridine-4-oxy)phenyl)-4-(4-fluorophenyl)-5-oxo-4,5-dihydro-thiazolo[5,4-b]pyridine-6-formamide in Embodiment 9, tetrahydropyrrole was replaced with morpholine, so as to obtain the target product. $^1$H NMR (300 MHz, $CDCl_3$) δ 11.92 (br, 1H), 9.30 (br, 1H), 9.04 (s, 1H), 9.03 (s, 1H), 8.11 (d, 1H, J=8.1 Hz), 8.03 (dd, 1H, J=12.9, 12.6 Hz), 7.73~7.78 (m, 2H), 7.50~7.56 (m, 3H), 7.32~7.37 (m, 2H), 6.62 (dd, 1H, J=6.0, 2.1 Hz), 3.53 (t, 4H, J=4.5 Hz), 3.38 (t, 4H, J=4.7 Hz).

By adopting the method similar to that in Embodiment 9 to Embodiment 11, the following compounds can be prepared.

| Serial Number | Structural Formula | Structure Characterization |
|---|---|---|
| Embodiment 12 | 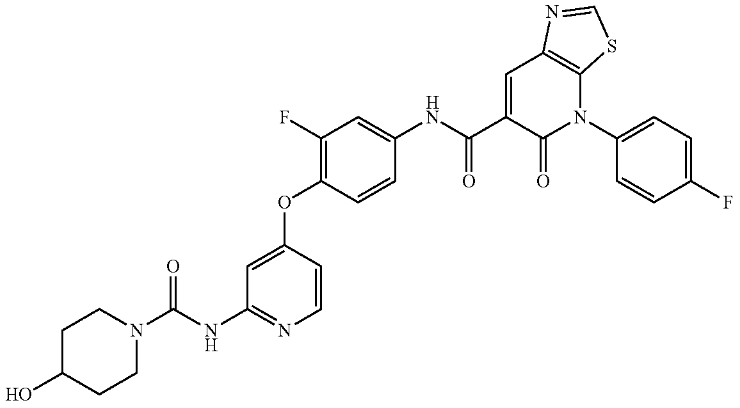 [SMILES: O=C(Nc1ccc(Oc2ccnc(NC(=O)N3CCC(O)CC3)c2)c(F)c1)c1cc2ncsc2n(-c2ccc(F)cc2)c1=O] | ESI-MS: m/z 619; $^1$H NMR (300 MHz, DMSO-$d_6$) δ 11.92 (br, 1H), 9.20 (br, 1H), 9.05 (s, 1H), 9.04 (s, 1H), 8.10 (d, 1 H, J = 5.7 Hz), 8.03 (dd, 1 H, J = 12.9, 12.9 Hz), 7.73~7.78 (m, 2 H), 7.50~7.57 (m, 3H), 7.31~7.37 (m, 2 H), 6.58 (dd, 1 H, J = 5.7, 6.0 Hz), 4.66 (br, 1 H, J = 4.5 Hz), 3.77 (t, 2 H, J = 6.9 Hz), 3.59~3.63 (m, 1H), 2.96~3.04 (m, 2H), 1.65~1.70 (m, 2H), 1.22~1.31 (m, 2H). |
| Embodiment 13 | 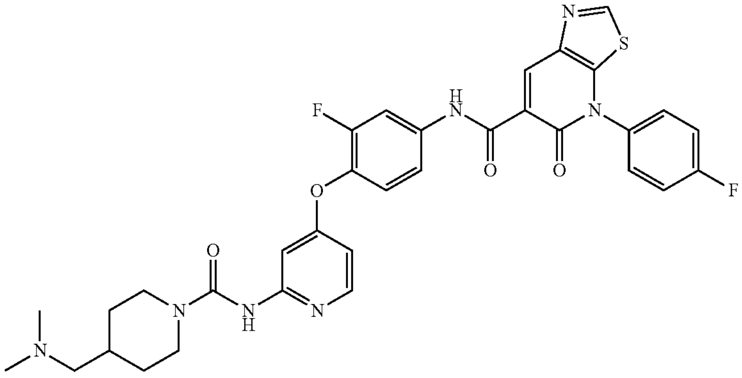 [SMILES: CN(C)CC1CCN(C(=O)Nc2cc(Oc3ccc(NC(=O)c4cc5ncsc5n(-c5ccc(F)cc5)c4=O)cc3F)ccn2)CC1] | EIS-MS: m/z 660 |
| Embodiment 14 | 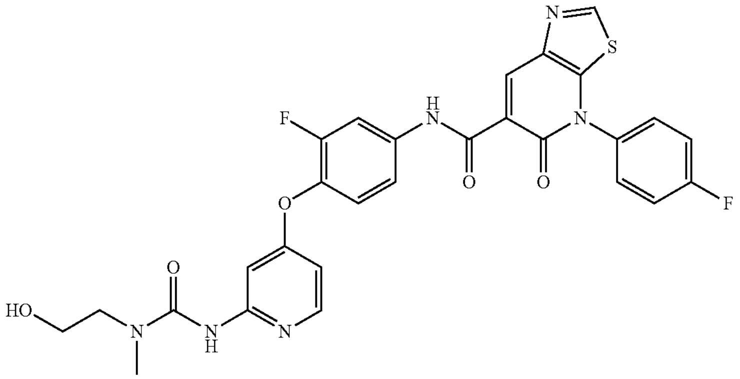 [SMILES: CN(CCO)C(=O)Nc1cc(Oc2ccc(NC(=O)c3cc4ncsc4n(-c4ccc(F)cc4)c3=O)cc2F)ccn1] | EIS-MS: m/z 593; $^1$H NMR (300 MHz, $CDCl_3$) δ 11.92 (br, 1H), 9.12 (br, 1H), 9.05 (s, 1H), 9.04 (s, 1H), 8.00~8.08 (m, 2H), 7.72~7.78 (m, 2H), 7.51~7.56 (m, 3H), 7.31~7.37 (m, 2H), 6.59 (dd, 1H, J = 6.0, 5.7 Hz), 5.33 (br, 1H), 3.53 (t, 2H, J = 4.8 Hz), 3.33 (s, 2H), 2.86 (br, 3H). |
| Embodiment 15 | 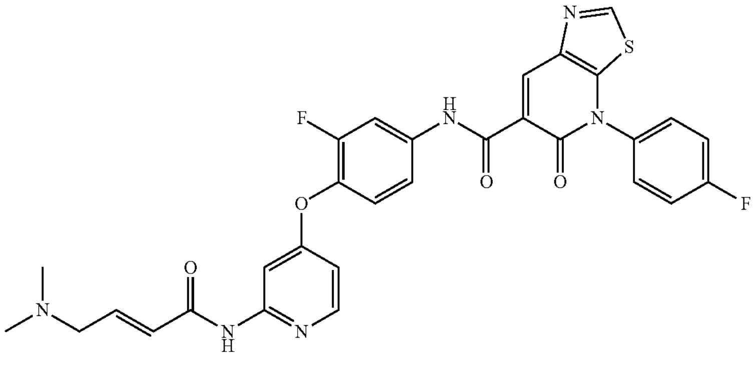 [SMILES: CN(C)C/C=C/C(=O)Nc1cc(Oc2ccc(NC(=O)c3cc4ncsc4n(-c4ccc(F)cc4)c3=O)cc2F)ccn1] | EIS-MS: m/z 603; $^1$H NMR (300 MHz, DMSO-$d_6$): δ 11.93 (s, 1H), 10.74 (s, 1H), 9.04 (d, 2H), 8.21 (d, 1H), 8.04 (d, 1H), 7.74 (m, 3H), 7.50~7.55 (m, 3H), 7.37 (t, 1H), 6.67~6.74 (m, 2H), 6.39 (d, 1H), 3.01~3.15 (m, 2H), 2.19 (s, 6H). |

-continued

| Serial Number | Structural Formula | Structure Characterization |
| --- | --- | --- |
| Embodiment 16 | 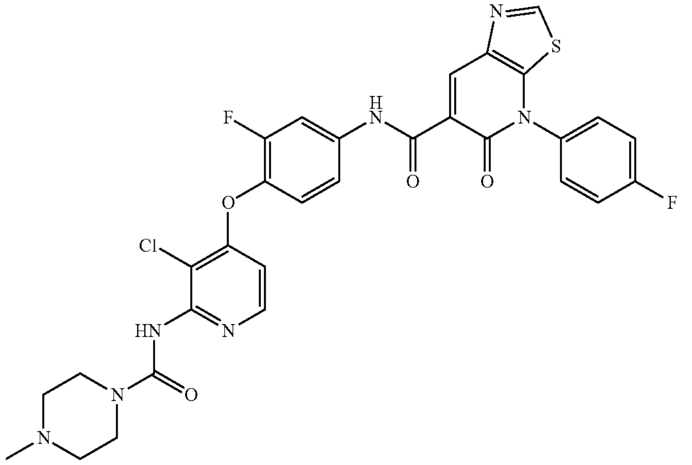 [SMILES: CN1CCN(C(=O)Nc2nccc(Oc3ccc(NC(=O)c4cc5ncsc5n(-c5ccc(F)cc5)c4=O)cc3F)c2Cl)CC1] | EIS-MS: m/z 652 |
| Embodiment 17 | 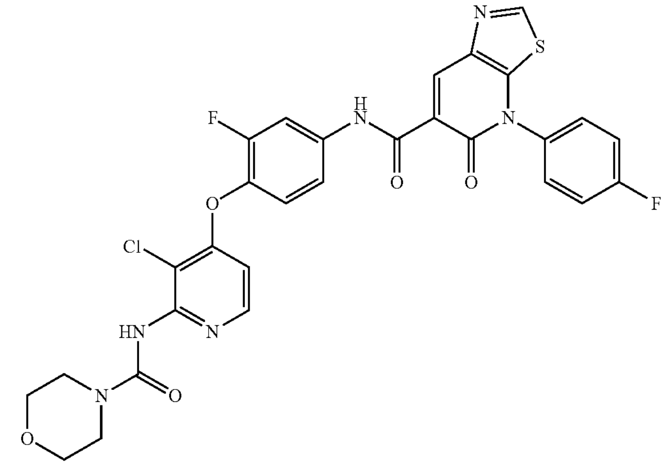 [SMILES: O=C(Nc1ccc(Oc2ccnc(NC(=O)N3CCOCC3)c2Cl)c(F)c1)c1cc2ncsc2n(-c2ccc(F)cc2)c1=O] | EIS-MS: m/z 639 |

Embodiment 18

N-(4-(2-aminopyridine-4-oxy)-3-fluorophenyl)-4-(2-(2-hydroxyethyl)phenyl)-5-oxo-4,5-dihydro-thiazolo[5,4-b]pyridine-6-formamide, having the structural formula below:

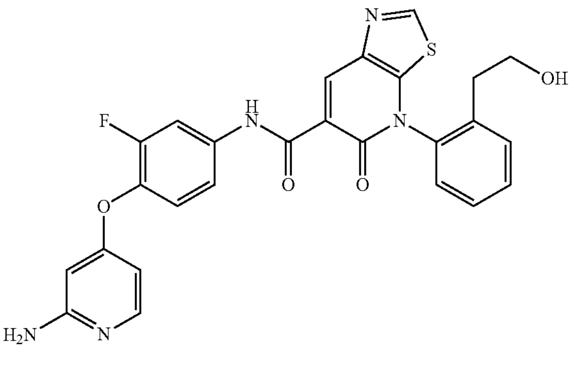 [SMILES: Nc1cc(Oc2ccc(NC(=O)c3cc4ncsc4n(-c4ccccc4CCO)c3=O)cc2F)ccn1]

Step 1. Synthesis of 2-tert-butyldiphenylsilyloxyethyl-aniline, through the reaction equation below:

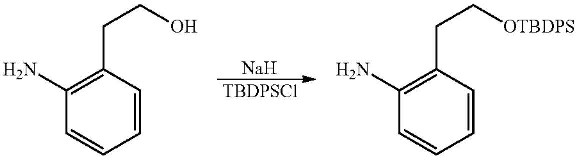

Under protection of nitrogen, 2-aminophenylethanol (1.30 g, 9.5 mmol) was dissolved in anhydrous tetrahydrofuran (100 mL), the resulting solution was slowly added dropwise to a suspension of sodium hydride (60%, 0.42 g, 10.4 mmol) in anhydrous tetrahydrofuran (20 mL), the mixture was stirred for 15 min at room temperature, and added with tert-butyldiphenylchlorosilane (2.86 g, 10.4 mmol), and stirred for 20 hrs at room temperature. The reaction system was added with water, and extracted with methyl tert-butyl ester. The extracts were combined, dried with anhydrous sodium sulfate, and concentrated under reduced pressure, to obtain a brown oil (3.75 g).

Step 2. Synthesis of 2-tert-butyldiphenylsilyloxyethyl-phenyl isothiocyanate, through the reaction equation below:

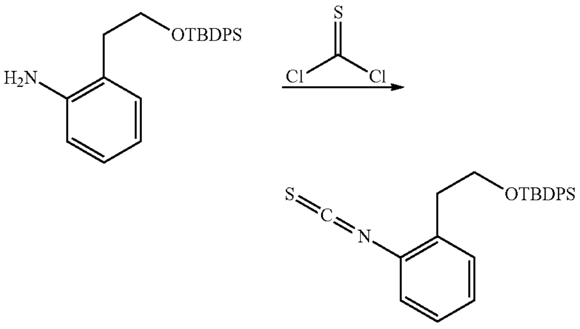

2-tert-butyldiphenylsilyloxyethyl-aniline (3.75 g) obtained in Step 1 was dissolved in ethyl acetate (50 mL), and triethylamine (3.1 mL, 22 mmol) was added. The mixture was cooled to 0° C., added with a solution of thiophosgene (0.84 mL) in ethyl acetate (10 mL), and then stirred for 2 hrs at room temperature. Water was carefully added to the mixture, and the ethyl acetate phase was washed with water and saturated brine, dried with anhydrous sodium sulfate, and concentrated under reduced pressure, to obtain a red oil (4.5 g).

Step 3. Synthesis of ethyl 5-(2-(2-(tert-butyldiphenylsilyloxo)ethyl)phenylamino) thiazole-4-formate, through the reaction equation below:

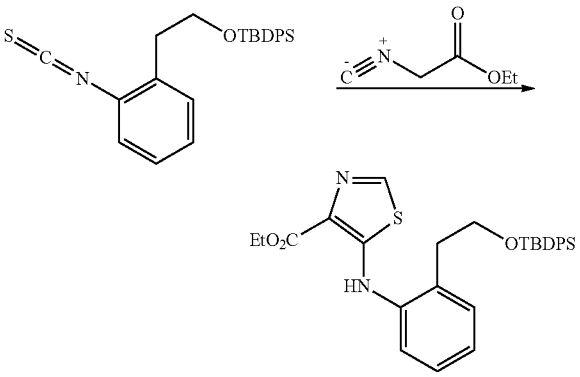

Potassium tert-butoxide (1.34 g, 12 mmol) was dissolved in anhydrous tetrahydrofuran (50 mL), and ethyl isocyanoacetate (1.1 mL, 10 mmol) was slowly added dropwise at room temperature. The mixture was stirred for a while, 2-tert-butyldiphenylsilyloxyethyl-phenyl isothiocyanate (4.5 g) obtained in Step 2 was added portionwise, and the mixture was stirred for 2 hrs at room temperature. Glacial acetic acid was added dropwise, to adjust the pH value to 6, and the reaction solution was added with water, and extracted with ethyl acetate. The ethyl acetate phase was washed with saturated brine, dried with anhydrous sodium sulfate, and concentrated, and the residue was subjected to silica gel column chromatography (petroleum ether/ethyl acetate=1/0 to 5/1), to obtain a light yellow solid (3.2 g, three-step yield 60%). $^1$H NMR (300 MHz, $CDCl_3$) δ 9.77 (s, 1H), 7.89 (s, 1H), 7.53~7.25 (m, 14H), 4.43 (q, 2H, J=6.9 Hz), 3.86 (t, 2H, J=6.0 Hz), 2.98 (t, 2H, J=6.0 Hz), 1.44 (t, 3H, J=6.9 Hz), 0.96 (s, 9H).

Step 4. Synthesis of ethyl 5-(2-(2-(tert-butyldiphenylsilyloxo)ethyl)phenyl-2-methoxycarbonylacetamido)thiazole-4-formate, through the reaction equation below:

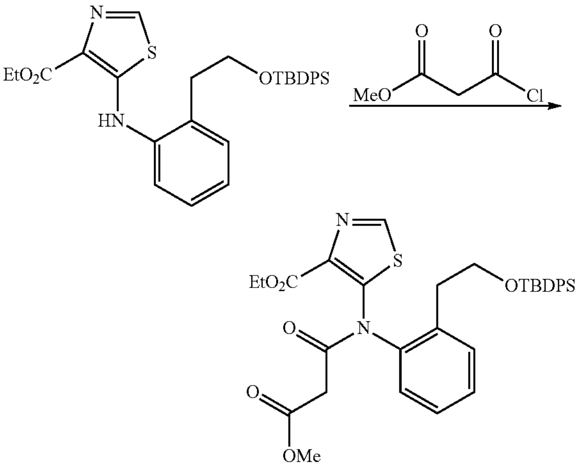

Under protection of nitrogen, ethyl 5-(2-(2-(tert-butyldiphenylsilyloxo)ethyl)phenylamino)thiazole-4-formate (2.2 g, 4.1 mmol) was dissolved in 1,2-dichloroethane (30 mL), methyl malonyl chloride (2.0 mL, 18.6 mmol) was added, and the mixture was stirred for 3 hrs at reflux. The mixture was cooled to room temperature, a saturated sodium bicarbonate solution was carefully added dropwise, the organic phase was washed with saturated brine, dried with anhydrous sodium sulfate, and concentrated under reduced pressure, and then subjected to silica gel column chromatography, to obtain a stiff oil (1.4 g, 54%).

Step 5. Synthesis of 4-(2-(2-(tert-butyldiphenylsilyloxy)ethyl)phenyl)-6-(methoxycarbonyl)-5-oxo-4,5-dihydro-thiazolo[5,4-b]pyridine-7-oxy sodium salt, through the reaction equation below:

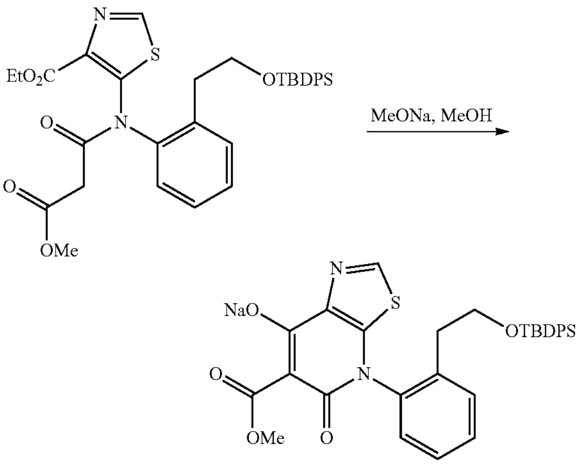

Ethyl 5-(2-(2-(tert-butyldiphenylsilyloxo)ethyl)phenyl-2-methoxycarbonylacetamido) thiazole-4-formate (1.27 g, 2.0 mmol) was dissolved in anhydrous methanol, the resulting solution was added dropwise to a solution of sodium methoxide (0.13 g, 2.4 mmol) in anhydrous methanol (10 mL), and then the mixture was stirred overnight at room temperature. The resulting solid was filtered and dried, to obtain a white solid (0.84 g, 69%).

Step 6. Synthesis of methyl 4-(2-(2-(tert-butyldiphenylsilyloxy)ethyl)phenyl)-5-oxo-4,5-dihydro-thiazolo[5,4-b] pyridine-6-formate, through the reaction equations below:

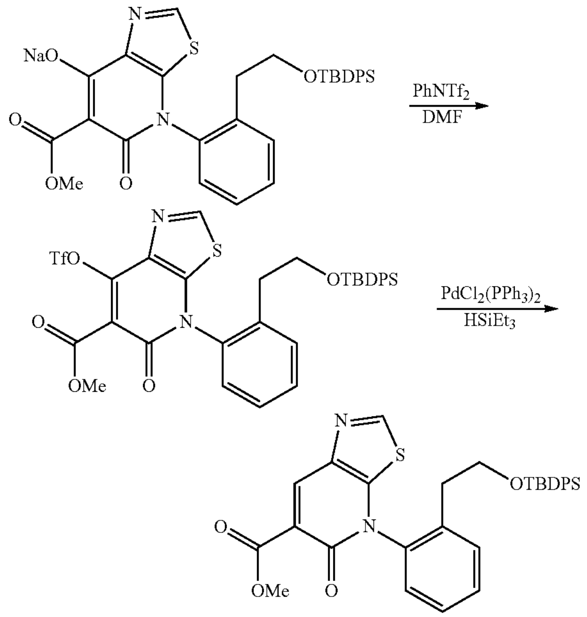

4-(2-(2-(tert-butyldiphenylsilyloxy)ethyl)phenyl)-6-(methoxycarbonyl)-5-oxo-4,5-dihydro-thiazolo[5,4-b]pyridine-7-oxy sodium salt (0.84 g, 1.38 mmol) was suspended in anhydrous DMF (20 mL), $PhNTf_2$ (0.84 g, 2.58 mmol) was added, and the mixture was stirred overnight at room temperature. $PdCl_2$ $(PPh_3)_2$ (70 mg) and triethylsilane (0.33 g, 2.8 mmol) were added to the reaction solution, the mixture was heated to 80° C. and stirred for 2 hrs. DMF was evaporated under reduced pressure, and the residue was dissolved in ethyl acetate. The ethyl acetate phase was washed with water and saturated brine, dried with anhydrous sodium sulfate, and concentrated under reduced pressure, and the residue was subjected to silica gel column chromatography, to obtain a light yellow solid (0.69 g, 88%). $^1$H NMR (300 MHz, $CDCl_3$) 8.85 (s, 1H), 8.37 (s, 1H), 7.52-7.17 (m, 14H), 3.93 (s, 3H), 3.73 (m, 2H), 2.70 (m, 2H), 0.97 (s, 9H).

Step 7. Synthesis of 4-(2-(2-(tert-butyldiphenylsilyloxy)ethyl)phenyl)-5-oxo-4,5-dihydro-thiazolo[5,4-b]pyridine-6-formic acid, through the reaction equation below:

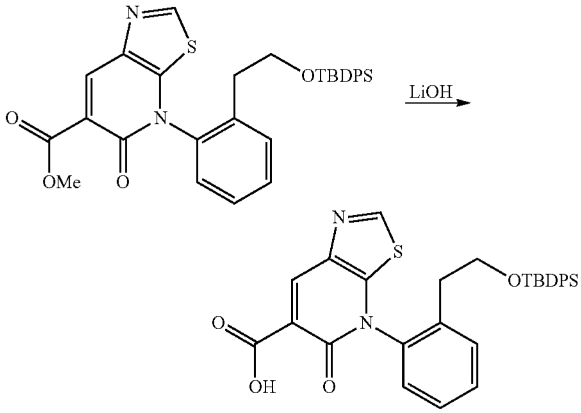

Methyl 4-(2-(2-(tert-butyldiphenylsilyloxy)ethyl)phenyl)-5-oxo-4,5-dihydro-thiazolo[5,4-b]pyridine-6-formate (0.69 g, 1.2 mmol) was dissolved in tetrahydrofuran (20 mL), a solution of $LiOH.H_2O$ (0.21 g, 4.8 mmol) in water (20 mL) was added, and the mixture was stirred overnight at room temperature. The mixture was cooled with ice water, and 3N hydrochloric acid was added dropwise to acidify the mixture to a pH value of 5 to 6. The mixture was extracted with dichloromethane, and the extracts were combined, dried with anhydrous sodium sulfate, and concentrated under reduced pressure, to obtain a light yellow solid (0.65 g, 98%).

Step 8. Synthesis of N-(4-(2-aminopyridine-4-oxy)-3-fluorophenyl)-4-(2-(2-hydroxyethyl)phenyl)-5-oxo-4,5-dihydro-thiazolo[5,4-b]pyridine-6-formamide, through the reaction equations below:

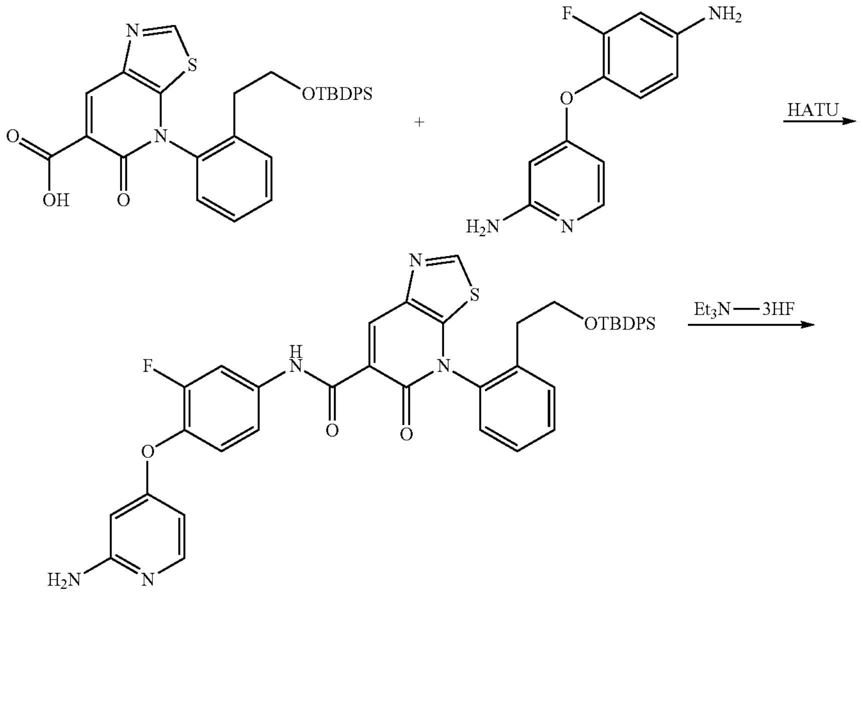

-continued

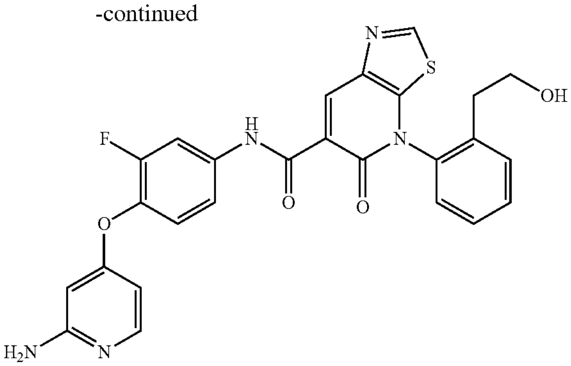

Under protection of nitrogen, 4-(2-(2-(tert-butyldiphenylsilyloxy)ethyl)phenyl)-5-oxo-4,5-dihydro-thiazolo[5,4-b]pyridine-6-formic acid (119 mg, 0.2 mmol) was dissolved in anhydrous DMF (5 mL), diisopropylethyl amine (52 mg, 0.4 mmol) and HATU (76 mg, 0.2 mmol) were added, and the mixture was stirred for 15 min at room temperature. 3-fluoro-4-(2-aminopyridine-4-oxy)aniline (44 mg, 0.2 mmol) was added, and stirred continuously for 6 hrs at 40° C. The reaction system was added with water, and stirred for 15 min and filtered. The solid was dried to obtain a crude product (140 mg). The crude product was dissolved in tetrahydrofuran (5 mL), triethylamine trihydrofluoride (1.0 mL) was added, and the mixture was stirred for 24 hrs at room temperature. Tetrahydrofuran was evaporated under reduced pressure, and a saturated sodium bicarbonate solution (20 mL) was carefully added to the residue. The mixture was extracted with dichloromethane, dried with anhydrous sodium sulfate, and concentrated under reduced pressure, and the residue tetrahydrofuran-petroleum ether was recrystallized, to obtain a white solid (34 mg, 33%). $^1$H NMR (DMSO-$d_6$, 300 MHz): δ 11.93 (s, 1H), 9.10 (s, 1H), 9.06 (s, 1H), 8.01 (dd, 1H, J=12.6, 2.4 Hz), 7.79 (d, 1H, J=6.0 Hz), 7.60~7.49 (m, 6H), 7.31 (m, 1H), 6.09 (br, 2H), 5.81 (d, 1H, J=2.1 Hz), 4.56 (br, 1H), 3.43 (m, 2H), 2.51 (m, 2H); ESI-MS: m/z 518 (M+H).

By adopting the method in Embodiment 18, substituted aniline in Embodiment 2 to Embodiment 5 was used to replace 3-fluoro-4-(2-aminopyridine-4-oxy)aniline, the following compounds can be prepared:

| Serial Number | Structural Formula | Structure Characterization |
|---|---|---|
| Embodiment 19 | 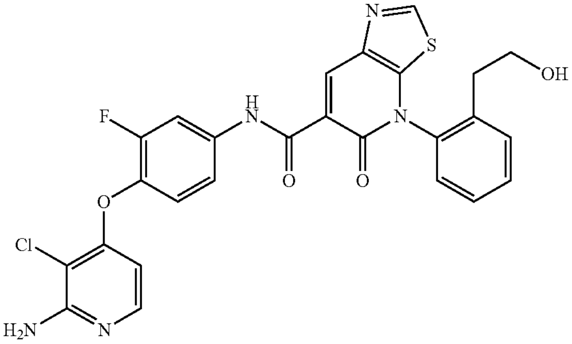 [SMILES: Nc1nccc(Oc2ccc(NC(=O)c3cc4ncsc4n(-c4ccccc4CCO)c3=O)cc2F)c1Cl] | $^1$H NMR (DMSO-$d_6$, 300 MHz) δ 11.95 (s, 1H), 9.09 (s, 1H), 9.05 (s, 1H), 8.03 (dd, 1H, J = 13.2, 2.1 Hz), 7.74 (d, 1H, J = 5.4 Hz), 7.60~7.49 (m, 5H), 7.32 (m, 1H), 6.44 (br, 2H), 5.92 (d, 1H, J = 5.4 Hz), 4.58 (br, 1H), 3.45 (m, 2H), 2.51 (m, 2H); ESI-MS: m/z 552 (M + H). |
| Embodiment 20 | 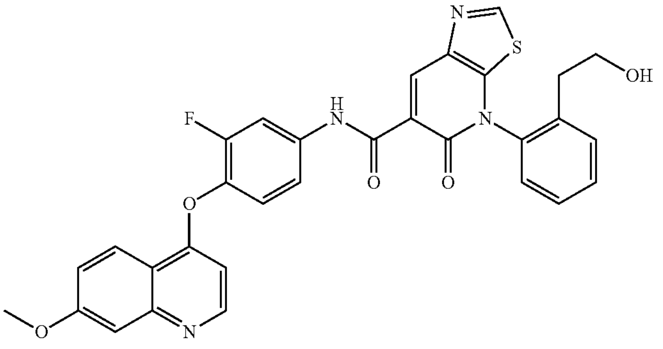 [SMILES: COc1ccc2c(Oc3ccc(NC(=O)c4cc5ncsc5n(-c5ccccc5CCO)c4=O)cc3F)ccnc2c1] | $^1$H NMR (DMSO-$d_6$, 300 MHz) δ 11.99 (s, 1H), 9.11 (s, 1H), 9.06 (s, 1H), 8.60 (d, 1H, J = 4.8 Hz), 8.22 (d, 1H, J = 9.0 Hz), 8.09 (dd, 1H, J = 12.6, 2.1 Hz), 7.61~7.40 (m, 7H), 7.29 (dd, 1H, J = 9.0, 3.0 Hz), 6.48 (d, 1H, J = 5.1 Hz), 4.60 (br, 1H), 3.93 (s, 3H), 3.45 (m, 2H), 2.53~2.49 (m, 2H); ESI-MS: m/z 583 (M + H). |

-continued

| Serial Number | Structural Formula | Structure Characterization |
|---|---|---|
| Embodiment 21 | 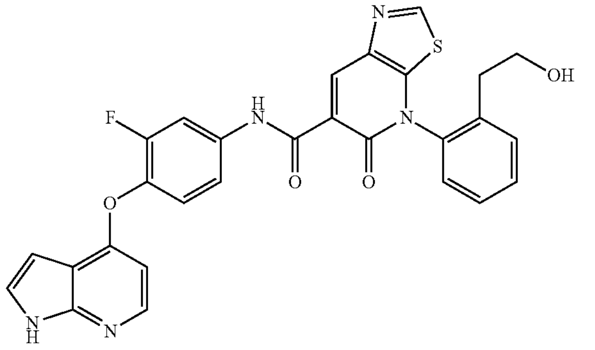 [SMILES: O=C(Nc1ccc(Oc2ccnc3[nH]ccc23)c(F)c1)c1cc2ncsc2n(-c2ccccc2CCO)c1=O] | $^1$H NMR (DMSO-$d_6$, 300 MHz) δ 11.96 (s, 1H), 11.79 (br, 1H), 9.10 (s, 1H), 9.06 (s, 1H), 8.07~8.02 (m, 2H), 7.61~7.51 (m, 5H), 7.40~7.35 (m, 2H), 7.38 (d, 1H, J = 5.4 Hz), 6.22 (br, 1H), 4.58 (br, 1H), 3.53~3.36 (m, 2H), 2.53~2.50 (m, 2H); ESI-MS: m/z 542 (M + H). |
| Embodiment 22 | 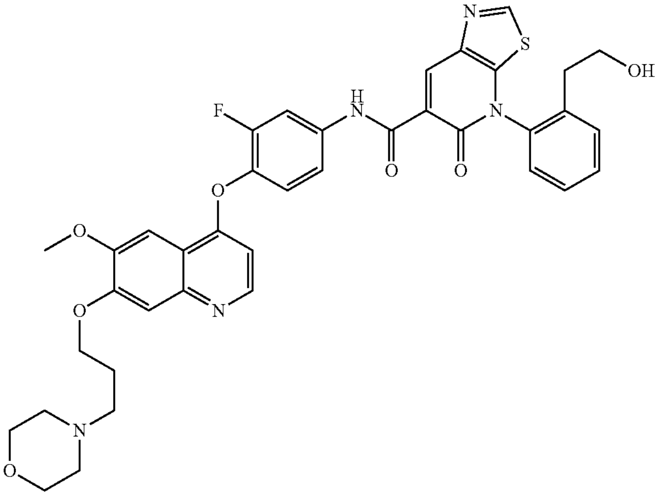 [SMILES: COc1cc2c(Oc3ccc(NC(=O)c4cc5ncsc5n(-c5ccccc5CCO)c4=O)cc3F)ccnc2cc1OCCCN1CCOCC1] | $^1$H NMR (DMSO-$d_6$, 300 MHz) δ 11.99 (s, 1H), 9.10 (s, 1H), 9.06 (s, 1H), 8.46 (d, 1H, 4.8 Hz), 8.09 (dd, 1H, J = 12.6, 2.4 Hz), 7.61~7.45 (m, 7H), 7.39 (s, 1H), 6.46 (d, 1H, J = 5.1 Hz), 4.58 (br, 1H), 4.18 (t, 2H, J = 6.0 Hz), 3.93 (s, 3H), 3.58 (m, 4H), 3.46 (m, 2H), 2.53 (m, 2H), 2.42 (m, 2H), 2.38 (m, 4H), 1.97 (m, 2H); ESI-MS: m/z 726 (M + H). |

Embodiment 23

N-(4-(2-amino-3-chloropyridine-4-oxy)-3-fluorophenyl)-2-(dimethylamino)-4-(4-fluorophenyl)-5-oxo-4,5-dihydrothiazole[5,4-b]pyridine-6-formamide, through the reaction equations below:

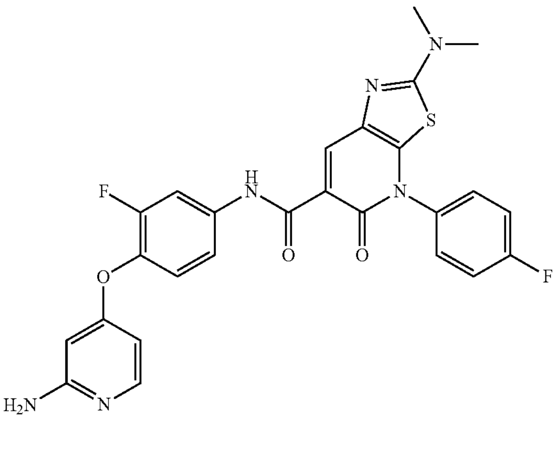 [SMILES: CN(C)c1nc2cc(C(=O)Nc3ccc(Oc4ccnc(N)c4)c(F)c3)c(=O)n(-c3ccc(F)cc3)c2s1]

Step 1. Synthesis of 2-amino-5-methoxy-thiazolo[5,4-b]pyridine, through the reaction equation below:

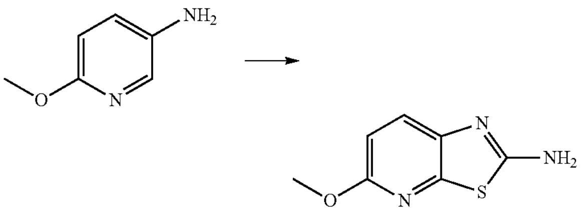

6-methoxy-3-aminopyridine (20 g, 161 mmol) was dissolved in glacial acetic acid (400 mL), the temperature was controlled to be below 20° C., and a solution of potassium thiocyanate (79.9 g, 822 mmol) in glacial acetic acid (20 mL) was added dropwise, and then a solution of liquid bromine (10 mL) in glacial acetic acid (20 mL) was added dropwise. The mixture was stirred for 2 hrs, and then heated to room temperature, and filtered. The cake was washed in sequence with glacial acetic acid (100 mL) and petroleum ether, and then added portionwise to a saturated sodium bicarbonate solution, and the mixture was extracted with ethyl acetate. The extracts were combined, dried with anhydrous sodium sulfate, and concentrated under reduced pressure, to obtain a red solid (21 g, 72%). $^1$H NMR (300 MHz, $CDCl_3$) δ 7.67 (d, 1H, J=9.0 Hz), 6.70 (d, 1H, J=9.0 Hz), 5.13 (br, 2H), 3.94 (s, 3H).

Step 2. Synthesis of 2-bromo-5-methoxy-thiazolo[5,4-b]pyridine, through the reaction equation below:

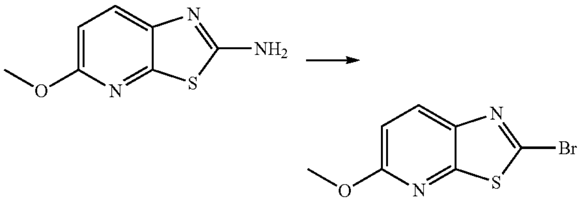

Under protection of nitrogen, $CuBr_2$ (14.8 g, 66.2 mmol) was suspended in anhydrous acetonitrile (100 mL), isoamyl nitrite (11.0 mL, 82.8 mL) (20 min) was slowly added dropwise. 2-amino-5-methoxy-thiazolo[5,4-b]pyridine (10.0 g, 55.2 mmol) was added, and the mixture was stirred for 2 hrs at reflux. The mixture was cooled to room temperature, and the solvent was evaporated under reduced pressure. A saturated sodium bicarbonate solution and ethyl acetate were added to the residue, and the mixture was filtered. The filtrate was washed with saturated brine, dried with anhydrous sodium sulfate, and concentrated under reduced pressure. The crude product was subjected to silica gel column chromatography for purification, to obtain a red solid (7.7 g, 57%). $^1$H NMR (300 MHz, $CDCl_3$) δ 8.05 (d, 1H, J=9.0 Hz), 6.83 (d, 1H, J=9.0 Hz), 3.99 (s, 3H).

Step 3. Synthesis of 5-methoxy-2-N,N-dimethylaminothiazolo[5,4-b]pyridine, through the reaction equation below:

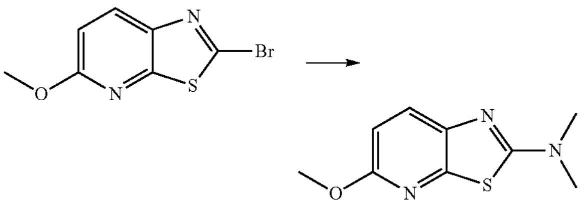

2-bromo-5-methoxy-thiazolo[5,4-b]pyridine (5.5 g, 22.5 mmol) was dissolved in acetonitrile (100 mL), an aqueous solution (33%, 32 mL) of dimethylamine was added, and the mixture was stirred overnight at room temperature. After the reaction was completed, the solvent was evaporated under reduced pressure, and the residue was dissolved with ethyl acetate, washed with saturated brine, dried with anhydrous sodium sulfate, and concentrated under reduced pressure. The crude product was subjected to silica gel column chromatography for purification, to obtain the target product (3.85 g, 82%). $^1$H NMR (300 MHz, $CDCl_3$) δ 7.67 (d, 1H, J=9.0 Hz), 6.66 (d, 1H, J=9.0 Hz), 3.92 (s, 3H), 3.16 (s, 6H).

Step 4. Synthesis of 6-bromo-5-methoxy-2-N,N-dimethylaminothiazolo[5,4-b]pyridine, through the reaction equation below:

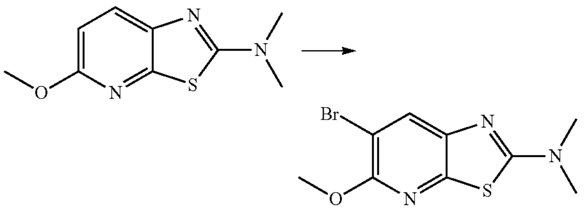

Under protection of nitrogen, 5-methoxy-2-N,N-dimethylaminothiazolo[5,4-b]pyridine (3.85 g, 18.4 mmol) was dissolved in anhydrous DMF (90 mL), N-bromosuccinimide (4.26 g, 23.9 mmol) was added portionwise with stirring, and then the mixture was heated to 75° C. and stirred for 2 hrs. The mixture was cooled to room temperature, DMF was evaporated under reduced pressure, and the residue was dissolved with ethyl acetate, dried with anhydrous sodium sulfate, and concentrated under reduced pressure, to obtain a yellow solid (5.0 g, 94%). $^1$H NMR (300 MHz, $CDCl_3$) δ 7.93 (s, 1H), 4.01 (s, 3H), 3.19 (s, 6H).

Step 5. Synthesis of 2-(dimethylamino)-5-methoxy-thiazolo[5,4-b]pyridine-6-formonitrile, through the reaction equation below:

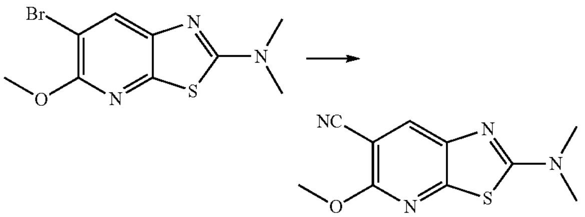

Under protection of nitrogen, 6-bromo-5-methoxy-2-N,N-dimethylaminothiazolo[5,4-b]pyridine (2.96 g, 10.3 mmol) was dissolved in anhydrous DMF (50 mL), anhydrous zinc cyanide (2.41 g, 20.6 mmol), zinc powder (20 mg, 0.31 mmol), dppf (683 mg, 1.23 mmol) and $Pd_2(dba)_3$ (564 mg, 0.60 mmol) were added, and the mixture was heated to 100° C. and stirred for 1 hr. The mixture was cooled to room temperature, DMF was evaporated under reduced pressure, and the residue was subjected to silica gel column chromatography, to obtain a yellow solid (2.1 g, 87%).

Step 6. Synthesis of 2-(dimethylamino)-5-oxo-4,5-dihydro-thiazolo[5,4-b]pyridine-6-formate, through the reaction equations below:

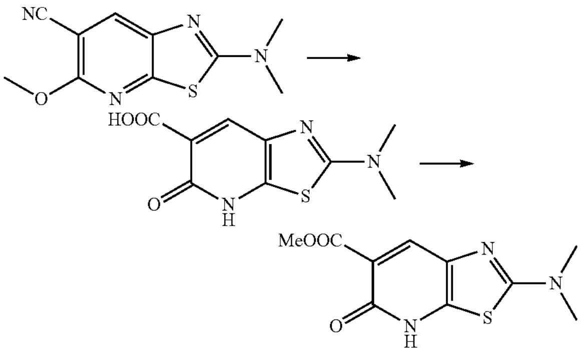

2-(dimethylamino)-5-methoxy-thiazolo[5,4-b]pyridine-6-formonitrile (500 mg, 2.13 mmol) was dissolved in hydrobromic acid (40%, 3 mL), and the mixture was stirred for 2 hrs at reflux. Hydrobromic acid was evaporated under reduced pressure, and the residue was dried to obtain a crude product 2-(dimethylamino)-5-oxo-4,5-dihydro-thiazolo[5,4-b]pyridine-6-formic acid (520 mg). The crude product was dissolved in anhydrous methanol (10 mL), and under protection of nitrogen, thionyl chloride (1.0 mL) was added dropwise, and the mixture was stirred overnight at reflux. The mixture was cooled to room temperature, the solvent was evaporated at room temperature, and the residue was dissolved in dichloromethane, carefully washed with a saturated sodium bicarbonate solution, dried with anhydrous sodium sulfate, and concentrated under reduced pressure, to obtain a white solid methyl 2-(dimethylamino)-5-oxo-4,5-dihydro-thiazolo[5,4-b]pyridine-6-formate (229 mg, 42%). $^1$H NMR (300 MHz, $CDCl_3$) δ 11.30 (br, 1H), 8.20 (s, 1H), 3.99 (s, 3H), 3.20 (s, 6H).

Step 7. Synthesis of methyl 2-(dimethylamino)-4-(4-fluorophenyl)-5-oxo-4,5-dihydro-thiazolo[5,4-b]pyridine-6-formate, through the reaction equation below:

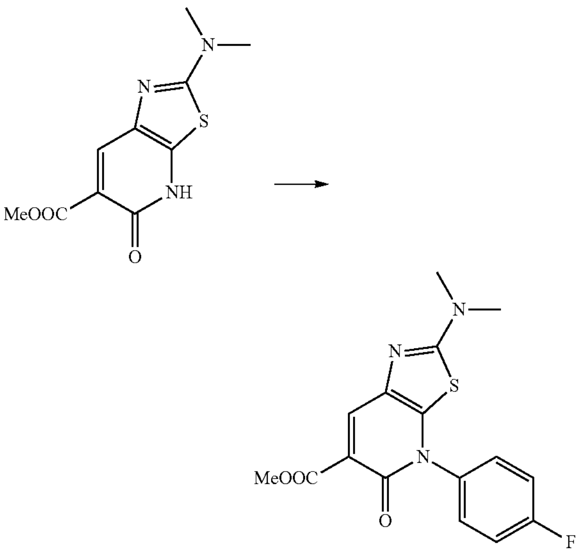

Under dry conditions, methyl 2-(dimethylamino)-5-oxo-4,5-dihydro-thiazolo[5,4-b]pyridine-6-formate (900 mg, 3.55 mmol) was dissolved in anhydrous acetonitrile (15 mL), 4-fluorophenylboronic acid (994 mg, 7.71 mmol), cuprous iodide (169 mg, 0.89 mmol), 2,2,6,6-tetramethylpiperidine nitrogen oxide (694 mg, 4.44 mmol), pyridine (1.1 mL) and activated molecular sieve powder (200 mg) were added, an anhydrous calcium chloride drying tube was added at the bottle neck, the mixture was stirred for 24 hrs at 40° C. After the reaction was completed, the system was directly concentrated under reduced pressure, and the residue was subjected to silica gel column chromatography for purification, to obtain a white solid (400 mg, 32%). $^1$H NMR (300 MHz, $CDCl_3$) δ 8.29 (s, 1H), 7.09-7.04 (m, 4H), 3.91 (s, 3H), 3.19 (s, 6H).

Step 8. Synthesis of 2-(dimethylamino)-4-(4-fluorophenyl)-5-oxo-4,5-dihydro-thiazolo[5,4-b]pyridine-6-formic acid, through the reaction equation below:

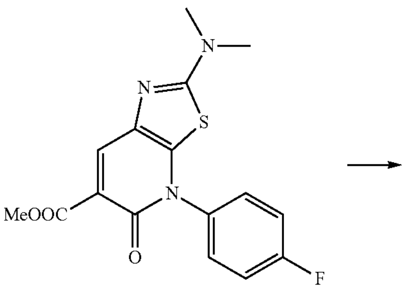

-continued

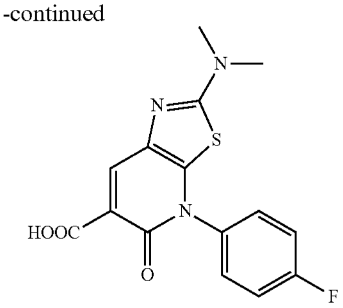

Methyl 2-(dimethylamino)-4-(4-fluorophenyl)-5-oxo-4,5-dihydro-thiazolo[5,4-b]pyridine-6-formate (100 mg, 0.29 mmol) was dissolved in tetrahydrofuran (1 mL), an aqueous solution (1 mL) of $LiOH.H_2O$ (100 mg, 2.3 mmol) was added, and the mixture was stirred for 3 hrs at room temperature. TLC showed that the raw materials disappeared, the reaction solution was cooled with ice water, 3N hydrochloric acid was added dropwise to acidify the reaction solution to a pH value of 3 to 4, and then the reaction solution was extracted with dichloromethane. The extracts were combined, washed with saturated brine, dried with anhydrous sodium sulfate, and concentrated under reduced pressure, to obtain a white solid (79 mg, 62%). $^1$H NMR (300 MHz, $CDCl_3$) δ 8.50 (s, 1H), 7.16~7.13 (m, 4H), 3.21 (s, 6H).

Step 9. Synthesis of N-(4-(2-amino-3-chloropyridine-4-oxy)-3-fluorophenyl)-2-(dimethylamino)-4-(4-fluorophenyl)-5-oxo-4,5-dihydro-thiazolo[5,4-b]pyridine-6-formamide, having the structural formula below:

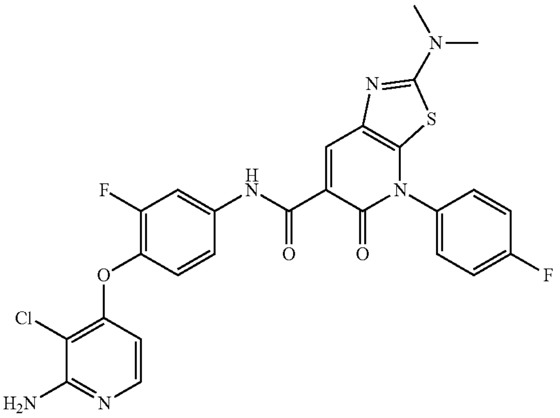 [SMILES: CN(C)c1nc2cc(C(=O)Nc3ccc(Oc4ccnc(N)c4Cl)c(F)c3)c(=O)n(-c3ccc(F)cc3)c2s1]

Under protection of nitrogen, 2-(dimethylamino)-4-(4-fluorophenyl)-5-oxo-4,5-dihydro-thiazolo[5,4-b]pyridine-6-formic acid (50 mg, 1.5 mmol) was dissolved in anhydrous DMF (2 mL), HATU (57 mg, 0.15 mmol) and diisopropylethyl amine (39 mg, 0.30 mmol) were added, and the mixture was stirred for 15 min at room temperature. 3-fluoro-4-(2-amino-3-chloropyridine-4-oxy)aniline (38 mg, 0.15 mmol) was added, and the mixture was stirred overnight at room temperature. TLC showed that the reaction was completed, water (5 mL) was added, the mixture was extracted with ethyl acetate, and the extracts were combined, washed with saturated brine, dried with anhydrous sodium sulfate, and concentrated under reduced pressure. The crude product was separated by silica gel preparative plate, to obtain a white solid (29 mg, 34%). $^1$H NMR (300 MHz, DMSO-$d_6$) δ 10.77 (s, 1H), 8.04 (s, 1H), 7.92 (d, 1H, J=12.3 Hz), 7.72 (d, 1H, J=5.1 Hz), 7.50 (d, 1H, J=8.4 Hz), 7.34 (t, 1H, J=9.0 Hz), 7.25~7.22 (m, 4H), 6.44 (br, 2H), 5.91 (d, 1H, J=5.7 Hz), 3.13 (s, 6H); ESI-MS: m/z 569 (M+H).

By adopting similar method, the following compounds can be prepared:
| Serial Number | Structural Formula | Structure Characterization |
|---|---|---|
| Embodiment 24 | 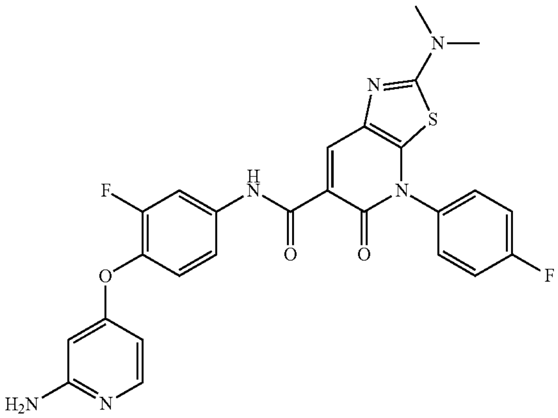 [SMILES: CN(C)c1nc2cc(C(=O)Nc3ccc(Oc4ccnc(N)c4)c(F)c3)c(=O)n(-c3ccc(F)cc3)c2s1] | ESI-MS: m/z 535 (M + H). |
| Embodiment 25 | 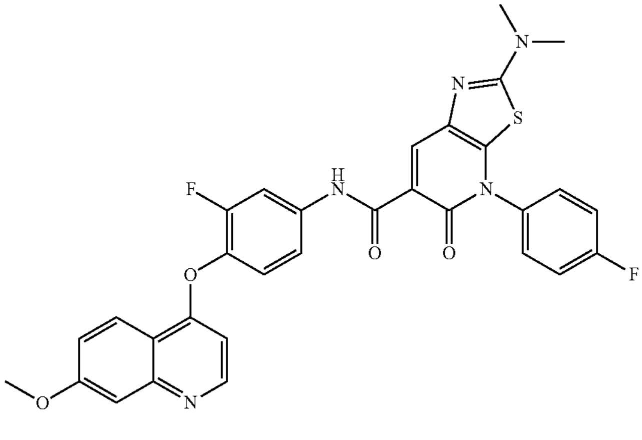 [SMILES: COc1ccc2c(Oc3ccc(NC(=O)c4cc5nc(N(C)C)sc5n(-c5ccc(F)cc5)c4=O)cc3F)ccnc2c1] | $^1$H NMR (300 MHz, DMSO-$d_6$) δ 10.81 (s, 1H), 8.60 (d, 1H, J = 3.9 Hz), 8.22 (d, 1H, J = 9.3 Hz), 8.07 (s, 1H), 7.99 (d, 1H, J = 12.9 Hz), 7.59~7.48 (m, 2H), 7.43 (d, 1H, J = 8.4 Hz), 7.27~7.24 (m, 5H), 6.47 (d, 1H, J = 5.1 Hz), 3.93 (s, 3H), 3.14 (s, 6H); ESI-MS: m/z 600 (M + H). |
| Embodiment 26 | 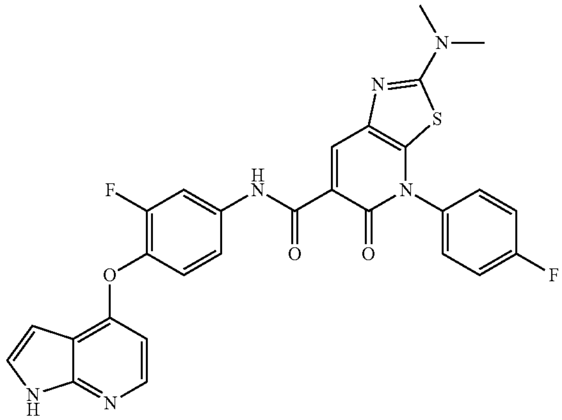 [SMILES: CN(C)c1nc2cc(C(=O)Nc3ccc(Oc4ccnc5[nH]ccc45)c(F)c3)c(=O)n(-c3ccc(F)cc3)c2s1] | $^1$H NMR (300 MHz, DMSO-$d_6$) δ 11.78 (s, 1H), 10.76 (s, 1H), 8.07~8.04 (m, 2H), 7.94 (d, 1H, J = 12.9 Hz), 7.52 (d, 1H, J = 8.7 Hz), 7.40~7.37 (m, 2H), 7.27~7.23 (m, 4H), 6.38 (d, 1H, J = 6.0 Hz), 6.26 (s, 1H), 3.14 (s, 6H); ESI-MS: m/z 559 (M + H). |

-continued

| Serial Number | Structural Formula | Structure Characterization |
| --- | --- | --- |
| Embodiment 27 | 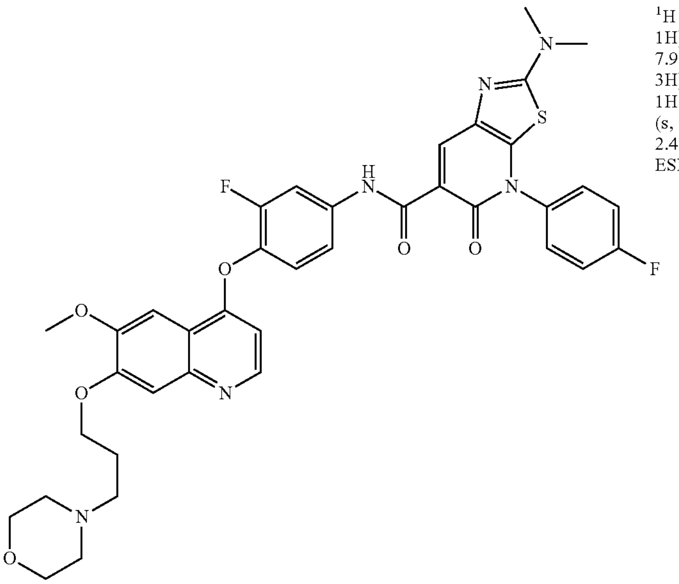 | $^1H$ NMR (300 MHz, DMSO-$d_6$) 10.81 (s, 1H), 8.44 (d, 1H, J = 5.4 Hz), 8.07 (s, 1H), 7.97 (dd, 1H, J = 13.2, 2.1 Hz), 7.60~7.44 (m, 3H), 7.39 (s, 1H), 7.40~7.38 (m, 4H), 6.45 (d, 1H, J = 5.1 Hz), 4.18 (t, 2H, J = 6.6 Hz), 3.94 (s, 3H), 3.59~3.54 (m, 4H), 3.14 (s, 6H), 2.47~2.41 (m, 6H), 1.99~1.95 (m, 2H); ESI-MS: m/z 743 (M+H). |

Embodiment 28

N-(4-(2-aminopyridine-4-oxy)-3-fluorophenyl)-7-(4-fluorophenyl)-1-methyl-6-oxo-6,7-dihydro-1H-pyrazolo[3,4-b]pyridine-5-formamide, having the structural formula below:

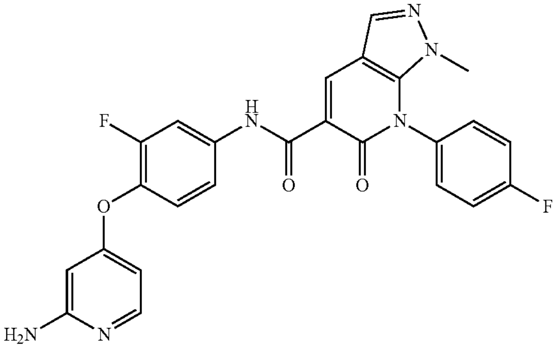 [SMILES: Cn1ncc2cc(C(=O)Nc3ccc(Oc4ccnc(N)c4)c(F)c3)c(=O)n(-c3ccc(F)cc3)c21]

Step 1. Synthesis of 5-amino-4-cyano-1-methyl-1H-pyrazole, through the reaction equation below:

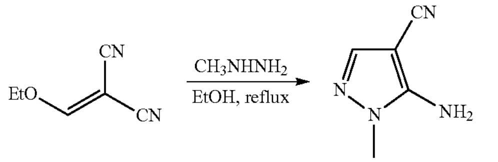

Ethoxymethylenemalononitrile (24.4 g, 20 mmol) and acetonitrile (9.2 g, 20 mmol) were added to anhydrous ethanol (300 mL), and the mixture was stirred for 2 hrs at reflux. The mixture was cooled to room temperature, the solvent was evaporated under reduced pressure, and the residue was added with water (200 mL), and stirred for half an hour. The mixture was filtered, and the cake was dried, to obtain a yellow solid (19.0 g, 78%).

$^1H$ NMR (DMSO-$d_6$, 300 MHz) δ 12.00 (s, 1H), 6.54 (br, 2H), 3.50 (s, 3H).

Step 2. Synthesis of 5-amino-4-aldo-1-methyl-1H-pyrazole, through the reaction equation below:

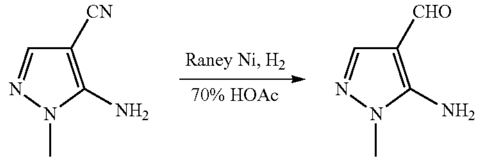

5-amino-4-cyano-1-methyl-1H-pyrazole (2.0 g, 16.4 mmol) was dissolved in 70% HOAc (30 mL), a Raney Ni catalyst (wet weight 1.5 g) was added, and the mixture was severely stirred for 6 hrs at 30 psi hydrogen pressure. After the reaction was completed, the mixture was filtered, the cake was washed with acetic acid, and the filtrates were combined and concentrated under reduced pressure, to obtain a green stiff jelly (5.0 g).

Step 3. Synthesis of ethyl 1-methyl-6-oxo-6,7-dihydro-1H-pyrazolo[3,4-b]pyridine-5-formate, through the reaction equation below:

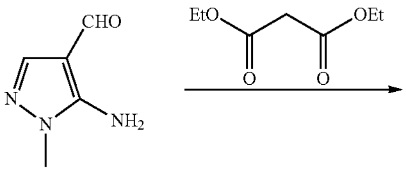

-continued

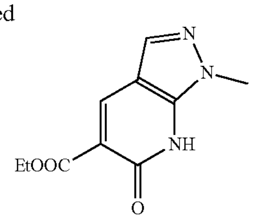

The stiff jelly (5.0 g) obtained in Step 2 was dissolved in anhydrous ethanol (150 mL), diethyl malonate (12.0 mL) and piperidine (8.0 mL) were added, and the mixture was stirred for 20 hrs at reflux under protection of nitrogen. The mixture was cooled to room temperature, the solvent was evaporated under reduced pressure, and the residue was subjected to silica gel column chromatography for purification, to obtain a white solid (1.6 g, two-step yield 44%). $^{1}H$ NMR ($CDCl_3$, 300 MHz) δ12.00 (s, 1H), 8.65 (s, 1H), 7.96 (s, 1H), 4.46 (q, 2H, J=7.5 Hz), 4.03 (s, 3H), 1.44 (t, 3H, J=7.5 Hz).

Step 4. Synthesis of ethyl 7-(4-fluorophenyll)-1-methyl-6-oxo-6,7-dihydro-1H-pyrazolo[3,4-b]pyri dine-5-formate, through the reaction equation below:

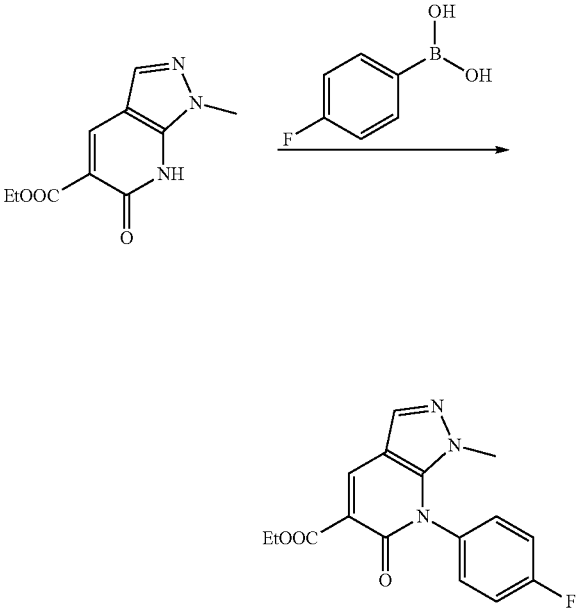

Ethyl 1-methyl-6-oxo-6,7-dihydro-1H-pyrazolo[3,4-b]pyridine-5-formate (0.89 g, 4.0 mmol) was dissolved in anhydrous dichloromethane (30 mL), 4-fluorophenylboronic acid (1.12 g, 8.0 mmol), anhydrous copper acetate (1.45 g, 8.0 mmol), 2,2,6,6-tetramethylpiperidine nitrogen oxide (0.78 g, 5.0 mmol), pyridine (2.0 mL) and activated molecular sieve powder (2.0 g) were added, and the mixture was stirred for 20 hrs at room temperature (an anhydrous calcium chloride drying tube was added at the bottle neck). After the reaction was completed, the mixture was directly concentrated under reduced pressure, and the residue was subjected to silica gel column chromatography, to obtain a white solid (0.248 g, 20%).

Step 5. Synthesis of 7-(4-fluorophenyl)-1-methyl-6-oxo-6,7-dihydro-1H-pyrazolo[3,4-b]pyridine-5-formic acid

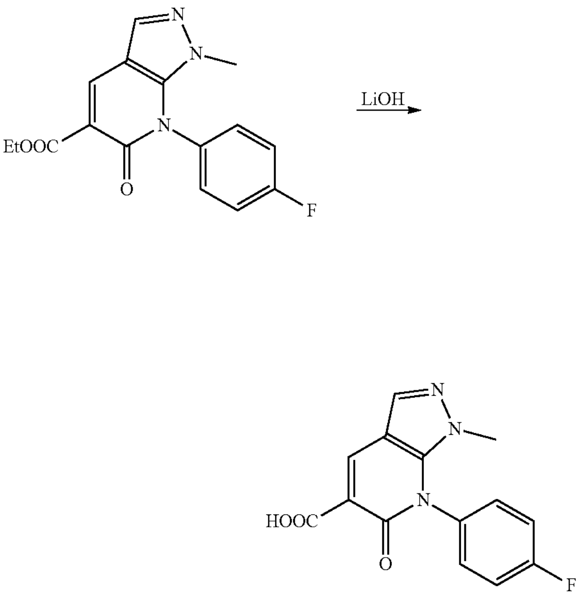

Ethyl 7-(4-fluorophenyll)-1-methyl-6-oxo-6,7-dihydro-1H-pyrazolo[3,4-b]pyridine-5-formate (180 mg, 0.57 mmol) was dissolved in tetrahydrofuran (3 mL), an aqueous solution (3 mL) of $LiOH.H_2O$ (120 mg, 2.86 mmol) was added, and the mixture was stirred overnight at room temperature. TLC detected that the raw materials disappeared, the mixture was cooled with ice water, and 3N hydrochloric acid was added dropwise to acidify the mixture to a pH value of 3. The reaction solution was extracted with dichloromethane, and the extracts were combined, dried with anhydrous sodium sulfate, and concentrated under reduced pressure, to obtain a light yellow solid (160 mg, 98%).

$^{1}H$ NMR ($CDCl_3$, 300 MHz) δ 8.93 (s, 1H), 8.06 (s, 1H), 7.26-7.14 (m, 4H), 3.86 (s, 3H), 1.44 (t, 3H, J=7.5 Hz).

Step 6. Synthesis of N-(4-(2-aminopyridine-4-oxy)-3-fluorophenyl)-7-(4-fluorophenyl)-1-methyl-6-oxo-6,7-dihydro-1H-pyrazolo[3,4-b]pyridine-5-formamide, through the reaction equation below:

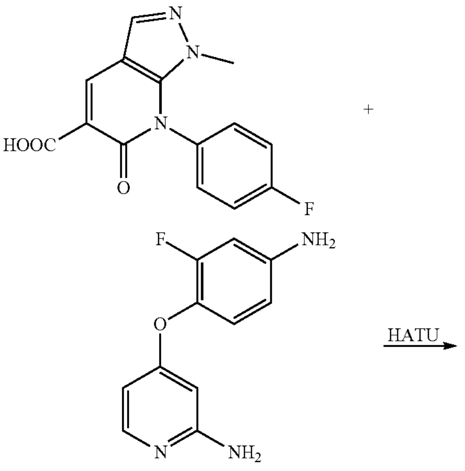

-continued

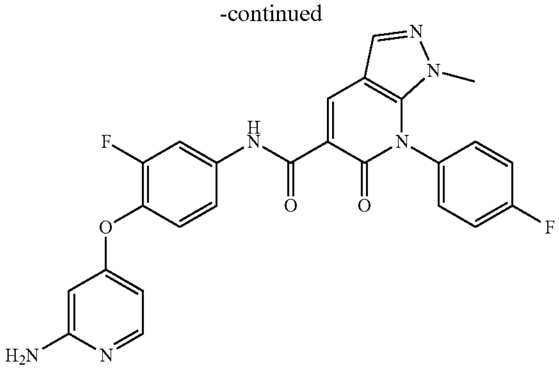

Under protection of nitrogen, 7-(4-fluorophenyl)-1-methyl-6-oxo-6,7-dihydro-1H-pyrazolo[3,4-b]pyridine-5-formic acid (57 mg, 0.2 mmol) was dissolved in anhydrous DMF (3 mL), diisopropylethyl amine (52 mg, 0.4 mmol) and HATU (76 mg, 0.2 mmol) were added, and the mixture was stirred for 15 min at room temperature. 3-fluoro-4-(2-aminopyridine-4-oxy)aniline (44 mg, 0.2 mmol) was added, and the mixture was heated to 40° C. and stirred overnight. After the reaction was completed, the system was added with water, and extracted with ethyl acetate, and the extracts were combined, washed with saturated brine, dried with anhydrous sodium sulfate, concentrated under reduced pressure, and subjected to silica gel column chromatography (dichloromethane/methanol=20/1), to obtain a white solid (64 mg, 66%). $^1$H NMR (DMSO-$d_6$, 300 MHz) δ10.75 (s, 1H), 8.57 (s, 1H), 8.17 (s, 1H), 7.94 (dd, 1H, J=12.6, 2.4 Hz), 7.80 (d, 1H, J=6.0 Hz), 7.51 (dd, 1H, J=6.0, 2.4 Hz), 7.42~7.27 (m, 5H), 6.24 (dd, 1H, J=6.0, 2.4 Hz), 6.18 (br, 2H), 5.82 (d, 1H, J=2.1 Hz), 3.78 (s, 3H); ESI-MS: m/z 489 (M+H).

Following the similar methods, the following compounds can be prepared:

| Serial Number | Structural Formula | Structure Characterization |
|---|---|---|
| Embodiment 29 | 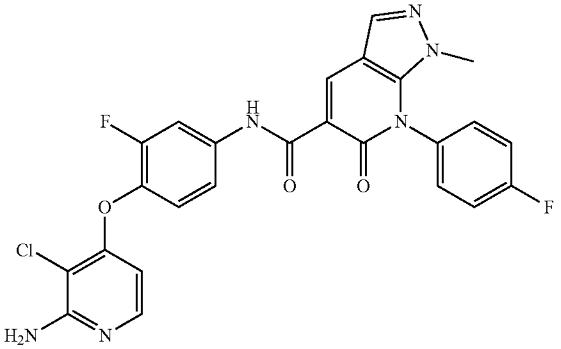 [SMILES: Cn1ncc2cc(C(=O)Nc3ccc(Oc4ccnc(N)c4Cl)c(F)c3)c(=O)n(-c3ccc(F)cc3)c21] | $^1$H NMR (DMSO-$d_6$, 300 MHz) δ 10.75 (s, 1H), 8.58 (s, 1H), 8.17 (s, 1H), 7.95 (dd, 1H, J = 12.6, 2.4 Hz), 7.73 (d, 1H, J = 6.0 Hz), 7.51 (d, 1H, J = 8.1 Hz), 7.42~7.26 (m, 5H), 6.42 (br, 2H), 5.92 (d, 1H, J = 2.1 Hz), 3.78 (s, 3H); ESI-MS: m/z 523 (M + H). |
| Embodiment 30 | 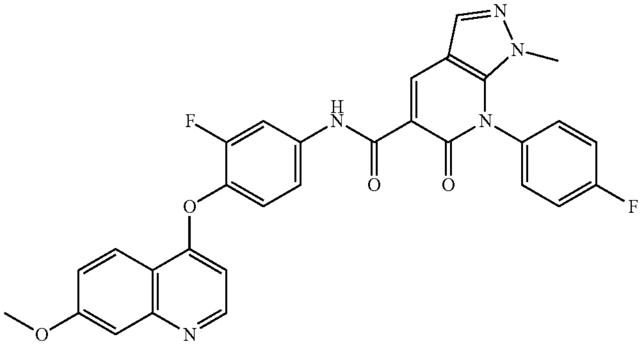 [SMILES: COc1ccc2c(Oc3ccc(NC(=O)c4cc5cnn(C)c5n(-c5ccc(F)cc5)c4=O)cc3F)ccnc2c1] | $^1$H NMR (DMSO-$d_6$, 300 MHz) δ 10.80 (s, 1H), 8.61~8.58 (m, 2H), 8.23 (d, 1H, J = 9.0 Hz), 8.28 (s, 1H), 8.01 (dd, 1H, J = 13.2, 1.8 Hz), 7.62~7.43 (m, 2H), 7.42~7.26 (m, 6H), 6.48 (d, 1H, 5.1 Hz), 3.93 (s, 3H), 3.79 (s, 3H). ESI-MS: m/z 554 (M + H). |
| Embodiment 31 | 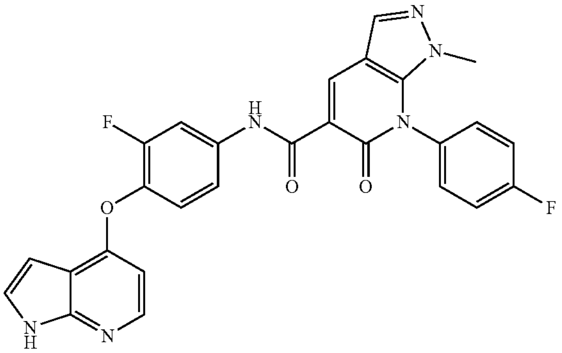 [SMILES: Cn1ncc2cc(C(=O)Nc3ccc(Oc4ccnc5[nH]ccc45)c(F)c3)c(=O)n(-c3ccc(F)cc3)c21] | $^1$H NMR (DMSO-$d_6$, 300 MHz) δ 11.78 (s, 1H), 10.76 (s, 1H), 8.60 (s, 1H), 8.17 (s, 1H), 8.05 (d, 1H, J = 5.4 Hz), 7.96 (d, 1H, J = 12.4 Hz), 7.54 (d, 1H, J = 6.0 Hz), 7.44~7.27 (m, 6H), 6.37 (d, 1H, J = 5.4 Hz), 6.26 (s, 1H), 3.78 (s, 3H); ESI-MS: m/z 513 (M + H). |

-continued

| Serial Number | Structural Formula | Structure Characterization |
| --- | --- | --- |
| Embodiment 32 | 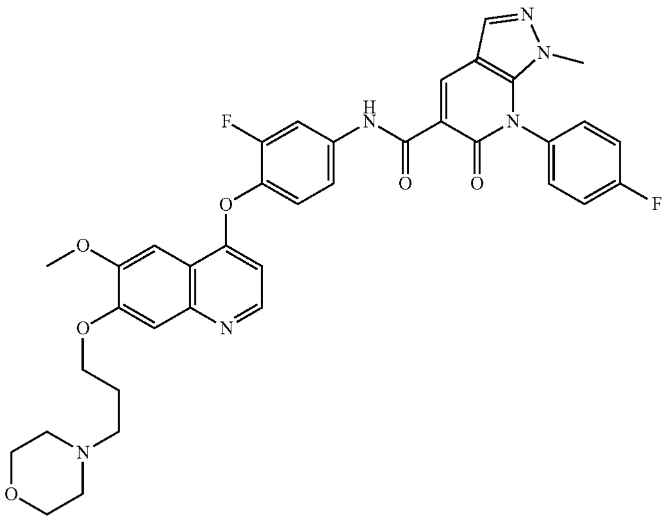 [SMILES: COc1cc2c(Oc3ccc(NC(=O)c4cc5cnn(C)c5n(-c5ccc(F)cc5)c4=O)cc3F)ccnc2cc1OCCCN1CCOCC1] | $^1H$ NMR (DMSO-$d_6$, 300 MHz) δ 10.79 (s, 1H), 8.60 (s, 1H), 8.45 (d, 1H, J = 4.8 Hz), 8.18 (s, 1H), 8.02 (dd, 1H, J = 13.2, 2.1 Hz), 7.57~7.26 (m, 10H), 6.46 (d, 1H, J = 5.7 Hz), 4.19 (t, 2H, J = 6.3 Hz), 3.94 (s, 3H), 3.78 (s, 3H), 3.61~3.55 (m, 4H), 2.47~2.30 (m, 4H), 1.97 (t, 2H, J = 6.3 Hz), 1.23~1.20 (m, 2H); ESI-MS: m/z 697 (M + H). |

Embodiment 33

N-(4-(2-amino-3-chloropyridine-4-oxy)-3-fluorophenyl)-4-(4-fluorophenyl)-3-methyl-5-oxo-4,5-dihydro-3H-imidazolo[4,5-b]pyridine-6-formamide, having the structural formula below:

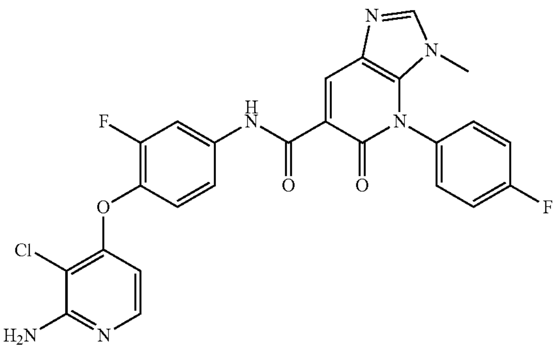 [SMILES: Cn1cnc2cc(C(=O)Nc3ccc(Oc4ccnc(N)c4Cl)c(F)c3)c(=O)n(-c3ccc(F)cc3)c21]

Step 1. Synthesis of ethyl 3-methyl-5-oxo-4,5-dihydro-3H-imidazolo[4,5-b]pyridine-6-formate, through the reaction equation below:

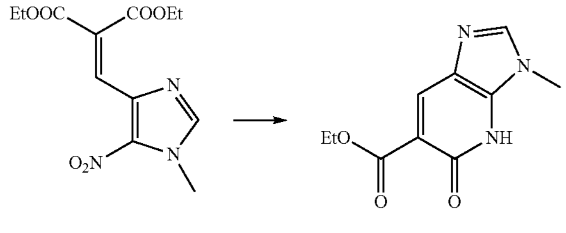 [SMILES: CCOC(=O)C(=Cc1ncn(C)c1[N+](=O)[O-])C(=O)OCC ; CCOC(=O)c1cc2ncn(C)c2[nH]c1=O]

Raw material 2-((1-methyl-5-nitro-1H-imidazol-4-yl)methylene)diethyl malonate (290 mg, 0.98 mmol, referring to document: Letters in Organic Chemistry, 2004, 1, 326-330) was dissolved in glacial acetic acid (25 mL), reduced iron powder (0.56 g, 10 mmol) was added, and the mixture was stirred for 2 hrs at reflux. The mixture was cooled to room temperature, glacial acetic acid was evaporated under reduced pressure, and the residue was carefully added with a saturated sodium bicarbonate solution to adjust the pH value to be greater than 7, and extracted with dichloromethane. The extracts were combined, washed with saturated brine, dried with anhydrous sodium sulfate, and concentrated under reduced pressure, to obtain a yellow solid (150 mg, 69%).

Step 2. Synthesis of ethyl 4-(4-fluorophenyl)-3-methyl-5-oxo-4,5-dihydro-3H-imidazolo[4,5-b]pyridine-6-formate, through the reaction equation below:

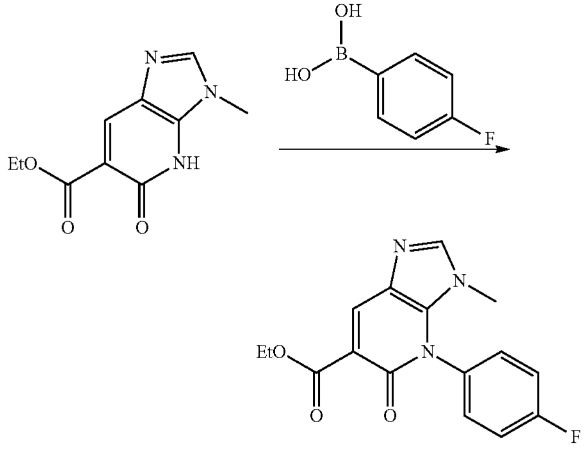

Under dry conditions, ethyl 3-methyl-5-oxo-4,5-dihydro-3H-imidazolo[4,5-b]pyridine-6-formate (150 mg, 0.68 mmol) was dissolved in anhydrous dichloromethane (30 mL), and 4-fluorophenylboronic acid (190 mg, 1.36 mmol), anhydrous copper acetate (247 mg, 1.36 mmol), 2,2,6,6-tetramethylpiperidine nitrogen oxide (128 mg, 0.82 mmol), pyridine (0.5 mL) and activated molecular sieve powder (0.5 g) were added. An anhydrous calcium chloride drying tube was added at the bottle neck, and the mixture was stirred for 24 hrs at room temperature. After the reaction was completed, the reaction solution was directly concentrated under reduced pressure, and the crude product was subjected to silica gel column chromatography for purification, to obtain a white solid (150 mg, 70%).

Step 3. Synthesis of 4-(4-fluorophenyl)-3-methyl-5-oxo-4,5-dihydro-3H-imidazolo[4,5-b]pyridine-6-formic acid, through the reaction equation below:

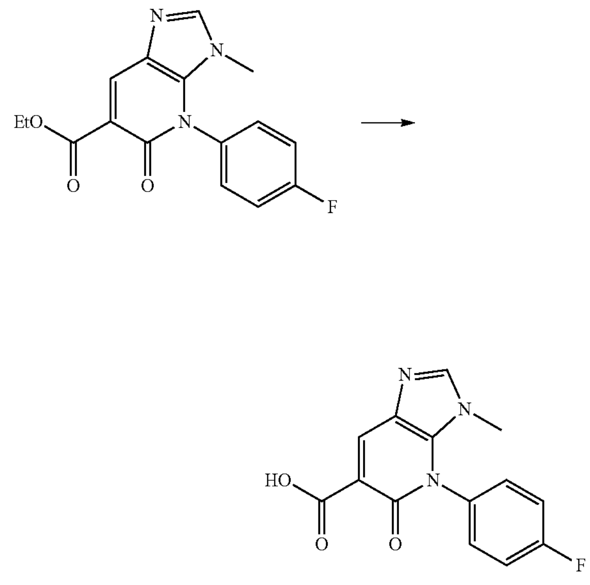 [SMILES: CCOC(=O)c1cc2ncn(C)c2n(-c2ccc(F)cc2)c1=O ; Cn1cnc2cc(C(=O)O)c(=O)n(-c3ccc(F)cc3)c21]

Ethyl 4-(4-fluorophenyl)-3-methyl-5-oxo-4,5-dihydro-3H-imidazolo[4,5-b]pyridine-6-formate (150 mg, 0.47 mmol) was dissolved in tetrahydrofuran (5 mL), an aqueous solution (5 mL) of $LiOH.H_2O$ (100 mg, 2.38 mmol) was added, and the mixture was stirred overnight at room temperature. After the reaction was completed, the reaction solution was cooled with ice water, and 3N hydrochloric acid was added dropwise to acidify the reaction solution to a pH value of 3. The reaction solution was extracted with dichloromethane, and the extracts were combined and dried with anhydrous sodium sulfate, and concentrated under reduced pressure, to obtain the crude target product (90 mg, 75%).

Step 4. Synthesis of N-(4-(2-amino-3-chloropyridine-4-oxy)-3-fluorophenyl)-4-(4-fluorophenyl)-3-methyl-5-oxo-4,5-dihydro-3H-imidazolo[4,5-b]pyridine-6-formamide, having the structural formula below:

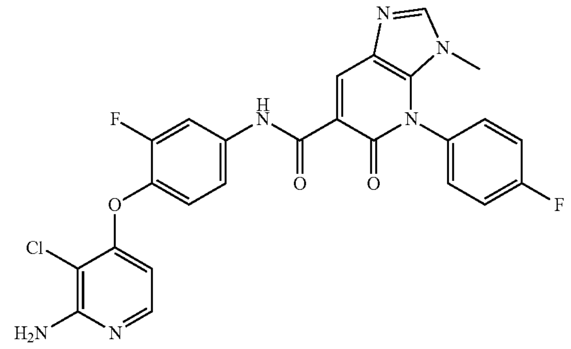 [SMILES: Cn1cnc2cc(C(=O)Nc3ccc(Oc4ccnc(N)c4Cl)c(F)c3)c(=O)n(-c3ccc(F)cc3)c21]

Under protection of nitrogen, 4-(4-fluorophenyl)-3-methyl-5-oxo-4,5-dihydro-3H-imidazolo[4,5-b]pyridine-6-formic acid (30 mg, 0.104 mmol) was dissolved in anhydrous DMF (3 mL), diisopropylethyl amine (1 drop) and HATU (40 mg, 0.104 mmol) were added, and the mixture was stirred for 15 min at room temperature. 3-fluoro-4-(2-aminopyridine-4-oxy)aniline (27 mg, 0.104 mmol) was added, and the mixture was heated to 30° C. and stirred overnight. After the reaction was completed, the system was added with water, and extracted with ethyl acetate, and the extracts were combined, washed with saturated brine, dried with anhydrous sodium sulfate, concentrated under reduced pressure, and then subjected to silica gel column chromatography (dichloromethane/methanol=20/1), to obtain a white solid (36 mg, 66%). $^1H$ NMR (300 MHz, DMSO-$d_6$) δ 10.74 (s, 1H), 8.41 (s, 1H), 8.40 (s, 1H), 7.95 (dd, 1H, J=13.5, 2.7 Hz), 7.75 (d, 1H, J=5.7 Hz), 7.53 (d, 1H, J=9.3 Hz), 7.40~7.22 (m, 5H), 6.67 (br, 2H), 5.99 (d, 1H, J=6.0 Hz), 3.63 (s, 3H); ESI-MS: m/z 523 (M+H).

By adopting the similar methods, the following compound can be prepared:

| Serial Number | Structural Formula | Structure Characterization |
|---|---|---|
| Embodiment 34 | 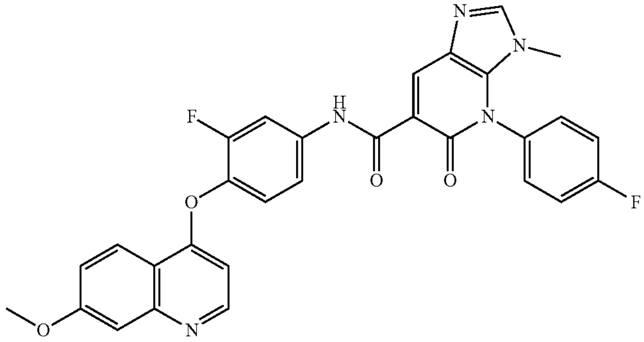 | $^1H$ NMR (DMSO-$d_6$, 300 MHz) δ 10.82 (s, 1H), 8.89 (d, 1H, J = 6.6 Hz), 8.49~8.41 (m, 3H), 8.08 (dd, 1H, J = 13.5, 1.8 Hz), 7.64~7.48 (m, 4H), 7.35~7.22 (m, 4H), 6.92 (d, 1H, J = 5.4 Hz), 4.01 (s, 3H), 3.64 (s, 3H); ESI-MS: m/z 523 (M + H). |

-continued
| Serial Number | Structural Formula | Structure Characterization |
|---|---|---|
| Embodiment 35 | 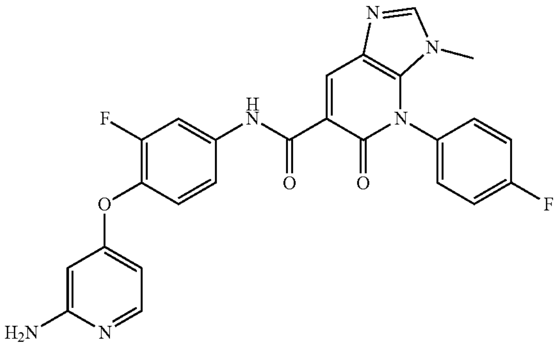 | ESI-MS: m/z 489 (M + H). |
| Embodiment 36 | 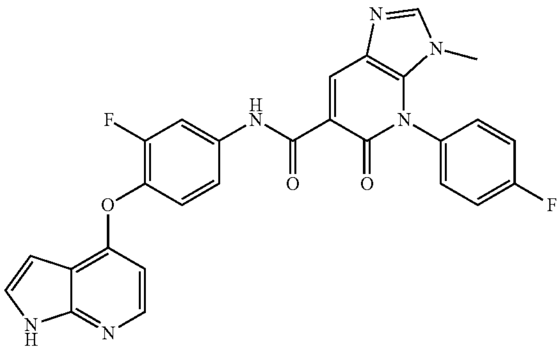 [SMILES: Cn1cnc2cc(C(=O)Nc3ccc(Oc4ccnc5[nH]ccc45)c(F)c3)c(=O)n(-c3ccc(F)cc3)c21] | ESI-MS: m/z 513 (M + H). |
| Embodiment 37 | 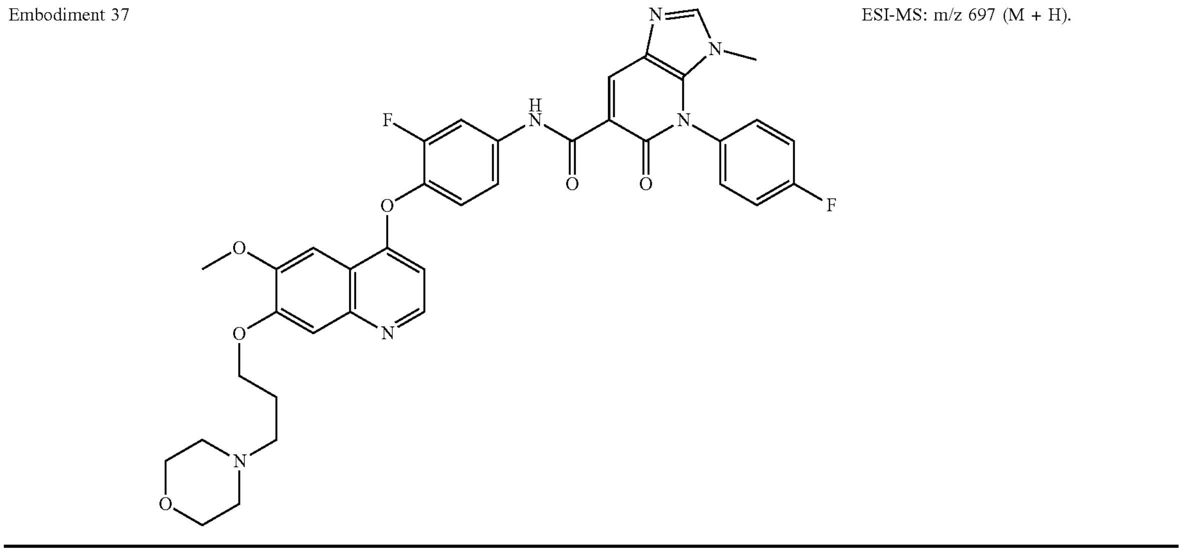 | ESI-MS: m/z 697 (M + H). |

Embodiment 38

N-(4-(2-amino-3-chloropyridine-4-oxy)-3-fluorophenyl)-5-(4-fluorophenyl)-4-methyl-6-oxo-3,4,5,6-tetrahydro-2H-pyrido[3,2-b][1,4]oxazine-7-formamide

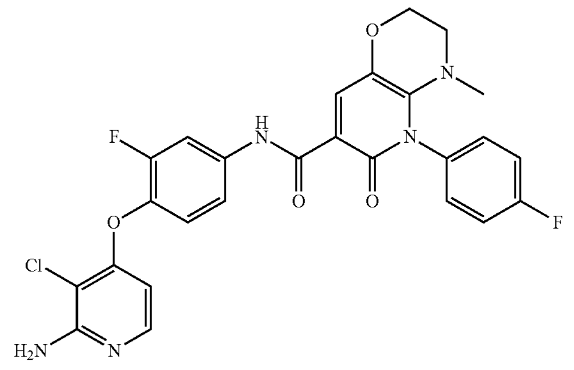 [SMILES: CN1CCOc2cc(C(=O)Nc3ccc(Oc4ccnc(N)c4Cl)c(F)c3)c(=O)n(-c3ccc(F)cc3)c21]

Step 1. Synthesis of 1-(7-bromo-2H-pyrido[3,2-b][1,4]oxazin-4 (3H)-yl)ethyl ketone, through the reaction equation below:

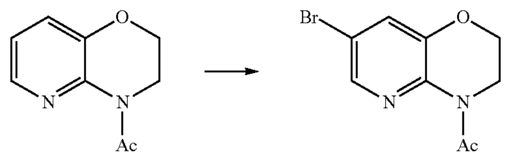 [SMILES: CC(=O)N1CCOc2cccnc21 ; CC(=O)N1CCOc2cc(Br)cnc21]

Under protection of nitrogen, 1-(2H-pyrido[3,2-b][1,4]oxazin-4 (3H)-yl)ethyl ketone (26.0 g, 146 mmol, referring to document: Journal of Medicinal Chemistry, 2007, 50, 3730-3742.) was dissolved in anhydrous DMF (240 mL), NBS (33.8 g, 190 mmol) was added portionwise, and the mixture was heated to 75° C. and stirred for 2 hrs. The mixture was cooled to room temperature, DMF was evaporated under reduced pressure, and the residue was added with dichloromethane and dissolved, washed with saturated brine, dried with anhydrous sodium sulfate, and concentrated under reduced pressure, to obtain a light yellow solid (41.0 g, approximately 100%).

Step 2. Synthesis of 4-acetyl-3,4-dihydro-2H-pyrido[3,2-b][1,4]oxazine-7-formonitrile, through the reaction equation below:

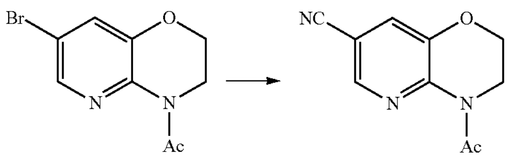 [SMILES: CC(=O)N1CCOc2cc(Br)cnc21 ; CC(=O)N1CCOc2cc(C#N)cnc21]

Under protection of nitrogen, 1-(7-bromo-2H-pyrido[3,2-b][1,4]oxazin-4 (3H)-yl)ethyl ketone (10.0 g, 38.9 mmol), $Zn(CN)_2$ (9.14 g, 77.8 mmol) were dissolved in anhydrous DMF (20 mL), and zinc powder (153 mg, 2.33 mmol), dppf (2.59 g, 4.67 mmol) and $Pd_2$ $(dba)_3$ (2.14 g, 2.33 mmol) were added, and the mixture was stirred overnight at reflux. After the reaction was completed, the mixture was cooled to room temperature, DMF was evaporated under reduced pressure, and the residue was dissolved in dichloromethane, dried with anhydrous sodium sulfate, and concentrated under reduced pressure. The residue was subjected to silica gel column chromatography (ethyl acetate/petroleum ether) for purification, to obtain an offwhite solid (5.0 g, 63%). $^1H$ NMR (300 MHz, $CDCl_3$) δ 8.23 (d, 1H, J=2.4 Hz), 7.42 (d, 1H, J=2.4 Hz), 4.30 (t, 2H, J=4.5 Hz), 4.09 (t, 2H, J=4.5 Hz), 2.65 (s, 3H).

Step 3. Synthesis of 3,4-dihydro-2H-pyrido[3,2-b][1,4]oxazine-7-formic acid, through the reaction equation below:

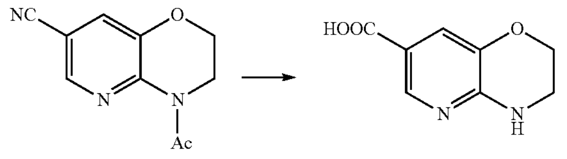 [SMILES: CC(=O)N1CCOc2cc(C#N)cnc21 ; O=C(O)c1cnc2c(c1)OCCN2]

4-acetyl-3,4-dihydro-2H-pyrido[3,2-b][1,4]oxazine-7-formonitrile (5.0 g) was dissolved in ethanol (60 mL), 10% aqueous solution (60 mL) of potassium hydroxide was added, and the mixture was stirred overnight at reflux. After the reaction was completed, the mixture was cooled to room temperature, ethanol was evaporated under reduced pressure, the residual alkali solution was added dropwise with 1N hydrochloric acid for acidification, extracted with dichloromethane, and the extracts were combined, dried with anhydrous sodium sulfate, and concentrated under reduced pressure, to obtain a light yellow solid (4.0 g, 72%).

Step 4. Synthesis of methyl 3,4-dihydro-2H-pyrido[3,2-b][1,4]oxazine-7-formate, through the reaction equation below:

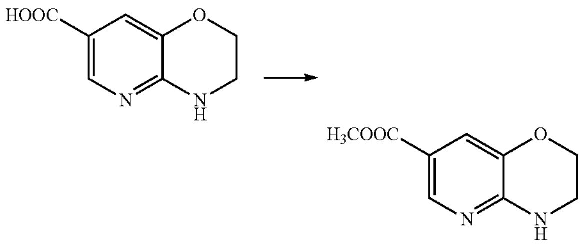

Under protection of nitrogen, 3,4-dihydro-2H-pyrido[3,2-b][1,4]oxazine-7-formic acid (1.0 g, 5.5 mmol) was dissolved in anhydrous methanol (15 mL), and thionyl chloride (1.0 mL) was added dropwise. The mixture was stirred for 2 hrs at reflux, and then cooled to room temperature, and concentrated under reduced pressure. The residue was dissolved in dichloromethane, the mixture was carefully washed with a saturated sodium bicarbonate solution and saturated brine, dried with anhydrous sodium sulfate, and concentrated under reduced pressure, to obtain a white solid (1.0 g, 93%).

Step 5. Synthesis of methyl 4-methyl-3,4-dihydro-2H-pyrido[3,2-b][1,4]oxazine-7-formate, through the reaction equation below:

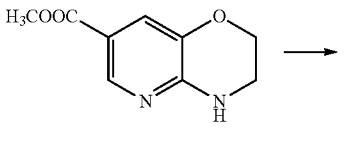

-continued

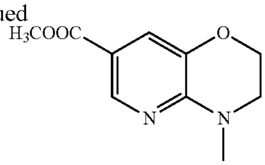

Under protection of nitrogen, methyl 3,4-dihydro-2H-pyrido[3,2-b][1,4]oxazine-7-formate (500 mg, 2.57 mmol) was dissolved in anhydrous tetrahydrofuran (10 mL), sodium hydride (60%, 74 mg, 1.85 mmol) was added, the mixture was stirred for 15 min at room temperature, iodomethane (1.83 g, 12.9 mmol) was added, and the mixture was stirred overnight at room temperature. The solvent was evaporated under reduced pressure, and the residue was dissolved in dichloromethane, washed with saturated brine, dried with anhydrous sodium sulfate, and concentrated under reduced pressure. The residue was subjected to silica gel column chromatography, to obtain a white solid (250 mg, 47%).

Step 6. Synthesis of methyl 4-methyl-6-oxo-3,4,5,6-tetrahydro-2H-pyrido[3,2-b][1,4]oxazine-7-formate, through the reaction equation below:

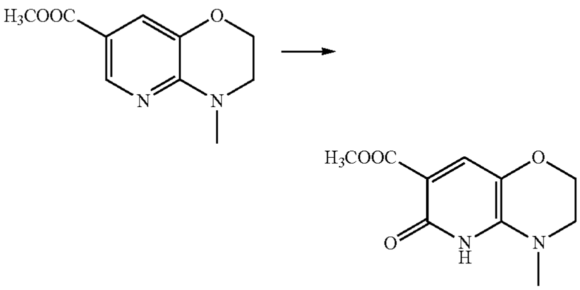

Methyl 4-methyl-3,4-dihydro-2H-pyrido[3,2-b][1,4]oxazine-7-formate (500 mg, 2 mmol) was dissolved in dichloromethane (5 mL), m-chloroperoxybenzoic acid (605 mg, 3 mmol) was added, and the mixture was stirred for 60 hrs at room temperature. After the reaction was completed, dichloromethane was added to dilute the reaction solution, and the mixture was carefully washed with a saturated sodium bicarbonate solution three times, then washed with saturated brine, dried with anhydrous sodium sulfate, and concentrated under reduced pressure. The residue was added with acetic anhydride (10 mL), and stirred for 4 hrs at reflux. The mixture was cooled to room temperature, acetic anhydride was evaporated under reduced pressure, the residue was dissolved in dichloromethane, and the dichloromethane solution was carefully washed with a saturated sodium bicarbonate solution, and concentrated under reduced pressure, to obtain a black oil. The black oil was dissolved in methanol (10 mL), anhydrous sodium carbonate (725 mg, 6.84 mmol) was added, and the mixture was stirred for 2 hrs at room temperature. Methanol was evaporated under reduced pressure, the residue was dissolved in dichloromethane, and the dichloromethane solution was washed with saturated brine, dried with anhydrous sodium sulfate, and concentrated under reduced pressure. The residue was subjected to silica gel column chromatography for purification, to obtain a white solid (210 mg, 49%). $^1$H NMR (300 MHz, $CDCl_3$) δ 8.44 (s, 1H), 7.43 (s, 1H), 4.14 (t, 2H, J=4.5 Hz), 3.87 (s, 3H), 3.52 (t, 2H, J=4.5 Hz), 3.22 (s, 3H).

Step 7. Synthesis of methyl 5-(4-fluorophenyl)-4-methyl-6-oxo-3,4,5,6-tetrahydro-2H-pyrido[3,2-b][1,4]oxazine-7-formate, through the reaction equation below:

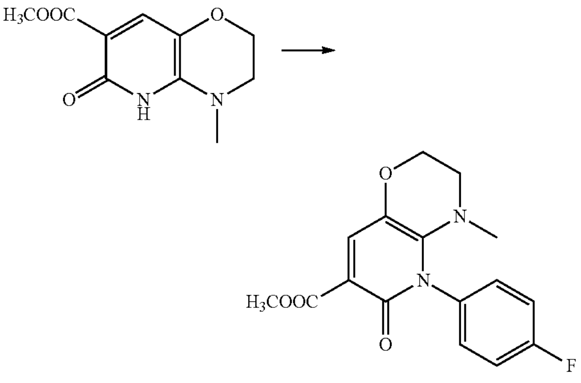

Methyl 4-methyl-6-oxo-3,4,5,6-tetrahydro-2H-pyrido[3,2-b][1,4]oxazine-7-formate (100 mg, 0.45 mmol) was dissolved in anhydrous acetonitrile (5 mL), and 4-fluorophenylboronic acid (125 mg, 0.90 mmol), cuprous iodide (21 mg, 0.11 mmol), 2,2,6,6-tetramethylpiperidine nitrogen oxide (87 mg, 0.56 mmol), pyridine (0.3 mL) and activated molecular sieve powder (100 mg) were added. An anhydrous calcium chloride drying tube was added at the bottle neck, and the mixture was heated to 40° C. and stirred for 60 hrs. The reaction mixture was directly concentrated under reduced pressure, and the residue was subjected to silica gel column chromatography, to obtain a white solid (65 mg, 42%). $^1$H NMR (300 MHz, $CDCl_3$) δ 7.54 (s, 1H), 7.07-7.01 (m, 4H), 4.15 (t, 2H, J=4.5 Hz), 3.83 (s, 3H), 3.44 (t, 2H, J=4.5 Hz), 2.86 (s, 3H).

Step 8. Synthesis of 5-(4-fluorophenyl)-4-methyl-6-oxo-3,4,5,6-tetrahydro-2H-pyrido[3,2-b][1,4]oxazine-7-formic acid, through the reaction equation below:

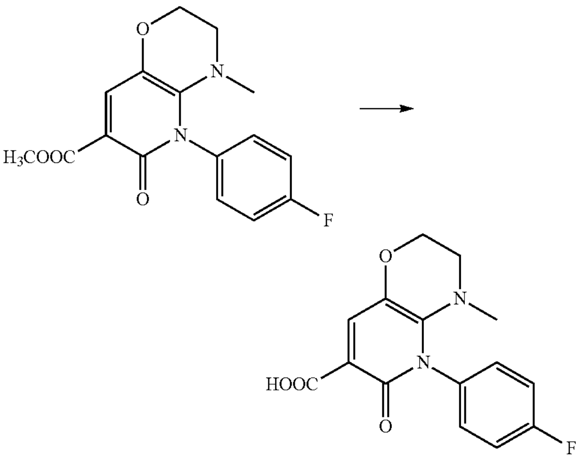

Methyl 5-(4-fluorophenyl)-4-methyl-6-oxo-3,4,5,6-tetrahydro-2H-pyrido[3,2-b][1,4]oxazine-7-formate (100 mg, 0.31 mmol) was dissolved in tetrahydrofuran (5 mL), an aqueous solution (5 mL) of $LiOH.H_2O$ (100 mg, 2.3 mmol) was added, and the mixture was heated to 40° C. and stirred overnight. After the reaction was completed, the reaction solution was cooled with ice water, and 3N hydrochloric acid was added dropwise to acidify the reaction solution to a pH value of 4 to 5. The mixture was extracted with ethyl acetate, and the extracts were combined, dried with anhydrous sodium sulfate, and concentrated under reduced pressure. The residue was subjected to silica gel column chromatography for purification, to obtain the target product (59 mg, 62%). $^1$H NMR (300 MHz, $CDCl_3$) δ 7.64 (s, 1H), 7.17-7.08 (m, 4H), 5.30 (s, 1H), 4.15 (t, 2H, J=4.5 Hz), 3.46 (t, 2H, J=4.5 Hz), 2.85 (s, 3H).

Step 9. Synthesis of N-(4-(2-amino-3-chloropyridine-4-oxy)-3-fluorophenyl)-5-(4-fluorophenyl)-4-methyl-6-oxo-3,4,5,6-tetrahydro-2H-pyrido[3,2-b][1,4]oxazine-7-formamide, having the structural formula below:

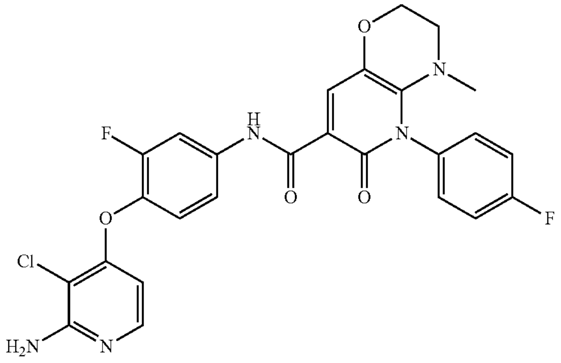 [SMILES: CN1CCOc2cc(C(=O)Nc3ccc(Oc4ccnc(N)c4Cl)c(F)c3)c(=O)n(-c3ccc(F)cc3)c21]

Under protection of nitrogen, 5-(4-fluorophenyl)-4-methyl-6-oxo-3,4,5,6-tetrahydro-2H-pyrido[3,2-b][1,4]oxazine-7-formic acid (45 mg, 0.15 mmol) was dissolved in anhydrous DMF (2 mL), diisopropylethyl amine (38 mg, 0.30 mmol) and HATU (56 mg, 0.15 mmol) were added, and the mixture was stirred for 15 min at room temperature. 3-fluoro-4-(2-amino-3-chloropyridine-4-oxy)aniline (38 mg, 0.15 mmol) was added, and the mixture was heated to 40° C. and stirred overnight. After the reaction was completed, the system was added with water, and extracted with ethyl acetate, and the extracts were combined, dried with anhydrous sodium sulfate, and concentrated under reduced pressure. The residue was subjected to silica gel column chromatography for purification, to obtain a white solid (40 mg, 50%). $^1$H NMR (300 MHz, DMSO-$d_6$) δ 10.03 (s, 1H), 7.90 (d, 1H), 7.71 (s, 1H), 7.37 (s, 1H), 7.18-7.32 (m, 5H), 6.41 (s, 2H), 5.88 (d, 2H), 4.15 (t, 2H), 3.46 (t, 2H), 2.79 (s, 3H); ESI-MS: m/z 540 (M+H).

By adopting methods similar to that in Embodiment 38, the following compounds can be prepared:

| Serial Number | Structural Formula | Structure Characterization |
|---|---|---|
| Embodiment 39 | 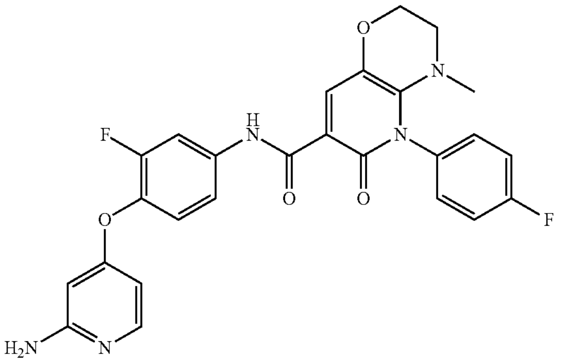 [SMILES: CN1CCOc2cc(C(=O)Nc3ccc(Oc4ccnc(N)c4)c(F)c3)c(=O)n(-c3ccc(F)cc3)c21] | ESI-MS: m/z 506 (M + H). |
| Embodiment 40 | 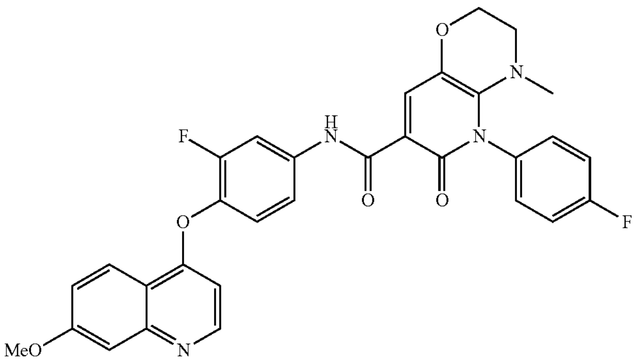 [SMILES: COc1ccc2c(Oc3ccc(NC(=O)c4cc5c(n(-c6ccc(F)cc6)c4=O)N(C)CCO5)cc3F)ccnc2c1] | $^1$H NMR (300 MHz, DMSO-$d_6$) δ 10.08 (s, 1H), 8.59 (d, 1H), 8.22 (d, 1H), 7.97 (d, 1H), 7.52 (d, 1H), 7.38~7.44 (m, 3H), 7.21~7.32 (m, 5H), 6.45 (d, 1H), 4.16 (t, 2H), 3.93 (s, 3H), 3.42 (t, 2H), 2.80 (s, 3H); ESI-MS: m/z 571 (M + H). |

-continued

| Serial Number | Structural Formula | Structure Characterization |
|---|---|---|
| Embodiment 41 | 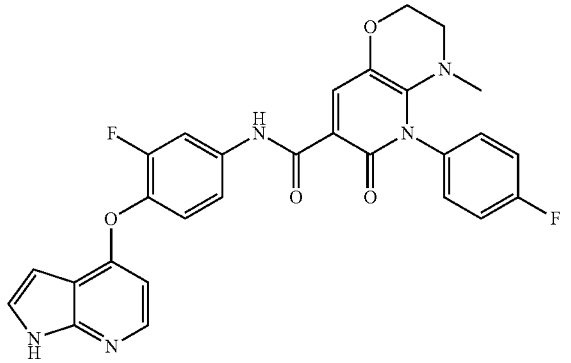 [SMILES: CN1CCOc2cc(C(=O)Nc3ccc(Oc4ccnc5[nH]ccc45)c(F)c3)c(=O)n(-c3ccc(F)cc3)c21] | $^1$H NMR (300 MHz, DMSO-$d_6$) δ 11.71 (s, 1H), 10.04 (s, 1H), 8.04 (d, 1H), 7.91 (d, 1H), 7.47 (d, 1H), 7.36~7.38 (m, 1H), 7.23~7.27 (m, 6H), 6.36 (d, 1H), 6.23 (s, 1H), 4.16 (t, 2H), 3.46 (t, 2H), 2.80 (s, 3H); ESI-MS: m/z 531 (M + H). |
| Embodiment 42 | 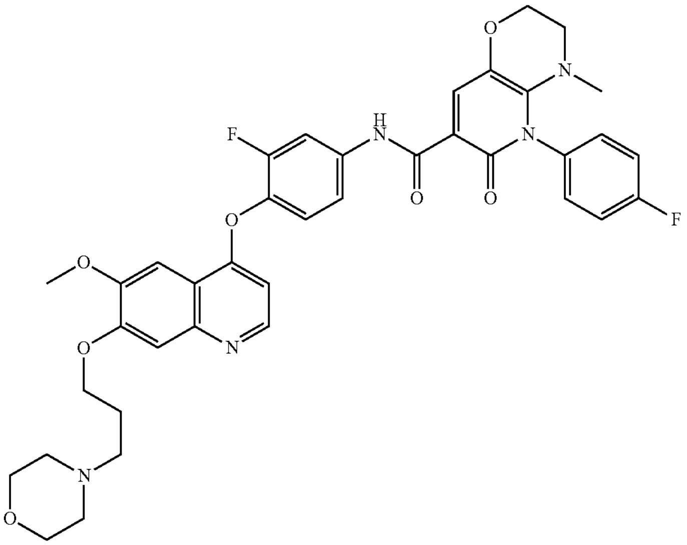 [SMILES: COc1cc2c(Oc3ccc(NC(=O)c4cc5c(n(-c6ccc(F)cc6)c4=O)N(C)CCO5)cc3F)ccnc2cc1OCCCN1CCOCC1] | $^1$H NMR (300 MHz, DMSO-$d_6$) δ 10.07 (s, 1H), 8.46 (d, 1H), 7.97 (d, 1H), 7.52 (d, 2H), 7.38~7.44 (m, 3H), 7.23~7.26 (m, 4H), 6.44 (s, 1H), 4.18 (m, 4H), 3.94 (s, 3H), 3.61 (s, 4H), 3.45 (m, 2H), 2.80 (s, 3H), 2.49 (m, 4H), 2.47 (m, 2H), 2.02 (s, 2H); ESI-MS: m/z 714 (M + H). |

Embodiment 43

N-(4-(2-aminopyridine-4-oxy)-3-fluorophenyl)-5-(4-fluorophenyl)-1-methyl-6-oxo-2,3,5,6-tetrahydro-1H-pyrido[2,3-b][1,4]oxazine-7-formamide, having the structural formula below:

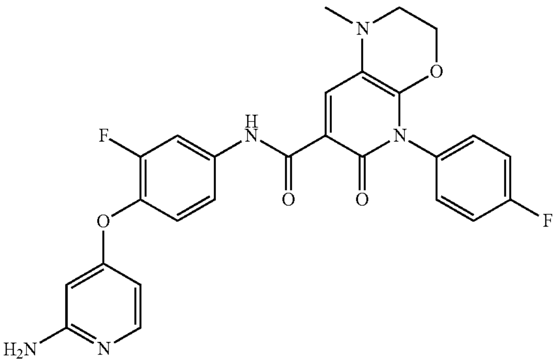 [SMILES: CN1CCOc2c1cc(C(=O)Nc1ccc(Oc3ccnc(N)c3)c(F)c1)c(=O)n2-c1ccc(F)cc1]

Step 1. Preparation of methyl 6-(2-methoxy-2-carbonylethoxy)-5-nitronicotinate, through the reaction equation below:

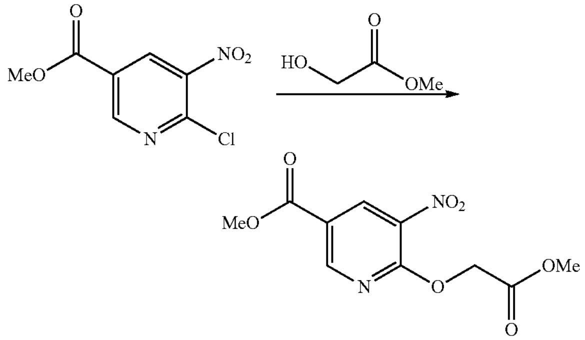

Methyl 6-chloro-5-nitronitronicotinate (5.0 g, 23 mmol) was dissolved in a mixed solvent of tetrahydrofuran (60 mL) and DMF (30 mL), methyl glycolate (2.1 mL, 27.7 mmol) and potassium carbonate (9.57 g, 69.3 mmol) were added, and the mixture was stirred for 16 hrs at 40° C. TLC showed that the raw materials were not reacted completely, methyl glycolate (1 mL) and potassium carbonate (2 g) was additionally added, and the mixture was continuously stirred for 8 hrs at 40° C. Tetrahydrofuran was evaporated under reduced pressure, and the residue was added to water (40 mL), extracted with ethyl acetate multiple times, the organic phase was washed with water and saturated brine, and dried with anhydrous sodium sulfate, and the solvent was evaporated under reduced pressure, to obtain the compound (5.1 g, 82%) as a brown solid. $^1$H NMR (300 MHz, $CDCl_3$) δ 8.95 (d, 1H), 8.90 (d, 1H), 5.15 (s, 2H), 3.97 (s, 3H), 3.78 (s, 3H).

Step 3. Preparation of methyl 2-oxo-2,3-dihydro-1H-pyrido[2,3-b][1,4]oxazine-7-formate, through the reaction equation below:

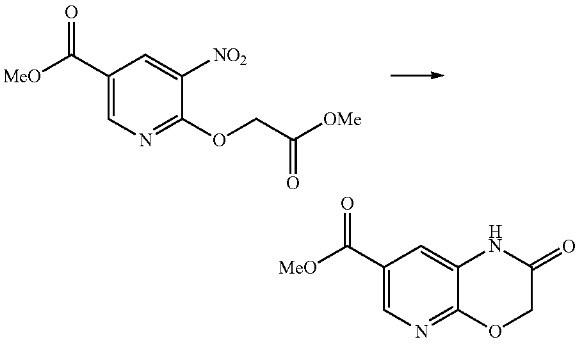

Under protection of nitrogen, methyl 6-(2-methoxy-2-carbonylethoxy)-5-nitronicotinate (5.0 g, 18.5 mmol) and iron powder (4.13 g, 74.0 mmol) were added to glacial acetic acid (75 mL), and the mixture was heated to 70° C. and stirred for 2 hrs. Glacial acetic acid was evaporated under reduced pressure, the residue was added to water (50 mL), and the pH value of the solution was adjusted to 6 with $K_3PO_4.3H_2O$. The mixture was filtered, the resulting filtrate was extracted with ethyl acetate, and the resulting solid was immersed in methanol and washed. The washing liquid was combined with the extract obtained previously, and the organic solvent was evaporated under reduced pressure, to obtain a yellow solid (2.4 g, 62%).

Step 4. Preparation of methyl 1-methyl-2-oxo-2,3-dihydro-1H-pyrido[2,3-b][1,4]oxazine-7-formate, through the reaction equation below:

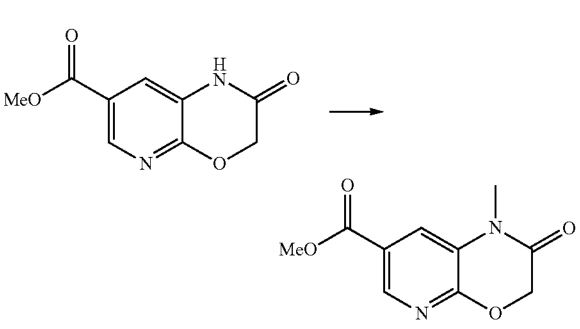

Under protection of nitrogen, raw material (1.0 g, 4.8 mmol) was added to a solution of NaH (55%, 210 mg, 4.8 mmol) in DMF (5 mL), the mixture was stirred for 30 min, iodomethane (0.36 mL, 5.76 mmol) was added dropwise, and the mixture was stirred for 18 hrs at room temperature. Water (9 mL) was added for quenching, and the mixture was stirred for 10 min, and then stood still. The solid was precipitated, filtered, and the resulting solid was dried, to obtain a yellow solid (600 mg, 56%). $^1$H NMR (300 MHz, DMSO-$d_6$) δ 8.40 (s, 1H), 7.81 (s, 1H), 4.96 (s, 2H), 3.86 (s, 3H), 3.29 (s, 3H).

Step 5. Preparation of methyl 1-methyl-2,3-dihydro-1H-pyrido[2,3-b][1,4]oxazine-7-formate, through the reaction equation below:

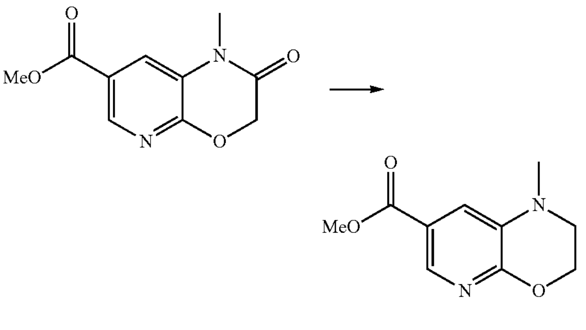

Under protection of nitrogen, methyl 1-methyl-2-oxo-2,3-dihydro-1H-pyrido[2,3-b][1,4]oxazine-7-formate (2.0 g, 9 mmol) was dissolved in anhydrous tetrahydrofuran (50 mL), the solution was cooled to 0° C., a tetrahydrofuran solution (2.0 M, 18 mL, 36 mmol) of borane-methyl sulfide complex was slowly added to the system, the system was heated to 40° C. and stirred for 2.5 hrs. 1N hydrochloric acid (40 mL) was added, the mixture was heated to reflux and stirred for 1 hr, and then cooled to room temperature, and sodium bicarbonate powder was carefully added portionwise, to adjust the pH value of the system to be greater than 7. The mixture was extracted with ethyl acetate repeatedly, the organic phase was washed with saturated brine, and then dried with anhydrous sodium sulfate, and ethyl acetate was evaporated under reduced pressure. The residue was subjected to silica gel column chromatography, to obtain a bright yellow solid (1.4 g, 75%). $^1$H NMR (300 MHz, $CDCl_3$) δ 8.24 (s, 1H), 7.41 (s, 1H), 4.49 (t, 2H), 3.88 (s, 3H), 3.29 (t, 2H), 2.93 (s, 3H).

Step 6. Preparation of methyl 1-methyl-6-oxo-2,3,5,6-tetrahydro-1H-pyrido[2,3-b][1,4]oxazine-7-formate

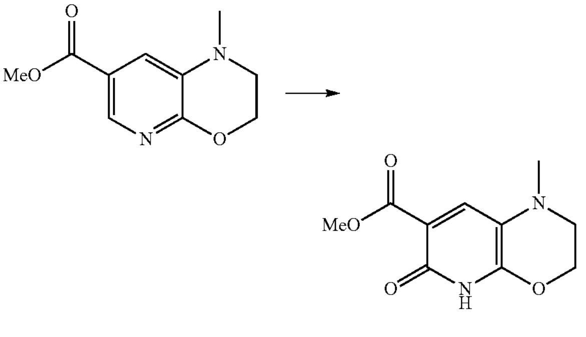

Methyl 1-methyl-2,3-dihydro-1H-pyrido[2,3-b][1,4]oxazine-7-formate (1.0 g, 4.8 mmol) was dissolved in dichloromethane (50 mL), m-chloroperoxybenzoic acid (85%, 1.21 g) was added, and the mixture was stirred for 16 at room temperature. The raw materials were not reacted completely, m-chloroperoxybenzoic acid (200 mg, 1 mmol) was additionally added, and the mixture was continuously stirred for 5 hrs at room temperature. After the reaction was completed, sodium bicarbonate powder (504 mg, 6 mmol) was added, and after stirring for a while, the solid was filtered off, and the solvent was evaporated under reduced pressure, to obtain a compound (1.1 g) as a yellow solid. Under protection of nitrogen, the yellow compound was added to acetic anhydride (20 mL), and the mixture was heated to reflux and stirred for 4 hrs. The solvent was evaporated under reduced pressure, to obtain a black oil (1.5 g). The oil was dissolved in methanol (20 mL), anhydrous sodium carbonate (1.93 g, 18.25 mmol) was added, and the mixture was stirred for 16 hrs at room temperature. Methanol was evaporated under reduced pressure, and the residue was subjected to silica gel column chromatography, to obtain the target compound (200 mg, 19%).

Step 7. Preparation of methyl 5-(4-fluorophenyl)-1-methyl-6-oxo-2,3,5,6-tetrahydro-1H-pyrido[2,3-b][1,4]oxazine-7-formate

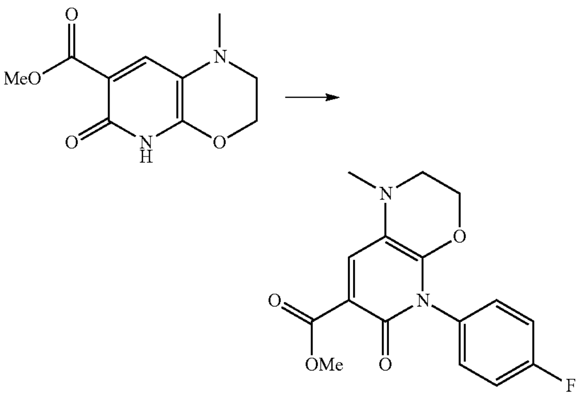

Methyl 1-methyl-6-oxo-2,3,5,6-tetrahydro-1H-pyrido[2,3-b][1,4]oxazine-7-formate (100 mg, 0.45 mmol) was dissolved in anhydrous acetonitrile (5 mL), and 4-fluorophenylboronic acid (125 mg, 0.90 mmol), cuprous iodide (21 mg, 0.11 mmol), 2,2,6,6-tetramethylpiperidine nitrogen oxide (87 mg, 0.56 mmol), pyridine (0.3 mL) and activated molecular sieve powder (100 mg) were added. An anhydrous calcium chloride drying tube was added at the bottle neck, and the mixture was heated to 40° C. and stirred for 60 hrs. The reaction mixture was directly concentrated under reduced pressure, and the residue was subjected to silica gel column chromatography, to obtain a white solid (45 mg, 29%).

Step 8. Preparation of 5-(4-fluorophenyl)-1-methyl-6-oxo-2,3,5,6-tetrahydro-1H-pyrido[2,3-b][1,4]oxazine-7-formic acid

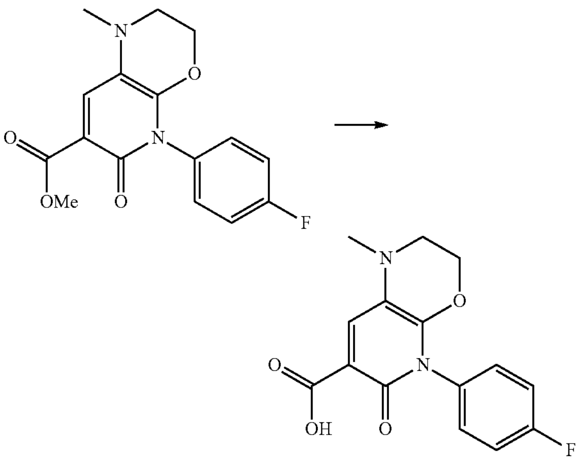

Methyl 5-(4-fluorophenyl)-1-methyl-6-oxo-2,3,5,6-tetrahydro-1H-pyrido[2,3-b][1,4]oxazine-7-formate (100 mg, 0.31 mmol) was dissolved in tetrahydrofuran (5 mL), an aqueous solution (5 mL) of $LiOH.H_2O$ (100 mg, 2.3 mmol) was added, and the mixture was heated to 40° C. and stirred overnight. After the reaction was completed, the reaction solution was cooled with ice water, and 3N hydrochloric acid was added dropwise to acidify the mixture to a pH value of 4 to 5. The mixture was extracted with ethyl acetate, and the extracts were combined, dried with anhydrous sodium sulfate, and concentrated under reduced pressure. The residue was subjected to silica gel column chromatography for purification, to obtain the target product (69 mg, 72%). ESI-MS: m/z 305 (M+H).

Step 9. N-(4-(2-aminopyridine-4-oxy)-3-fluorophenyl)-5-(4-fluorophenyl)-1-methyl-6-oxo-2,3,5,6-tetrahydro-1H-pyrido[2,3-b][1,4]oxazine-7-formamide, having the structural formula below:

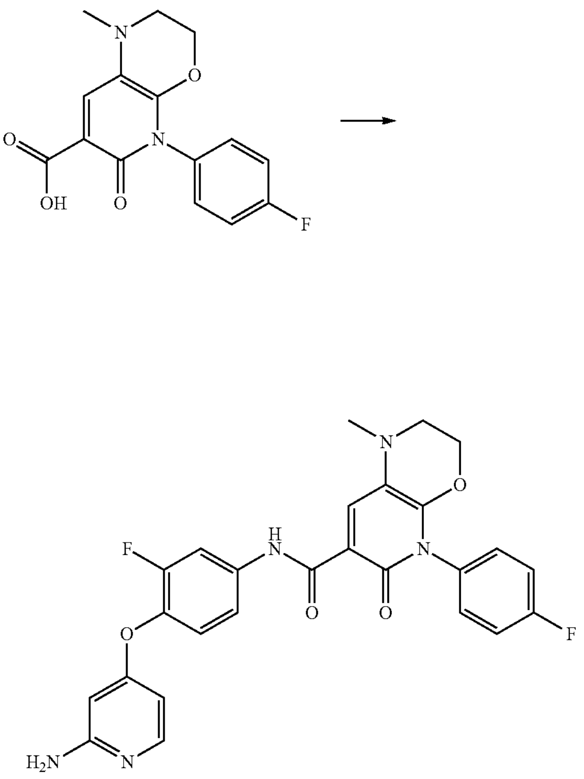

Under protection of nitrogen, 5-(4-fluorophenyl)-1-methyl-6-oxo-2,3,5,6-tetrahydro-1H-pyrido[2,3-b][1,4]oxazine-7-formic acid (45 mg, 0.15 mmol) was dissolved in anhydrous DMF (2 mL), diisopropylethyl amine (38 mg, 0.30 mmol) and HATU (56 mg, 0.15 mmol) were added, and the mixture was stirred for 15 min at room temperature. 3-fluoro-4-(2-aminopyridine-4-oxy)aniline (33 mg, 0.15 mmol) was added, and the mixture was heated to 40° C. and stirred overnight. After the reaction was completed, the system was added with water, and extracted with ethyl acetate. The extracts were combined, dried with anhydrous sodium sulfate, and concentrated under reduced pressure. The residue was subjected to silica gel column chromatography for purification, to obtain a white solid (39 mg, 51%). ESI-MS: m/z 506 (M+H).

By adopting methods similar to that in Embodiment 43, the following compounds can be prepared:
| Serial Number | Structure | Structure Characterization |
|---|---|---|
| Embodiment 44 | 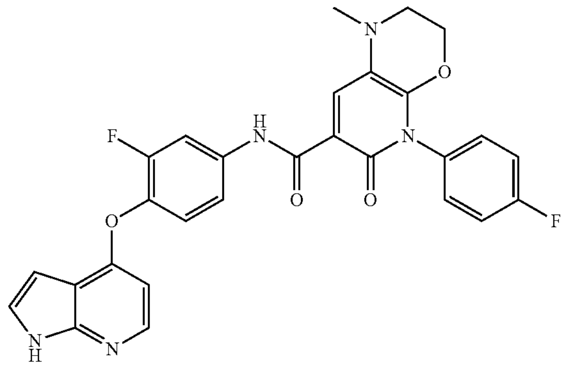 [SMILES: CN1CCOc2c1cc(C(=O)Nc1ccc(Oc3ccnc4[nH]ccc34)c(F)c1)c(=O)n2-c1ccc(F)cc1] | ESI-MS: m/z 531 (M + H). |
| Embodiment 45 | 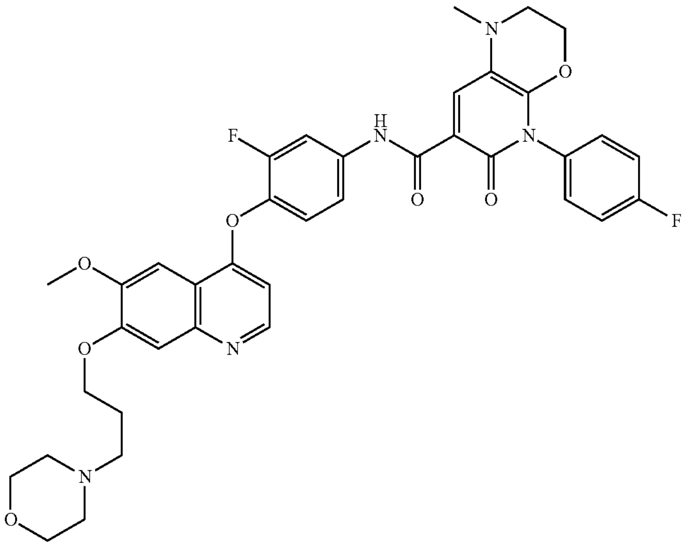 [SMILES: COc1cc2c(Oc3ccc(NC(=O)c4cc5c(n(-c6ccc(F)cc6)c4=O)OCCN5C)cc3F)ccnc2cc1OCCCN1CCOCC1] | ESI-MS: m/z 714 (M + H). |
| Embodiment 46 | 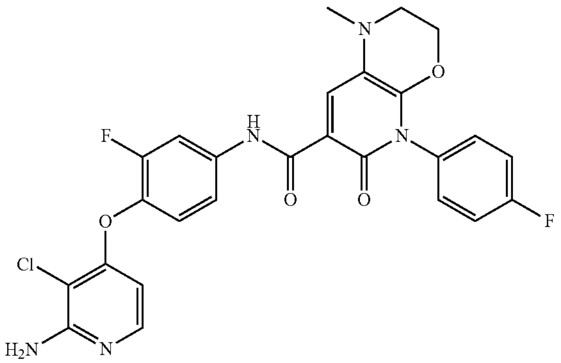 [SMILES: CN1CCOc2c1cc(C(=O)Nc1ccc(Oc3ccnc(N)c3Cl)c(F)c1)c(=O)n2-c1ccc(F)cc1] | ESI-MS: m/z 540 (M + H). |

-continued

| Serial Number | Structure | Structure Characterization |
| --- | --- | --- |
| Embodiment 47 | 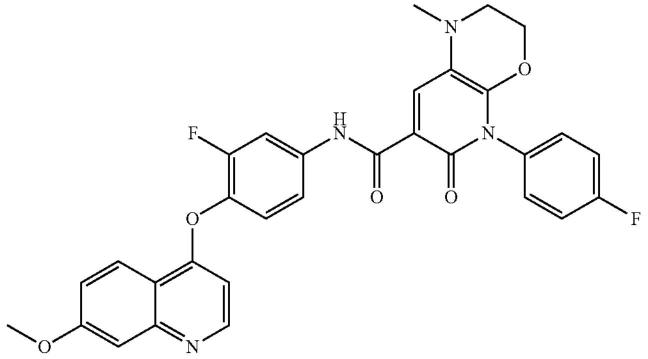 [SMILES: COc1ccc2c(Oc3ccc(NC(=O)c4cc5c(n(-c6ccc(F)cc6)c4=O)OCCN5C)cc3F)ccnc2c1] | ESI-MS: m/z 571 (M + H). |

Embodiment 48

N-(4-(2-aminopyridine-4-oxy)-3-fluorophenyl)-7-ethoxy-4-(4-fluorophenyl)-5-oxo-4,5-dihydro-thiazolo[5,4-b]pyridine-6-formamide, having the structural formula below:

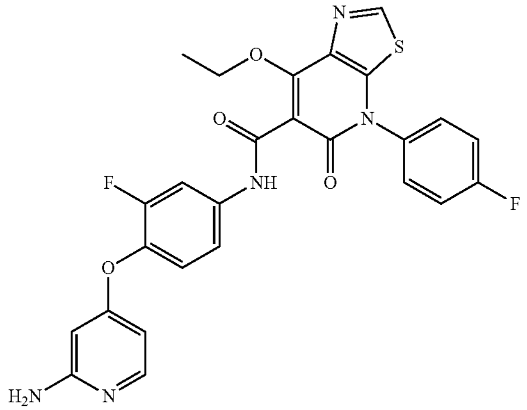 [SMILES: CCOc1c(C(=O)Nc2ccc(Oc3ccnc(N)c3)c(F)c2)c(=O)n(-c2ccc(F)cc2)c2scnc12]

Step 1. Preparation of methyl 7-ethoxy-4-(4-fluorophenyl)-5-oxo-4,5-dihydro-thiazolo[5,4-b]pyridine-6-formate, through the reaction equation below:

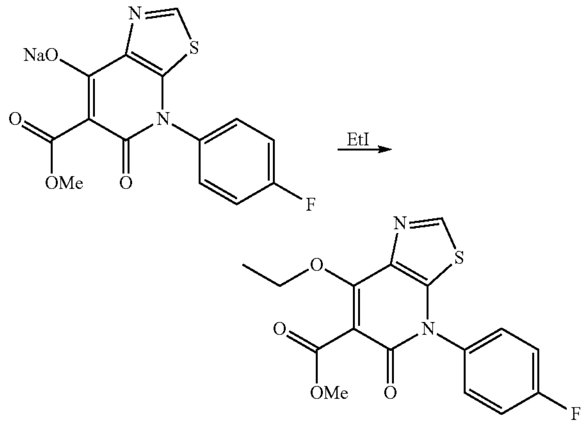

4-(4-fluorophenyl)-6-(methoxycarbonyl)-5-oxo-4,5-dihydro-thiazolo[5,4-b]pyridine-7-oxy sodium salt was obtained following the preparation method in Embodiment 1. The compound (3.42 g, 10 mmol) was suspended in DMF (20 mL), iodoethane (1.87 g, 12 mmol) was added, and the mixture was stirred overnight at room temperature. The solvent was evaporated under reduced pressure, and the residue was dissolved in dichloromethane, washed with water and saturated brine, concentrated, and subjected to column chromatography, to obtain the target product (1.82 g, 52%). ESI-MS: m/z 349.

Step 2. Preparation of 7-ethoxy-4-(4-fluorophenyl)-5-oxo-4,5-dihydro-thiazolo[5,4-b]pyridine-6-formic acid, through the reaction equation below:

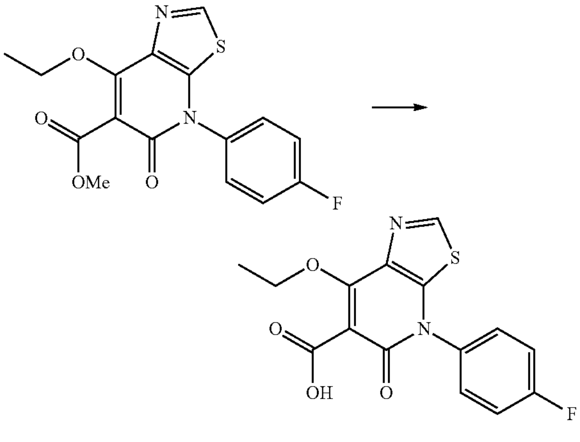

Methyl 7-ethoxy-4-(4-fluorophenyl)-5-oxo-4,5-dihydro-thiazolo[5,4-b]pyridine-6-formate (560 mg, 1.6 mmol) was suspended in a mixed solvent of tetrahydrofuran (3.5 mL) and water (3.5 mL), $LiOH.H_2O$ (136 mg, 3.24 mmol) was added, and the mixture was stirred for half an hour at room temperature. The reaction mixture was concentrated under reduced pressure, and the residue was acidified with 1N hydrochloric acid to a pH value of 5, and filtered, to obtain a yellow solid (540 mg, ~100%). ESI-MS: m/z 335.

Step 3. N-(4-(2-aminopyridine-4-oxy)-3-fluorophenyl)-7-ethoxy-4-(4-fluorophenyl)-5-oxo-4,5-dihydro-thiazolo[5,4-b]pyridine-6-formamide, through the reaction equation below:

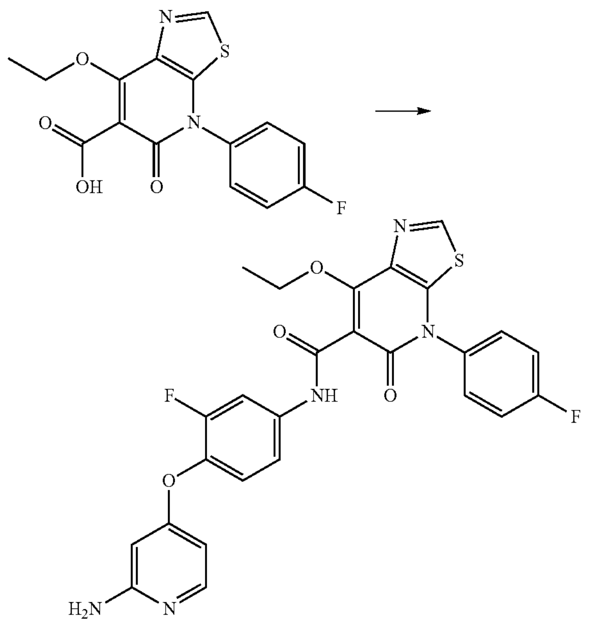

Under protection of nitrogen, 7-ethoxy-4-(4-fluorophenyl)-5-oxo-4,5-dihydro-thiazolo[5,4-b]pyridine-6-formic acid (50 mg, 1.5 mmol) was dissolved in anhydrous DMF (2 mL), HATU (57 mg, 0.15 mmol) and diisopropylethyl amine (39 mg, 0.30 mmol) were added, and the mixture was stirred for 15 min at room temperature. 3-fluoro-4-(2-aminopyridine-4-oxy)aniline (33 mg, 0.15 mmol) was added, and the mixture was stirred overnight at room temperature. TLC showed that the reaction was completed, water (5 mL) was added, and the mixture was extracted with ethyl acetate. The extracts were combined, and washed with saturated brine, dried with anhydrous sodium sulfate, and concentrated under reduced pressure. The crude product was separated by using a silica gel preparation plate, to obtain a white solid (29 mg, 36%). ESI-MS: m/z 536 (M+H); $^1$H NMR (300 MHz, DMSO-$d_6$) δ 10.64 (s, 1H), 8.92 (s, 1H), 7.85 (dd, 1H), 7.78 (d, 1H), 7.62-7.57 (m, 2H), 7.55-7.41 (m, 3H), 7.29 (t, 1H), 6.17 (dd, 1H), 5.95 (br, 2H), 5.77 (s, 1H), 4.83 (q, 2H), 1.33 (t, 3H).

By adopting methods similar to that in Embodiment 48, the following compounds can be prepared:

| Serial Number | Structural Formula | Structure Characterization |
| --- | --- | --- |
| Embodiment 49 | 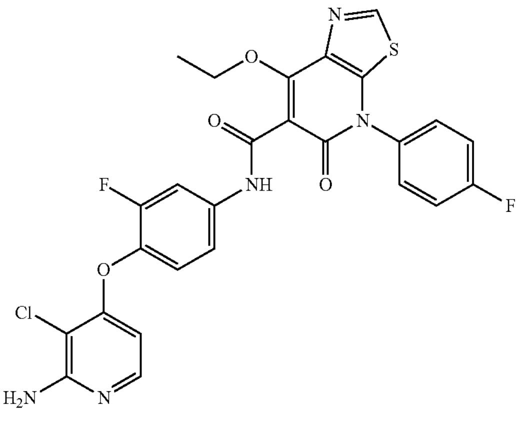 [SMILES: CCOc1c(C(=O)Nc2ccc(Oc3ccnc(N)c3Cl)c(F)c2)c(=O)n(-c2ccc(F)cc2)c2scnc12] | ESI-MS: m/z 570 (M + H); $^1$H NMR (300 MHz, DMSO-$d_6$) δ 10.64 (s, 1H), 8.92 (s, 1H), 7.86 (dd, 1H), 7.73 (d, 1H), 7.62-7.44 (m, 2H), 7.49-7.43 (m, 3H), 7.31 (t, J = 10.5, 1H), 6.40 (br, 2H), 5.94 (d, 1H), 4.83 (m, 2H), 4.05 (m, 2H), 1.33 (s, 3H). |
| Embodiment 50 | 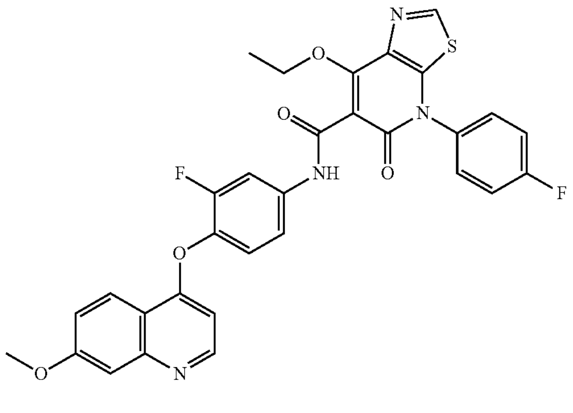 [SMILES: CCOc1c(C(=O)Nc2ccc(Oc3ccnc4cc(OC)ccc34)c(F)c2)c(=O)n(-c2ccc(F)cc2)c2scnc12] | ESI-MS: m/z 601 (M + H); $^1$H NMR (300 MHz, DMSO-$d_6$) δ 10.69 (s, 1H), 8.92 (s, 1H), 8.59 (d, 1H), 8.23 (d, 1H), 7.92 (dd, 1H), 7.31-7.28 (m, 7H), 7.29 (dd, 1H), 6.49 (d, 1H), 4.84 (p, 2H), 3.93 (s, 3H), 1.35 (t, 3H). |

-continued

| Serial Number | Structural Formula | Structure Characterization |
|---|---|---|
| Embodiment 51 | 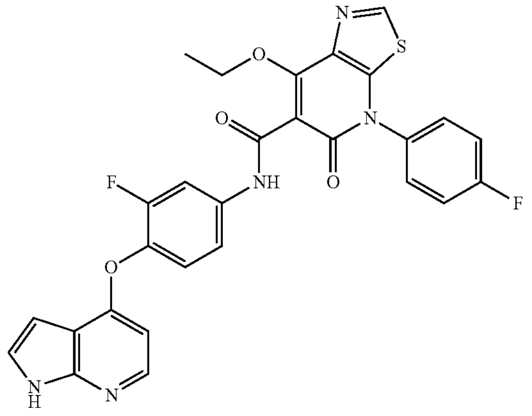 [SMILES: CCOc1c(C(=O)Nc2ccc(Oc3ccnc4[nH]ccc34)c(F)c2)c(=O)n(-c2ccc(F)cc2)c2scnc12] | ESI-MS: m/z 560 (M + H); $^1$H NMR (300 MHz, DMSO-$d_6$) δ 13.27 (s, 1H), 10.69 (s, 1H), 8.92 (s, 1H), 8.23 (d, J = 5.1 Hz, 1H), 7.93 (d, J = 11.7 Hz, 1H), 7.63-7.49 (m, 2H), 7.49-7.39 (m, 4H), 6.21 (d, J = 5.1 Hz, 1H), 4.85 (q, 2H, J = 6.9 Hz), 2.61 (s, 3H), 1.34 (t, 3H, J = 7.2 Hz). |

Embodiment 52

N-(4-(2-aminopyridine-4-oxy)-3-fluorophenyl)-7-(dimethylamino)-4-(4-fluorophenyl)-5-oxo-4,5-dihydro-thiazolo [5,4-b]pyridine-6-formamide, having the structural formula below:

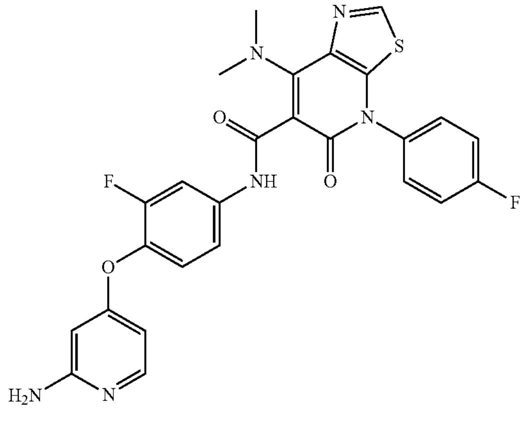 [SMILES: CN(C)c1c(C(=O)Nc2ccc(Oc3ccnc(N)c3)c(F)c2)c(=O)n(-c2ccc(F)cc2)c2scnc12]

Step 1. Preparation of methyl 7-(dimethylamino)-4-(4-fluorophenyl)-5-oxo-4,5-dihydro-thiazolo[5,4-b]pyridine-6-formate, through the reaction equations below:

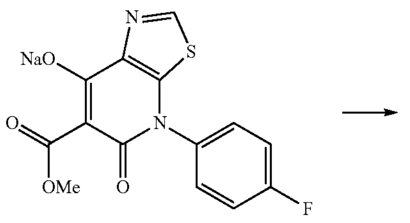

-continued

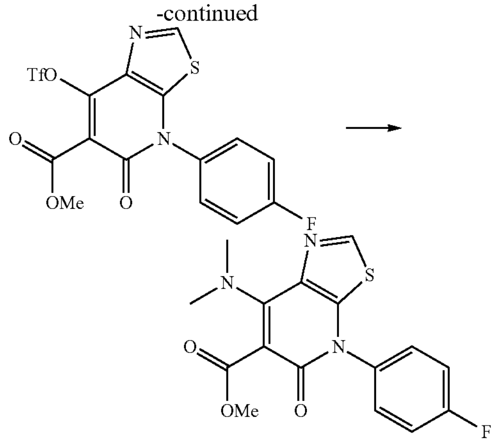

4-(4-fluorophenyl)-6-(methoxycarbonyl)-5-oxo-4,5-dihydro-thiazolo[5,4-b]pyridine-7-oxy sodium salt was obtained following the preparation method in Embodiment 1. The compound (3.42 g, 10 mmol) was suspended in DMF, $PhNTf_2$ (3.9 g, 12 mmol) was added, and the mixture was stirred overnight at room temperature. A solution (2M, 10 mL) of dimethylamine in tetrahydrofuran was added, and the mixture was stirred overnight at room temperature. The solvent was evaporated under reduced pressure, and the residue was dissolved in dichloromethane, washed with water and saturated brine, dried, concentrated, and subjected to column chromatography, to obtain a light yellow solid (1.5 g, 43%). ESI-MS: m/z 348 (M+H).

Step 2. Preparation of 7-(dimethylamino)-4-(4-fluorophenyl)-5-oxo-4,5-dihydro-thiazolo[5,4-b]pyridine-6-formic acid, through the reaction equation below:

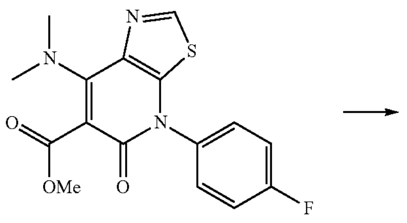

-continued

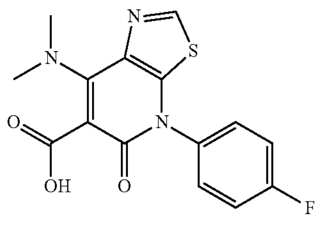

Methyl 7-(dimethylamino)-4-(4-fluorophenyl)-5-oxo-4,5-dihydro-thiazolo[5,4-b]pyridine-6-formate (348 mg, 1.0 mmol) was suspended in a mixed solvent of tetrahydrofuran (3 mL) and water (3 mL), $LiOH.H_2O$ (126 mg, 3.0 mmol) was added, and the mixture was stirred for 4 hrs at room temperature. The reaction mixture was concentrated under reduced pressure, and the residue was acidified with 1N hydrochloric acid to a pH value of 6, and filtered, to obtain a yellow solid (280 mg, 84%). ESI-MS: m/z 334.

Step 3. N-(4-(2-aminopyridine-4-oxy)-3-fluorophenyl)-7-(dimethylamino)-4-(4-fluorophenyl)-5-oxo-4,5-dihydro-thiazolo[5,4-b]pyridine-6-formamide, through the reaction equation below:

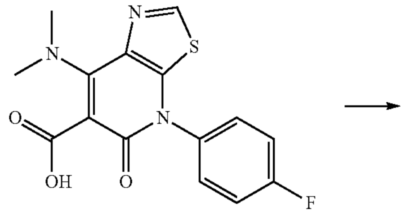

-continued

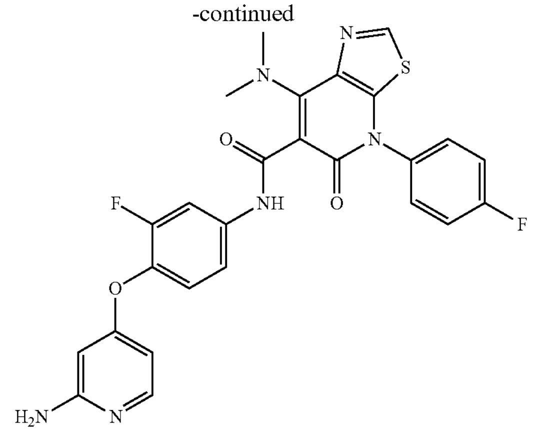

Under protection of nitrogen, 7-(dimethylamino)-4-(4-fluorophenyl)-5-oxo-4,5-dihydro-thiazolo[5,4-b]pyridine-6-formic acid (50 mg, 1.5 mmol) was dissolved in anhydrous DMF (2 mL), HATU (57 mg, 0.15 mmol) and diisopropylethyl amine (39 mg, 0.30 mmol) were added, and the mixture was stirred for 15 min at room temperature. 3-fluoro-4-(2-aminopyridine-4-oxy)aniline (33 mg, 0.15 mmol) was added, and the mixture was stirred overnight at room temperature. TLC showed that the reaction was completed, water (20 mL) was added, and the mixture was extracted with ethyl acetate. The extracts were combined, and washed with saturated brine, dried with anhydrous sodium sulfate, and concentrated under reduced pressure. The crude product was separated by using a silica gel preparation plate, to obtain a white solid (49 mg, 61%). ESI-MS: m/z 535 (M+H); $^1H$ NMR (300 MHz, DMSO-$d_6$) δ 10.67 (s, 1H), 8.80 (s, 1H), 7.89 (dd, 1H, J=13.8, 2.4 Hz), 7.77 (d, 1H, J=6.0 Hz), 7.49-7.44 (m, 2H), 7.45-7.41 (m, 3H), 7.27 (t, 1H, J=11.5 Hz), 6.16 (dd, 1H, J=5.4, 2.1 Hz), 5.98 (br, 2H), 5.76 (s, 1H), 3.29 (s, 6H).

By adopting methods similar to that in Embodiment 52, the following compounds can be prepared:

| Serial Number | Structural Formula | Structure Characterization |
|---|---|---|
| Embodiment 53 | 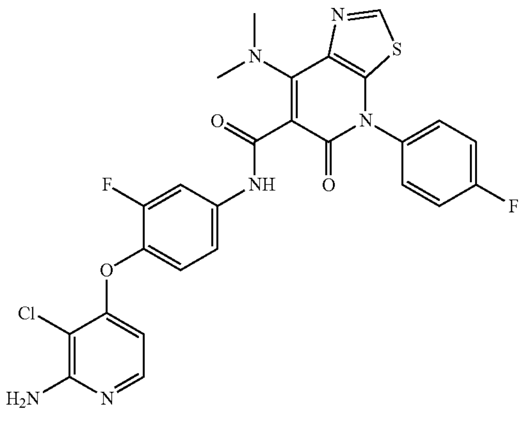 [SMILES: CN(C)c1c(C(=O)Nc2ccc(Oc3ccnc(N)c3Cl)c(F)c2)c(=O)n(-c2ccc(F)cc2)c2scnc12] | ESI-MS: m/z 569 (M + H); $^1H$ NMR (300 MHz, DMSO-$d_6$) δ 10.71 (s, 1H), 8.80 (s, 1H), 7.89 (dd, 1H, J = 13.3 Hz, 2.7 Hz), 7.73 (d, 1H, J = 5.7 Hz), 7.61-7.44 (m, 2H), 7.49-7.41 (m, 3H), 7.29 (t, 1H, J = 11.5 Hz), 6.47 (br, 2H), 5.92 (d, 1H, J = 6.0 Hz), 3.29 (s, 6H). |

-continued
| Serial Number | Structural Formula | Structure Characterization |
|---|---|---|
| Embodiment 54 | 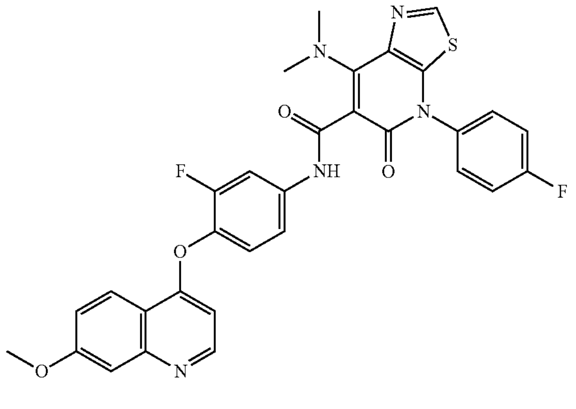 [SMILES: COc1ccc2c(Oc3ccc(NC(=O)c4c(N(C)C)c5ncsc5n(-c5ccc(F)cc5)c4=O)cc3F)ccnc2c1] | ESI-MS: m/z 601 (M + H); $^1$H NMR (300 MHz, DMSO-$d_6$) δ 10.75 (s, 1H), 8.81 (s, 1H), 8.59 (d, 1H, J = 5.1 Hz), 8.22 (d, 1H, J = 9.0 Hz), 7.98 (d, 1H, J = 13.2 Hz), 7.61-7.41 (m, 7H), 7.28 (dd, 1H, J = 11.1, 1.8 Hz), 6.46 (d, 1H, J = 5.1 Hz), 3.93 (s, 3H), 3.30 (s, 6H). |
| Embodiment 55 | 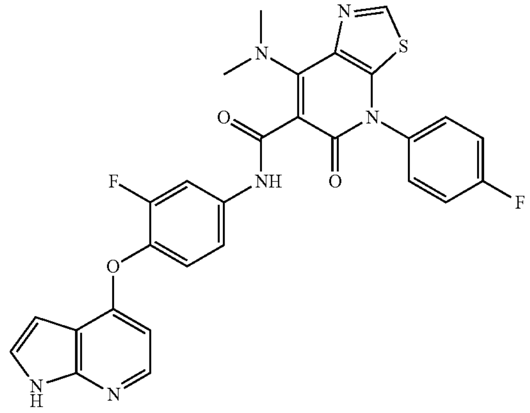 [SMILES: CN(C)c1c(C(=O)Nc2ccc(Oc3ccnc4[nH]ccc34)c(F)c2)c(=O)n(-c2ccc(F)cc2)c2scnc12] | ESI-MS: m/z 559 (M + H); $^1$H NMR (300 MHz, DMSO-$d_6$) δ 13.27 (s, 1H), 10.75 (s, 1H), 8.80 (s, 1H), 8.23 (d, 1H, J = 5.7 Hz), 7.96 (dd, 1H, J = 13.2, 1.5 Hz), 7.61-7.44 (m, 2H), 7.49-7.41 (m, 4H), 6.19 (d, 1H, J = 6.3 Hz), 3.29 (s, 6H), 2.60 (s, 3H). |
| Embodiment 56 | 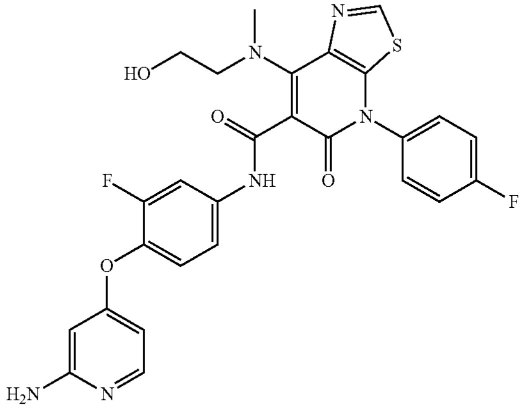 [SMILES: CN(CCO)c1c(C(=O)Nc2ccc(Oc3ccnc(N)c3)c(F)c2)c(=O)n(-c2ccc(F)cc2)c2scnc12] | ESI-MS: m/z 564 (M + H); $^1$H NMR (300 MHz, DMSO-$d_6$) δ 10.71 (s, 1H), 8.82 (s, 1H), 7.89 (dd, 1H, J = 13.2, 2.1 Hz), 7.79 (d, 1H, J = 5.7 Hz), 7.51-7.46 (m, 2H), 7.45-7.41 (m, 3H), 7.29 (t, 1H), 6.21 (dd, 1H, J = 5.7, 2.1 Hz), 6.11 (br, 2H), 5.79 (s, 1H), 4.81 (t, 1H), 4.05 (m, 2H), 3.71 (m, 2H), 3.13 (s, 3H). |

-continued

| Serial Number | Structural Formula | Structure Characterization |
|---|---|---|
| Embodiment 57 | 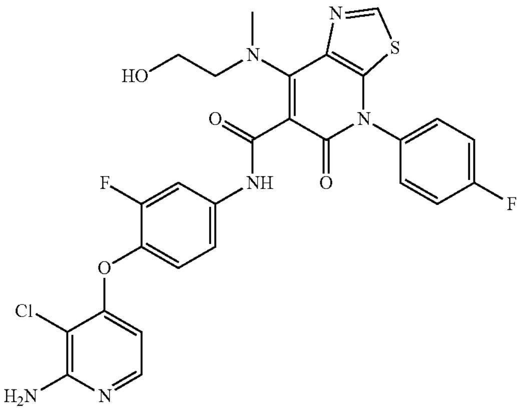 [SMILES: CN(CCO)c1c(C(=O)Nc2ccc(Oc3ccnc(N)c3Cl)c(F)c2)c(=O)n(-c2ccc(F)cc2)c2scnc12] | ESI-MS: m/z 599 (M + H); $^{1}$H NMR (300 MHz, DMSO-d$_6$) δ 10.73 (s, 1H), 8.82 (s, 1H), 7.89 (dd, 1H, J = 13.5, 2.7 Hz), 7.73 (d, 1H, J = 5.4 Hz), 7.61-7.44 (m, 2H), 7.49-7.41 (m, 3H), 7.31 (t, 1H, J = 11.5), 6.51 (br, 2H), 5.94 (d, 1H, J = 5.4 Hz), 4.05 (m, 2H), 4.05 (m, 2H), 3.40 (m, 2H), 3.12 (s, 3H). |
| Embodiment 58 | 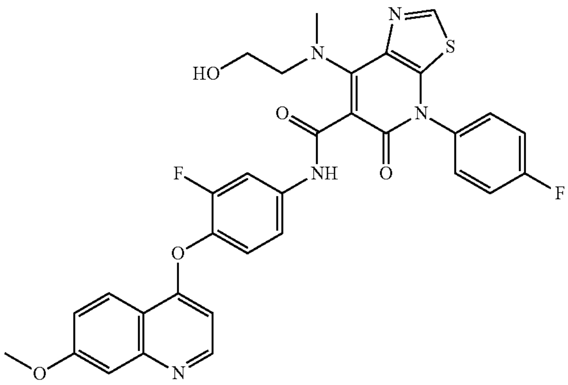 [SMILES: COc1ccc2c(Oc3ccc(NC(=O)c4c(N(C)CCO)c5ncsc5n(-c5ccc(F)cc5)c4=O)cc3F)ccnc2c1] | ESI-MS: m/z 629 (M + H); $^{1}$H NMR (300 MHz, DMSO-d$_6$) δ 10.76 (s, 1H), 8.83 (s, 1H), 8.59 (d, 1H, J = 5.1 Hz), 8.22 (d, 1H, J = 9.0 Hz), 7.99 (dd, 1H, J = 13.2, 1.8 Hz), 7.61-7.41 (m, 7H), 7.29 (dd, 1H, J = 11.2, 1.8 Hz), 6.47 (d, 1H, J = 5.4 Hz), 4.82 (t, 3H), 4.06 (m, 2H), 3.97 (s, 3H), 3.71 (m, 2H), 3.14 (s, 3H). |
| Embodiment 59 | 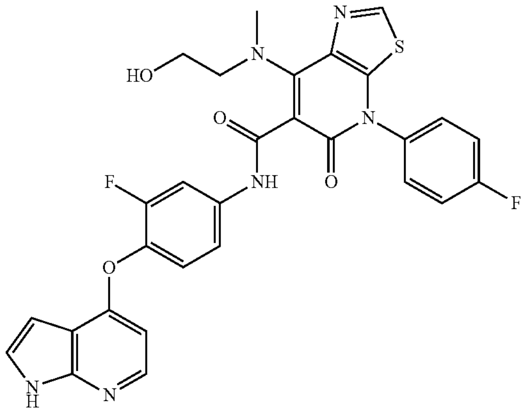 [SMILES: CN(CCO)c1c(C(=O)Nc2ccc(Oc3ccnc4[nH]ccc34)c(F)c2)c(=O)n(-c2ccc(F)cc2)c2scnc12] | ESI-MS: m/z 589 (M + H); $^{1}$H NMR (300 MHz, DMSO-d$_6$) δ 13.27 (s, 1H), 10.77 (s, 1H), 8.82 (s, 1H), 8.23 (d, 1H, J = 5.4 Hz), 7.96 (dd, 1H, J = 13.2 Hz, 2.4 Hz), 7.62-7.49 (m, 2H), 7.49-7.41 (m, 4H), 6.19 (d, 1H, J = 5.1 Hz), 4.81 (br, 1H), 4.06 (m, 2H), 3.71 (m, 2H), 3.13 (s, 3H), 2.60 (s, 3H). |

Biological Test Embodiment 1

Determination of Inhibitory Activity of Compound to c-Met Kinases

The inhibitory activity of the compound to c-Met kinases in vitro is determined through the following method.

The method described below can be used to determine the inhibiting capacity of the compound of the present invention on the c-Met kinase activity, and the inhibiting capacity is represented by $IC_{50}$. The half inhibitory concentration $IC_{50}$ (a concentration of the compound for inhibiting the enzyme activity to 50%) of the compound is obtained by: mixing and reacting a certain amount of kinase with a specific substrate and different concentrations of test compound, and then labeling the substrate with an anti-phosphotyrosine antibody and a radioisotope labeled antibody, and finally quantitatively determining the c-Met kinase activity through a time-resolved fluorescence method.

The specific experiment is implemented by using a Z'-LYTE kinase assay kit (Invitrogen, item PV4122). First, the test compound is diluted into 8 different concentrations from 100 μM at an interval of 1:5 with an ATP solution (Invitrogen, item PV3227); 5 μL 2×c-Met (Invitrogen, item PV3143) and 2×Z'-LYTE Tyr 6 substrate peptide are respectively taken up, and added to a 384-well microtiter plate, 5 μL diluted different concentrations of test compound are added in sequence, and the lid is closed. The microtiter plate is incubated for 60 min at room temperature (20° C. to 25° C.); and then 5 μL starter reagent A is added, and the lid is closed. The microtiter plate is incubated for 60 min at room temperature (20° C. to 25° C.); and then 5 μL termination reagent is added to the reaction well, to terminate the reaction. Finally, the fluorescence intensity ($OD_{400}$) of each well is determined in a fluorescence analyzer (excitation wavelength: 400 nm). The inhibition rate is calculated, and the half inhibitory concentration ($IC_{50}$) of the compound is calculated according to the inhibition rates of different concentrations.

For a negative control group, except that test compound (replaced by 5 μL ATP solution) is not added, all the other reagents are added. In addition, an enzyme-free control group (that is, blank group) is set.

$$\text{Inhibition rate} = \left(1 - \frac{OD \text{ of the compound} - OD \text{ of the blank group}}{OD \text{ of the negative control group} - OD \text{ of the blank group}}\right) \times 100\%$$

The inhibition of some compounds of the present invention on c-Met kinase is shown below:

| Embodiment Serial Number | Strength of activity | Embodiment Serial Number | Strength of activity |
|---|---|---|---|
| 1 | ++ | 31 | ++ |
| 2 | +++ | 32 | + |
| 3 | ++ | 33 | ++ |
| 4 | +++ | 34 | +++ |
| 5 | +++ | 35 | + |
| 6 | ++ | 36 | ++ |
| 7 | ++ | 37 | +++ |
| 8 | ++ | 38 | + |
| 9 | +++ | 39 | ++ |
| 10 | + | 40 | +++ |
| 11 | ++ | 41 | ++ |
| 12 | ++ | 42 | + |
| 13 | ++ | 43 | ++ |
| 14 | ++ | 44 | − |
| 15 | ++ | 45 | + |
| 16 | + | 46 | ++ |
| 17 | +++ | 47 | +++ |
| 18 | + | 48 | + |
| 19 | +++ | 49 | +++ |
| 20 | + | 50 | ++ |
| 21 | ++ | 51 | + |
| 22 | − | 52 | ++ |
| 23 | ++ | 53 | +++ |
| 24 | +++ | 54 | + |
| 25 | + | 55 | ++ |
| 26 | ++ | 56 | +++ |
| 27 | ++ | 57 | + |
| 28 | + | 58 | +++ |
| 29 | +++ | 59 | + |
| 30 | + | | |

Remark: "+" represents 100 nM < $IC_{50} \leq$ 1 uM; "++" represents 10 nM < $IC_{50}$ < 100 nM; "+++" represents $IC_{50}$ < 10 nM; and "−" represents having no activity.

Biological Test Embodiment 2

Inhibition of the Compound on In Vitro Proliferation of Human Gastric Cancer Cell SNU-5

Method:

Human gastric cancer cells SNU-5 are cultured in an IMDM medium containing 20% fetal bovine serum, and the culture conditions are 37° C. and 5% CO2. Tumor cells are inoculated in a 96-well plate, and after 24-hr sidewall growth, 9 different concentrations of (1 to 30000 nM) an agent are added, after 72-hr agent treatment, the medium is discarded, the cells are fixed by cold trichloroacetic acid, and then dyed with a sulforhodamine B (SRB) solution. Unbound SRB is washed off, and SRB bound with protein was dissolved with Tris, the OD is determined at a wavelength of 510 nm by a microplate reader, and the cell growth inhibition rate is calculated according to the following equation:

$$\text{Inhibition rate} = (\text{OD of control well} - \text{OD of administered well}) / \text{OD of control well} \times 100\%$$

According to the inhibition rates of different concentrations, the half inhibitory concentration $IC_{50}$ is calculated by using a Logit method.

The inhibition of compounds of some embodiments of the present invention on SNU-5 is shown below:

| Embodiment Serial Number | Strength of activity | Embodiment Serial Number | Strength of activity |
|---|---|---|---|
| 1 | +++ | 21 | +++ |
| 2 | ++ | 22 | + |
| 3 | ++ | 23 | ++ |
| 4 | ++ | 24 | ++ |
| 5 | +++ | 25 | + |
| 6 | ++ | 26 | ++ |
| 7 | ++ | 28 | + |
| 8 | + | 29 | +++ |
| 9 | ++ | 31 | ++ |
| 10 | +++ | 32 | ++ |
| 12 | ++ | 36 | + |
| 16 | ++ | 37 | ++ |
| 17 | ++ | 38 | + |
| 18 | + | 51 | ++ |
| 20 | +++ | | |

Remarks: "+" represents 500 nM < IC50 < 5 uM; "++" represents 100 nM < IC50 < 500 nM; and "+++" represents IC50 < 100 nM.

Biological Test Embodiment 3

Efficacy of the Compound on Human Malignant Glioma U87-MG Xenografts in Nude Mice Method:

The human malignant glioma U87-MG is purchased from ATCC (American Type Culture Collection), America.

BALB/cA-nude nude mice (♀, 6-7 weeks old) are purchased from Shanghai SLAC Laboratory Animal Co. Ltd. Breeding environment: SPF grade.

In vitro-cultured malignant glioma U87-MG cells are inoculated subcutaneously in nude mice, and after the tumor grows to a size of 100 to 250 $mm^3$, the animals are randomly divided into groups ($d_0$). The dose of the test agent is 100 mg/kg, and the agent is orally administered once per day for continuous 16 days. The volume of the tumor is measured two to three times per week, the mice are weighed, and the data is recorded. The tumor volume (V) is calculated according to the equation: $V=1/2 \times a \times b^2$, where a and b respectively represent length and width.

The antineoplastic efficacy is evaluated according to tumor inhibition rate, and the tumor inhibition rate is calculated according to the equation below:

$$\text{Tumor inhibition rate} = 1-(T-T_0)/(C-C_0),$$

where T and C are respectively tumor volumes of the test agent group mice and the blank group mice at the end of the experiment; and $T_0$ and $C_0$ are tumor volumes at the start of the experiment.

The inhibition of compounds of some embodiments of the present invention on human malignant glioma U87-MG xenografts in nude mice is shown below:

| Embodiment Serial Number | Tumor Inhibition Rate (%) |
|---|---|
| 1 | 62 |
| 2 | 16 |
| 3 | 91 |
| 4 | 26 |
| 5 | 74 |

What is claimed is:

1. A heterocyclic pyridone compound, being a compound represented by General Formula (I):

(I)

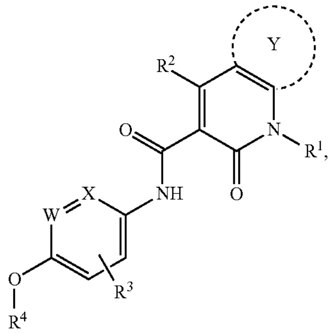

or an enantiomer, diastereomer, or conformational isomer of said compound, or a mixture thereof, or a pharmaceutically acceptable salt of said compound, wherein $R^1$ is selected from hydrogen, alkyl, substituted alkyl, cycloalkyl, substituted cycloalkyl, aryl, substituted aryl, heteroaryl, substituted heteroaryl, arylalkyl, substituted arylalkyl, heteroarylalkyl, substituted heteroarylalkyl and $C(=O)NR^{10}R^{11}$;

$R^2$ is selected from hydrogen, halogen, alkoxy, amino, alkyl, substituted alkyl, cycloalkyl, substituted cycloalkyl, hydroxy alkyl, amino alkyl, aryl, substituted aryl, heteroaryl, substituted heteroaryl, arylalkyl, substituted arylalkyl, heteroarylalkyl, substituted heteroarylalkyl, heterocyclic group, and substituted heterocyclic group;

$R^3$ is selected from hydrogen, halogen, alkyl and heteroaryl;

$R^4$ is selected from groups having Structural Formulas (1) to (5) below, wherein Z═CH or N;

(1)

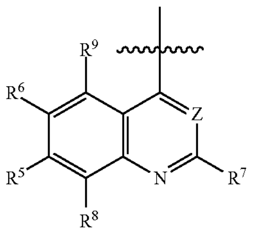

-continued (2)

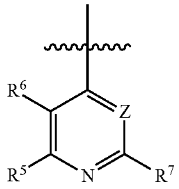

(3)

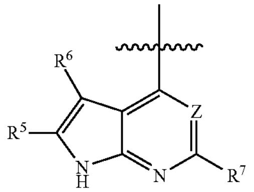

(4)

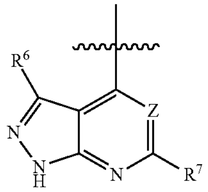

(5)

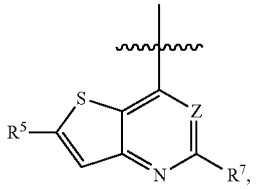

$R^5$ is selected from H, $OCH_3$, $NH_2$, $NH(C{=}O)R^{12}$, $NHC(=O)NR^{10}R^{11}$, $O(CH_2)_nOR^{12}$ (n is 1 to 4), $NR^{10}R^{11}$ or a heterocyclic group, or a substituted heterocyclic group and an aromatic heterocyclic group;

$R^6$, $R^7$, $R^8$, $R^9$, $R^{10}$, $R^{11}$, $R^{12}$ are simultaneously or non-simultaneously selected from hydrogen, halogen, alkyl, substituted alkyl, cycloalkyl, substituted cycloalkyl, aryl, substituted aryl, heteroaryl, substituted heteroaryl, alkenyl, substituted alkenyl, alkynyl, substituted alkynyl, substituted aminoalkyl, substituted alkylamino, arylamino, substituted arylamino, heteroaryl amino, substituted heteroaryl amino, a heterocyclic group and a substituted heterocyclic group;

W and X are selected from CH and N; and

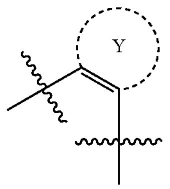

is a group having Structural Formula below:

(6)

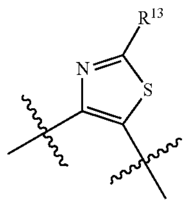

wherein $R^{13}$ is selected from hydrogen, alkyl, substituted alkyl, cycloalkyl, substituted cycloalkyl, alkoxyl, aryl, substituted aryl, heteroaryl, substituted heteroaryl, alkenyl, substituted alkenyl, alkynyl, substituted alkynyl, substituted aminoalkyl, substituted alkylamino, arylamino, substituted arylamino, heteroaryl amino, substituted heteroaryl amino, a heterocyclic group and a substituted heterocyclic group.

2. The heterocyclic pyridone compound according to claim 1, wherein Z is CH, and $R^7$, $R^8$ and $R^9$ are respectively H.

3. The heterocyclic pyridone compound according to claim 1, wherein $R^4$ is selected from groups having Structural Formulas (45) to (52) below:

(45)

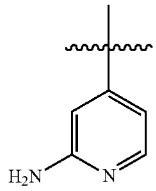

(46)

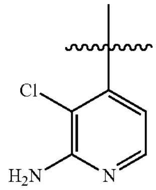

(47)

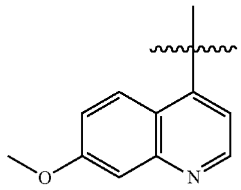

(48)

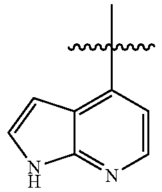

-continued (49)

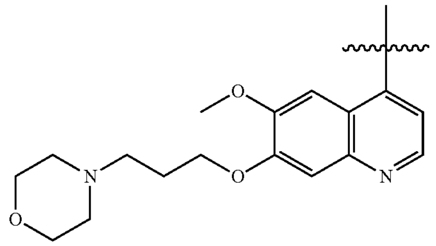

(50)

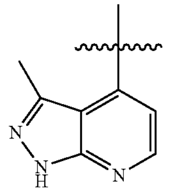

(51)

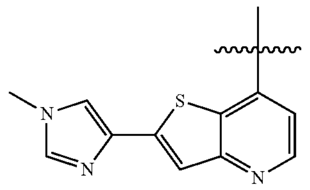

(52)

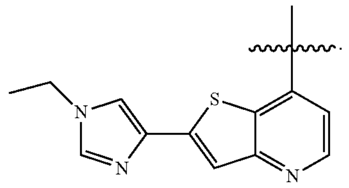

4. The heterocyclic pyridone compound according to claim 1, wherein $R^1$ is selected from phenyl, p-fluorophenyl, 2-hydroxyethyl phenyl and benzyl.

5. The heterocyclic pyridone compound according to claim 1, wherein $R^2$ is selected from hydrogen, halogen, alkoxy and amino.

6. The heterocyclic pyridone compound according to claim 1, wherein W and X are CH, $R^3$ is florine.

7. The heterocyclic pyridone compound according to claim 1, wherein the compound represented by General Formula (I) is selected from compounds having Structural Formulas (I-1) to (I-27) and (I-48) to (I-59) below:

I-1
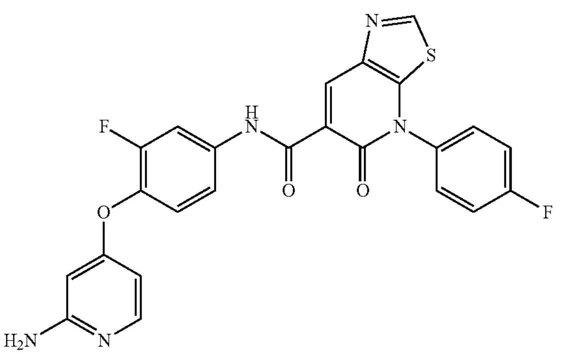
I-2
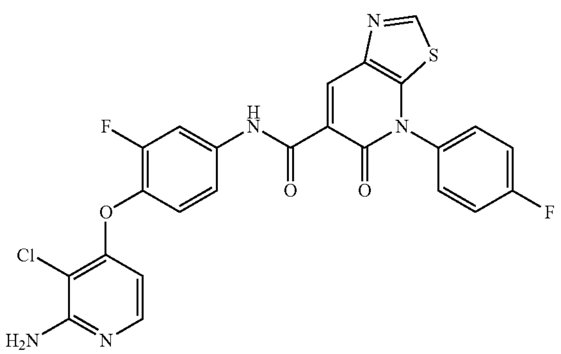
I-3
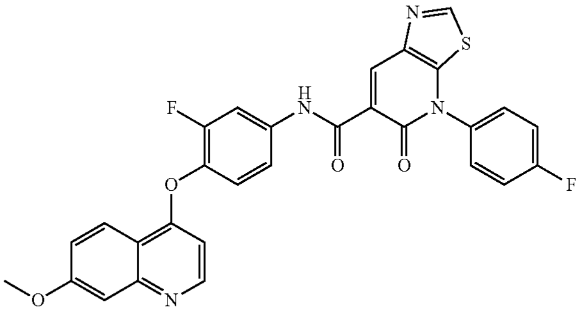
I-4
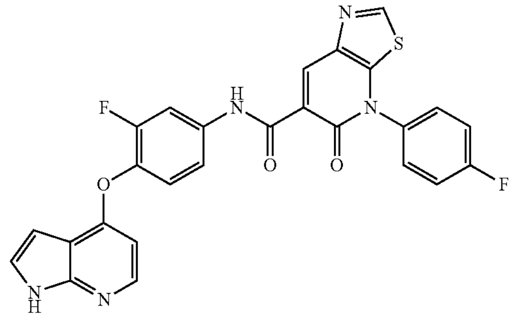
I-5
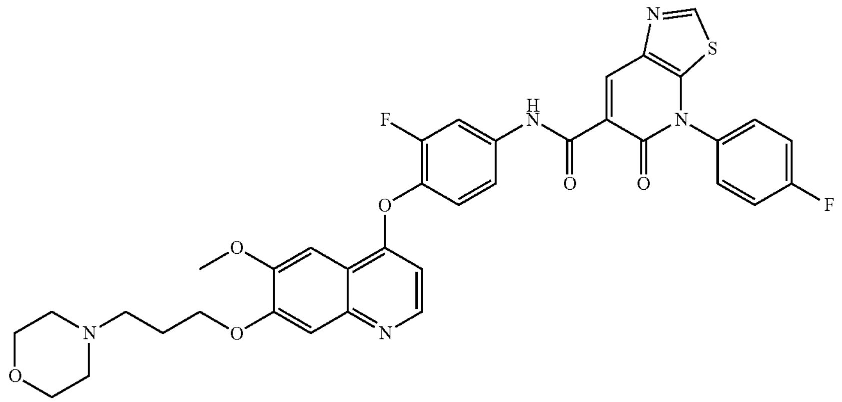
I-6
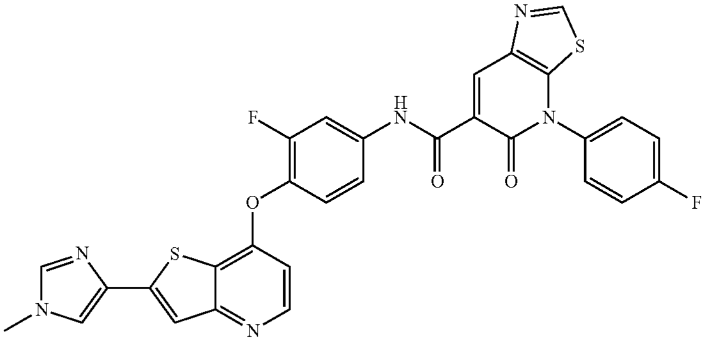

-continued
I-7
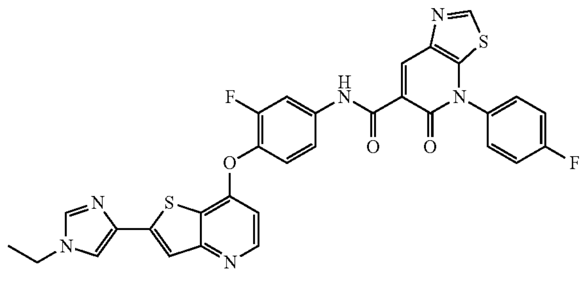
I-8
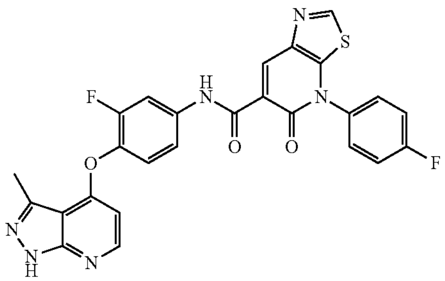
I-9
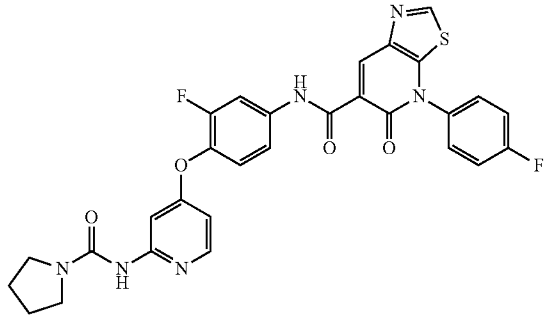
I-10
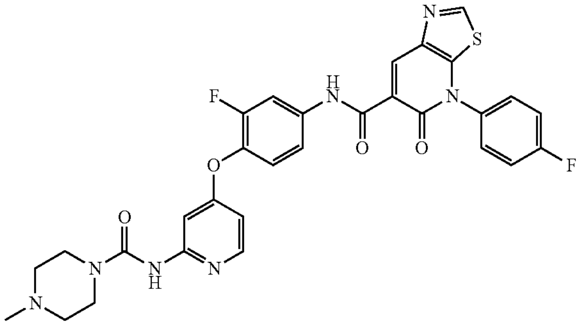
I-11
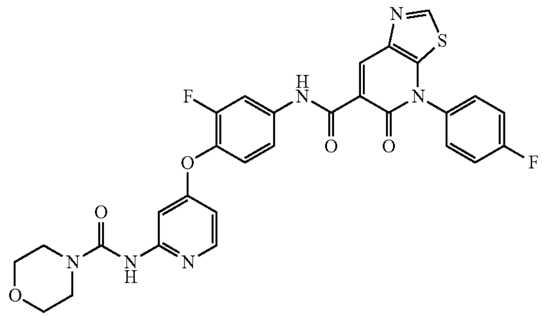
I-12
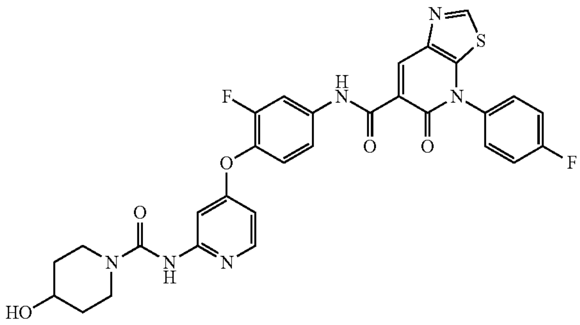
I-13
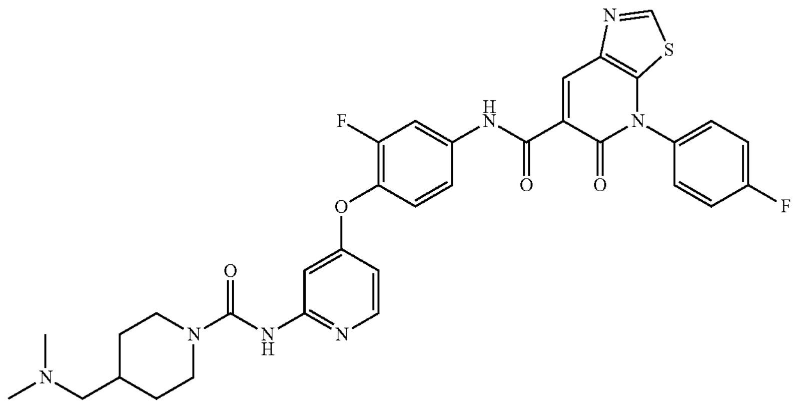

-continued
I-14
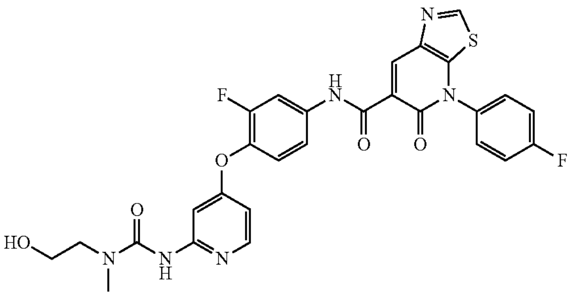
I-15
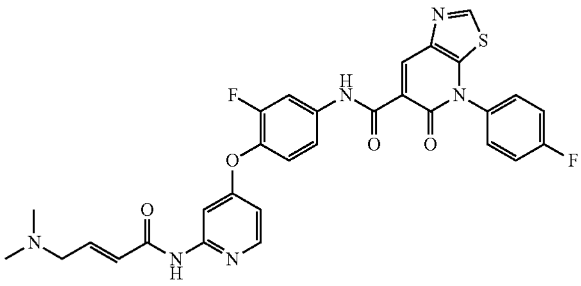
I-16
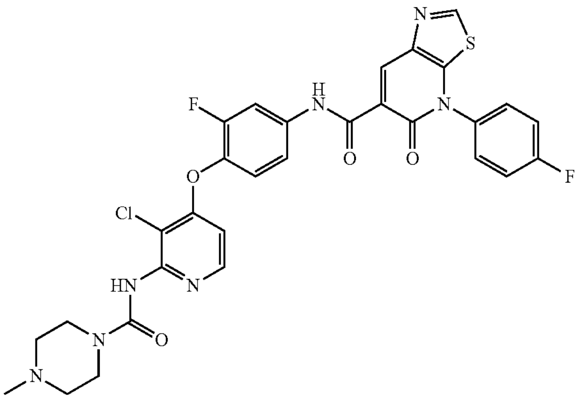
I-17
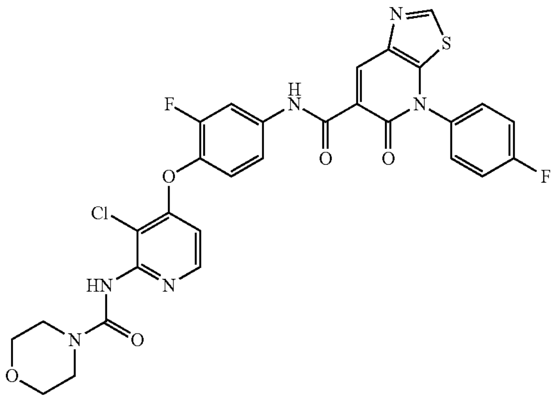
I-18
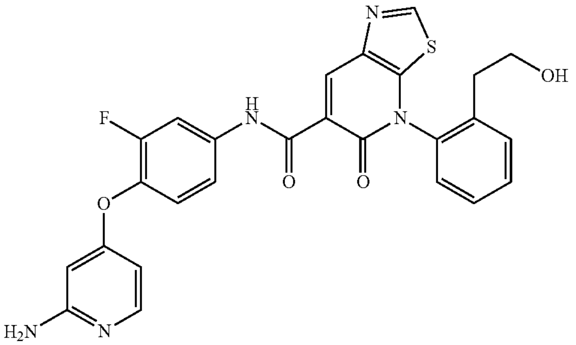
I-19
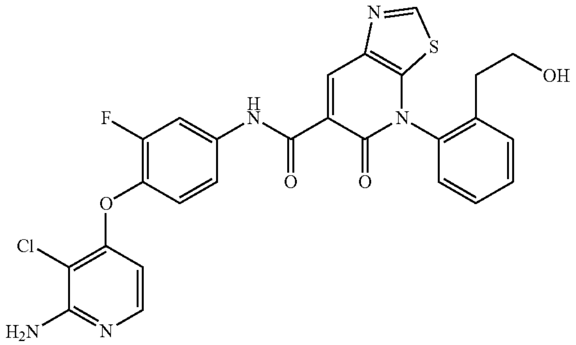
I-20
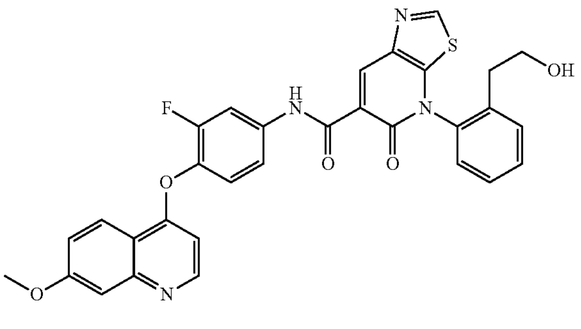
I-21
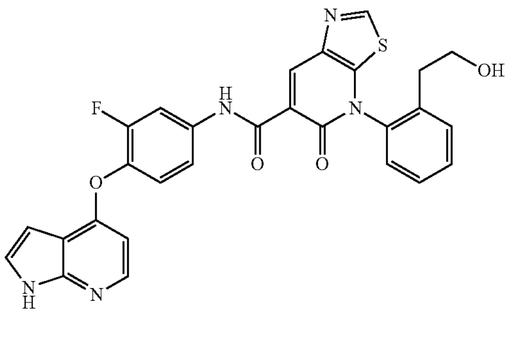

-continued
I-22
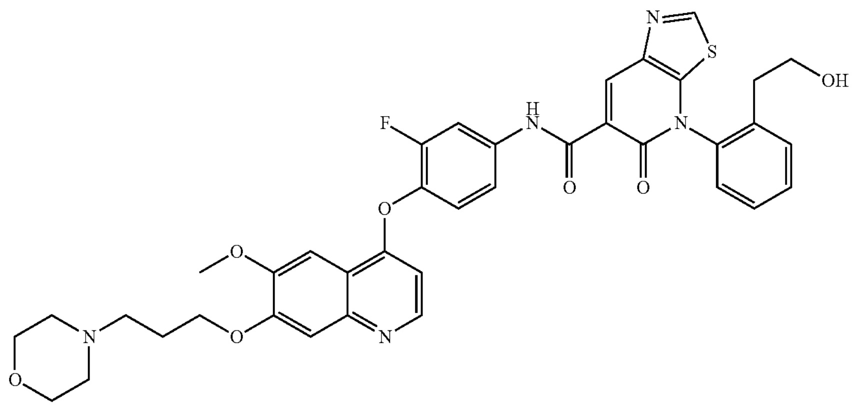
I-23
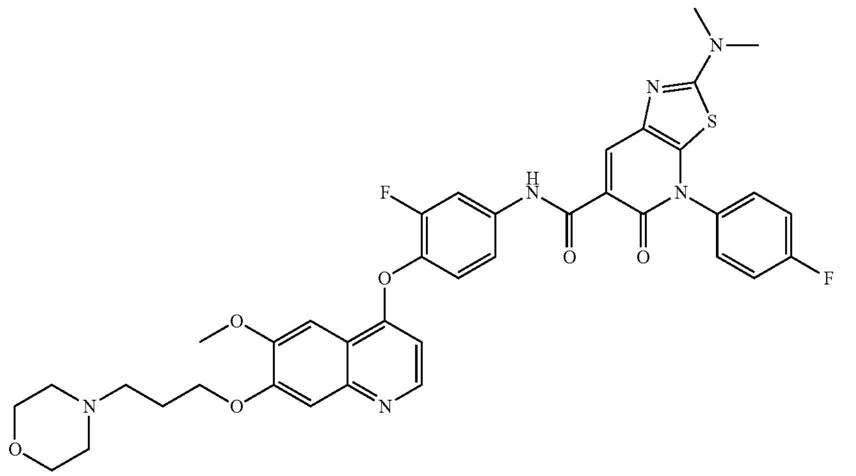
I-24
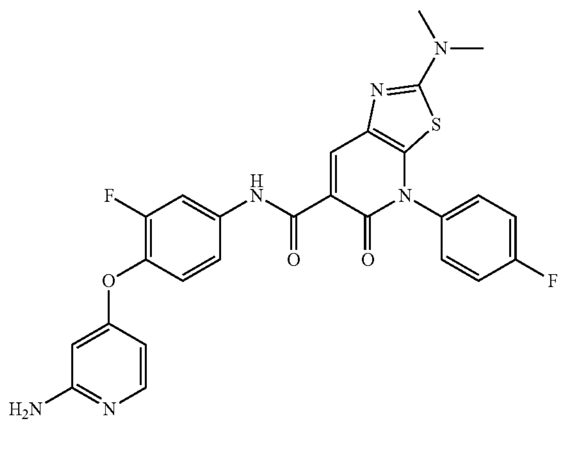
I-25
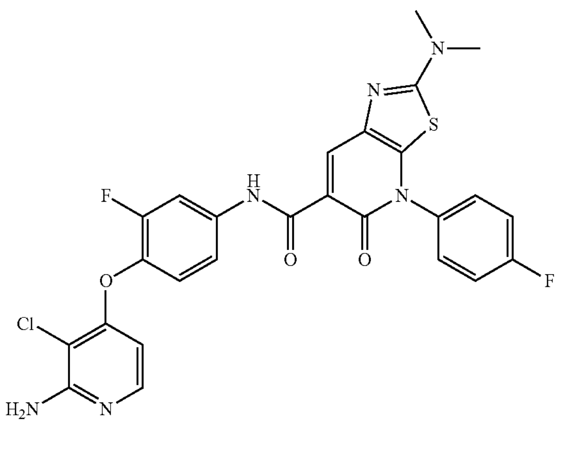

-continued
I-26
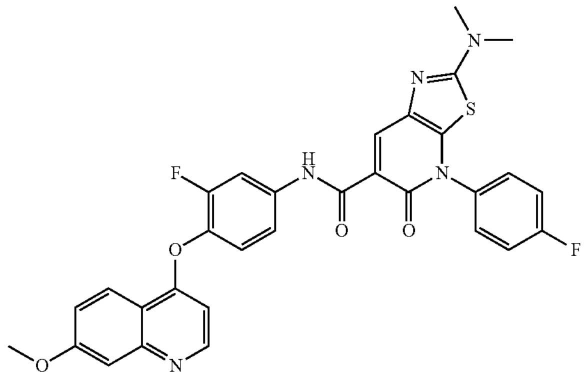
I-27
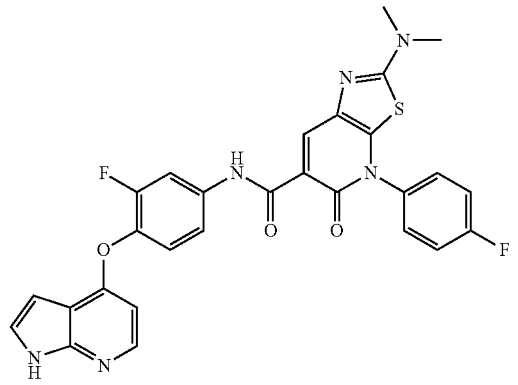
I-48
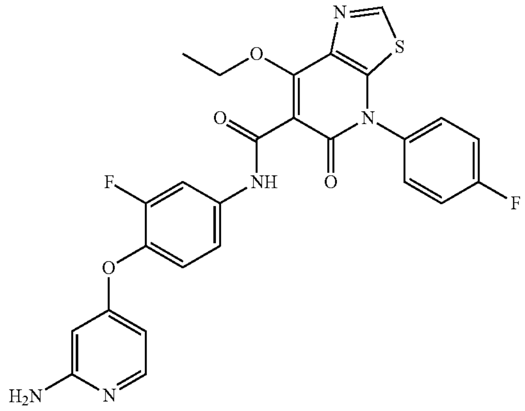
I-49
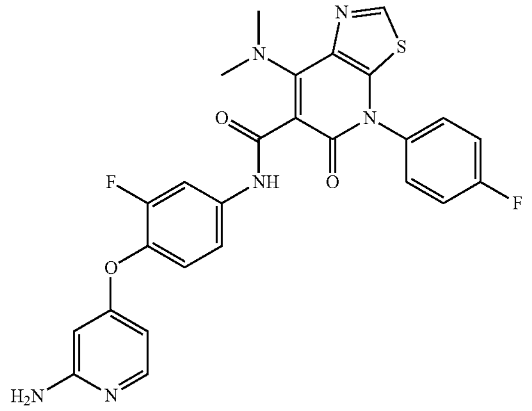
I-50
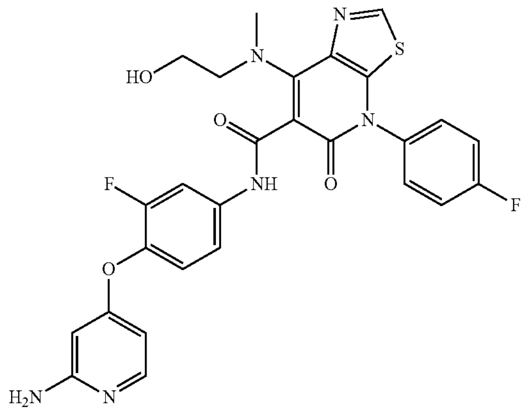
I-51
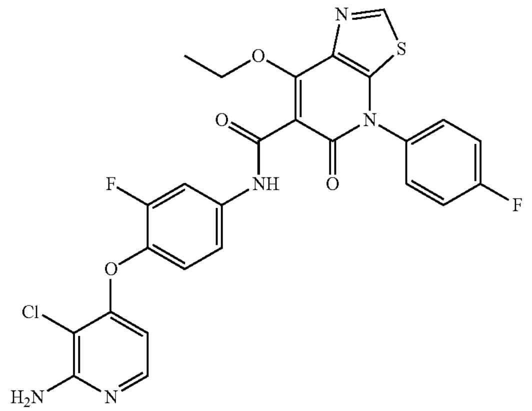
I-52
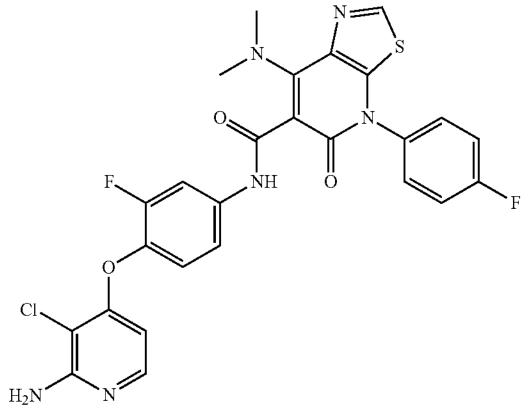
I-53
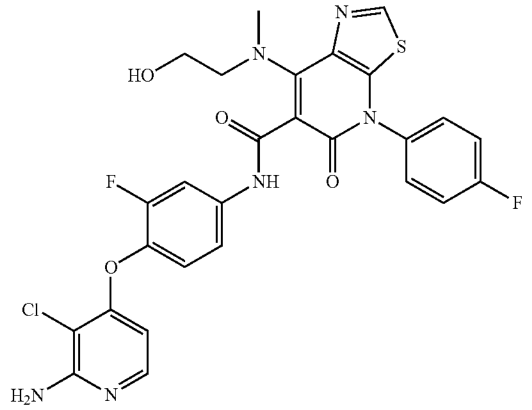

-continued

I-54

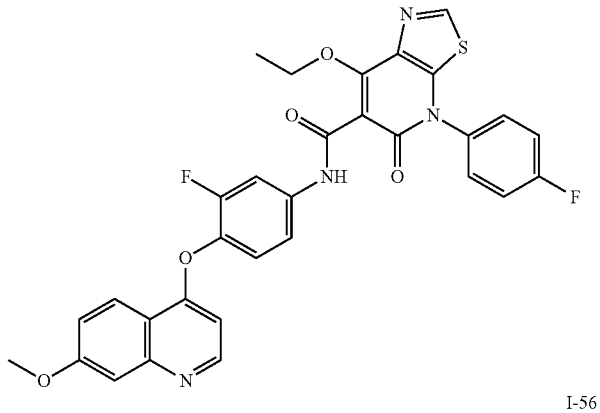

I-55

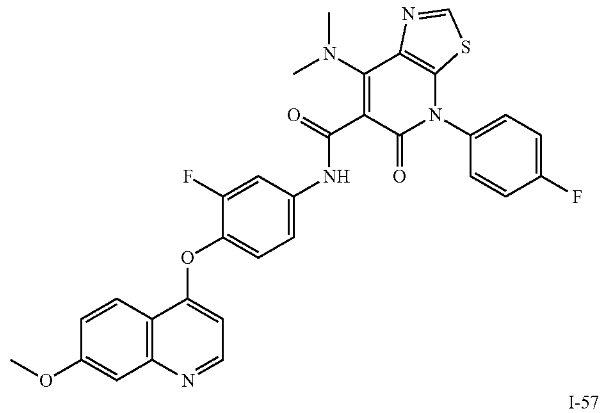

I-56

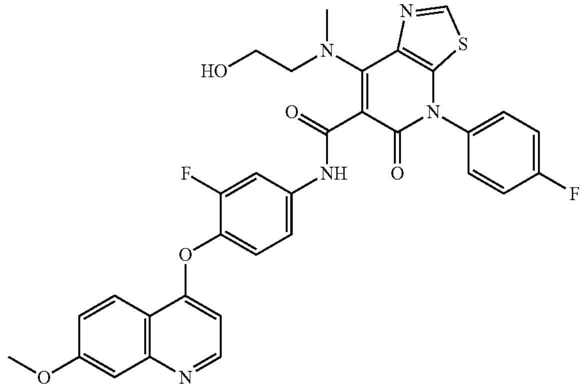

I-57

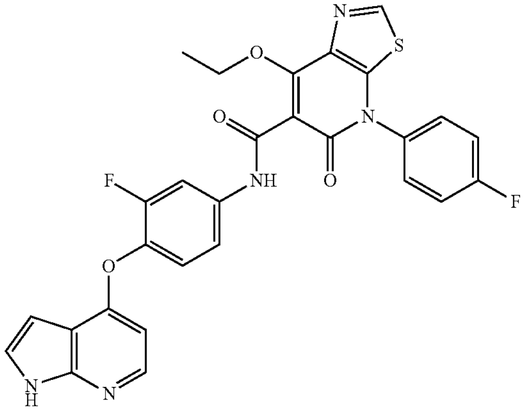

I-58

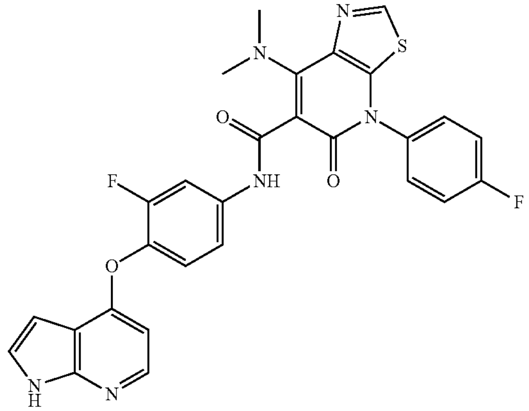

I-59

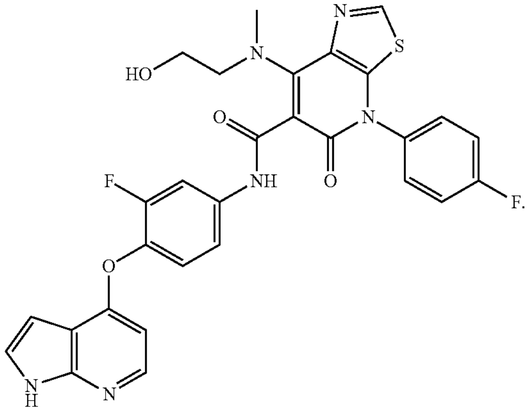

8. The heterocyclic pyridone compound according to claim 1, wherein the heterocyclic pyridone compound represented by General Formula (I) is an enantiomer, diastereomer, a conformational isomer, or a mixture thereof, or in the form of a pharmaceutically acceptable salt.

9. The heterocyclic pyridone compound according to claim 8, wherein the pharmaceutically acceptable salt is a hydrochloride, sulfate, phosphate, trifluoroacetate, methanesulfonate, trifluoromethanesulfonate, p-toluenesulfonate, tartrate, maleate, fumarate, succinate or malate of the compound represented by General Formula (I).

10. A pharmaceutical composition, comprising a therapeutically effective amount of the heterocyclic pyridone compound represented by General Formula (I) according to claim 1 and a pharmaceutically acceptable excipient.

* * * * *